United States Patent
Savariar et al.

(10) Patent No.: US 10,596,259 B2
(45) Date of Patent: Mar. 24, 2020

(54) TUMOR RADIOSENSITIZATION WITH MONOMETHYL AURISTATIN E (MMAE) AND DERIVATIVES THEREOF

(71) Applicant: The Regents of the University of California, Oakland, CA (US)

(72) Inventors: Elamprakash N. Savariar, San Diego, CA (US); Sunil J. Advani, Encinitas, CA (US); Roger Y. Tsien, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 32 days.

(21) Appl. No.: 15/161,123

(22) Filed: May 20, 2016

(65) Prior Publication Data
US 2017/0080088 A1 Mar. 23, 2017

Related U.S. Application Data

(60) Provisional application No. 62/164,429, filed on May 20, 2015.

(51) Int. Cl.
| | |
|---|---|
| A61K 41/00 | (2006.01) |
| A61K 38/05 | (2006.01) |
| A61K 47/64 | (2017.01) |
| A61K 47/65 | (2017.01) |
| A61K 47/55 | (2017.01) |
| A61N 5/10 | (2006.01) |

(52) U.S. Cl.
CPC .......... *A61K 41/0038* (2013.01); *A61K 38/05* (2013.01); *A61K 47/55* (2017.08); *A61K 47/64* (2017.08); *A61K 47/645* (2017.08); *A61K 47/65* (2017.08); *A61N 2005/1098* (2013.01)

(58) Field of Classification Search
CPC ................ A61K 41/0038; A61K 47/55; A61N 2005/1098; A61N 5/10
See application file for complete search history.

(56) References Cited

U.S. PATENT DOCUMENTS

| | | |
|---|---|---|
| 4,466,919 A | 8/1984 | Weingarten |
| 4,507,389 A | 3/1985 | Weingarten |
| 5,434,073 A | 7/1995 | Dawson et al. |
| 5,674,980 A | 10/1997 | Frankel et al. |
| 5,747,641 A | 5/1998 | Frankel et al. |
| 5,910,300 A | 6/1999 | Tournie et al. |
| 6,083,486 A | 7/2000 | Weissleder et al. |
| 6,306,993 B1 | 10/2001 | Rothbard et al. |
| 6,348,185 B1 | 2/2002 | Piwnica-Worms |
| 6,592,847 B1 | 7/2003 | Weissleder et al. |
| 7,431,915 B2 | 10/2008 | Jiang et al. |
| 7,985,401 B2 | 7/2011 | Jiang et al. |
| 8,110,554 B2 | 2/2012 | Jiang et al. |
| 8,486,373 B2 | 7/2013 | Weissleder et al. |
| 8,642,561 B2 | 2/2014 | Jiang et al. |
| 9,072,792 B2 | 7/2015 | Jiang et al. |
| 9,682,151 B2 | 6/2017 | Tsien |
| 9,695,251 B2 | 7/2017 | Tsien |
| 9,808,532 B2 | 11/2017 | Tsien |
| 2001/0021763 A1 | 9/2001 | Harris et al. |
| 2002/0009786 A1 | 1/2002 | Tang et al. |
| 2003/0176335 A1 | 9/2003 | Zhang et al. |
| 2004/0009122 A1 | 1/2004 | Klaveness et al. |
| 2004/0241096 A1 | 12/2004 | Bogdanov et al. |
| 2005/0069494 A1 | 3/2005 | Li et al. |
| 2005/0042034 A1 | 5/2005 | Jiang et al. |
| 2005/0107583 A1 | 5/2005 | Jiang et al. |
| 2006/0041105 A1 | 2/2006 | Jiang et al. |
| 2007/0041904 A1 | 2/2007 | Jiang et al. |
| 2009/0004118 A1 | 1/2009 | Nie et al. |
| 2011/0160147 A1 | 6/2011 | Dal Pozzo et al. |
| 2012/0014873 A1 | 1/2012 | Jiang et al. |
| 2012/0134922 A1 | 5/2012 | Tsien et al. |
| 2012/0148610 A1 | 6/2012 | Doronina et al. |
| 2013/0020537 A1 | 1/2013 | Maruno et al. |

(Continued)

FOREIGN PATENT DOCUMENTS

| | | |
|---|---|---|
| EP | 2 399 939 A2 | 12/2011 |
| WO | WO 01/75067 A2 | 10/2001 |

(Continued)

OTHER PUBLICATIONS

Lin et al., Cancer Research, 63, 3413-3417, Jun. 15, 2003. (Year: 2003).*
Abdollahi, A. et al., "Inhibition of $\alpha_v\beta_3$ Integrin Survival Signaling Enhances Antiangiogenic and Antitumor Effects of Radiotherapy," *Clin Cancer Res.*, Sep. 1, 2005, 11(17), pp. 6270-6279.
Adams, S.R. et al., "Anti-tubulin drugs conjugated to anti-ErbB antibodies selectively radiosensitize," *Nature Communications*, Oct. 4, 2016, 7:13019, pp. 1-11.

(Continued)

*Primary Examiner* — James H Alstrum-Acevedo
*Assistant Examiner* — Kaipeen E Yang
(74) *Attorney, Agent, or Firm* — Morgan Lewis & Bockius LLP

(57) ABSTRACT

Disclosed herein, the invention pertains to methods and compositions that find use in radiosensitization of tumors and tumor samples based on the ability of a tumor sample to cleave a MTS molecule of the present invention. The MTS molecules of the present invention have a formula as disclosed herein and wherein A is a peptide with a sequence comprising 5 to 9 consecutive acidic amino acids, wherein the amino acids are selected from: aspartates and glutamates; B is a peptide with a sequence comprising 5 to 20 consecutive basic amino acids; X and Y are linkers; P is an optional pre-targeting moiety; M is an optional macromolecular carrier; and T is a radiosensitization agent for delivery to a target, including for example a therapeutic compound.

4 Claims, 64 Drawing Sheets

Specification includes a Sequence Listing.

(56) References Cited

U.S. PATENT DOCUMENTS

| | | |
|---|---|---|
| 2013/0078188 A1 | 3/2013 | Tsien et al. |
| 2013/0176335 A1 | 7/2013 | Sugiyama et al. |
| 2015/0031852 A1 | 1/2015 | Liu et al. |

FOREIGN PATENT DOCUMENTS

| | | |
|---|---|---|
| WO | WO 2005/042034 A1 | 5/2005 |
| WO | WO 2006/125134 A1 | 11/2006 |
| WO | WO 2011/008992 A2 | 1/2011 |
| WO | WO 2011/008996 A2 | 1/2011 |
| WO | WO 2013/019681 A2 | 2/2013 |
| WO | WO 2014/120837 A2 | 8/2014 |

OTHER PUBLICATIONS

Advani, S.J. et al., "Increased oncolytic efficacy for high-grade gliomas by optimal integration of ionizing radiation into the replicative cycle of HSV-1," Gene Therapy, 2011, vol. 18, pp. 1098-1102.

Advani, S.J. et al., "Preferential Replication of Systemically Delivered Oncolytic Vaccinia Virus in Focally Irradiated Giloma Xenografts," Clin Cancer Res., 2012; 18(9), pp. 2579-2590.

Aguilera, T.A. et al., "Systemic in vivo distribution of activatable cell penetrating peptides is superior to that of cell penetrating peptides," Integr. Biol., 2009 vol. 1, pp. 371-381.

Akashi, Y. et al., "The novel microtubule-interfering agent TZT-1027 enhances the anticancer effect of radiation in vitro and in vivo," British Journal of Cancer, 2007, vol. 96, pp. 1532-1539.

Arnold, D. et al., "Substrate specificity of cathepsins D and E determined by N-terminal and C-terminal sequencing of peptide pools," Eur. J. Biochem., 1997, vol. 249, pp. 171-179.

Bai, R. et al., "Dolastatin 10, a powerful cytostatic peptide derived from a marine animal. Inhibition of tubulin polymerization mediated through the vinca alkaloid binding domain," Biochem Pharmacol., 1990; 39:1941-49.

Bartles, J.R. et al., "Identification and charactzerization of espin, an actin-binding protein localized to the F-actin0rich junctionla plaques of Sertoli cell ectoplasmic specializations," Journal of Cell Science, 1996, vol. 109, No. 6, pp. 1229-1239.

Bhorade, R. et al., "Macrocyclic Chelators with Paramagnetic Cations Are Internalized into Mammalian Cells via a HIV-Tat Derived Membrane Translocation Peptide," Bioconjugate Chemistry, May 1, 2000, vol. 11, No. 3, pp. 301-305.

Blum, G. et al., "Noninvasive optical imaging of cysteine protease activity using fluorescently quenched activity-based probes," Nature Chemical Biology, Oct. 2007, vol. 3, No. 10, pp. 668-677.

Breij, E.C.W. et al., "An Antibody-Drug Conjugate That Targets Tissue Factor Exhibits Potent Therapeutic Activity against a Broad Range of Solid Tumors," Cancer Res., Feb. 15, 2014, 74(4):1214-1226.

Bremer, C. et al., "In vivo molecular target assessment of matrix metalloproteinase inhibition," Nature Medicine, Jun. 2001, vol. 7, No. 6, pp. 743-748.

Bremer, C. et al., "Optical Imaging of Matrix Metalloproteinase-2 Activity in Tumors: Feasibility Study in a Mouse Model," Radiology, 2001, vol. 221, pp. 523-529.

Bremer, C. et al., "Optical Imaging of Spontaneous Breast Tumors Using Protease Sensing 'Smart' Optical Probes," Invest Radiol., Jun. 6, 2005, 40(6):321-327.

Buckel, L. et al., "Tumor Radiosensitization by Monomethyl Auristatin E; Mechanism of Action and Trageted Delivery," Cancer Res., Apr. 1, 2015, 75(7), pp. 1376-1387.

Chaurand, P. et al., "Molecular imaging of thin mammalian tissue sections by mass spectrometry," Curr Opinion Biotechnol., 2006; 17(4):431-436.

Chen, B. et al., "Thrombin Activity Associated with Neuronal Damage during Acute Focal Ischemia," The Journal of Neuroscience, May 30, 2012, vol. 32, No. 22, pp. 7622-7631.

Chen, E.I. et al., "A Unique Substrate Recognition Profile for Matrix Metalloprotinase-2," The Journal of Biological Chemistry, Feb. 8, 2002, vol. 277, No. 6, pp. 4485-4491.

Chen, J. et al., "'Zipper' Molecular Beacons: A Generalized Strategy to Optimize the Performance of Activatable Protease Probes," Bioconjugate Chem., 2009, vol. 20, pp. 1836-1842.

Cooks, R.J. et al., "Ambient Mass Spectrometry," Science, 2006; 311(5767):1566-1570.

Crisp, J.L. et al., "Dual Targeting of Integrin $\alpha_v\beta_3$ and Matrix Metalloproteinase-2 for Optical Imaging of Tumors and Chemotherapeutic Delivery," Mol Cancer Ther., Jun. 2014, 13:6, pp. 1514-1525.

Derossi et al., "Trojan peptides: the penetratin system for intracellular delivery," Trends in Cell Biology, 1998, 8:84-87.

Doronina, S.O. et al., "Development of potent monoclonal antibody auristatin conjugates for cancer therapy," Nat Biotechnol., 2003; 21:778-84.

Egami, T. et al., "Up-regulation of integrin $\beta3$ in radioresistant pancreatic cancer impairs adenovirus-mediated gene therapy," Cancer Science, Oct. 2009, vol. 100, No. 10, pp. 1902-1907.

Fujita, M. et al., "X-ray irradiation and Rho-kinase inhibitor additively induce invasiveness of the cells of the pancreatic cancer line, MIAPaCa-2, which exhibits mesenchymal and amoeboid motility," Cancer Sci., Apr. 2011, vol. 102, No. 4, pp. 792-798.

Futaki et al., "Stearylated Arginine-Rich Peptides: A New Class of Transfection Systems," Bioconj. Chem., 2001, 12:1005-1011.

Gallwitz, M. et al., "The Extended Cleavage Specificity of Human Thrombin," PLoS One, Feb. 2012, vol. 7, Issue 2, e31756, pp. 1-16.

Giustini, A.J. et al., "Ionizing radiation increases systemic nanoparticle tumor accumulation," Nanomedicine 2012;8:818-21.

Golub, T.R. et al., "Molecular Classification of Cancer: Class Discovery and Class Prediction by Gene Expression Monitoring," Science, Oct. 15, 1999, vol. 286, pp. 531-537.

Gounaris, E. et al., "Live Imaging of Cysteine-Cathepsin Activity Reveals Dynamics of Focal Inflammation, Angiogenesis, and Polyp Growth," PLoS One, Aug. 2008, vol. 3, No. 8, e2916, pp. 1-9.

Hallahan, D. et al., "Integrin-mediated targeting of drug delivery to irradiated tumor blood vessels," Cancer Cell, Jan. 2003, vol. 3, pp. 63-74.

Hallahan, D.E. et al., "Radiation-mediated control of drug delivery," Am J Clin Oncol., 2001; 24:473-80.

Hallahan, D.E. et al., et al., "Spatial and temporal control of gene therapy using ionizing radiation," Nat Med., 1995;1:786-91.

Hallbrink, M. et al., "Cargo delivery kinetics of cell-penetrating peptides," Biochimica et Biophysica Acta, 2001, vol. 1515, pp. 101-109.

Harir, G. et al., "Radiation-Guided Drug Delivery to Mouse Models of Lung Cancer," Clin Cancer Res., Oct. 15, 2010, 16(1); pp. 4968-4977.

Hutteman, M. et al., "Optimization of Near-Infrared Fluorescent Sentinel Lymph Node Mapping for Vulvar Cancer," Am J Obstet Gynecol., Jan. 2012, vol. 206, No. 1, pp. 89.e1-89.e5.

Ifa, D.R. et al., "Ambient Ionization Mass Spectrometry for Cancer Diagnosis and Surgical Margin Evaluation," Clinical Chemistry, 2016, 62:1, pp. 111-123.

Jaffer, F.A. et al., "In Vivo Imaging of Thrombin Activity in Experimental Thrombi With Thrombin-Sensitive Near-Infrared Molecular Probe," Arterioscler Thromb Vasc Biol., 2002, vol. 22, pp. 1929-1935.

Jiang, T. et al., "Tumor imaging by means of proteolytic activation of cell-penetrating peptides," PNAS, Dec. 21, 2004, pp. 17867-17872, vol. 101, No. 51.

Joh, D.Y. et al., "Selective Targeting of Brain Tumors with Gold Nanoparticle-Induced Radiosensitization," PLoS One, Apr. 2013, vol. 8, No. 4, e62425, pp. 1-10.

Kumar, A. et al., "Increased tyoe-IV collagenase (MMP-2 and MMP-9) activity following preoperative radiotherapy in rectal cancer," British Journal of Cancer, 2000, 82(4), pp. 960-965.

Lanekoff, I. et al., "Automated Platform for High-Resolution Tissue Imaging Using Nanospray Desorption Electrospray Ionization Mass Spectrometry," Anal Chem., 2012; 84(19):8351-8356.

Laskin, J. et al., "Ambient Mass Spectrometry Imaging Using Direct Liquid Extraction Techniques," Anal. Chem., 2016; 88(1):52-73.

(56) References Cited

OTHER PUBLICATIONS

Levenson, R. et al., "Review Article: Modern Trends in Imaging X: Spectral imaging in preclinical research and clinical pathology," Anal Cell Pathol, 2012, vol. 35, pp. 339-361.

Levi, J. et al., "Design, Synthesis and Imaging of an Activatable Photoacoustic Probe," J Am Chem Soc., Aug. 18, 2010, vol. 132, No. 32, pp. 11264-11269.

Li, C. et al., "Tumor Irradiation Enhances the Tumor-specific Distribution of Poly(L-glutamate acid)-conjugated Paclitaxel and Its Antitumor Efficacy," Clinical Cancer Research, Jul. 2000, vol. 6, pp. 2829-2834.

Liauw, S.L. et al., "New paradigms and future challenges in radiation oncology: an update of biological targets and technology," Sci Transl Med., 2013;5:173sr2.

Lin, S.H. et al., "Opportunities and Challenges in the Era of Molecularly Targeted Agents and Radiation Therapy," J Natl Cancer Inst., 2013, vol. 105, pp. 686-693.

Linder, K.E. et al., "Synthesis, In Vitro Evaluation, and In Vivo Metabolism of Fluor/Quencher Compounds Containing IRDye 800CW and Black Hole Quencher-3 (BHQ-3)," Bioconjugate Chemistry, 2011, vol. 22, pp. 1287-1297.

Liu, F-F. et al., "Lessons Learned from Radiation Oncology Clinical Trials," Clin Cancer Res., 2013, 19(22):6089-6100.

Ma, D. et al., "Potent Antitumor Activity of an Auristatin-Conjugated, Fully Human Monoclonal Antibody to Prostate-Specific Membrane Antigen," Clin Cancer Res., 2006, 12(8):2591-2596.

Maitz, M.F. et al., "Bio-responsive polymer hydrogels homeostatically regulate blood coagulation," Nature Communications, 2013, pp. 1-7.

Miller, S.M. et al., "Nanomedicine in chemoradiation," Ther Deliv., 2013;4: 239-50.

Moding, E.J. et al., "Strategies for optimizing the response of cancer and normal tissues to radiation," Nat Rev Drug Discov., 2013; 12:526-42.

Mullard, A., "Maturing antibody-drug conjugate pipeline hits 30," Nat Rev Drug Discov., 2013;12:329-32.

Nguyen, Q.T. et al., "Fluorescence-guided surgery with live molecular navigation—a new cutting edge," Nature Reviews Cancer, Sep. 2013, vol. 13, pp. 653-662.

Nguyen, Q.T. et al., "Surgery with molecular fluorescence imaging using activatable cell-penetrating peptides decreases residual cancer and improves survival," PNAS, Mar. 2, 2010, vol. 107, No. 9, pp. 4317-4322.

Olson, E.S. et al., "Activatable cell penetrating peptides linked to nanoparticles as dual probes for in vivo fluorescence and MR imaging of proteases," PNAS, Mar. 2, 2010, vol. 107, No. 9, pp. 4311-4316.

Olson, E.S. et al., "In vivo characterization of activatable cell penetrating peptides for targeting protease activity in cancer," Integr. Biol., 2009, vol. 1, pp. 382-393.

Olson, E.S. et al., "In vivo fluorescence imaging of atherosclerotic plaques with activatable cell-penetrating peptides targeting thrombin activity," Integr Biol (Camb), Jun. 2012, vol. 4, No. 6, pp. 595-605.

Olson, E.S., "Activatable cell penetrating peptides for imaging protease activity in vivo," Electronic Theses and Dissertations UC San Diego, 2008, 152 pages.

Passarella, R.J. et al., "Targeted Nanoparticles That Deliver a Sustained, Specific Release of Paclitaxel to Irradiated Tumors," Cancer Res., Jun. 1, 2010, 70(11); pp. 4550-4559.

Pretz, J.L. et al., "Chemoradiationtherapy: localized esophageal, gastric, and pancreatic cancer," Surg Oncol Clin N Am., 2013;22:511-24.

Proimmune, "think peptides® the source for all peptides for your research," 2012, pp. 1- 15.

Raleigh, D.R. et al., "Molecular targets and mechanisms of radiosensitization using DNA damage response pathways," Future Oncol., 2013; 9:219-223.

Rieken, S. et al., "Targeting $\alpha_v\beta_3$ and $\alpha_v\beta_5$ inhibits photon-induced hypermigration of malignant glioma cells," Radiation Oncology, 2011, 6(132):pp. 1-7.

Rothbard, J. B. et al., "Conjugation of arginine oligomers to cyclosporin A facilitates topical delivery and inhibition of inflammation," Nature Medicine, Nov. 2000, vol. 6, No. 11, pp. 1253-1257.

Rothbard, J.B. et al., "Arginine-Rich Molecular Transporters for Drug Delivery: Role of Backbone Spacing in Cellular Uptake," J. Med. Chem., 2002, vol. 45, pp. 3612-3618.

Ryppa, C. et al., "In Vitro and In Vivo Evaluation of Doxorubicin Conjugates with the Divalent Peptide E-[c(RGDfK)$_2$] that Targets Integrin $\alpha_v\beta_3$," Bioconjugate Chem., 2008, vol. 19, pp. 1414-1422.

Savariar, E.N. et al., "Real-time In Vivo Molecular Detection of Primary Tumors and Metastases with Ratiometric Activatable Cell-Penetrating Peptides," Cancer Res., 2012, 73(2); pp, 855-864.

Scherer, R.L. et al., "Optical imaging of matrix metalloproteinase-7 activity in vivo using a proteolytic nanobeacon," Mol Imaging, 2008, vol. 7, No. 3, pp. 118-131.

Sievers, E.L. et al., "Antibody-drug conjugates in cancer therapy," Annu Rev Med., 2013;64:15-29.

Speake, W.J. et al., "Radiation induced MMP expression from rectal cancer is short lived but contributes to in vitro invasion," Eur J Surg Oncol., 2005;31:869-74.

Sperling, C. et al., "Thrombin-responsive hydrogels with varied cleavage kinetics," Society for Biomaterials, 2013, Abstract #208, 1 page.

Stary, H. et al., "A Definition of Advanced Type of Atherosclerotic Lesions and a Histologicial Classification of Atherosclerosis: A Report From the Committee on Vascular Lesions of the Council on Arteriosclerosis, American Heart Association," Circulation, Sep. 1995, vol. 92, No. 5, pp. 355-374.

Stone, G.W. et al., "A Prospective Natural-History Study of Coronary Atherosclerosis," The New England Journal of Medicine, Jan. 20, 2011, vol. 364, No. 3, pp. 226-235.

Tishler, R.B. et al., "Taxol: a novel radiation sensitizer," Int J Radiat Oncol Biol Phys., 1992; 122:613-7.

Tseng, W.W. et al., "Development of an Orthotopic Model of Invasive Pancreatic Cancer in an Immunocompetent Murine Host," Clinical Cancer Research, Jul. 15, 2010, vol. 16, No. 14, pp. 3684-3695.

Tsien, R.Y. et al., "Practical design criteria for a dynamic ratio imaging system," Cell Calcium, 1990, vol. 11, pp. 93-109.

Tsien, R.Y., "Indicators Based on Fluorescence Resonance Energy Transfer (FRET)," Imaging in Neuroscience and Development, Jul. 2009, vol. 4, No. 7, pp. 1-7.

Tung, C-H. et al., "A Novel Near-Infrared Fluorescence Sensor for Detection of Thrombin Activation in Blood," ChemBioChem, 2002, vol. 3, pp. 207-211.

Tung, C-H. et al., "Arginine containing peptides as delivery vectors," Advanced Drug Delivery Reviews, 2003, vol. 55, pp. 281-294.

Ullrich, K.J. et al., "Controluminal para-aminohippurate (PAH) transport in the proximal tubule of the rat kidney," Pflügers Arch., 1989, vol. 415, pp. 342-350.

Van Berkel, S.S. et al., "Fluorogenic Peptide-Based Substrates for Monitoring Thrombin Acitivity," ChemMedChem, 2012, vol. 7, pp. 606-617.

Van Dam, G.M. et al., "Intraoperative tumor-specific fluorescence imaging in ovarian cancer by folate receptor-α targeting: first in-human results," Nature Medicine, 2011, vol. 17, pp. 1315-1319.

Van Duijnhoven, S.M.J. et al., "Tumor Targeting of MMP-2/9 Activatable Cell-Penetrating Imaging Probes is Caused by Tumor-Independent Activation," J Nucl Med, 2011, vol. 52, pp. 279-286.

Van Vlerken, L.E. et al., "Poly(ethylene glycol)-modified Nanocarriers for Tumor-targeted and Intracellular Delivery," Pharmaceutical Research, Aug. 2007, vol. 24, No. 8, pp. 1404-1414.

Vartak, D.G. et al., "In vitro evaluation of functional interaction of integrin αvβ3 and matrix metalloprotease-2," Mol Pharm., 2009, vol. 6, No. 6, pp. 1856-1867.

Wadia et al., "Protein transduction technology," Curr Opinion. Biotech., 2002, 13:52-56.

Wang, Y. et al., "Efficacy and safety of dendrimer nanoparticles with coexpression of tumor necrosis factor-α and herpes simplex virus

(56) References Cited

OTHER PUBLICATIONS thymidine kinase in gene radiotherapy of the human uveal melanoma OCM-1 cell line," *International Journal of Nanomedicine*, 2013, vol. 8, pp. 3805-3816.
Wang, Y. et al., "Visualizing the mechanical activation of SRC," *Nature*, Apr. 21, 2005, pp. 1040-1045, vol. 434.
Wender, P.A. et al., "The design, synthesis, and evaluation of molecules that enable or enhance cellular uptake: Peptoid molcular transporters," *PNAS*, Nov. 21, 2000, vol. 97, No. 24, pp. 13003-13008.
Werner, M.E. et al., "Preclinical evaluation of Genexol-PM, a nanoparticle formulation of paclitaxel, as a novel radiosensitizer for the treatment of non-small cell lung cancer," *Int J Radiat Oncol Biol Phys*., 2013;86:463-8.
Whitney, M. et al., "Parallel in Vivo and in Vitro Selection Using Phage Display Identifies Protease-dependent Tumor-targeting Peptides," *The Journal of Biological Chemistry*, Jul. 16, 2010, vol. 285, No. 29, pp. 22532-22541.
Xu, W. et al., "RGD-conjugated gold nanorods induce Radiosensitization in melanoma cancer cells by down regulating $\alpha_3\beta_3$ expression," *International Journal of Nanomedicine*, 2012, vol. 7, pp. 915-924.
Zhang, L. et al., "Preparation of functionally active cell-permeable peptides by single-step ligation of two peptide modules," *Proc. Natl. Acad. Sci. USA*, Aug. 1998, vol. 95, pp. 9184-9189.
Zhu, L. et al., "Dual-Functional, Receptor-Targeted Fluorogenic Probe for In Vivo Imaging of Extracellular Protease Expressions," *Bioconjugate Chemistry*, Jun. 15, 2011, vol. 22, No. 6, pp. 1001-1005.
Znati, C. et al., "Effect of Radiation on Interstitual Fluid Pressure and Oxygenation in a Human Tumor Xenograft," *Cancer Research*, Mar. 1, 1996, vol. 56, pp. 964-968.

\* cited by examiner

Figure 2
Synthesis of cyclicRGD-ACPP-MMAE
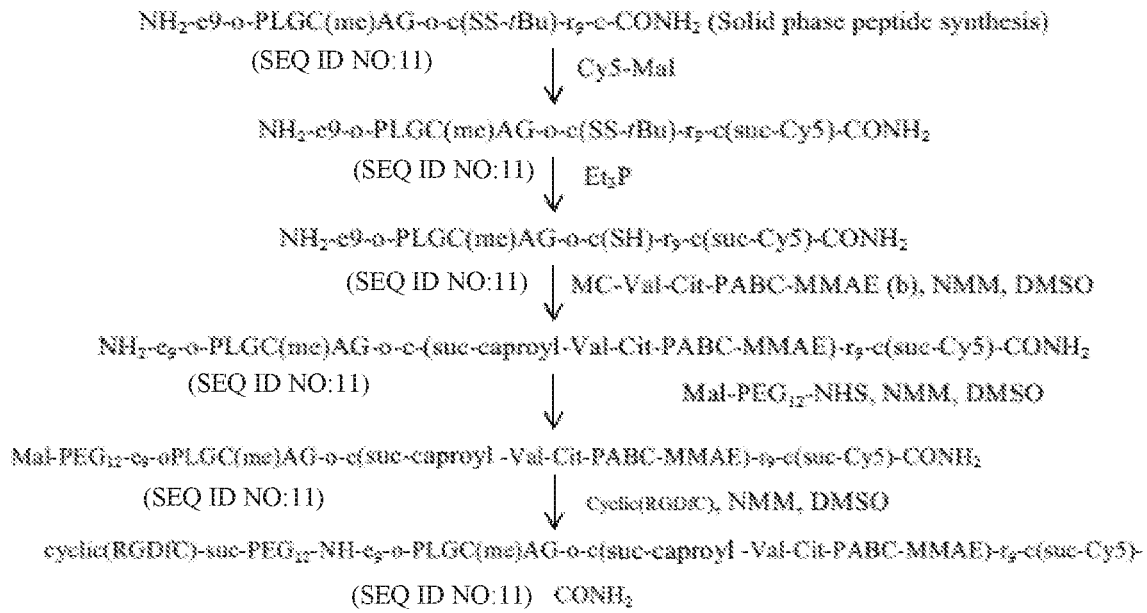
*Scheme 1: Synthesis of cRGD-ACPP-MMAE*
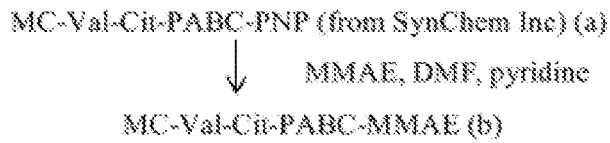
*Scheme 2: Synthesis of MC-Val-Cit-PABC-MMAE*
Schemes show synthesis of CyclicRGD-ACPP-MMAE (Scheme 1), MC-Val-Cit-PABC-MMAE (Scheme 2). Lower case letters represent D amino acids, "o" denotes 5-amino-3-oxopentanoyl, a short hydrophilic spacer -, "suc" refers to succinimido.

*Figure 7B*
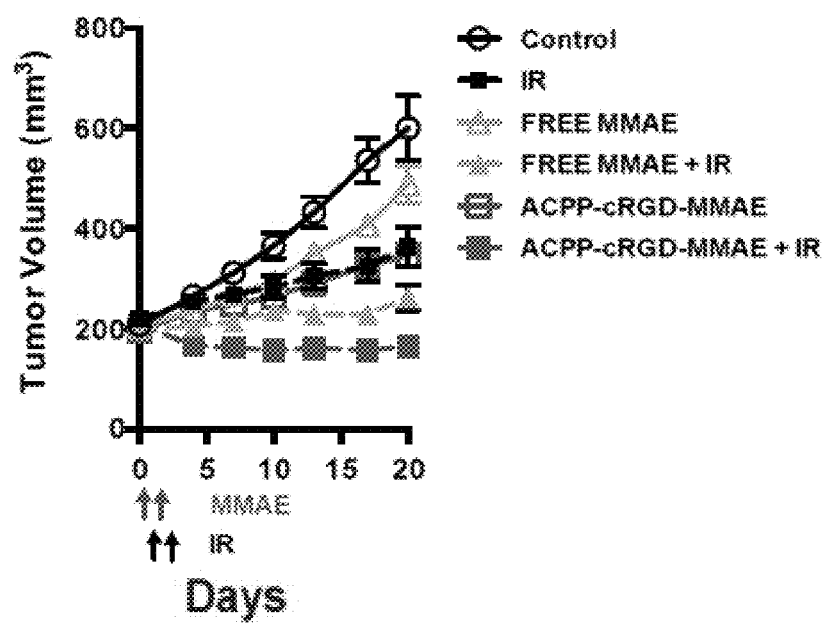
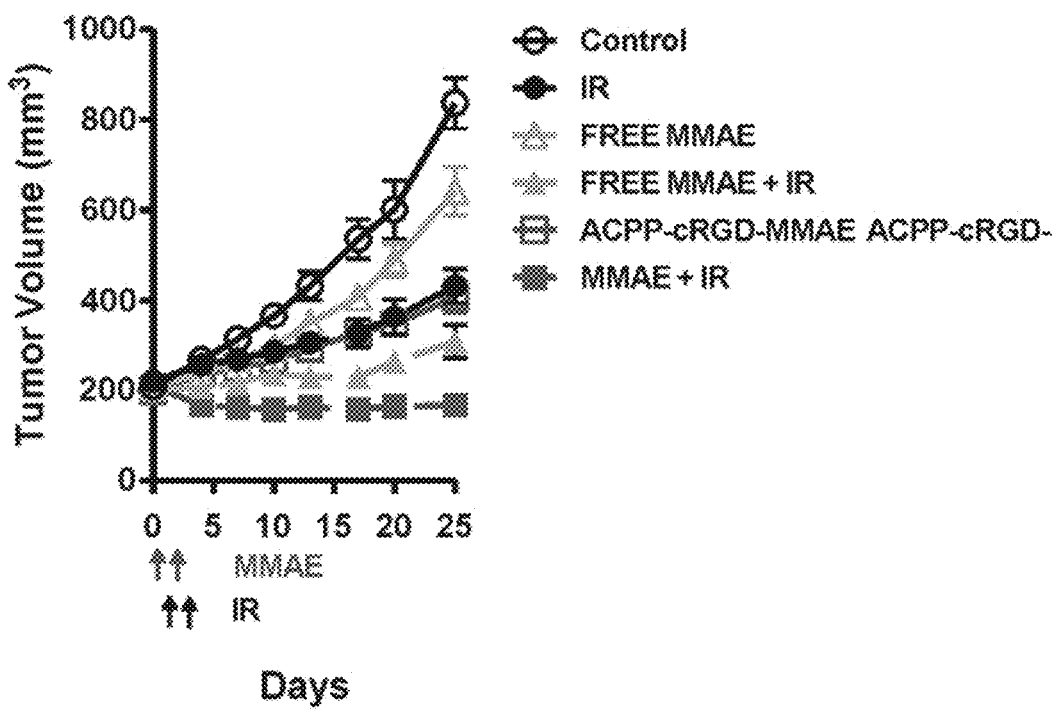

*Figure 9*

|  | V(end) / V(0) ≤ 1 | | |
|---|---|---|---|
|  | PANC-1, Fig 7B (top) | PANC-1, Fig 7C | HCT-116, Fig 7D |
| Control | 0% | 0% | 0% |
| IR | 20% | 0% | 30% |
| Free MAME | 0% |  |  |
| Free MMAE + IR | 40% |  |  |
| ACPP-cRGD-MMAE | 0% | 7% | 0% |
| ACPP-cRGD-MMAE + IR | 90% | 57% | 90% |

|  | V(end) / V(0) ≤ 1 | | |
|---|---|---|---|
|  | PANC-1, Fig 7B (bottom) | PANC-1, Fig 7C | HCT-116, Fig 7D |
| Control | 0% | 0% | 0% |
| IR | 0% | 0% | 30% |
| Free MAME | 0% |  |  |
| Free MMAE + IR | 10% |  |  |
| ACPP-cRGD-MMAE | 0% | 7% | 0% |
| ACPP-cRGD-MMAE + IR | 80% | 57% | 90% |

*Figure 14*

2-Way ANOVA with Tukey's Multiple Comparisons Group and P value significance in GraphPad Prism,

| Comparison | Significance |
|---|---|
| Control vs. IR | **** |
| Control vs. FREE MMAE | ** |
| Control vs. FREE MMAE + IR | **** |
| Control vs. ACPP-cRGD-MMAE | **** |
| Control vs. ACPP-cRGD-MMAE + IR | **** |
| IR vs. FREE MMAE | *** |
| IR vs. FREE MMAE + IR | * |
| IR vs. ACPP-cRGD-MMAE | ns |
| IR vs. ACPP-cRGD-MMAE + IR | **** |
| FREE MMAE vs. FREE MMAE + IR | **** |
| FREE MMAE vs. ACPP-cRGD-MMAE | **** |
| FREE MMAE vs. ACPP-cRGD-MMAE + IR | **** |
| FREE MMAE + IR vs. ACPP-cRGD-MMAE | ns |
| FREE MMAE + IR vs. ACPP-cRGD-MMAE + IR | * |
| ACPP-cRGD-MMAE vs. ACPP-cRGD-MMAE + IR | **** |

| Symbol | Meaning |
|---|---|
| ns | $P > 0.05$ |
| * | $P \leq 0.05$ |
| ** | $P \leq 0.01$ |
| *** | $P \leq 0.001$ |
| **** | $P \leq 0.0001$ |

*Figure 15*

2-Way ANOVA with Tukey's Multiple Comparisons Group and P value significance in GraphPad Prism,

| | |
|---|---|
| Control vs. ACPP-cRGD--MMAE | **** |
| Control vs. IR | **** |
| Control vs. ACPP-cRGD-MMAE+IR | **** |
| ACPP-cRGD--MMAE vs. IR | ns |
| ACPP-cRGD--MMAE vs. ACPP-cRGD-MMAE+IR | **** |
| IR vs. ACPP-cRGD-MMAE+IR | **** |

| Symbol | Meaning |
|---|---|
| ns | $P > 0.05$ |
| * | $P \leq 0.05$ |
| ** | $P \leq 0.01$ |
| *** | $P \leq 0.001$ |
| **** | $P \leq 0.0001$ |

Figure 16

2-Way ANOVA with Tukey's Multiple Comparisons Group and P value significance in GraphPad Prism.

| Comparison | Significance |
|---|---|
| Control vs. ACPP-cRGD--MMAE | * |
| Control vs. IR | **** |
| Control vs. ACPP-cRGD-MMAE+IR | **** |
| ACPP-cRGD--MMAE vs. IR | **** |
| ACPP-cRGD--MMAE vs. ACPP-cRGD-MMAE+IR | **** |
| IR vs. ACPP-cRGD-MMAE+IR | * |

| Symbol | Meaning |
|---|---|
| ns | $P > 0.05$ |
| * | $P \leq 0.05$ |
| ** | $P \leq 0.01$ |
| *** | $P \leq 0.001$ |
| **** | $P \leq 0.0001$ |

*Figure 17*
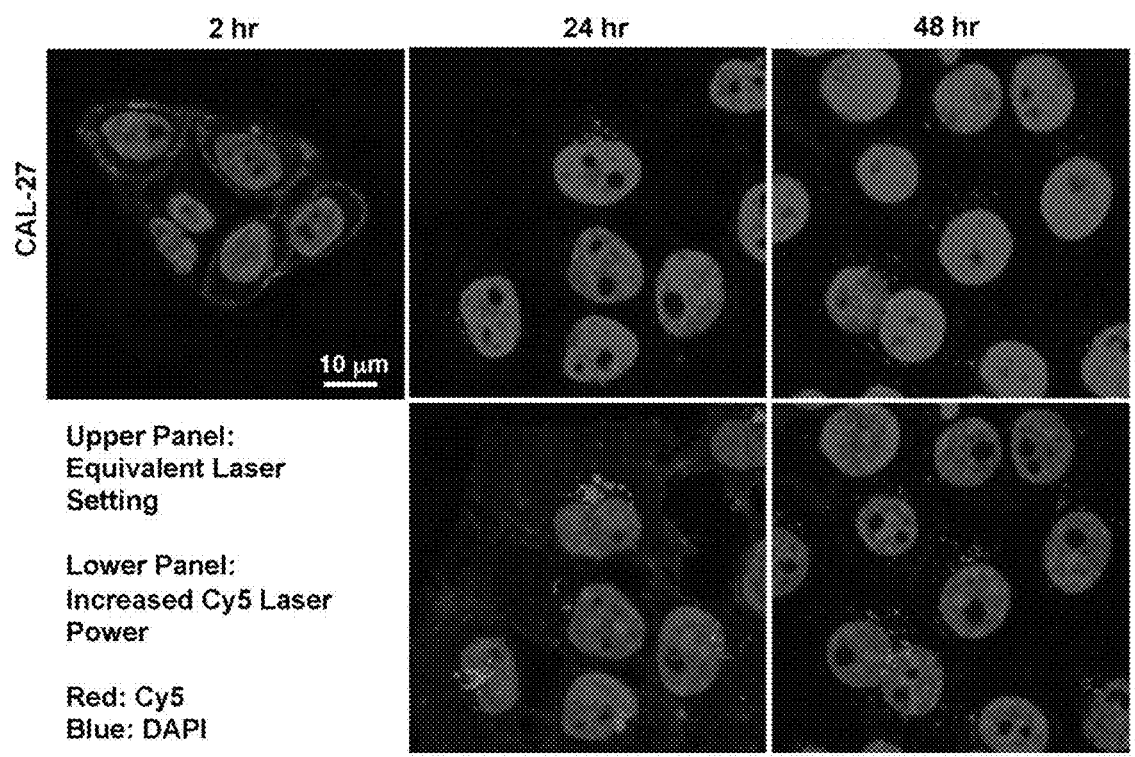
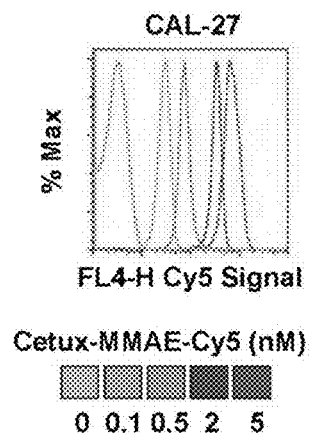
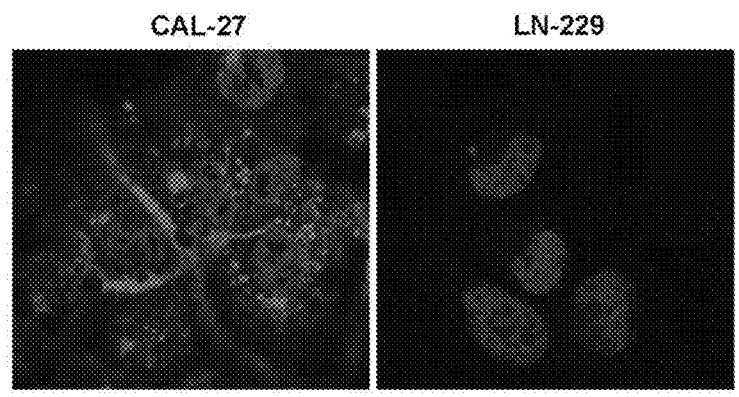

*Figure 20*
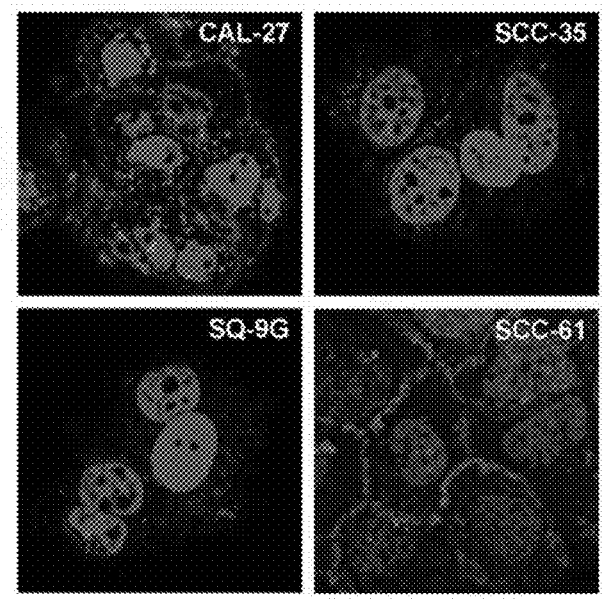
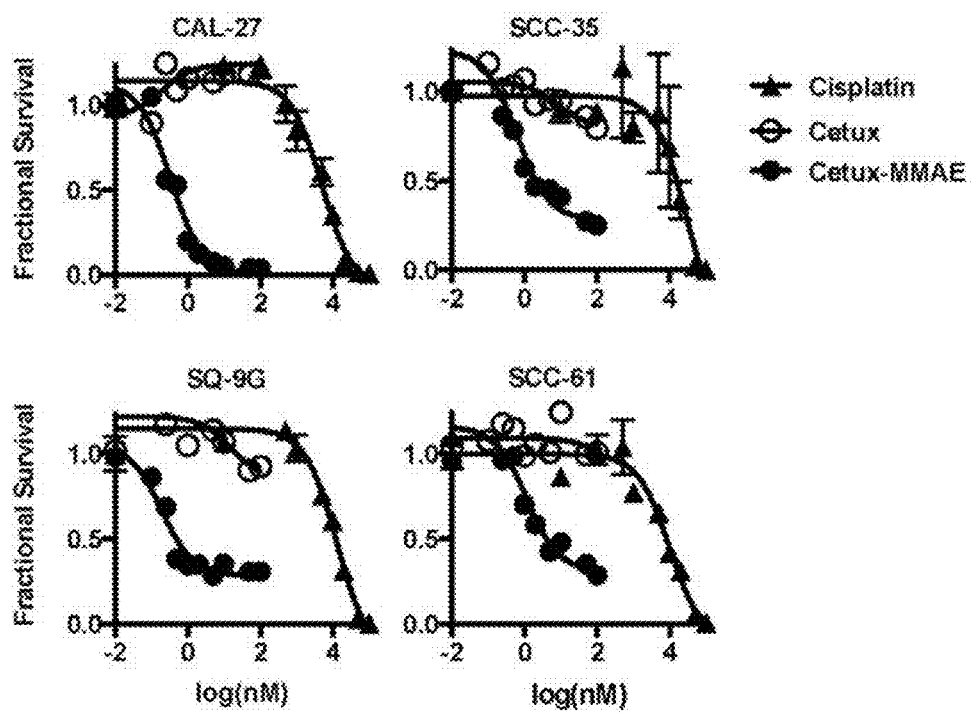

*Figure 21*
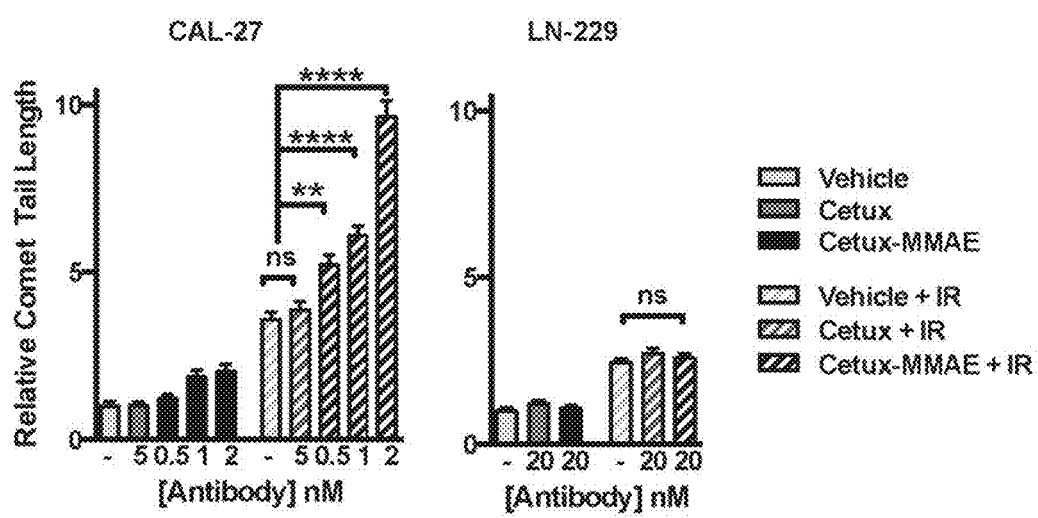
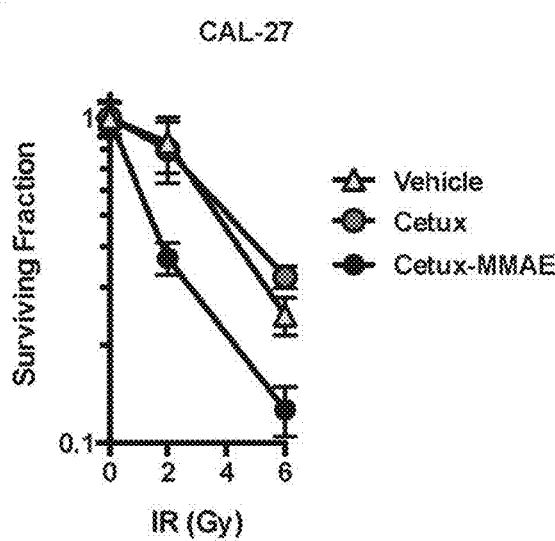 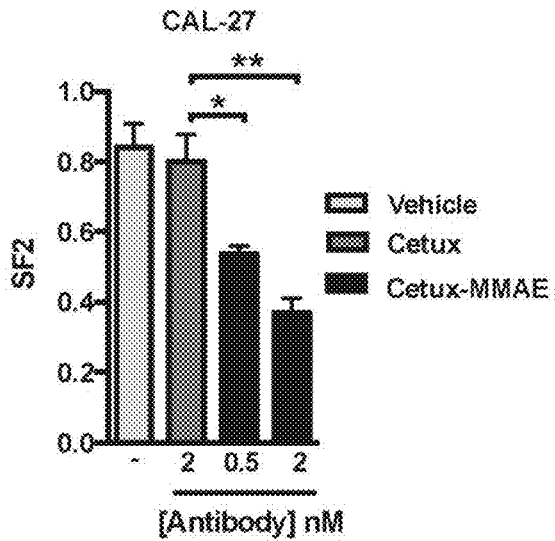

*Figure 29*
A
Unilateral Right Thigh HNSCC Tumor Xenografts
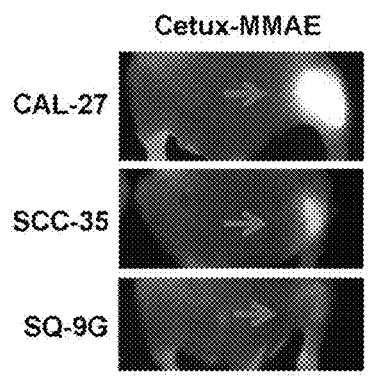
B
Bilateral Thigh Tumor Xenografts
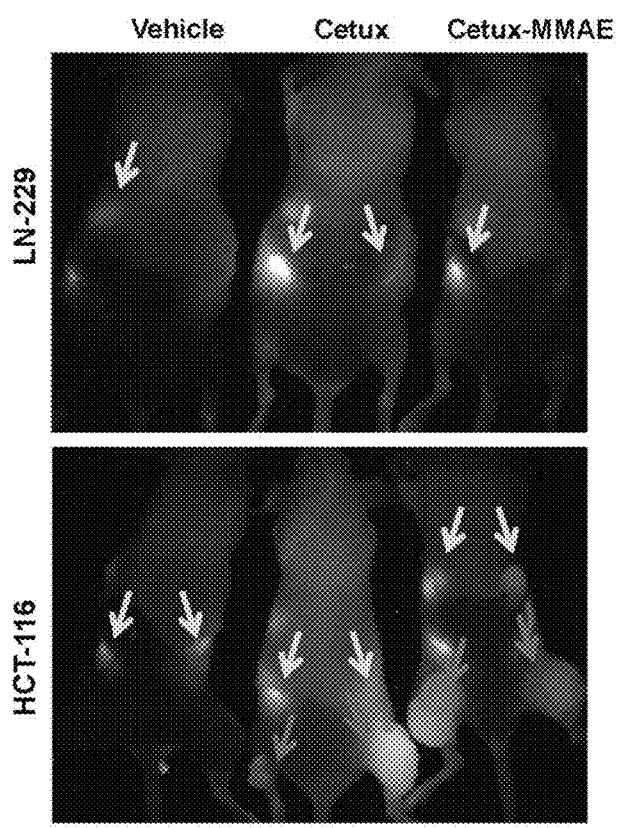
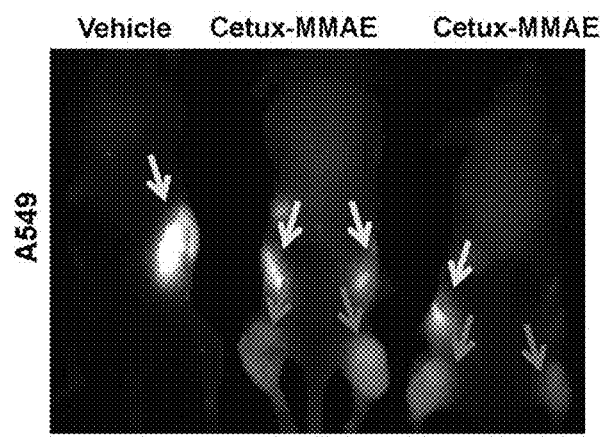

*Figure 32*
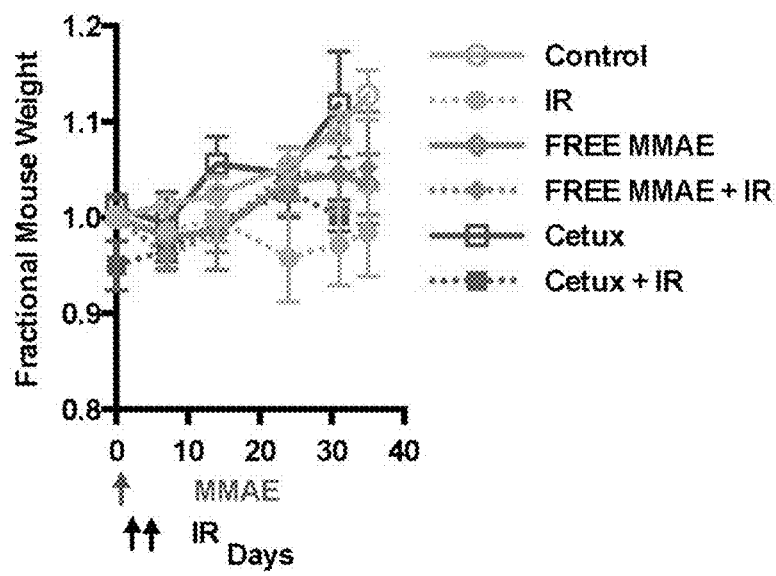
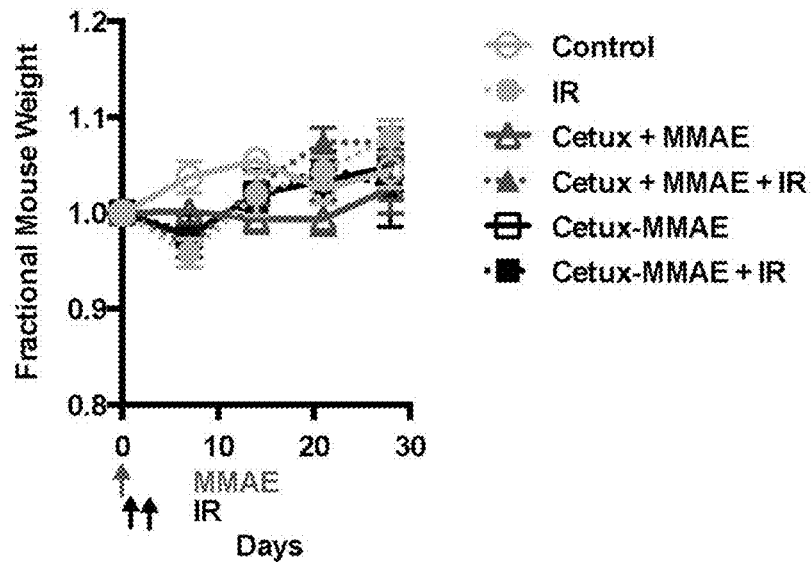

*Figure 43*
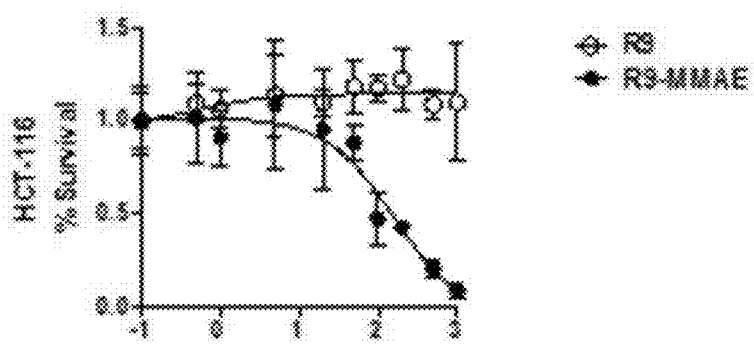
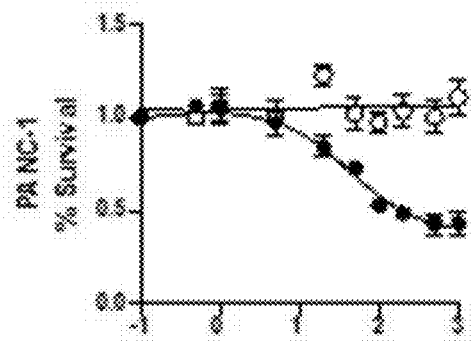
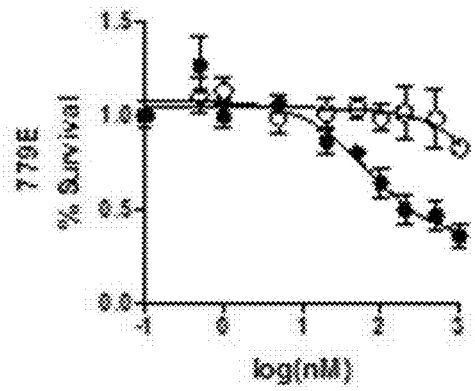

TUMOR RADIOSENSITIZATION WITH MONOMETHYL AURISTATIN E (MMAE) AND DERIVATIVES THEREOF

CROSS-REFERENCE TO RELATED APPLICATION

This application claims the benefit of U.S. Provisional Application No. 62/164,429, filed May 20, 2015, which is incorporated herein by reference in its entirety for all purposes.

STATEMENT OF FEDERALLY-SPONSORED RESEARCH

This invention was made with government support under W81XWH-09-1-0699 awarded by the Army and under CA158448 awarded by the National Institutes of Health. The government has certain rights in this invention.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Oct. 2, 2019, entitled 008075_5042_US_ST25.txt which is 20,000 bytes in size.

BACKGROUND OF THE INVENTION

Introduction

Cell membranes delimit the outer boundaries of cells, and regulate transport into and out of the cell interior. Made primarily of lipids and proteins, cell membranes provide a hydrophilic surface enclosing a hydrophobic interior across which materials must pass before entering a cell. Although many small, lipophilic compounds are able to cross cell membranes passively, most compounds, particles and materials must rely on active mechanisms in order to gain entry into a living cell.

Transmembrane Transport

Regulation of transport into and out of a cell is vital for its continued viability. For example, cell membranes contain ion channels, pumps, and exchangers capable of facilitating the transmembrane passage of many important substances. However, transmembrane transport is selective: in addition to facilitating the entry of desired substances into a cell, and facilitating the exit of others, a major role of a cell membrane is to prevent uncontrolled entry of substances into the cell interior. This barrier function of the cell membrane makes difficult the delivery of markers, drugs, nucleic acids, and other exogenous material into cells.

Over the last decade, peptide sequences that can readily enter a cell have been identified. For example, the Tat protein of the human immunodeficiency virus 1 (HIV-1) is able to enter cells from the extracellular environment (e.g., Fawell et al. P.N.A.S. 91:664-668 (1994)). Such uptake is reviewed in, for example, Richard et al., J. Biol. Chem. 278(1):585-590 (2003).

Such molecules that are readily taken into cells may also be used to carry other molecules into cells along with them. Molecules that are capable of facilitating transport of substances into cells have been termed "membrane translocation signals" (MTS) as described in Tung et al., *Advanced Drug Delivery Reviews* 55:281-294 (2003). The most important MTS are rich in amino acids such as arginine with positively charged side chains. Molecules transported into cell by such cationic peptides may be termed "cargo" and may be reversibly or irreversibly linked to the cationic peptides. An example of a reversible linkage is found in Zhang et al., *P.N.A.S.* 95:9184-9189 (1994)).

MTS molecules are discussed in, for example, Wender et al., *P.N.A.S.* 97:1300313008 (2000); Hallbrink et al., *Biochim. Biophys. Acta* 1515:101-109 (2001); Derossi et al., *Trends in Cell Biology* 8:84-87 (1998); Rothbard et al., 1 *Med. Chem.* 45:3612-3618 (2002); Rothbard et al., *Nature Medicine* 6(11):1253-1247 (2000); Wadia et al., *Curr. Opinion Biotech.* 13:52-56 (2002); Futaki et al; *Bioconj. Chem.* 12:1005-1011 (2001); Rothbard et al., U.S. Pat. No. 6,306,993; Frankel et al., U.S. Pat. No. 6,316,003; Rothbard et al., U.S. Pat. No. 6,495,663; Monahan et al., U.S. Pat. No. 6,630,351 and Jiang et al., WO 2005/042034.

Cancer Surgery

In cancer surgery, positive margins, defined as tumor cells present at the cut edge of the surgical specimen, have been associated with increased local recurrence and a poor prognosis (Haque R., et al., *BMC Ear Nose Throat Disord.* 16:2 (2006)). As in most solid tumors, salvage surgery (i.e., re-excision of the positive margin) or adjuvant chemotherapy and/or radiation not only cause extra trauma and expense but also often fail to remediate the poor outcome (Haque R., et al., *BMC Ear Nose Throat Disord.* 16:2 (2006); Singletary S. *Am. J. Surg.* 184:383-393 (2002); Meric F., et al., *Cancer* 97:926-933 (2003); Snijder R., et al., *Annals of Thoracic Surg.* 65 (1998); Nagtegaal I D, Quirke P., *J. Clin. On.* 26:303-312 (2008); Dotan Z, et al., *J. Urol.* 178:2308-2312 (2007); and Wieder J. A., *J. Urol.* 160:299-315 (1998)).

The reason for this observation is likely multifactorial and related in part to the difficulty in identifying the residual cancer during repeat surgery. Therefore, development of more sensitive imaging and diagnostic assays for more accurate detection of positive surgical margins during the primary operation would be one of the most effective means to minimize patient suffering and expense and to improve survival.

As the field of molecularly targeting fluorescent markers for early cancer detection and intraoperative margin evaluation progresses and more enzymatically activatable probes (Jiang T., et al. *P.N.A.S. USA.* 101:17867-17872 (2004); Aguilera T. A., et al., *Integr. Biol.* 1:371-381 (2009); Olson E. S., et al., *Integr Biol (Camb).* 1:382-393 (2009); Olson E. S., et al., *PNAS USA.* 107:4311-4316 (2010); Nguyen Q. T., *PNAS USA.* 107:4317-4322 (2010); Blum G., et al., *Nat Chem Biol.* 3:668-677 (2007); Gounaris E., et al., *PLoS One.* 3:e2916 (2008); Bremer C., et al., *Invest Radiol.* 40:321-327 (2005)) are becoming available for clinical use, methods such as those described herein personalized would be useful in a variety of treatment, diagnostic, prognostic applications.

Radiosensitization

Activatable cell penetrating peptides (ACPPs; also referred to herein as MTS molecules) are peptide based molecules in which a polycationic sequence, typically comprising 8-12 arginines, is connected via an enzyme cleavable linker to a polyanionic sequence, typically comprising a matching number of glutamates. The present application provides disclosure of a new subclass of ACPP (MTS) that accommodates pretargeting agent/ligand and prodrug attached by a linker cleavable after endocytosis. Herein is demonstrated that pre-targeted ACPP (one exemplary embodiment of which is cRGD-MMP-MMAE) produces tumor specific radiosensitization. Herein is also demonstrated that MMAE itself can be used as a radiosensitizer. Such radiosensitizers can include antibody-MMAE conjugates that are currently approved for clinical use. All forms of auristatin can also be employed with the present methods as radiation sensitizing agents.

MMAE has been used in antibody-drug conjugates for targeted chemotherapy. By demonstrating the potential of MMAE as a radiosensitizer, the present application extends the usefulness of antibody-MMAE conjugates to being employed with the targeted radiosensitization according to the methods of the present invention, which methods have the potential to decrease toxicity and improve efficacy. Likewise, by conjugating the MMAE to the ACPPs/MTS molecules of the present invention (such as for example, cyclic RGD pre-targeted ACPP through a cathepsin cleavable linker), tumor specific radiosensitization and tumor regression at much lower dose than what is used for MMAE chemotherapy or MMAE containing peptide based targeted chemotherapy alone can be achieved.

Overall, there remains a need in the art for additional treatment, specifically methods for radiosensitization or to decrease toxicity and improve efficacy. The present invention meets these needs and provides methods for treatment, diagnosis, prognosis and characterization of tumors which can find use in a variety of personalized medicine applications.

All patents and publications, both supra and infra, are hereby incorporated by reference in their entirety.

SUMMARY OF THE INVENTION

In some embodiments, the present invention provides a method for inducing radiosensitization comprising administering to a subject in need thereof a molecule comprising the formula:

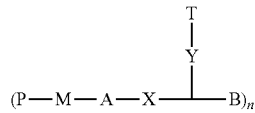

wherein the molecule comprises:
an optional pre-targeting moiety P;
an optional macromolecular carrier M;
a peptide A with a sequence comprising 5 to 9 consecutive acidic amino acids, wherein the amino acids are selected from the group consisting of aspartates and glutamates;
a first cleavable linker X;
a second cleavable linker Y;
a radiosensitizing agent T;
a peptide B with a sequence comprising 5 to 20 consecutive basic amino acids;
the T-Y pair is attached to either end of B; and
n is an integer between 1 and 20;
wherein said subject is radiosensitized.

In some embodiments of the method, a peptide A has a sequence comprising 5 to 9 consecutive glutamates.

In some embodiments of the method, a peptide B has a sequence comprising 5 to 12 consecutive arginines.

In some embodiments of the method, X is selected from the group consisting of (SEQ ID NO: 1) DPRSFL, (SEQ ID NO:2) PPRSFL, (SEQ ID NO:3) Norleucine-TPRSFL, and (SEQ ID NO:4) PLGC(Me)AG.

In some embodiments of the method, M is a macromolecular carrier selected from the group consisting of a dendrimer, dextran, a PEG polymer, albumin, and lipid-coated perfluorocarbon droplet. In some embodiments of the method, M is a PEG polymer. In some embodiments, n is 1.

In some embodiments of the method, P is cyclic RGD (cRGD).

In some embodiments of the method, Y is Val-Cit-(p-amido)benzyloxycarbonyl.

In some embodiments of the method, T is an auristatin or a derivative thereof. In some embodiments of the method, T is monomethyl auristatin E (MMAE).

In some embodiments, the present invention provides a method for inducing radiosensitization comprising administering to a subject in need thereof a molecule comprising the formula:

$$(A\text{-}X\text{-}B)_n\text{-}M\text{-}(Y\text{-}T)_i$$

wherein the molecule comprises:
a macromolecular carrier M bound to A or B;
a peptide A with a sequence comprising 5 to 9 consecutive acidic amino acids, wherein the amino acids are selected from the group consisting of aspartates and glutamates;
a first cleavable linker X;
a second cleavable linker Y;
a radiosensitizing agent T;
a peptide B with a sequence comprising 5 to 20 consecutive basic amino acids; and
n and i are independently selected integers between 1 and 20;
wherein said subject is radiosensitized.

In some embodiments of the method, a peptide A has a sequence comprising 5 to 9 consecutive glutamates.

In some embodiments of the method, a peptide B has a sequence comprising 5 to 12 consecutive arginines.

In some embodiments of the method, X is selected from the group consisting of (SEQ ID NO: 1) DPRSFL, (SEQ ID NO:2) PPRSFL, (SEQ ID NO:3) Norleucine-TPRSFL, and (SEQ ID NO:4) PLGC(Me)AG.

In some embodiments of the method, M is a macromolecular carrier selected from: a dendrimer, dextran, a PEG polymer, albumin, and lipid-coated perfluorocarbon droplet. In some embodiments of the method, M is a PEG polymer. In some embodiments, n is 1.

In some embodiments of the method, Y is Val-Cit-(p-amido)benzyloxycarbonyl.

In some embodiments of the method, T is an auristatin or a derivative thereof. In some embodiments of the method, T is monomethyl auristatin E (MMAE).

In some embodiments, the present invention provides the molecule of the invention is administered prior to administration of a radiation therapy.

In some embodiments, the present invention provides the molecule of the invention is administered concurrently with administration of a radiation therapy.

In some embodiments of the method, the molecule is cleaved in vivo in the presence of a tumor in the subject.

In some embodiments, the present invention provides a composition for inducing radiosensitization in a subject, wherein said composition comprises a molecule comprising the formula:

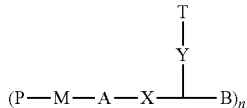

wherein the molecule comprises:
an optional pre-targeting moiety P;
an optional macromolecular carrier M;
a peptide A with a sequence comprising 5 to 9 consecutive acidic amino acids, wherein the amino acids are selected from the group consisting of aspartates and glutamates;
a first cleavable linker X;
a second cleavable linker Y;
a radiosensitizing agent T;
a peptide B with a sequence comprising 5 to 20 consecutive basic amino acids;
the T-Y pair is attached to either end of B; and
n is an integer between 1 and 20.

In some embodiments of the composition, the peptide A has a sequence comprising 5 to 9 consecutive glutamates.

In some embodiments of the composition, the peptide B has a sequence comprising 5 to 12 consecutive arginines.

In some embodiments of the composition, X is selected from the group consisting of (SEQ ID NO: 1) DPRSFL, (SEQ ID NO:2) PPRSFL, (SEQ ID NO:3) Norleucine-TPRSFL, and (SEQ ID NO:4) PLGC(Me)AG.

In some embodiments of the composition, M is a macromolecular carrier selected from: a dendrimer, dextran, a PEG polymer, albumin, or lipid-coated perfluorocarbon droplet. In some embodiments of the composition, M is a PEG polymer. In some embodiments of the composition, n is 1.

In some embodiments of the composition, P is cyclic RGD (cRGD).

In some embodiments of the composition, Y is Val-Cit-(p-amido)benzyloxycarbonyl.

In some embodiments of the composition, T is an auristatin or a derivative thereof.

In some embodiments of the composition, T is monomethyl auristatin E (MMAE).

In some embodiments of the composition, the composition comprises a pharmaceutically acceptable buffer.

In some embodiments of the composition, composition is administered to a subject prior to administration of a radiation therapy.

In some embodiments of the composition, the composition e is administered concurrently with administration of a radiation therapy.

In some embodiments of the composition, the molecule is capable of being cleaved in vivo in upon administration to a subject with a tumor.

In some embodiments, the present invention provides a composition for inducing radiosensitization in a subject, wherein said composition comprises a molecule comprising the formula:

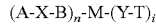

wherein the molecule comprises:
a macromolecular carrier M bound to A or B;
a peptide A with a sequence comprising 5 to 9 consecutive acidic amino acids, wherein the amino acids are selected from the group consisting of aspartates and glutamates;
a first cleavable linker X;
a second cleavable linker Y;
a radiosensitizing agent T;
a peptide B with a sequence comprising 5 to 20 consecutive basic amino acids; and
n and i are independently selected integers between 1 and 20.

In some embodiments of the composition, the peptide A has a sequence comprising 5 to 9 consecutive glutamates.

In some embodiments of the composition, the peptide B has a sequence comprising 5 to 12 consecutive arginines.

In some embodiments of the composition, X is selected from the group consisting of (SEQ ID NO: 1) DPRSFL, (SEQ ID NO:2) PPRSFL, (SEQ ID NO:3) Norleucine-TPRSFL, and (SEQ ID NO:4) PLGC(Me)AG.

In some embodiments of the composition, M is a macromolecular carrier selected from the group consisting of a dendrimer, dextran, a PEG polymer, albumin, and lipid-coated perfluorocarbon droplet. In some embodiments of the composition, M is a PEG polymer. In some embodiments of the composition, n is 1.

In some embodiments of the composition, Y is Val-Cit-(p-amido)benzyloxycarbonyl.

In some embodiments of the composition, T is an auristatin or a derivative thereof.

In some embodiments of the composition, T is monomethyl auristatin E (MMAE).

In some embodiments of the composition, the composition comprises a pharmaceutically acceptable buffer.

In some embodiments of the composition, the composition e is administered to a subject prior to administration of a radiation therapy.

In some embodiments of the composition, the composition is administered concurrently with administration of a radiation therapy.

In some embodiments of the composition, the molecule is capable of being cleaved in vivo in upon administration to a subject with a tumor.

BRIEF DESCRIPTION OF THE DRAWINGS

FIG. 2: Synthesis of cyclicRGD-ACPP-MMAE. Schemes showing synthesis of CyclicRGD-ACPP-MMAE (Scheme 1), MC-Val-Cit-PABC-MMAE (Scheme 2). Lower case letters represent D amino acids, "o" denotes 5-amino-3-oxopentanoyl, a short hydrophilic spacer -, "suc" refers to succinimido.

FIG. 7A-D: Combination of ACPP-cRGD-MMAE with IR significantly reduced the tumor growth. HCT-116 or PANC-1 tumor xenografts were grown subcutaneously in athymic nude mice. A) ACPP-cRGD-MMAE localizes to tumor xenografts following IV administration. Following growth of bilateral subcutaneous tumors, the right hindlimb tumor was irradiated while the remainder of the mouse including the left subcutaneous tumor was shielded to block >95% of the delivered IR does. Cy5 labeled ACPP-cRGD was IV injected into tumor bearing mice and mice were imaged 6 hrs later with skin on (top) and skin removed (bottom). B) PANC-1 tumor xenografts bearing mice were IV injected with 6 nM of Free MMAE or ACPP-cRGD-MMAE days 0 and 1. For IR treated tumor xenografts, 3 Gy was delivered on days 1 and 2. On days 1 IR was given 6 hrs after IV injection of MMAE. PANC-1 tumor xenografts were measured twice a week. C) PANC-1 tumor xenografts bearing mice were IV injected with 6 nM ACPP-cRGD-MMAE days 0, 1, and 2. For IR treated tumor xenografts, 3 Gy was delivered on days 1, 2 and 3. On days 1 and 2, IR was given 6 hrs after IV injection of ACPP-cRGD-MMAE. PANC-1 tumor xenografts were measured twice a week. D) HCT-116 tumor xenografts were treated IR on day 0 with 6 Gy and then 3 Gy on days 1 and 2. A dose of 7.5 nM ACPP-cRGD-MMAE was IV injected on both days 0 and 1, 6 hrs after IR. HCT-116 tumor xenografts were measured every other day.

FIG. 9: Sustained tumor growth inhibition following treatment with ACPP-cRGD-MMAE and IR. Percent of treated PANC-1 and HCT-116 tumor xenografts that at day 20, 40, 14 (PANC-1 (FIG. 7B, top and bottom), PANC2 (FIG. 7C), HCT-116 (FIG. 7D) respectively) post initiation of treatment were smaller than the starting tumor volume on day 0, V(end)/V(0)≤1.

FIG. 14: 2 Way ANOVA Analysis with Tukey's Multiple Comparisons Testing. PANC-1 xenograft experiment in FIG. 7B comparing Free MMAE and ACPP-cRGD-MMAE with IR.

FIG. 15: 2 Way ANOVA Analysis with Tukey's Multiple Comparisons Testing. PANC-1 xenograft experiment in FIG. 7D testing ACPP-cRGD-MMAE with IR.

FIG. 16: 2 Way ANOVA Analysis with Tukey's Multiple Comparisons Testing. HCT-116 xenograft experiment in FIG. 7C testing ACPP-cRGD-MMAE with IR.

FIG. 17: Cetuximab-MMAE-Cy5 binds to cells in an EGFR-1 dependent manner. A) CAL-27 cells exposed to cetuximab-MMAE-Cy5 for 2-48 hours and Cy5 fluorescence (red) imaged. Nuclei were stained with DAPI (blue). The upper panel was imaged with similar laser settings. For samples fixed at 24 and 48 hrs, images were also taken at increased laser power setting for Cy5. B) Flow cytometry assessment of cetuximab-MMAE-Cy5 cell surface binding. CAL-27 cells were incubated on ice with increasing concentrations of cetuximab-MMAE-Cy5. C) Cy5 fluorescence of CAL-27 and LN-229 cells exposed to cetuximab-MMAE-Cy5 for 24 hrs.

FIG. 20: Cetuximab-MMAE has increased potency compared to chemotherapies used concurrently with IR in HNSCC. A) CAL-27, SQ-9G, SCC-35 and SCC-61 were exposed to cetuximab-MMAE-Cy5 overnight and Cy5 fluorescence (red) imaged. Nuclei were stained with DAPI (blue). B) CAL-27, SQ-9G, SCC-35 and SCC-61 cells were treated with increasing concentrations of cisplatin, cetuximab or cetuximab-MMAE-Cy5 for 72 hours. Cell viability was measured, normalized to vehicle treated cells and plotted as fractional survival±SD.

FIG. 21: Cetuximab-MMAE-Cy5 radiosensitizes tumor cells in an EGFR dependent manner. A) CAL-27 and LN-229 cells were treated with cetuximab-Cy5 or cetuximab-MMAE-Cy5 overnight and then irradiated with 6 Gy. Comet tail length was measured using neutral comet assay. Data was normalized to vehicle treated, non-irradiated cells and plotted as relative comet tail length±SEM. B, C) Clonogenic cell survival of CAL-27 cells treated with cetuximab-Cy5 or cetuximab overnight followed by 0-6 Gy. Cell viability was normalized to vehicle treated, non-irradiated cells and plotted as fractional survival±SD. *P<0.05, P<0.01, *P<0.0001.

FIG. 29: Cetuximab-MMAE-Cy5 accumulates in EGFR expressing tumor xenografts. For HNSCC tumor xenografts, CAL-27, SCC-35 and SQ-9G tumor cells were only implanted in the right hindlimb. For LN229, HCT-116 and A549 tumor bearing mice, tumors were grown in both the left and right thigh. 0.5 nmoles of cetuximab-MMAE-Cy5 or cetuximab-Cy5 was IV injected into tumor bearing mice as indicated. Mice were imaged 48 hrs later for Cy5 fluorescence. Red arrows point to tumor Cy5 fluorescence. Yellow arrows point to gut autofluorescence.

FIG. 32: Effect on body weight in mice treated with cetuximab-MMAE in combination with IR. Individual mouse body weights were normalized to each mouse's weight on initiation of treatment, Day 0. A) Fractional body weights from mice in experiment in FIG. 6C. B) Fractional body weights from mice in experiment in FIG. 6D. Data is plotted as mean fractional body weight±SEM.

FIG. 43: Polycation conjugated MMAE is cytotoxic to tumor cells. HCT-116, PANC-1, and 779E cells were exposed to polycation alone ($r_9$) or conjugated to MMAE ($r_9$-MMAE) at varying concentrations for 72 hours at which time cell viability was assessed. Cell viability was normalized to vehicle treated cells and plotted as percent survival±SD.

DETAILED DESCRIPTION OF THE INVENTION

Introduction

Figure 1:
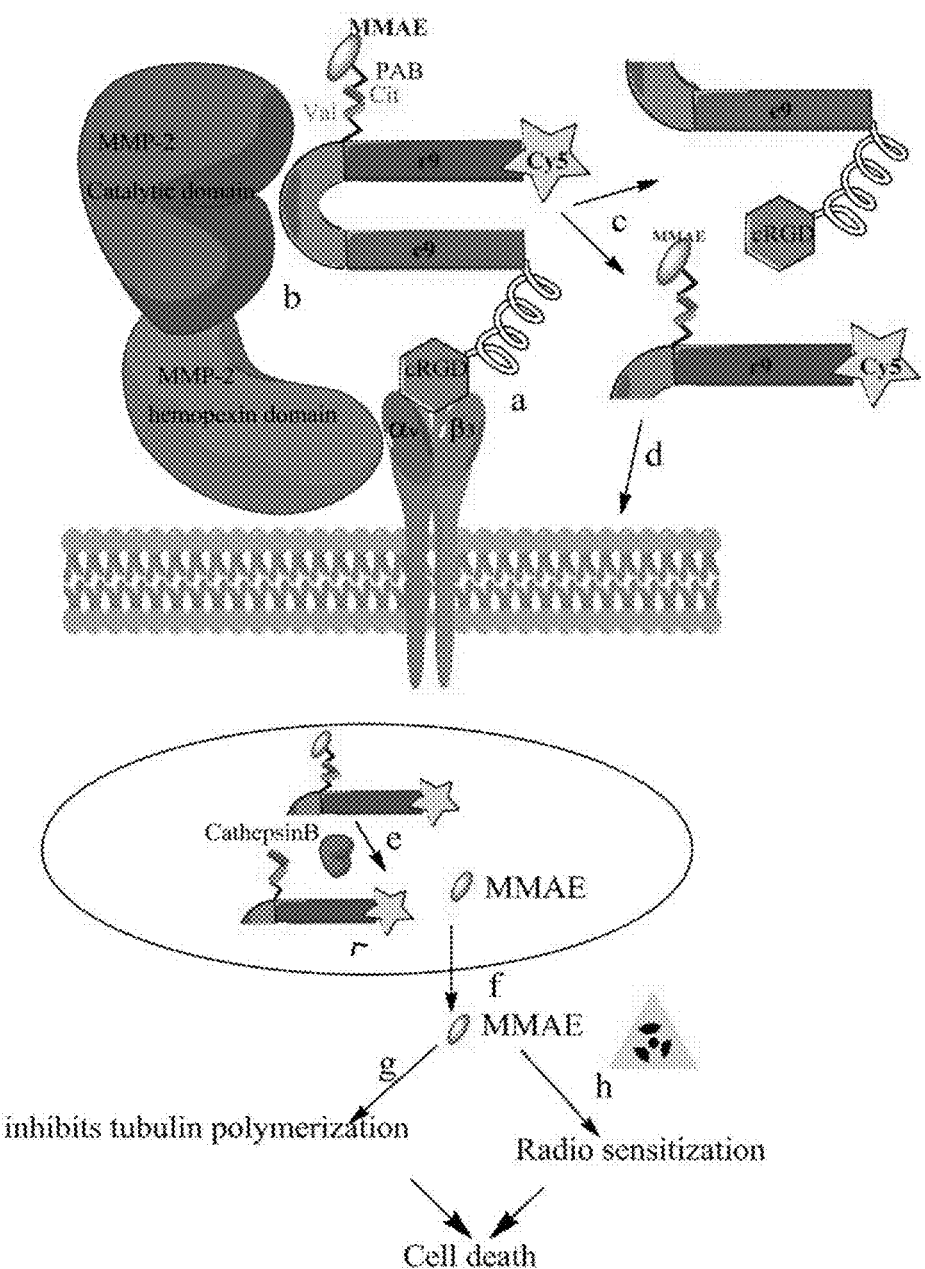
FIG. 1: A schematic representation shows the presence of MMP-2 and αvβ3 in close proximity, which enhances cleavage of ACPP. The released MMAE-$r_9$-Cy5 fragment is taken up into endosomes and lysosomes, where the 2nd linker (zigzag line) is cleaved by enzymes such as cathepsin B to release active MMAE, which can diffuse across the organellar membranes into the cytosol where it binds extremely tightly to microtubules.

Activatable cell penetrating peptides (ACPPs) are peptide based molecules in which a polycationic sequence, typically comprising 8-12 arginines, is connected via an enzyme cleavable linker to a polyanionic sequence, typically comprising a matching number of glutamates. ACPP is described in greater detail in US 2012/0134922 as well as PCT/US2014/013687, herein incorporated by reference in their entireties.

The ACPP described herein includes a first cleavable linker X that separates the acidic peptide domain from the basic peptide domain. The second cleavable linker Y is a cleavable linker linked to a compound, such as a therapeutic agent, that is preferably an intracellularly cleavable linker. The position of the second cleavable linker can be positioned anywhere along the basic peptide domain, the interface between the first cleavable marker and the basic peptide domain, or on the first cleavable linker. If the second cleavable linker is positioned on the first cleavable linker, it should be positioned such that following cleavage of the first cleavable linker, the second cleavable linker and its associated cargo remains associated with the basic peptide domain to allow delivery of the cargo into the cell, and does not interfere with the cleavage of the first cleavable linker.

Disclosed is a new sub class of ACPP that accommodates 1) pretargeting agent/ligand, 2) prodrug attached by a linker cleavable after endocytosis, and 3) contrast or imaging agent. This allows ACPP to be used as a molecular dual targeted theranostic agent. The pre-targeted ACPP embodiments described herein synergistically enhance tumor contrast, reduce tumor growth, and enhance the overall survival rate in a patient in need thereof.

The present invention is also based in part on the discovery that ex vivo cleavage of ratiometric MTSs (ACPPs) by tumor extract correlates with in-vivo MTS (ACPP) fluorescence uptake and increased emission ratio in cancer, particularly carcinoma. In some embodiments, measuring the ability of individual tumors to cleave MTSs (ACPPs) and assessing the percentage of enzymatically positive tumors in a clinical population provides valuable data in that the ex vivo cleavage data can be correlated with MTS (ACPP) performance in vivo. In some embodiments, the ex vivo cleavage assay may be further developed into a personalized screening assay to determine eligibility to use MTSs (ACPPs) during a given patient procedure such as for example surgery. In some embodiments, the present invention provides methods for assessing the distribution of human surgical specimens with respect to their ability to cleave the MTSs (ACPPs) and the correlation of the MTS with clinical grade and outcome. Methods and compositions useful in such methods are provided herein.

Certain Definitions

The following terms have the meanings ascribed to them unless specified otherwise.

The terms cell penetrating peptide (CPP), activatable cell penetrating peptide (ACPP), membrane translocating sequence (MTS) and protein transduction domain are used interchangeably. As used herein, the terms mean a peptide (polypeptide or protein) sequence that is able to translocate across the plasma membrane of a cell. In some embodiments, a CPP facilitates the translocation of an extracellular molecule across the plasma membrane of a cell. In some embodiments, the CPP translocates across the plasma membrane by direct penetration of the plasma membrane, endocytosis-mediated entry, or the formation of a transitory structure. In some embodiments the MTS is not transported across the membrane of a cell, but is employed in an ex vivo assay or application.

As used herein, the term "aptamer" refers to a DNA or RNA molecule that has been selected from random pools based on their ability to bind other molecules with high affinity specificity based on non-Watson and Crick interactions with the target molecule (see, e.g., Cox and Ellington, *Bioorg. Med. Chem.* 9:2525-2531 (2001); Lee et al., *Nuc. Acids Res.* 32:D95-D100 (2004)). In some embodiments, the aptamer binds nucleic acids, proteins, small organic compounds, vitamins, inorganic compounds, cells, and even entire organisms.

The terms "polypeptide," "peptide" and "protein" and derivatives thereof as used herein, are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds. As used herein, the terms "peptide" refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a β-ester, a thioamide, phosphonamide, carbamate, hydroxylate, and the like (see, e.g., Spatola, *Chem. Biochem. Amino Acids and Proteins* 7: 267-357 (1983)), where the amide is replaced with a saturated amine (see, e.g., Skiles et al., U.S. Pat. No. 4,496,542, which is incorporated herein by reference, and Kaltenbronn et al., (1990) Pp. 969-970 in *Proc. 11th American Peptide Symposium*, ESCOM Science Publishers, The Netherlands, and the like)).

The term "amino acid" and derivatives thereof as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be either D amino acids or L amino acids. In peptide sequences throughout the specification, lower case letters indicate the D isomer of the amino acid (conversely, upper case letters indicate the L isomer of the amino acid).

Amino acids may be referred to herein by either their commonly known three letter symbols or by the one-letter symbols recommended by the IUPAC-IUB Biochemical Nomenclature Commission.

Nucleotides, likewise, may be referred to by their commonly accepted single-letter codes.

One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

As used herein, a "linker" or "spacer" is any molecule capable of binding (e.g., covalently) portions an MTS molecule as disclosed herein together. Linkers include, but are not limited to, straight or branched chain carbon linkers, heterocyclic carbon linkers, peptide linkers, polyether linkers and short hydrophilic molecules. Exemplary linkers can include but are not limited to NH—$CH_2$—$CH_2$—O—$CH_2$—CO— and 5-amino-3-oxopentanoyl. For example, poly(ethylene glycol) linkers are available from Quanta Biodesign, Powell, Ohio. These linkers optionally have amide linkages, sulfhydryl linkages, or heterofunctional linkages.

As used herein, the term "label" refers to any molecule that facilitates the visualization and/or detection of a MTS molecule disclosed herein. In some embodiments, the label is a fluorescent moiety.

The term "carrier" or "macromolecular carrier" means an inert molecule that increases (a) plasma half-life and (b) solubility. In some embodiments, a carrier increases plasma half-life and solubility by reducing glomerular filtration. In some embodiments, a carrier increases tumor uptake due to enhanced permeability and retention (EPR) of tumor vasculature. Exemplary macromolecular carriers include but are not limited to dendrimers, dextrans, PEG polymers, albumins, or lipid-coated perfluorocarbon droplets.

The term "thrombin" means an enzyme (EC 3.4.21.5) that cleaves fibrinogen molecules into fibrin monomers. Thrombin, acting through its G-protein coupled receptor PAR-I, is a key player in a wide range of vascular and extravascular disease processes throughout the body, including cancer, cardiovascular diseases, acute kidney injury, and stroke. In certain instances, thrombin activity increases over the course of atherosclerotic plaque development. In some embodiments, thrombin activity is a biomarker for atherosclerotic plaque development.

The term "reactive oxygen species" or "ROS" includes peroxide compounds or compounds with peroxide activity. Examples include but are not limited to hydrogen peroxide. Hydrogen peroxide is represented by the formula $H_2O_2$. Hydrogen peroxide is commonly found endogenously in living organisms. $H_2O_2$ plays an active role in the regulation of various physiological processes; however, its overabundance results in oxidative stress that can lead to extensive cellular damage. Indeed, high levels of $H_2O_2$ have been implicated in many pathological conditions including inflammation, diabetes, cardiovascular diseases, neurodegenerative disorders and cancer.

The terms "individual," "patient," or "subject" are used interchangeably. As used herein, they mean any mammal (i.e., species of any orders, families, and genus within the taxonomic classification animalia: chordata: vertebrata: mammalia). In some embodiments, the mammal is a human. None of the terms require or are limited to situation characterized by the supervision (e.g., constant or intermittent) of a health care worker (e.g., a doctor, a registered nurse, a nurse practitioner, a physician's assistant, an orderly, or a hospice worker).

As used herein, the term "medical professional' means any health care worker. By way of non-limiting example, the health care worker may be a doctor, a registered nurse, a nurse practitioner, a physician's assistant, an orderly, or a hospice worker.

The terms "administer," "administering", "administration," and derivatives thereof as used herein, refer to the methods that may be used to enable delivery of agents or compositions to the desired site of biological action These methods include, but are not limited to parenteral injection (e.g., intravenous, subcutaneous, intraperitoneal, intramuscular, intravascular, intrathecal, intravitreal, infusion, or local) Administration techniques that are optionally employed with the agents and methods described herein, include e.g., as discussed in Goodman and Gilman, *The Pharmacological Basis of Therapeutics*, current edition, Pergamon, and Remington's, Pharmaceutical Sciences (current edition), Mack Publishing Co, Easton, Pa.

The term "pharmaceutically acceptable" and derivatives thereof as used herein, refers to a material that does not abrogate the biological activity or properties of the agents described herein, and is relatively nontoxic (i.e., the toxicity of the material significantly outweighs the benefit of the material) In some instances, a pharmaceutically acceptable material may be administered to an individual without causing significant undesirable biological effects or significantly interacting in a deleterious manner with any of the components of the composition in which it is contained.

The term "surgery" and derivatives thereof as used herein, refers to any methods for that may be used to manipulate, change, or cause an effect by a physical intervention These methods include, but are not limited to open surgery, endoscopic surgery, laparoscopic surgery, minimally invasive surgery, and robotic surgery.

The terms "neoplasm" or "neoplasia" and derivatives thereof as used herein, include any non-normal or non-standard cellular growth. Neoplasms can include tumors and cancers of any variety of stages, from benign to metastatic. Neoplasms can be primary or metastatic growths and can occur anywhere in a subject. Neoplasms can include neoplasms of the lung, skin, lymph, brain, nerves, muscle, breast, prostate, testis, pancreases, liver, kidneys, stomach, muscle, gastrointestinal, bone and blood. Neoplasms can be solid and non-solid tumors.

The terms "sample" or "samples" and derivatives thereof as used herein, include any samples obtained from a subject with can be employed with the methods described herein. Samples can include but are not limited to urine, blood, lymph, tears, mucus, saliva, biopsy or other sample tissue samples. Sample can be frozen, refrigerated, previously frozen, and/or stored for minutes, hours, days, weeks, months, years. Sampling techniques, handling and storage are well known and any such techniques for obtaining samples for use with the present invention are contemplated.

The following symbols, where used, are used with the indicated meanings Fl=fluorescein, aca=ahx=X=ammohexanoyl linker (—HN—(CH$_2$)$_5$CO-) aminohexanoyl, C=L-cysteine, E=L-glutamate, R=L-arginine, D=L-aspartate, K=L-lysine, A=L-alanine, r=D-arginine, c=D-cysteine, e=D-glutamate, P=L-proline, L=L-leucine, G=glycine, V=valine, I=isoleucine, M=methionine, F=phenylalanine, Y=tyrosine, W=tryptophan, H=histidine, Q=glutamine, N=asparagine, S=serine, T=threonine, o is 5-amino-3-oxapentanoyl linker, and C(me) is S-methylcysteine.

MTS Peptides

In some embodiments, a generic structure for peptides having features of the invention are selected from the following:

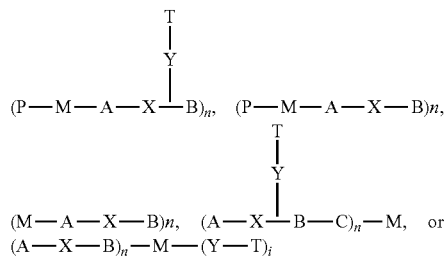

where P is an optional pre-targeting moiety; M is an optional macromolecular carrier; T is a compound for delivery to a target, including for example a therapeutic compound (also referred to herein as a "warhead"); peptide portion B includes between about 5 to about 20 basic amino acids; X is a cleavable linker portion, in some embodiments cleavable under physiological conditions; Y is a cleavable linker portion, in some embodiments cleavable under physiological conditions; and wherein peptide portion A includes between about 2 to about 20 acidic amino acids. In some embodiments of molecules having features of the invention, n and i are independently selected integers between 1 and 20. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments of molecules having features of the invention, peptide portion B includes between about 5 to about 20, or between about 9 to about 16 basic amino acids, and may be a series of basic amino acids (e.g., arginines, histidines, lysines, or other basic amino acids). In some embodiments of molecules having features of the invention, peptide portion A includes between about 2 to about 20, or between about 5 to about 20 acidic amino acids, and may be series of acidic amino acids (e.g., glutamates and aspartates or other acidic amino acids). A schematic representation of a MTS molecule having features of the invention comprising a basic portion B, a linker portion X, and an acidic portion A is presented in FIG. 1A of WO 2005/042034. In embodiments, MTS molecules having features of the invention may be cyclic molecules, as schematically illustrated in FIG. 1B of WO 2005/04203. Thus, MTS molecules having features of the invention may be linear molecules, cyclic molecules, or may be linear molecules including a cyclic portion.

In some embodiments, A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X is a linker that is cleavable by a protease.

In some embodiments, A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; and M is a macromolecular carrier.

Regulation of transport into and out of a cell is important for its continued viability. For example, cell membranes contain ion channels, pumps, and exchangers capable of facilitating the transmembrane passage of many important substances. However, transmembrane transport is selective in addition to facilitating the entry of desired substances into a cell, and facilitating the exit of others, a major role of a cell membrane is to prevent uncontrolled entry of substances into the cell interior. This barrier function of the cell membrane makes difficult the delivery of markers, drugs, nucleic acids, and other exogenous material into cells.

As discussed above, molecules including a multiple basic amino acids, such as a series of basic amino acids, are often taken up by cells. However, the present inventors have discovered that molecules having structures including a basic portion B, a linker portion X and/or Y and an acidic portion A are not taken up by cells. An acidic portion A may include amino acids that are not acidic. Acidic portion A may comprise other moieties, such as negatively charged moieties. In some embodiments acidic portion A does not include an amino acid. In embodiments of MTS molecules having features of the present disclosure, an acidic portion A may be a negatively charged portion, in some embodiments having about 2 to about 20 negative charges at physiological pH. A basic portion B may include amino acids that are not basic. Basic portion B may comprise other moieties, such as positively charged moieties. In some embodiments basic portion B does not include an amino acid. In embodiments of MTS molecules having features of the invention, a basic portion B may be a positively charged portion, having between about 5 and about 20 positive charges at physiological pH. Including an acidic portion A is effective to inhibit or prevent the uptake of a portion B into cells. Such a block of uptake that would otherwise be effected by the basic amino acids of portion B may be termed a "veto" of the uptake by the acidic portion A. The present inventors have made the further surprising discovery that cleavage of linker X, allowing the separation of portion A from portion B is effective to allow the uptake of portion B into cells.

In a some embodiments, MTS molecules of the present disclosure include the following:

$$\begin{matrix} & T \\ & | \\ & Y \\ & | \\ (P-M-A-X-B-C)_n, & (P-M-A-X-B-C)n, \\ & T & T \\ & | & | \\ & Y & Y \\ & | & | \\ (P-M-A-X-B-C)_n, & (A-X-B-C)_n-M, \\ & T \\ & | \\ & Y \\ & | \\ (P-M-A-X-B)_n, & (P-M-A-X-B)n, \\ & T \\ & | \\ & Y \\ & | \\ (M-A-X-B)n, & (A-X-B)n-M, \text{ or} \\ (A-X-B)_n-M-(Y-T)_i \end{matrix}$$

wherein P is an optional pre-targeting moiety; M is an optional macromolecular carrier, T is a compound for delivery to a target, including for example a therapeutic compound (also referred to herein as a "warhead"); A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound (also referred to herein as a "warhead"); and n is an integer between 1 and 20; and C is a detectable cargo moiety. In some embodiments of molecules having features of the invention, n and i are independently selected integers between 1 and 20. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. An acidic portion A may include amino acids that are not acidic. In some embodiments, A-X-B is joined to T with linker Y. Acidic portion A may comprise other moieties, such as negatively charged moieties. In some embodiments, cleavage of linker X leads to B and T remaining joined together. In some embodiments, B and T remained joined together until cleavage of linker Y occurs. In embodiments of MTS molecules having features of the invention, an acidic portion A may be a negatively charged portion, having about 2 to about 20 negative charges at physiological pH that does not include an amino acid. A basic portion B may include amino acids that are not basic. Basic portion B may comprise other moieties, such as positively charged moieties. In some embodiments basic portion B does not include an amino acid. In embodiments of MTS molecules having features of the invention, a basic portion B may be a positively charged portion, having between about 5 and about 20 positive charges at physiological pH. In some embodiments, the amount of negative charge in portion A is approximately the same as the amount of positive charge in portion B. In some embodiments, the T-Y pair is attached to either end of B.

A cargo moiety C (also referred to as a detectable moiety) and or compound T include, for example, a variety of detectable agents, including for example any detectable moiety for detection in an ex vivo assay, a contrast agent for diagnostic imaging, or a chemotherapeutic drug or radiation-sensitizer for therapy. B may be, for example, a peptide portion having between about 5 to about 20 basic amino acids, such as a series of basic amino acids (arginines are can be employed, as well as histidines, lysines or other basic amino acids). In some embodiments, X and/or Y is a cleavable linker that is cleavable under physiological conditions. A may be a peptide portion having between about 2 to about 20 about 2 to about 20 acidic amino acids, such as a series of acidic amino acids. In some embodiments of molecules having features of the invention, glutamates and aspartates are employed as acidic amino acids for peptide portion A.

A pre-targeting moiety P can include a variety of peptides for use in targeting the MTS molecules of the invention to a particular tissue, cell type and/or cell. A pre-targeting moiety P includes any moiety capable of binding a moiety on a target cell or in target cell location, including for example peptide moieties, antibodies, aptamers, chemical ligands, small molecule ligands, peptides, nucleotides/nucleic acids, peptide nucleic acids, locked nucleic acids and small molecule moieties as well as any derivatives thereof. In some embodiments, P includes any moiety capable of binding to cell and/or tissue involved in inflammation, diabetes, cardiovascular diseases, neurodegenerative disorders and cancer. In some embodiments, the receptor for which P is a legend can include any receptor differentially expressed on a neoplastic cell as compared to a non-neoplastic cell, including breast, prostate, liver, colon, lung, pancreas, stomach, brain, liver, kidney, bladder, blood or any other receptor known by those of skill in the art to be differentially expressed in cancer versus normal cells. In some embodiments, the receptor to which P is a ligand includes a receptor selected from but not limited to G-protein coupled receptors (GPCRs), androgen receptors (ARs), estrogen receptors (ERs), leptin receptors (LRs), growth hormone receptors (GHRs), transforming growth factor receptors (TGFs; including for example but not limited to TGF31, TGF32 and TGF33), epidermal growth factor receptors (EGFRs), HER2/neu receptors, breast cancer associated receptors (including for example but not limited to estrogen receptors), ErbB receptors, ErbB2 receptors, epidermal growth factor receptors (EGFRs), insulin like growth factor receptors (ILGFRs), HGF/Met receptors, tyrosine kinase receptors, pattern recognition receptors (PRRs), Toll-like receptors (TLRs) pathogen-associated molecular patterns (PAMP), killer activated and killer inhibitor receptors (KARs and KIRs), complement receptors, Fc receptors, B-cell receptors, T-cell receptors, cytokine receptors, RAGE, BTLA, protease activate receptors (PARs), nuclear receptors (including for example but not limited to PPARs), mineralocorticoid receptors, platelet ADP receptors, APJ receptor, muscarinic receptors (including for example but not limited to muscarinic acetylcholine receptor M2, M3 muscarinic receptor), glucorticoid receptors, adrenergic receptors, scavenger receptors, calcium sensing receptor (CaR), angiotension II receptor, bile acid receptors, corticosteroid receptors, Protease-activated receptors (PARs), interleukin receptors (including for example, but not limited to interleukin 1 receptors), AMPA receptors, insulin receptors, glucose receptors, cannabinoid receptors, chemokine receptors, N-methyl-D-aspartate (NDMA) receptors, adenosine receptors, peripheral benzodiazepine receptors, sigma-1 receptor, Trk receptors (including for example but not limited to TrkB receptor), nuclear hormone receptors, nicotinic receptors, nicotinic acetylcholine receptors (including for example but not limited to $\alpha 4\beta 2$ and IgG receptors) and integrins. In some embodiments, P is a ligand for capable of binding to $\alpha v\beta 3$ or $\alpha v\beta 5$. In some embodiments, P is a ligand capable of binding to $\alpha v\beta 3$. In some embodiments, P is a cyclic ligand. In some embodiments, P is cyclic RGD (cRGD).

The present inventors have made the surprising discovery that including an acidic portion A is also effective to inhibit or prevent the uptake into cells of molecules combining a portion B and a portion C and/or compound T. The present inventors have made the further discovery that cleavage of linker X and/or Y, allowing the separation of portion A from portion B is effective to allow the uptake of portions B and C into cells. Thus, delivery of cargo C can be controlled and enhanced by molecules having features of the invention.

For example, when peptide portion A contains about 5 to about 9 consecutive glutamates or aspartates, and X and/or Y is a flexible linker of about 2 to about 100, or about 6 to about 30 atoms in length, the normal ability of a peptide portion B (e.g., a sequence of nine consecutive arginine residues) to cause uptake into cells is blocked. Cleavage of linker X allows the separation of portion A from portion B and portion C and/or compound T, alleviating the veto by portion A. Thus, when separated from A, the normal ability of portion B to affect the uptake of cargo C into cells is regained. Such cellular uptake typically occurs near the location of the cleavage event. Thus, design of cleavable linker X and/or Y such that either is cleaved at or near a target cell is effective to direct uptake of cargo C and/or therapeutic moiety T into target cells. Extracellular cleavage of X and/or Y allows separation of A from the rest of the molecule to allow uptake into cells.

A MTS molecule having features of the invention may be of any length. In embodiments of MTS molecules having features of the invention, a MTS molecule may be about 7 to about 40 amino acids in length, not including the length of a linker X and/or Y, a cargo portion C and/or a moiety T. In other embodiments, particularly where multiple non-acidic (in portion A) or non-basic (in portion B) amino acids are included in one or both of portions A and B, portions A and B of a MTS molecule may together be about 50, or about 60, or about 70 amino acids in length. A cyclic portion of an MTS may include about 12 to about 60 amino acids, not including the length of a linker X and a cargo portion C. For example, a linear MTS molecule having features of the invention may have a basic portion B having between about 5 to about 20 basic amino acids (in some embodiments between about 9 to about 16 basic amino acids) and an acidic portion A having between about 2 to about 20 acidic amino acids (e.g., between about 5 to about 20, between about 5 to about 9 acidic amino acids). In some embodiments, a MTS molecule having features of the invention may have a basic portion B having between about 9 to about 16 basic amino acids and between about 5 to about 9 acidic amino acids.

Portions A and B may include either L-amino acids or D-amino acids. In embodiments of the invention, D-amino acids are employed for the A and B portions in order to minimize immunogenicity and nonspecific cleavage by background peptidases or proteases. Cellular uptake of oligo-D-arginine sequences is known to be as good or better than that of oligo-L-arginines. The generic structures of the molecules described above can be effective where A is at the amino terminus and where A is at the carboxy terminus, i.e. either orientation of the peptide bonds is permissible. However, in embodiments where X and/or Y is a peptide cleavable by a protease, it may be beneficial to join the C-terminus of X and/or Y to the N-terminus of B, so that the new amino terminus created by cleavage of X and/or Y contributes an additional positive charge that adds to the positive charges already present in B.

In some embodiments, a MTS molecule disclosed herein has the formula according to one of the following:

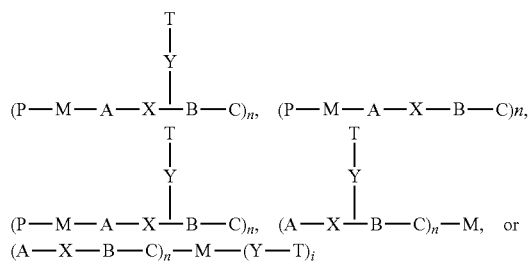

wherein C is a cargo moiety; T is a therapeutic moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X and/or Y is a linker that is cleavable by thrombin. In some embodiments, the acid amino acids are consecutive. In some embodiments, the acid amino acids are not consecutive. In some embodiments of molecules having features of the invention, n and i are independently selected integers between 1 and 20. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments, a MTS molecule disclosed herein has the formula according to one of the following:

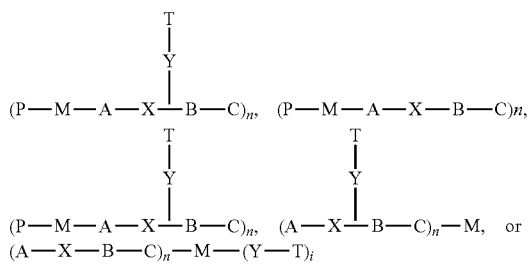

wherein C is a cargo moiety; T is a therapeutic moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X and/or Y is a linker that is cleavable by thrombin; M is a macromolecular carrier; and n is an integer between 1 and 20. In some embodiments of molecules having features of the invention, n and i are independently selected integers between 1 and 20. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20.

In some embodiments of molecules having features of the invention, peptide portion A includes between about 2 to about 20, or between about 5 to about 20 acidic amino acids, and may be series of acidic amino acids (e.g., glutamates and aspartates or other acidic amino acids). In some embodiments, A has a sequence comprising 5 to 9 consecutive glutamates. In some embodiments, portion A comprises 8 consecutive glutamates (i.e., EEEEEEEE or eeeeeeee).

An acidic portion A may include amino acids that are not acidic. Acidic portion A may comprise other moieties, such as negatively charged moieties. In embodiments of a MTS molecule disclosed herein, an acidic portion A may be a negatively charged portion, in some embodiments having about 2 to about 20 negative charges at physiological pH that does not include an amino acid. In some embodiments, the amount of negative charge in portion A is approximately the same as the amount of positive charge in portion B.

Portion A is either L-amino acids or D-amino acids. In embodiments of the invention, D-amino acids are can be employed in order to minimize immunogenicity and non-specific cleavage by background peptidases or proteases. Cellular uptake of oligo-D-arginine sequences is known to be as good as or better than that of oligo-L-arginines.

It will be understood that portion A may include non-standard amino acids, such as, for example, hydroxylysine, desmosine, isodesmosine, or other non-standard amino acids. Portion A may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion A may also include peptide mimetic moieties, including portions linked by non-peptide bonds and amino acids linked by or to non-amino acid portions.

The generic structures according to one of the following:

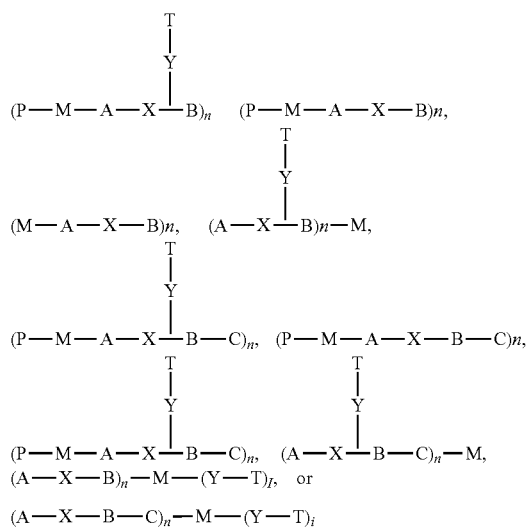

is effective where A is at the amino terminus or where A is at the carboxy terminus, i.e., either orientation of the peptide bonds is permissible. In some embodiments of molecules having features of the invention, n and i are independently selected integers between 1 and 20. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments, a MTS molecule disclosed herein has the formula according to one of the following:

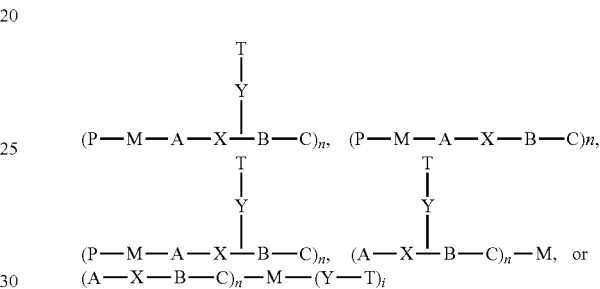

wherein C is a cargo moiety, A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X and/or Y is a linker that is cleavable by thrombin. In some embodiments of molecules having features of the invention, n and i are independently selected integers between 1 and 20. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20.

In some embodiments, a MTS molecule disclosed herein has the formula according to one of the following

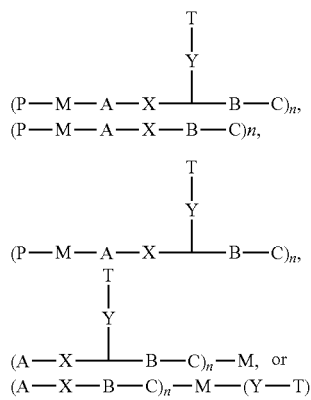

wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X and/or Y is a linker that is cleavable by thrombin; M is a macromolecular carrier; and n is an integer between 1 and 20. In some embodiments of molecules having features of the invention, n and i are independently selected integers between 1 and 20. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments of molecules having features of the disclosure, peptide portion B includes between about 5 to about 20, or between about 9 to about 16 basic amino acids, and may be a series of basic amino acids (e.g., arginines, histidines, lysines, or other basic amino acids). In some embodiments, portion B comprises 9 consecutive arginines (i.e., RRRRRRRRR or rrrrrrrrr). In some embodiments, the basic amino acids are consecutive. In some embodiments, the basic amino acids are not consecutive.

A basic portion B may include amino acids that are not basic. Basic portion B may comprise other moieties, such as positively charged moieties. In embodiments, a basic portion B may be a positively charged portion, having between about 5 and about 20 positive charges at physiological pH that does not include an amino acid. In some embodiments, the amount of negative charge in portion A is approximately the same as the amount of positive charge in portion B.

Portion B is either L-amino acids or D-amino acids. In some embodiments of the invention, D-amino acids are employed in order to minimize immunogenicity and non-specific cleavage by background peptidases or proteases. Cellular uptake of oligo-D-arginine sequences is known to be as good as or better than that of oligo-L-arginines.

It will be understood that portion B may include non-standard amino acids, such as, for example, hydroxylysine, desmosine, isodesmosine, or other non-standard amino acids. Portion B may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion B may also include peptide mimetic moieties, including portions linked by non-peptide bonds and amino acids linked by or to non-amino acid portions.

In embodiments where X and/or Y is a peptide cleavable by a protease, it may be beneficial to join the C-terminus of X and/or Y to the N-terminus of B, so that the new amino terminus created by cleavage of X and/or Y contributes an additional positive charge that adds to the positive charges already present in B.

Cargo portion C may be attached to B in any location or orientation. A cargo portion C need not be located at an opposite end of portion B than a linker X and/or Y. Any location of attachment of C to B is acceptable as long as that attachment remains after X and/or Y is cleaved. For example, a cargo portion C may be attached to or near to an end of portion B with linker X and/or Y attached to an opposite end of portion B. A cargo portion C may also be attached to or near to an end of portion B with linker X and/or Y attached to or near to the same end of portion B. In some embodiments of the invention, a linker X and/or Y may link to a cargo portion C which is linked to a basic portion B where a MTS molecule having features of the invention comprising a cargo portion C linked to multiple basic portions B, each of which basic portions B are linked to a linker portion X and/or Y, and via the linker to an acidic portion A.

A linker X and/or Y may be designed for cleavage in the presence of particular conditions or in a particular environment. In some embodiments, a linker X and/or Y is cleavable under physiological conditions. Cleavage of such a linker X and/or Y may, for example, be enhanced or may be affected by particular pathological signals or a particular environment related to cells in which cargo delivery is desired. The design of a linker X and/or Y for cleavage by specific conditions, such as by a specific enzyme, allows the targeting of cellular uptake to a specific location where such conditions obtain. Thus, one important way that MTS molecules having features of the invention provide specific detection of specific proteases presence is by the design of the linker portion X and/or Y to be cleaved by the protease. Thus, another important way that MTS molecules having features of the invention provide specific detection of hydrogen peroxide presence is by the design of the linker portion X and/or Y to be cleaved by hydrogen peroxide. The linker portion X and/or Y can be designed to be cleaved only by specific proteases or to be selective for specific proteases. After cleavage of a linker X and/or Y, the portions B-C of the molecule are then a simple conjugate of B and C, in some instances retaining a relatively small, inert stub remaining from a residual portion of linker X and/or Y.

A linker portion X and/or Y may be cleavable by conditions found in the extracellular environment, such as acidic conditions which may be found near cancerous cells and tissues or a reducing environment, as may be found near hypoxic or ischemic cells and tissues; by proteases or other enzymes found on the surface of cells or released near cells having a condition to be treated, such as diseased, apoptotic or necrotic cells and tissues; or by other conditions or factors. An acid-labile linker may be, for example, a cis-aconitic acid linker. A linker portion X and/or Y may also be cleaved extracellularly in an ex vivo reaction. Other examples of pH-sensitive linkages include acetals, ketals, activated amides such as amides of 2,3-dimethylmaleamic acid, vinyl ether, other activated ethers and esters such as enol or silyl ethers or esters, imines, iminiums, enamines, carbamates, hydrazones, and other linkages. A linker X may be an amino acid or a peptide. A linker portion X and/or Y may also be cleaved by hydrogen peroxide found in the extracellular environment, which can occur near and around cells during inflammation, diabetes, cardiovascular diseases, neurodegenerative disorders and cancer. A peptide linker may be of any suitable length, such as, for example, about 3 to about 30, or about 6 to about 24 atoms in sequence (e.g., a linear peptide about 1 to 10 or about 2 to 8 amino acids long). A cleavable peptide linker may include an amino acid sequence recognized and cleaved by a protease, so that proteolytic action of the protease cleaves the linker X and/or Y. A cleavable peptide linker may include an amino acid sequence recognized and cleaved by a hydrogen peroxide, so that hydrogen peroxide action cleaves the linker X and/or Y. In some embodiments, cleavage of X and/or Y can allow for categorization of the tumor microenvironment.

In some embodiments, X and/or Y is a cleavable linker. In some embodiments, a linker X and/or Y is designed for cleavage in the presence of particular conditions or in a particular environment In some embodiments, a linker X and/or Y is cleavable under physiological conditions Cleavage of such a linker X and/or Y may, for example, be enhanced or may be affected by particular pathological signals or a particular environment related to cells in which cargo delivery is desired The design of a linker X and/or Y for cleavage by specific conditions, such as by a specific enzyme (e.g., thrombin), allows the targeting of cellular uptake to a specific location where such conditions obtain Thus, one important way that MTS molecules provide specific targeting of cellular uptake to desired cells, tissues, or regions is by the design of the linker portion X and/or Y to be cleaved by conditions near such targeted cells, tissues, or regions. After cleavage of a linker X and/or Y, the portions B-C, B-C with T, or B with T of the molecule are then a simple conjugate of the recited parts, in some instances retaining a relatively small, inert stub remaining from a residual portion of linker X and/or Y. In some embodiments, cleavage of X and/or Y can allow for categorization of the tumor microenvironment. In some embodiments, cleavage of X and/or Y can allow for categorization of the tumor and the proteases expressed by the tumor.

In some embodiments, X and/or Y is cleavable by a protease associated with a disease, including but not limited to inflammation, diabetes, cardiovascular diseases, neurodegenerative disorders and cancer. In some embodiments, X and or Y is cleavable by a matrix metalloproteinase (including but not limited to MMP-2, MMP-9, MMP-7 and MMP-14), a hydrogen peroxidase, cathepsins (including but not limited to cathepsin B and cathepsin K), serine proteases (including but not limited to neutrophil serine proteases), mast cell proteases, elastases, gelatinases (including but not limited to MMP-2/gelatinase A and MMP-9/92-kDa gelatinase B), collagenases (including but not limited to MMP-1, MMP-3, MMP-8, and MMP-13), stromelysins (including but not limited to MMP-3, -7, -10, -11, and -12), tissue inhibitors of metalloproteinases (TIMPs; including but not limited to TIMP-1 and TIMP-2) cysteine proteases, threonine proteases, aspartic proteases, thrombin, plasmin, PSA, trypsin, uPA, TOP, caspase (including but not limited to caspase-3), β-amyloid proteases, calpains, and presenilinases. For a description of proteases, see, for example, Choi et al., *Theranostics,* 2(2): 156-178 (2012); incorporated herein by reference in its entirety. In some embodiments, cleavage of X and/or Y can allow for categorization of the disease microenvironment. In some embodiments, cleavage of X and/or Y can allow for categorization of the tumor and the proteases expressed by the diseased cell(s).

In some embodiments, X and/or Y is (SEQ ID NO:1) DPRSFL, (SEQ ID NO:2) PPRSFL, (SEQ ID NO:3) Norleucine-TPRSF, (SEQ ID NO:4) PLGC(Me)AG, 6-aminohexanoyl, 5-amino-3-oxapentanoyl, Val-Cit-(p-amido)benzyloxycarbonyl (Val-Cit-PAB), benzyloxycarbonyl-valine-citrulline (Z-val-cit), or a combination thereof. In some embodiments, X is (SEQ ID NO:1) DPRSFL, (SEQ ID NO:2) PPRSFL, (SEQ ID NO:3) Norleucine-TPRSF, (SEQ ID NO:4) PLGC(Me)AG, (SEQ ID NO:5) SSKLQ, (SEQ ID NO:6) GPLGIAGQ, (SEQ ID NO:7) Glu-Pro-Cit-Gly-Hof-Tyr-Leu, (SEQ ID NO:8) PVGLIG, D-Ala-Phe-Lys, or a combination thereof. In some embodiments, X and/or Y is a p-amido-benzyl ether. In some embodiments, X is 6-aminohexanoyl, 5-amino-3-oxapentanoyl, or a combination thereof. In some embodiments, Y is Val-Cit-(p-amido)benzyloxycarbonyl (Val-Cit-PAB).

In some embodiments, X and/or Y is cleaved by thrombin. In some embodiments, X and/or Y is substantially specific for thrombin, MMPs or elastases. In some embodiments, X and/or Y is cleaved by or is substantially specific for MMPs ((SEQ ID NO: 10) PLGLAG and (SEQ ID NO:4) PLGC(met)AG, elastases (SEQ ID NO:12) (RLQLK(acetyl)L, plasmin and/or thrombin. In some embodiments, X and/or Y is (SEQ ID NO:1) DPRSFL, (SEQ ID NO:2) PPRSFL, (SEQ ID NO:3) Norleucine-TPRSF, or (SEQ ID NO:4) PLGC(Me)AG. In some embodiments, X and/or Y is 6-aminohexanoyl, 5-amino-3-oxapentanoyl, or a combination thereof. In some embodiments, X and/or Y is a p-amido-benzyl ether, such as for example Val-Cit-(p-amido)benzyloxycarbonyl (Val-Cit-PAB). In some embodiments, X is (SEQ ID NO: 1) DPRSFL, (SEQ ID NO:2) PPRSFL, (SEQ ID NO:3) Norleucine-TPRSF, or (SEQ ID NO:4) PLGC (Me)AG. In some embodiments, X is 6-aminohexanoyl, 5-amino-3-oxapentanoyl, or a combination thereof. In some embodiments, Y is Val-Cit-(p-amido)benzyloxycarbonyl (Val-Cit-PAB). In some embodiments, the MMP 2,9 cleavable or substantially specific sequence is (SEQ ID NO: 10) PLGLAG and/or (SEQ ID NO:4) PLGC(met)AG. In some embodiments, the MMP cleavable or substantially specific sequences could include but are not limited to (SEQ ID NO: 13) RS-(Cit)-G-(homoF)-YLY, (SEQ ID NO:14) PLGLEEA, (SEQ ID NO:15) CRPAHLRDSG, (SEQ ID NO:16) SLAYYTA, (SEQ ID NO:17) NISDLTAG, (SEQ ID NO:18) PPSSLRVT, (SEQ ID NO:19) SGESLSNLTA, (SEQ ID NO:20) RIGFLR elastase cleavable or substantially specific sequence is (SEQ ID NO: 12) RLQLK(acetyl)L. In some embodiments, the plasmin cleavable or substantially specific sequence is (SEQ ID NO:21) RLQLKL. Thrombin selective substrates include (SEQ ID NO: 1) DPRSFL, (SEQ ID NO:2) PPRSFL, and (SEQ ID NO:3) Norleucine-TPRSFL. In some embodiments, the chymase cleavable or substantially specific sequence (SEQ ID NO:22) GVAYISGA. Urokinase-type plasminogen activator (uPA) and tissue plasminogen activator (tPA) cleavable or substantially specific sequence is (SEQ ID NO:23) YGRAAA. In some embodiments, the uPA cleavable or substantially specific sequence is (SEQ ID NO:24) YGPRNR. In some embodiments, X and Y are different cleavable linkers such that specific properties of the linkers are employed for delivery of cargo and therapeutic compounds to particular cells and/or cellular environments. In some embodiments, linker X and/or Y can be any combination of linkers described herein.

In some embodiments, X and/or Y is cleaved by a peroxide, including but not limited to hydrogen peroxide. Examples of X linkers cleaved by hydrogen peroxide include but are not limited to ACPP1 and/or ACPP2. The representative structure for ACPP 1 is:

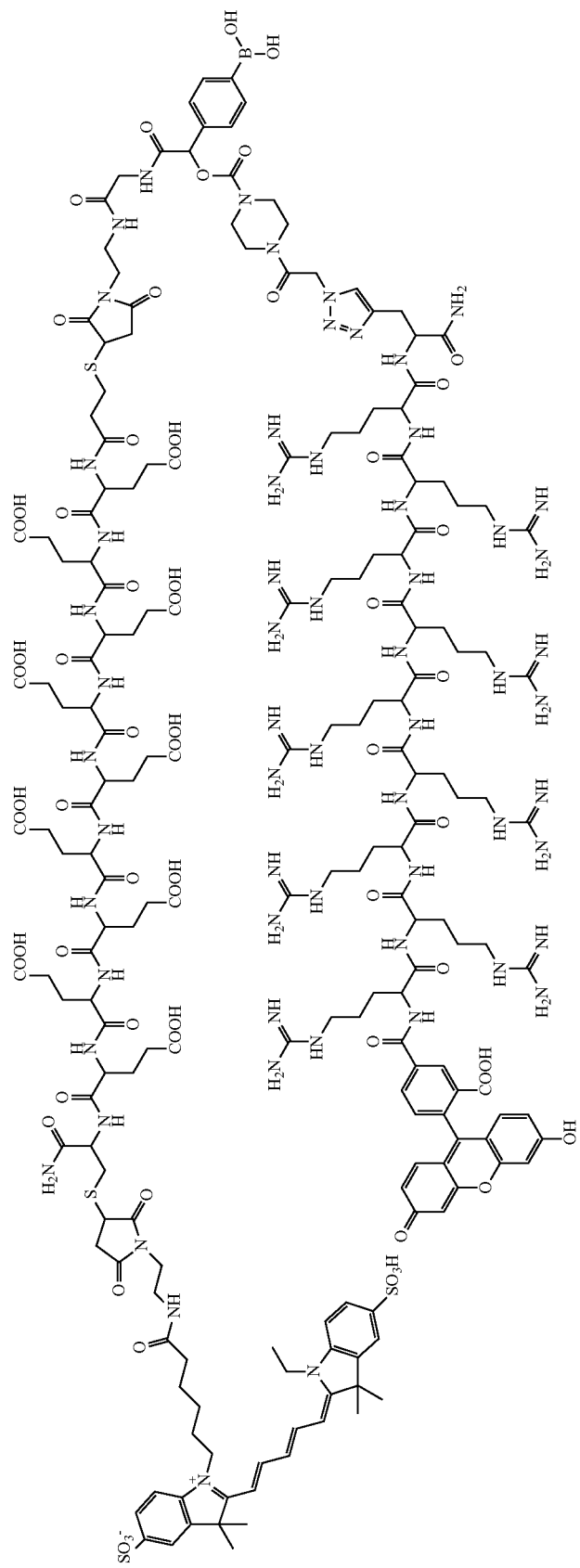

The representative structure for ACPP2 is:

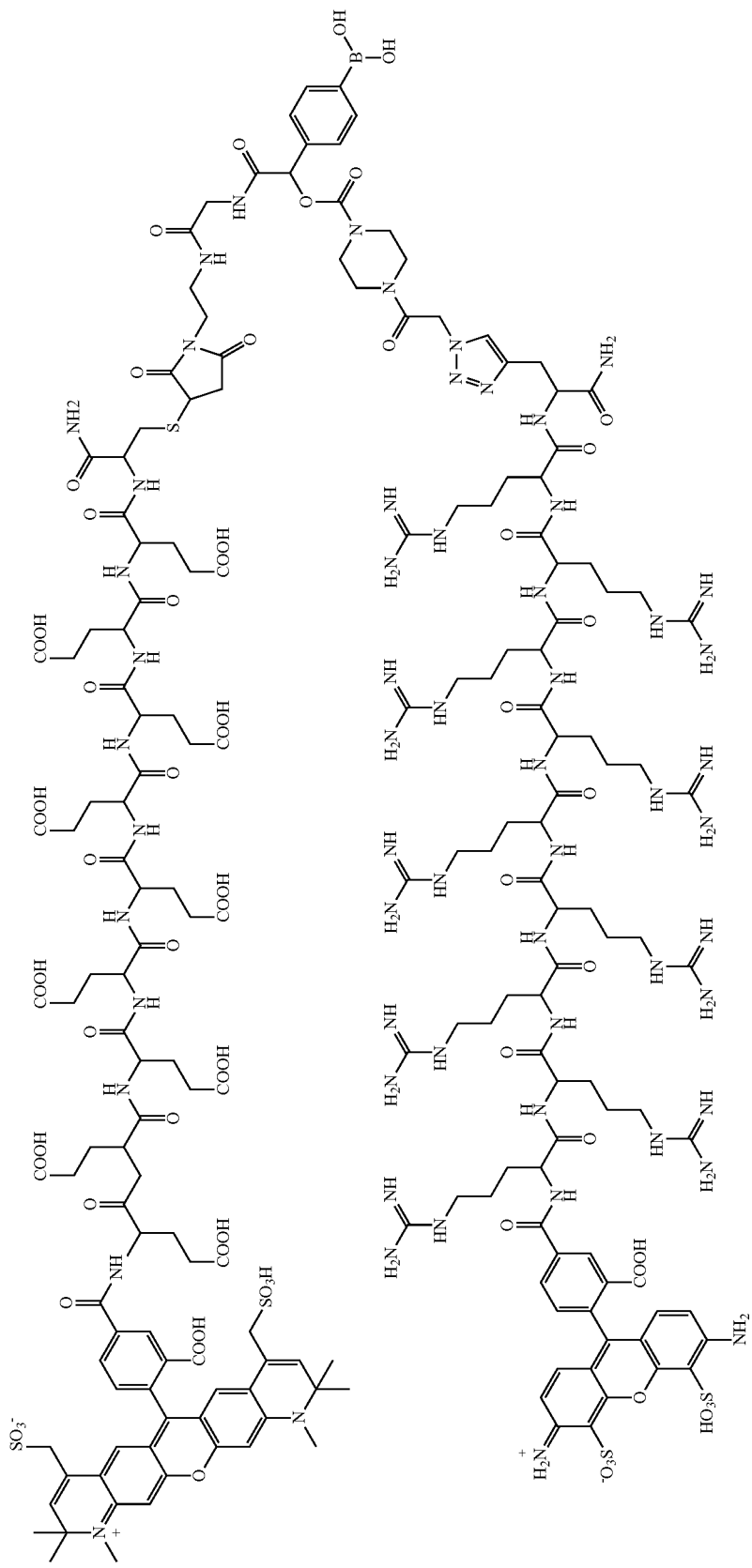

Other related structures cleavable by hydrogen peroxide are also contemplated by the present invention.

In some embodiments, a linker consisting of one or more amino acids is used to join peptide sequence A (i.e., the sequence designed to prevent uptake into cells) and peptide sequence B (i.e., the TS). Generally the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity.

In some embodiments, the linker is flexible. In some embodiments, the linker is rigid. In some embodiments, both linkers are flexible. In some embodiments, both linkers are rigid. In some embodiments, one linker is rigid and one linker is flexible.

In some embodiments, one or both linkers comprise a linear structure. In some embodiments, one or both linkers comprise a non-linear structure. In some embodiments, one or both linkers comprise a branched structure. In some embodiments, one or both linkers comprise a cyclic structure. In some embodiments, the linkers comprise the same structure. In some embodiments, the linkers comprise different structures.

In some embodiments, X and/or Y is about 5 to about 30 atoms in length. In some embodiments, X and/or Y is about 6 atoms in length. In some embodiments, X and/or Y is about 8 atoms in length. In some embodiments, X and/or Y is about 10 atoms in length. In some embodiments, X and/or Y is about 12 atoms in length. In some embodiments, X and/or Y is about 14 atoms in length. In some embodiments, X and/or Y is about 16 atoms in length. In some embodiments, X and/or Y is about 18 atoms in length. In some embodiments, X and/or Y is about 20 atoms in length. In some embodiments, X and/or Y is about 25 atoms in length. In some embodiments, X and/or Y is about 30 atoms in length.

In some embodiments, X and/or Y is cleaved by thrombin. In some embodiments, the linker is substantially specific for thrombin.

In some embodiments, the linker X and/or Y has a formula selected from: (SEQ ID NO: 1) DPRSFL, (SEQ ID NO:2) PPRSFL, or (SEQ ID NO:3) Norleucine-TPRSF. In some embodiments, linker is (SEQ ID NO:1) DPRSFL, (SEQ ID NO:2) PPRSFL, or (SEQ ID NO:3) Norleucine-TPRSF.

In some embodiments, the linker X and/or Y binds peptide portion A (i.e., the peptide sequence which prevents cellular uptake) to peptide portion B (i.e., the MTS sequence) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, X and/or Y comprises a peptide linkage. The peptide linkage comprises L-amino acids and/or D-amino acids. In embodiments of the invention, D-amino acids are employed in order to minimize immunogenicity and nonspecific cleavage by background peptidases or proteases. Cellular uptake of oligo-D-arginine sequences is known to be as good as or better than that of oligo-L-arginines.

It will be understood that a linker disclosed herein may include non-standard amino acids, such as, for example, hydroxylysine, desmosine, isodesmosine, or other non-standard amino acids. A linker disclosed herein may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. A linker disclosed herein may also include peptide mimetic moieties, including portions linked by non-peptide bonds and amino acids linked by or to non-amino acid portions.

In some embodiments, a MTS molecule disclosed herein comprises a single type of linker. Use of a single mechanism to mediate uptake of both imaging and therapeutic cargoes is particularly valuable, because imaging with noninjurious tracer quantities can be used to test whether a subsequent therapeutic dose is likely to concentrate correctly in the target tissue.

In some embodiments, a MTS molecule disclosed herein comprises different types of linkers. Use of multiple mechanisms to mediate uptake of both imaging and therapeutic cargoes is particularly valuable, because imaging with noninjurious tracer quantities can be used to test whether a subsequent therapeutic dose is likely to concentrate correctly in the target tissue.

In some embodiments, a MTS molecule disclosed herein comprises a plurality of linkers. Where a MTS molecule disclosed herein includes multiple linkages X and/or Y, separation of portion A from the other portions of the molecule requires cleavage of all linkages X and/or Y. Cleavage of multiple linkers X and/or Y may be simultaneous or sequential Multiple linkages X and/or Y may include linkages X having different specificities, linkages Y have different specificities and/or linkages X and/or Y having different specificities so that separation of portion A from the other portions of the molecule requires that more than one condition or environment ("extracellular signals") be encountered by the molecule. Cleavage of multiple linkers X and/or Y thus serves as a detector of combinations of such extracellular signals. For example, a MTS molecule may include two linker portions Xa and Xb connecting basic portion B with acidic portion A. Both linkers Xa and Xb must be cleaved before acidic portion A is separated from basic portion B allowing entry of portion B and cargo moiety C or therapeutic moiety T (if any) to enter a cell. For example, a MTS molecule may include two linker portions Ya and Yb connecting basic portion B with acidic portion A. Both linkers Ya and Yb must be cleaved before acidic portion A is separated from basic portion B allowing entry of portion B and cargo moiety C or therapeutic moiety T (if any) to enter a cell. For example, a MTS molecule may include four linker portions Xa, Xb, Ya and Yb connecting basic portion B with acidic portion A. All four linkers Xa, Xb, Ya and Yb must be cleaved before acidic portion A is separated from basic portion B allowing entry of portion B and cargo moiety C or therapeutic moiety T (if any) to enter a cell. It will be understood that a linker region may link to either a basic portion B or a cargo moiety C or therapeutic moiety T independently of another linker that may be present, and that, where desired, more than two linker regions X may be included.

Combinations of two or more linkers X and/or Y may be used to further modulate the detection of multiple proteases with a single MTS molecule, as well as targeting and delivery of molecules to desired cells, tissue or regions. Combinations of extracellular signals are used to widen or narrow the specificity of the cleavage of linkers X and/or Y if desired. Where multiple linkers X and/or Y are linked in parallel, the specificity of cleavage is narrowed, since each linker X must be cleaved before portion. A may separate from the remainder of the molecule. Where multiple linkers X and/or Y are linked in series, the specificity of cleavage is broadened, since cleavage on any one linker X and/or Y allows separation of portion A from the remainder of the molecule. For example, in order to detect either a protease OR hypoxia (i.e., to cleave X and/or Y in the presence of either protease or hypoxia), a linker X and/or Y is designed to place the protease-sensitive and reduction-sensitive sites in tandem, so that cleavage of either would suffice to allow separation of the acidic portion. Alternatively, in order to detect the presence of both a protease and hypoxia (i.e., to cleave X and/or Y in the presence of both protease and hypoxia but not in the presence of only one alone), a linker X and/or Y is designed to place the protease sensitive site between at least one pair of cysteines that are disulfide-bonded to each other In that case, both protease cleavage and disulfide reduction are required in order to allow separation of portion A.

One important class of signals is the hydrolytic activity of matrix metalloproteinases (MMPs), which are very important in the invasive migration of metastatic tumor cells. MMPs are also believed to play major roles in inflammation and stroke. MMPs are reviewed in Visse et al., *Circ. Res.* 92:827-839 (2003). MMPs may be used to cleave a linker X and/or Y and so to allow separation of acidic portion A from portions B and C, allowing cellular uptake of cargo C and/or therapeutic compound T (e.g., radiosensitizing agent T) so that cellular uptake of C and/or T is triggered by action of MMPs. Such uptake is typically in the vicinity of the MMPs that trigger cleavage of X and/or Y. Thus, uptake of molecules having features of the invention are able to direct cellular uptake of cargo C and or therapeutic compound T (e.g., radiosensitizing agent T) to specific cells, tissues, or regions having active MMPs in the extracellular environment.

For example, a linker X and/or Y that includes the amino-acid sequence PLGLAG (SEQ ID NO: 10) may be cleaved by the metalloproteinase enzyme MMP-2 (a major MMP in cancer and inflammation). Cleavage of such a linker X and/or Y occurs between the central G and L residues, causing cell uptake to increase by 10 to 20-fold. A great deal is known about the substrate preferences of different MMPs, so that linkers X and/or Y may be designed that are able to bias X and/or Y to be preferentially sensitive to particular subclasses of MMPs, or to individual members of the large MMP family of proteinases. For example, in some embodiments, linkers X and/or Y designed to be cleaved by membrane-anchored MMPs are particularly employed because their activity remains localized to the outer surface of the expressing cell. In alternative embodiments, linkers X and/or Y designed to be cleaved by a soluble secreted MMP are employed where diffusion of cargo C and/or therapeutic compound T (e.g., radiosensitizing agent T) away from the exact location of cleavage may be desired, thereby increasing the spatial distribution of the cargo C and/or therapeutic compound T (e.g., radiosensitizing agent T). Other linkers X and/or Y cleavable by other MMPs are discussed throughout the disclosure.

Hypoxia is an important pathological signal. For example, hypoxia is thought to cause cancer cells to become more resistant to radiation and chemotherapy, and also to initiate angiogenesis. A linker X and/or Y suitable for cleavage in or near tissues suffering from hypoxia enables targeting of portion B and C and/or T to cancer cells and cancerous tissues, infarct regions, and other hypoxic regions. For example, a linker X and/or Y that includes a disulfide bond is preferentially cleaved in hypoxic regions and so targets cargo delivery to cells in such a region. In a hypoxic environment in the presence of, for example, leaky or necrotic cells, free thiols and other reducing agents become available extracellularly, while the $O_2$ that normally keeps the extracellular environment oxidizing is by definition depleted. This shift in the redox balance should promote reduction and cleavage of a disulfide bond within a linker X and/or Y. In addition to disulfide linkages which take advantage of thiol-disulfide equilibria, linkages including quinones that fall apart when reduced to hydroquinones may be used in a linker X and/or Y designed to be cleaved in a hypoxic environment.

Necrosis often leads to release of enzymes or other cell contents that may be used to trigger cleavage of a linker X and/or Y. A linker X and/or Y designed for cleavage in regions of necrosis in the absence of hypoxia, for example, may be one that is cleaved by calpains or other proteases that may be released from necrotic cells. Such cleavage of linkers X by calpains would release the connected portions B-C and/or compound T (e.g., radiosensitizing agent T) from portion A allowing cargo C and/or therapeutic compound T (e.g., radiosensitizing agent T) to be taken up by diseased cells and by neighboring cells that had not yet become fully leaky.

Acidosis is also commonly observed in sites of damaged or hypoxic tissue, due to the Warburg shift from oxidative phosphorylation to anaerobic glycolysis and lactic acid production. Such local acidity could be sensed either by making an acid-labile linker X and/or Y (e.g., by including in X and/or Y an acetal or vinyl ether linkage). Alternatively, or in addition, acidosis may be used as a trigger of cargo C and/or therapeutic compound T (e.g., radiosensitizing agent T) uptake by replacing some of the arginines within B by histidines, which only become cationic below pH 7.

Molecules having features of the invention are suitable for carrying different cargoes C and/or compounds T, including different types of cargoes C and/or compounds T and different species of the same types of cargo C and/or compound T (e.g., radiosensitizing agent T), for uptake into cells. For example, different types of cargo include marker cargoes (e.g., fluorescent or radioactive label moieties) and different types of compounds T include therapeutic cargoes (e.g., chemotherapeutic molecules such as methotrexate or doxorubicin), or other cargoes C and/or compounds T. Where destruction of aberrant or diseased cells is therapeutically required, a cargo C and/or a compound T (e.g., radiosensitizing agent T) include a therapeutic cargo such as a "cytotoxic agent," i.e. a substance that inhibits or prevents the function of cells and/or causes destruction of cells. In some embodiments, a single molecule having features of the invention includes more than one cargo portion C and/or compound T (e.g., radiosensitizing agent T) so that a basic portion B may be linked to multiple cargoes C and/or compounds T. Such multiple cargoes C and/or compounds T include marker cargoes, therapeutic cargoes, or other cargoes. Multiple cargoes C and compounds T may allow, for example, delivery of both a radioactive marker and an ultrasound or contrast agent, allowing imaging by different modalities. Alternatively, for example, delivery of a radioactive cargo C along with an anti-cancer agent compound T (e.g., radiosensitizing agent T), providing enhanced anticancer activity, or delivery of a radioactive cargo with a fluorescent cargo, allowing multiple means of localizing and identifying cells which have taken up cargo C and/or compound T (e.g., radiosensitizing agent T).

Delivery of cargo C and/or compound T (e.g., radiosensitizing agent T) such as a fluorescent molecule may be used to visualize cells having a certain condition or cells in a region exhibiting a particular condition. For example, thrombosis (clot formation) may be visualized by designing a linker X and/or Y to be cleaved by any of the many proteases in the blood clot formation cascade for delivery of a cargo including a fluorescent or other marker to the region. Similarly, complement activation may be visualized by designing a linker X and/or Y to be cleaved by any one or more of the proteases in the complement activation cascades for delivery of a fluorescent or other marker to the region. Thus, fluorescent molecules are one example of a marker that may be delivered to target cells and regions upon release of a portion A upon cleavage of a linker X and/or Y.

Delivery of compound T (e.g., radiosensitizing agent T) such as a therapeutic compound (also referred to herein as a "warhead") may be used to treat cells having a certain condition or cells in a region exhibiting a particular condition. For example, neoplasia cells may be targeted by designing a linker X and/or Y to be cleaved by any of the many proteases produced by tumor cells, including for example MMPs. Thus, therapeutic compounds for the treatment of neoplasia are one example of compounds that may be delivered to target cells and regions upon release of a portion A and/or B upon cleavage of a linker X and/or Y.

A molecule having features of the invention may include one or more linkers X and/or Y so that an acidic portion A may be linked to portions B and C by one or more linkages. Such linkages connecting to portion A may be to portion B, to portion C, or to both portions B and C. Where a molecule having features of the invention includes multiple linkages X and/or Y, separation of portion A from the other portions of the molecule requires cleavage of all linkages X and/or Y. Cleavage of multiple linkers X and/or Y may be simultaneous or sequential. Multiple linkages X and/or Y may include linkages X and/or Y having different specificities, so that separation of portion A from the other portions of the molecule requires that more than one condition or environment ("extracellular signals") be encountered by the molecule. Cleavage of multiple linkers X and/or Y thus serves as a detector of combinations of such extracellular signals. In some embodiments, MTS molecule having includes two linker portions Xa and Xb connecting basic portion B with acidic portion A. In some embodiments, a cyclic MTS molecule includes two linker regions Xa and Xb connecting basic portion B with acidic portion A. In some embodiments, both linkers Xa and Xb must be cleaved before acidic portion A is separated from basic portion B allowing entry of portion B and cargo portion C (if any) to enter a cell. In some embodiments, MTS molecule having includes two linker portions Ya and Yb connecting basic portion B with acidic portion A. In some embodiments, a cyclic MTS molecule includes two linker regions Ya and Yb connecting basic portion B with acidic portion A. In some embodiments, both linkers Ya and Yb must be cleaved before acidic portion A is separated from basic portion B allowing entry of portion B and cargo portion C (if any) to enter a cell. In some embodiments, MTS molecule having includes two linker portions X and Y connecting basic portion B with acidic portion A. In some embodiments, a cyclic MTS molecule includes two linker regions X and Y connecting basic portion B with acidic portion A. In some embodiments, both linkers X and Y must be cleaved before acidic portion A is separated from basic portion B allowing entry of portion B and cargo portion C (if any) to enter a cell. In some embodiments, MTS molecule having includes four linker portions Xa, Xb, Ya and Yb connecting basic portion B with acidic portion A. In some embodiments, a cyclic MTS molecule includes four linker regions Xa, Xb, Ya and Yb connecting basic portion B with acidic portion A. In some embodiments, linkers Xa, Xb, Ya and Yb must be cleaved before acidic portion A is separated from basic portion B allowing entry of portion B and cargo portion C (if any) to enter a cell. In some embodiments, MTS molecule having includes more than two portions X and X connecting basic portion B with acidic portion A. In some embodiments, a cyclic MTS molecule includes two linker regions X and Y connecting basic portion B with acidic portion A. In some embodiments, both linkers X and Y must be cleaved before acidic portion A is separated from basic portion B allowing entry of portion B and cargo portion C (if any) to enter a cell. It will be understood that a linker region may link to either a basic portion B or a cargo portion C and/or compound T (e.g., radiosensitizing agent T) independently of another linker that may be present, and that, where desired, more than two linker regions X and/or Y may be included.

Combinations of two or more linkers X and/or Y may be used to further modulate the targeting and delivery of molecules to desired cells, tissue or regions. Boolean combinations of extracellular signals can be detected to widen or narrow the specificity of the cleavage of linkers X and/or Y if desired. Where multiple linkers X and/or Y are linked in parallel, the specificity of cleavage is narrowed, since each linker X and/or Y must be cleaved before portion A may separate from the remainder of the molecule. Where multiple linkers X and/or Y are linked in series, the specificity of cleavage is broadened, since cleavage on any one linker X allows separation of portion A from the remainder of the molecule. For example, in order to detect either a protease OR hypoxia (i.e., to cleave X and/or Y in the presence of either protease or hypoxia), a linker X and/or Y is designed to place the protease-sensitive and reduction-sensitive sites in tandem, so that cleavage of either would suffice to allow separation of the acidic portion A. Alternatively, in order to detect the presence of both a protease AND hypoxia (i.e., to cleave X and/or Y in the presence of both protease and hypoxia but not in the presence of only one alone), a linker X and/or Y is designed to place the protease sensitive site between at least one pair of cysteines that are disulfide-bonded to each other. In that case, both protease cleavage and disulfide reduction are required in order to allow separation of portion A.

D amino acids may be used in MTS molecules having features of the invention. For example, some or all of the peptides of portions A and B may be D-amino acids in some embodiments of the invention. In an embodiment of the invention suitable for delivering a detectable marker to a target cell, a MTS having features of the invention includes a contrast agent as cargo C and/or compound T (e.g., radiosensitizing agent T) attached to a basic portion B comprising 8 to 10 D-arginines. Acidic portion A may include D-amino acids as well. Similarly, a drug may be delivered to a cell by such molecules having a basic portion B including 8 to 10 D-arginines and an acidic portion A including acidic D-amino acids.

It will be understood that a MTS molecule having features of the invention may include non-standard amino acids, such as, for example, hydroxylysine, desmosine, isodesmosine, or other non-standard amino acids. A MTS molecule having features of the invention may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. A MTS molecule having features of the invention may also include peptide mimetic moieties, including portions linked by non-peptide bonds and amino acids linked by or to non-amino acid portions. For example, a MTS molecule having features of the invention may include peptoids, carbamates, vinyl polymers, or other molecules having non-peptide linkages but having an acidic portion cleavably linked to a basic portion having a cargo moiety.

The linker portion X and/or Y may be designed so that it is cleaved, for example, by proteolytic enzymes or reducing environment, as may be found near cancerous cells, or a hydrogen peroxide environment found near inflammatory diseases, neurodegenerative diseases, cardiovascular diseases, diabetes and cancer (neoplasia). Such an environment, or such enzymes or hydrogen peroxide, are typically not found near normal cells. In some embodiments, a cleavable linker X and/or Y is designed to be cleaved near diseased cells, including cancerous cells. In some embodiments, the cleavable linker is not cleaved near normal tissue. A capable of vetoing cellular uptake of a portion B, and of a portion B-C, and/or B-T blocking the entry of cargo and/or compound T (e.g., radiosensitizing agent T) into normal tissue.

In some embodiments, the linker portion X and/or Y may be cleaved, for example, by proteolytic enzymes, reducing environment or reactive oxygen species containing found near diseased cells, such as inflammatory diseased cells, neurodegenerative diseased cells, cardiovascular diseased cells, diabetic cells and cancerous cells to deliver a marker or a drug to cancerous cells. In some embodiments, a MTS molecule with a cleavable linker X and/or Y that is cleaved by proteolytic enzymes, by the reducing environment or by the reactive oxygen species containing environment near diseased cells is able to facilitate cargo entry into diseased tissue. Thus, the selective cleavage of the linker X and/or Y and the resulting separation of cargo C and/or compound T (e.g., radiosensitizing agent T) and basic portion B from acidic portion A allows the targeted uptake of cargo C and/or compound T (e.g., radiosensitizing agent T) into cells having selected features (e.g., enzymes), or located near to, a particular environment. Thus, molecules having features of the invention are able to selectively deliver cargo to target cells without doing so to normal or otherwise non-targeted cells.

In embodiments, a MTS molecule disclosed herein is a linear molecule. In embodiments, a MTS molecule disclosed herein is a cyclic molecule, as schematically illustrated in FIG. 1B of WO 2011/008996; incorporated herein by reference in its entirety. In embodiments, a MTS molecule disclosed herein comprises a cyclic portion and a linear portion.

A MTS disclosed herein may be of any length. In some embodiments, a MTS molecule disclosed herein is about 7 to about 40 amino acids in length, not including the length of a linker X and/or Y, a cargo moiety C and/or a compound T (e.g., radiosensitizing agent T). In other embodiments, particularly where multiple non-acidic (in portion A) or non-basic (in portion B) amino acids are included in one or both of portions A and B, portions A and B of a MTS molecule disclosed herein may together be about 50, or about 60, or about 70 amino acids in length. A cyclic portion of a MTS molecule disclosed herein may include about 12 to about 60 amino acids, not including the length of a linker X and/or Y, a cargo moiety C, and/or a compound T (e.g., radiosensitizing agent T). For example, a linear MTS molecule disclosed herein may have a basic portion B having between about 5 to about 20 basic amino acids (between about 9 to about 16 basic amino acids) and an acidic portion A having between about 2 to about 20 acidic amino acids (e.g., between about 5 to about 20, between about 5 to about 9 acidic amino acids). In some particular embodiments, a MTS molecule disclosed herein may have a basic portion B having between about 9 to about 16 basic amino acids and between about 5 to about 9 acidic amino acids. In some embodiments, A is consecutive glutamates (i.e., EEEEEEEE, E9, eeeeeeee, or e9 (SEQ ID NO: 90)), B is nine consecutive arginines (i.e., RRRRRRRRR, R9, rrrrrrrrr, or r9 (SEQ ID NO: 91)).

In some embodiments, the MTS is selected from: Suc-e9-XDPRSFL-r9-c(Cy5)-CONH2; Suc-e9-ODPRSFL-r9-c(Cy5)-CONH2; Suc-e9-Xdprsfl-r9-c(Cy5)-CONH2; cRGD-ACPP-MMAE; and (D-arg)9-Cy5 CPP-c(RGDfK)-(D-glu) 9.

A MTS molecule disclosed herein may be of any length. In some embodiments, a MTS molecule disclosed herein is about 7 to about 40 amino acids in length, not including the length of a linker X and/or Y, a cargo moiety C and/or compound T (e.g., radiosensitizing agent T). In other embodiments, particularly where multiple non-acidic (in portion A) or non-basic (in portion B) amino acids are included in one or both of portions A and B, portions A and B of a MTS molecule disclosed herein may together be about 50, or about 60, or about 70 amino acids in length. A cyclic portion of a MTS molecule disclosed herein may include about 12 to about 60 amino acids, not including the length of a linker X and/or Y, a cargo moiety and/or compound T (e.g., radiosensitizing agent T).

For example, a linear MTS molecule disclosed herein may have a basic portion B having between about 5 to about 20 basic amino acids (in some embodiments between about 9 to about 16 basic amino acids) and an acidic portion A having between about 2 to about 20 acidic amino acids (e.g., between about 5 to about 20, between about 5 to about 9 acidic amino acids). In some embodiments, a MTS molecule disclosed herein may have a basic portion B having between about 9 to about 16 basic amino acids and between about 5 to about 9 acidic amino acids. In some embodiments, A is 9 consecutive glutamates (i.e., EEEEEEEE, E9, eeeeeeee, or e9 (SEQ ID NO: 90)), B is nine consecutive arginines (i.e., RRRRRRRRR, R9, rrrrrrrrr, or r9 (SEQ ID NO: 91)), and X and/or Y is (SEQ ID NO:10) PLGLAG. In some embodiments, A is 9 consecutive glutamates (i.e., EEEEEEEE, E9, eeeeeeee, or e9 (SEQ ID NO: 90)), B is nine consecutive arginines (i.e., RRRRRRRRR, R9, rrrrrrrrr, or r9 (SEQ ID NO: 91)), and X and/or Y is (SEQ ID NO: 1) DPRSFL, (SEQ ID NO:2) PPRSFL, (SEQ ID NO:3) Norleucine-TPRSF, (SEQ ID NO:4) PLGC(Me)AG, 6-aminohexanoyl, 5-amino-3-oxapentanoyl, Val-Cit-(p-amido)benzyloxycarbonyl (Val-Cit-PAB) or a combination thereof. In some embodiments, A is 9 consecutive glutamates (i.e., EEEEEEEE, E9, eeeeeeee, or e9 (SEQ ID NO: 90)), B is nine consecutive arginines (i.e., RRRRRRRRR, R9, rrrrrrrrr, or r9 (SEQ ID NO: 91)), and X is (SEQ ID NO:10) PLGLAG, (SEQ ID NO:1) DPRSFL, (SEQ ID NO:2) PPRSFL, (SEQ ID NO:3) Norleucine-TPRSF, (SEQ ID NO:4) PLGC(Me)AG, or a combination thereof. In some embodiments, A is 9 consecutive glutamates (i.e., EEEEEEEE, E9, eeeeeeee, or e9 (SEQ ID NO: 90)), B is nine consecutive arginines (i.e., RRRRRRRRR, R9, rrrrrrrrr, or r9 (SEQ ID NO: 91)), and X is 6-aminohexanoyl, 5-amino-3-oxapentanoyl, or a combination thereof. In some embodiments, A is 9 consecutive glutamates (i.e., EEEEEEEE, E9, eeeeeeee, or e9 (SEQ ID NO: 90)), B is nine consecutive arginines (i.e., RRRRRRRRR, R9, rrrrrrrrr, or r9 (SEQ ID NO: 91)), and Y is Val-Cit-(p-amido)benzyloxycarbonyl (Val-Cit-PAB).

In some embodiments, the MTS molecule has a formula given below. It should be noted that in some instances the peptide sequence is given by the amino acid symbol and a number indicating the number of amino acids (for example, R9 translates to RRRRRRRRR (SEQ ID NO: 91) or nine consecutive L-arginines; and r9 translates to nine consecutive D-arginines or rrrrrrrrr and E9 translates to EEEEEEEEE (SEQ ID NO: 90) or nine consecutive L-glutamates; and e9 translates to nine consecutive D-glutamates or eeeeeeeee):

- cRGD-MMP-MMAE (Ligand=Cyclic(RGDfC); Substrate=(SEQ ID NO: 11) o-PLGC(Me)AG-o; o=5-amino-3-oxopentanoyl)
- cRAD-PEG6-MMAE (Ligand=Cyclic(RADfC); Substrate=PEG6-o; o=5-amino-3-oxopentanoyl)
- cRGD-PEG6-MMAE (Ligand=Cyclic(RGDfC); Substrate=PEG6-o; o=5-amino-3-oxopentanoyl)
- cRAD-MMP-MMAE (Ligand=Cyclic(RADfC); Substrate=(SEQ ID NO: 11) o-PLGC(Me)AG-o; o=5-amino-3-oxopentanoyl)
- Suc-eeeeeeeee-XDPRSFL-rrrrrrrrr-c(Cy5)-CONH2
- Suc-eeeeeeeee-ODPRSFL-rrrrrrrrr-c(Cy5)-CONH2
- Suc-eeeeeeeee-Xdprsfl-rrrrrrrrr-c(Cy5)-CONH2
- cRGD-ACPP-MMAE
- (rrrrrrrrr)-Cy5 CPP-c(RGDfK)-(eeeeeeeee)
- EDDDDKA-aca-R9-aca-C(Fl)-CONH2 (SEQ ID NO:27)
- Fl-aca-CRRRRRRRRR-aca-EEEEEEEEEC-CONH2 (SEQ ID NO:28)
- Fl-aca-CEEEE-aca-RRRRRRRRRC-CONH2 (SEQ ID NO:29)
- H2N-EEEEEDDDDKA-aca-RRRRRRRRRR-aca-C(Fl)-CONH2 (SEQ ID NO:30)
- H2N-EDDDDKA-aca-RRRRRRRRRR-aca-C(Fl)-CONH2 (SEQ ID NO:31)
- H2N-EEEEEDDDDK ARRRRRRRRR-aca-C(Fl)-CONH2 (SEQ ID NO:32)
- H2N-EEDDDDKA-aca-rrrrrrrrr-aca-C(Fl)-CONH2
- H2N-DDDDDDKARRRRRRRRR-aca-C(Fl)-CONH2 (SEQ ID NO:34)
- H2N-EEDDDDKAR-aca-RR-aca-RR-aca-RR-aca-RR-aca-C(Fl)-CONH2 (SEQ ID NO:35)
- H2N-eeeeee-aca-PLGLAG-rrrrrrrrr-aca-c(Fl)-CONH2
- EDA-aca-R,-aca-C(Fl)-CONH2 (SEQ ID NO:37)
- EDDDDKA-aca-R6-aca-C(DOX)-CONH2 (SEQ ID NO:38)
- EEEDDDEEEDA-aca-R9-aca-Y(12SI)-CONH2 (SEQ ID NO:39)
- ededdAAeeeDDDDKA-aca-R11-aca-C(Fl)-
- eddededDDDDDKA-aca-R6-AGA-R6-aca-C(DOX)-CONH2
- Ggedgddeeeeeeddeed-aca-PLGLAG-aca-R8-AAA-Ri2-aca-C(Fl)-CONH2
- eeddeeddKA-aca-R7-aca-C(Fl)-CONH2
- eDDDDKA-aca-RGRGRRR-aca-C(Fl)-CONH2)
- eddddeeeeee-aca-PLGLAGKA-aca-R10-aca-C(Fl)-CONH2
- eeeeeeeeeeeeeee-aca-DDDDKA-aca-R20-aca-C(Fl)-CONH2
- eeeeeeeeedddd-aca-DDDDK A-aca-R17-aca-Y125I)-CONH2
- ddddddddddddddd-aca-PLGLAG-aca-R14-aca-C(DOX)-CONH2
- NH2-eeeeee-ahx-PLG LAG-rrrrrrrrr-ahx-c(Fl)-CONH2, where "ahx" indicates ammohexanoic acid
- EEEEEDDDDKAXRRRRRRRRRRXC(Fl) (SEQ ID NO:49)
- EEEEEDDDDKARRRRRRRRRRXC(Fl) (SEQ ID NO:50)
- EDDDDKAXRRRRRRRRRRXC(Fl) (SEQ ID NO:51)
- EEDDDDKARXRRXRRXRRXRRXC(Fl) (SEQ ID NO:52)
- DDDDDDKARRRRRRRRRRXC(Fl) (SEQ ID NO:53)
- EEDDDDKAXrrrrrrrrrXC(Fl)
- eeeeeeXPLGLAGrrrrrrrrrXc(Fl)
- UeeeeeeecXPLGLAGrrrrrrrrrXk(Fl)
- eeeeeeXPLGLAGrrrrrrrrrXc(Cy5)
- UeeeeeeXPLGLAGrrrrrrrrrXc(Cy5)
- UeeeeeeecXPLGLAGrrrrrrrrrXk(Cy5)
- 11-kDa PEG]XeeeeeeeeeeXPLGLAGrrrrrrrrrXk(Cy5)
- 11-kDa PEG]XeeeeeeeeeeXLALGPGrrrrrrrrrXk(Cy5)
- Fl-XrrrrrrrrrXPLGLAGeeeeeeeee-βAla
- Fl-XrrrrrrrrrXSGRSAeeeeeeeee-βAla
- eeeeeeXSGRSAXrrrrrrrrrXc(Cy5)
- Fl-rrrrrrrrrc-SS-ceeeeeee
- succinyl-e8-XPLGLAG-r9-Xk, where X denotes 6-aminohexanoyl
- [11 kDa PEG]-X-e9-XPLGLAG-r9
- [11-kDa PEG]-X-e9-XPLGLAG-r9-Xk(Cy5)
- H2N-e6-XPLGLAG-r9-Xc(Cy5)-CONH2, where X=aminohexanoic acid)
- H2N-eeeeee-(ahx)-PLG LAG-rrrrrrrrr-(ahx)-c(Fluor)-CONH2
- XeeeeeeeeeXPLGLAGrrrrrrrrrXk
- eeeeeeeeeeXLALGPG-rrrrrrrrrXk(Cy5)
- mPEG(1 lkd)-S-CH2-CONH-ahx-e9-ahx-PLGLAG-r9-ahx-k-CONH2 mPEG-S-CH2CONH-e9-ahx-PLGLAG-r9-K[DOTA(Gd)]-CONH2
- (11 KDa-mPEG)-e9-XPLGLAG-r9-[DPK-99mTc(CO)3]
- (70 KDa-dextran)-e9-XPLGLAG-r9-[DPK-99mTc(CO)3]
- murine serum albumin)-e9-XPLGLAG-r9-[DPK-99mTc(CO)3]
- (PAMAM generation 5 dendrimer)-e9-XPLGLAX-r9-[DPK99mTc(CO)3]
- (70 KDa dextran)-e9-XPLGLAX-r9-(DOTA-111In)
- (11-KDa-mPEG)-e9-XPLGLAG-r9-K(DOTA-Gd)
- Suc9-(70 KDa dextran)-e9-XPLGLAG-r9-K(DOTA-Gd)
- Suc9-(70 KDa dextran)-e9-XPLGLAX-r9-K(DOTA-Gd)
- Suc9-(70 KDa dextran)-e9-XPLGLAG-r9-K(DOTA-Gd)
- cyclic[succinoyl-PLGLAG-c(11 KDa-mPEG)-e9-XPLGLAG-r9-K]-k(Cy5)
- Cy5-X-e6-XPLGLAG-r9-Xk(Cy5)
- Cy7-X-e6-XPLGLAG-r9-Xk(Cy5)
- 11 KDa mPEG-e9-PLGLAG-r9
- Ac-r9-k-NH2
- mPEG(1 lkd)-e9-XPLGLAG-r9-Xk-NH2
- e9-XPLGLAG-r9-Xk-NH2

TABLE 1

| Cap | Macromolecule | Polyanion | P4 | P3 | P2 | P1 | P1' | P2' | P3'...Pn' | Polycation | Cargo | C-term |
|---|---|---|---|---|---|---|---|---|---|---|---|---|
| Suc9 | Dextran (70 KDa) | e9 | X | P | L | G | L | A | G | r9 | K[DOTA(Gd)] | $NH_2$ |
| Suc | — | e9 | X | P | L | G | C(Me) | A | X | r9 | DPK | $NH_2$ |
| Suc | — | e9 | X | P | ThienylAla | G | C(Me) | A | X | r9 | DPK | $NH_2$ |
| Suc | — | e9 | X | P | F(4-Cl) | G | C(Me) | A | X | r9 | DPK | $NH_2$ |
| Suc | — | e8 | X | P | L | G | L | A | G | r9 | c[Cy5] | $NH_2$ |
| Suc | — | e8 | X | P | F(4-Cl) | G | C(Me) | M | X | r9 | c[Cy5] | $NH_2$ |
| Suc | — | e8 | X | P | F(4-Cl) | G | C(Me) | Y | X | r9 | c[Cy5] | $NH_2$ |
| Suc | — | e8 | X | P | F(4-Cl) | G | C(Me) | R | X | r9 | c[Cy5] | $NH_2$ |
| Suc | — | e8 | X | P | F(4-Cl) | G | C(Me) | PhGly | X | r9 | c[Cy5] | $NH_2$ |
| Suc | — | e8 | X | P | F(4-Cl) | G | C(Me) | C(Me) | X | r9 | c[Cy5] | $NH_2$ |
| — | Albumin | e9 | X | P | L | G | L | A | X | r9 | DPK | $NH_2$ |
| Suc | — | e8 | X | P | C(Me) | G | C(Me) | A | X | r9 | c[Cy5] | $NH_2$ |
| Suc | — | e8 | X | P | ThienylAla | G | C(Me) | A | X | r9 | c[Cy5] | $NH_2$ |
| Suc | — | e8 | X | P | F(4-Cl) | G | C(Me) | A | X | r9 | c[Cy5] | $NH_2$ |
| Suc | — | e8 | X | P | K(Dnp) | G | C(Me) | A | X | r9 | c[Cy5] | $NH_2$ |
| — | Albumin | e9 | X | P | L | G | L | A | X | r9 | DPK | $NH_2$ |
| Suc | — | e8 | X | P | L | G | C(Me) | M | X | r9 | c[Cy5] | $NH_2$ |
| Suc | — | e8 | X | P | L | G | C(Me) | Y | X | r9 | c[Cy5] | $NH_2$ |
| Suc127 | PAMAM-Gen5 | e9 | X | P | L | G | L | A | X | r9 | DPK | $NH_2$ |
| Suc | — | e8 | X | P | L | G | C(Me) | A | X | r9 | c[Cy5] | $NH_2$ |
| Suc9 | Dextran (70 KDa) | e9 | X | P | L | G | L | A | G | r9 | K[DOTA(Gd)] | $NH_2$ |
| Suc9 | Dextran (70 KDa) | e9 | X | P | L | G | L | A | X | r9 | k[Cy5] | $NH_2$ |
| Suc127 | PAMAM-Gen5 | e9 | — | — | — | — | — | — | — | r9 | Xc[Cy5] | $NH_2$ |
| — | — | — | — | — | — | — | — | — | — | r9 | Xc[Cy5] | $NH_2$ |
| Ac127 | PAMAM-Gen5 | e9 | X | P | L | G | L | A | X | r9 | k[Cy5] | $NH_2$ |
| Suc | — | e8 | X | P | L | G | L | F(4-NO2) | A | Xr9 | k[Cy5] | $NH_2$ |
| Suc127 | PAMAM-Gen5 | e9 | X | P | L | G | L | A | X | r9 | k[Cy5] | $NH_2$ |
| Suc63 | PAMAM-Gen4 | e9 | X | P | L | G | L | A | X | r9 | k[Cy5] | $NH_2$ |
| — | Albumin | e9 | X | P | L | G | L | A | G | r9 | DPK | $NH_2$ |
| Suc136 | Dextran (86 KDa) | e9 | X | P | L | G | L | A | X | r9 | k[Cy5] | $NH_2$ |
| Suc | — | e8 | X | P | L | G | L | A | X | r9 | k[Cy5] | $NH_2$ |
| Suc9 | Dextran (70 KDa) | e9 | X | P | L | G | L | A | X | r9 | K[DOTA(Gd)] | $NH_2$ |
| Suc9 | Dextran (70 KDa) | e9 | X | P | L | G | L | A | X | r9 | K[DOTA(Gd)] | $NH_2$ |
| Suc9 | Dextran (70 KDa) | e9 | X | P | L | G | L | A | G | r9 | k[Cy5] | $NH_2$ |
| Suc9 | Dextran (70 KDa) | e9 | X | P | L | G | L | A | G | r9 | DPK | $NH_2$ |
| Suc | — | e8 | X | p | l | g | l | a | g | r9 | k[Cy5] | $NH_2$ |
| — | Albumin | e9 | X | p | l | g | l | a | g | r9 | k[Cy5] | $NH_2$ |
| Suc9 | Dextran | e9 | X | p | l | g | l | a | g | r9 | k[Cy5] | $NH_2$ |
| Suc97 | Dextran (500 KDa) | e9 | X | P | L | G | L | A | G | r9 | k[Cy5] | $NH_2$ |
| — | Albumin | e9 | X | P | L | G | L | A | G | r9 | k[Cy5] | $NH_2$ |
| Suc9 | Dextran (70 KDa) | e9 | X | P | L | G | L | A | G | r9 | k[Cy5] | $NH_2$ |
| — | Albumin | e9 | X | P | L | G | L | A | G | r9 | k[Cy5] | $NH_2$ |
| Suc | | e8 | X | P | L | G | L | A | X | r9 | k[Cy5] | $NH_2$ |
| Suc9 | Dextran (70 KDa) | e9 | X | P | L | G | L | A | G | r9 | k[Cy5] | $NH_2$ |
| — | Albumin | e9 | X | P | L | G | L | A | G | r9 | k[Cy5] | $NH_2$ |
| — | Albumin | e9 | X | P | L | G | L | A | G | r9 | k[Cy5] | $NH_2$ |
| — | Albumin | e9 | X | P | L | G | L | A | G | r9 | k[Cy5] | $NH_2$ |
| Suc9 | Dextran (70 KDa) | e9 | X | P | L | G | L | A | G | r9 | k[Cy5] | $NH_2$ |
| Suc | nonconj. Albumin | e8 | X | P | L | G | L | A | G | r9X | k[Cy5] | $NH_2$ |
| Suc | — | e8 | X | P | L | G | L | A | G | r9X | k[Cy5] | $NH_2$ |
| — | Albumin | e9 | X | P | L | G | L | A | G | r9 | k[Cy5] | $NH_2$ |
| — | mPEG (5 KDa) | e9 | X | p | l | g | l | a | g | r9X | k[Cy5] | $NH_2$ |
| — | mPEG (11 KDa) | e9 | X | P | L | G | L | A | G | r9 | K[DOTA(Gd)] | $NH_2$ |
| — | mPEG (11 KDa) | e10 | X | P | L | G | F(4-NO2) | A | A | Xr9 | k[Cy5] | $NH_2$ |
| — | mPEG (11 KDa) | e10 | X | P | L | G | C(Me) | W | A | Qr9 | k[Cy5] | $NH_2$ |
| — | mPEG (11 KDa) | e9 | X | P | L | G | C(Me) | W | A | Qr9 | k[Cy5] | $NH_2$ |

In some embodiments, cargo C and/or compound T (e.g., radiosensitizing agent T) may be or comprise a fluorescent molecule such as fluorescein. Fluorescent cargo moieties enable easy measurement by fluorescence microscopy or flow cytometry in unfixed cultured cells. However, oligoarginine sequences, such as make up portion B, have been demonstrated to import a very wide varieties of cargoes C and/or compounds T, ranging from small polar molecules to nanoparticles and vesicles (Tung & Weissleder, Advanced Drug Delivery Reviews 55: 281-294 (2003)). Thus, in embodiments of the invention, a cargo portion C and/or compound T (e.g., radiosensitizing agent T) is any suitable cargo moiety capable of being taken up by a cell while connected to a basic portion B.

For example, for in vivo imaging purposes, C and/or T may be labeled with a positron-emitting isotope (e.g. $^{18}$F) for positron emission tomography (PET), gamma-ray isotope (e.g. $^{99m}$Tc) for single photon emission computed tomography (SPECT), a paramagnetic molecule or nanoparticle (e.g. $Gd^{3+}$ chelate or coated magnetite nanoparticle) for magnetic resonance imaging (MRI), a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound. For therapeutic purposes, for example, suitable classes of cargo C and/or compound T (e.g., radiosensitizing agent T) include but are not limited to: a) chemotherapeutic agents such as doxorubicin, mitomycin, paclitaxel, nitrogen mustards, etoposide, camptothecin, 5-fluorouracil, etc.; b) radiation sensitizing agents such as porphyrins for photodynamic therapy, or $^{10}$B clusters or $^{157}$Gd for neutron capture therapy; or c) peptides or proteins that modulate apoptosis, the cell cycle, or other crucial signaling cascades. Existing chemotherapeutic drugs may be used, although they may not be ideal, because they have already been selected for some ability to enter cells on their own. In some embodiments of the molecules of the invention, cargoes that are unable to enter or leave cells without the help of the polybasic portion B may be employed.

In some embodiments, cargo portion C and/or compound T (e.g., radiosensitizing agent T) include a fluorescent moiety, such as a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. Nos. 4,452,720; 5,227,487 and 5,543,295. In some embodiments, cargo C and/or compound T (e.g., radiosensitizing agent T) includes detection agents.

In some embodiments, a cargo portion C and/or a compound T (e.g., radiosensitizing agent T) may include a fluorescein dye. Typical fluorescein dyes include, but are not limited to, 5-carboxyfluorescein, fluorescein-5-isothiocyanate and 6-carboxyfluorescein; examples of other fluorescein dyes can be found, for example, in U.S. Pat. Nos. 6,008,379; 5,750,409; 5,066,580 and 4,439,356. In some embodiments, a cargo portion C and/or compound T (e.g., radiosensitizing agent T) includes a rhodamine dye, such as, for example, tetramethylrhodamine-6-isothiocyanate, 5-carboxytetramethyrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED*, and other rhodamine dyes. Other rhodamine dyes can be found, for example, in U.S. Pat. Nos. 6,080,852, 6,025,505, 5,936,087, 5,750,409. In some embodiments, a cargo portion C and/or compound T includes a cyanine dye, such as, for example, Cy3, Cy3B, Cy3.5, Cy5, Cy5.5, Cy 7, Alexa 647, IRDye-700DX and IRDYE 800CW.

Some of the above compounds or their derivatives will produce phosphorescence in addition to fluorescence, or will only phosphoresce. Some phosphorescent compounds include porphyrins, phthalocyanines, polyaromatic compounds such as pyrenes, anthracenes and acenaphthenes, and so forth, and may be, or may be included in, a cargo portion C. In some embodiments, a cargo portion C and/or compound includes a fluorescence quencher, such as, for example, a (4-dimethylamino-phenylazo)benzoic acid (DABCYL) group.

In some embodiments, a cargo moiety and/or compound T is all or part of a molecular beacon. In some embodiments a cargo moiety C and/or compound T is combined with a quencher moiety Q to form all or part of a molecular beacon. In some embodiments a cargo moiety C is combined with a quencher moiety Q (in some embodiments Q includes compound T) to form all or part of a molecular beacon. One or both of the complementary regions may be part of the cargo moiety. Where only one of the complementary regions (e.g., the fluorescent moiety) is part of the cargo moiety, and where the quencher moiety is part of the linker X and/or Y or the acidic portion A, then cleavage of the linker X and/or Y will allow fluorescence of the fluorescent portion and detection of the cleavage. Upon cellular uptake, the fluorescent portion of a molecular beacon will allow detection of the cell. For example, a quencher Q may be attached to an acidic portion A to form a MTS molecule having features of the MTS molecules of the present disclosure where cargo is fluorescent and is quenched by Q. The quenching of the cargo moiety by Q is relieved upon cleavage of X and/or Y, allowing fluorescent marking of a cell taking up portion B with cargo C and/or compound T. The combination of fluorescence quenching and selective uptake should increase contrast between tissues able to cleave X and/or Y compared to those that cannot cleave X and/or Y.

A pair of compounds may be connected to form a molecular beacon or FRET pair, having complementary regions with a fluorophore and a fluorescent quencher associated together so that the fluorescence of the fluorophore is quenched by the quencher. Such pairs can be useful as detection agents and any fluorescent pairs known or described herein can be employed with the present invention. One or both of the complementary regions may be part of the cargo portion C and/or compound T. Where only one of the complementary regions (e.g., the fluorescent moiety) is part of the cargo portion C and/or compound T, and where the quencher moiety is part of the linker X and/or Y or the acidic portion A, then cleavage of the linker X and/or Y will allow fluorescence of the fluorescent portion and detection of the cleavage. Upon cellular uptake, the fluorescent portion of a molecular beacon will allow detection of the cell. For example, a quencher Q may be attached to an acidic portion A to form a MTS molecule having features of the molecules as described in this disclosure where cargo C and/or compound T is fluorescent and is quenched by Q. The quenching of C and/or T by Q is relieved upon cleavage of X and/or Y, allowing fluorescent marking of a cell taking up portion B comprising C and/or T. The combination of fluorescence quenching and selective uptake should increase contrast between tissues able to cleave X and/or Y compared to those that cannot cleave X and/or Y.

In some embodiments, C, T and/or Q comprise all or part of a donor:acceptor FRET pair or a BRET (bioluminescence resonance energy transfer) pair. Donors can include any appropriate molecules listed herein or known in the art and as such include but are not limited to FITC; Cy3; EGFP; cyan fluorescent protein (CFP); EGFP; 6-FAM; fluorescein, IAEDANS, EDANS and BODIPY FL. Acceptors can include any appropriate molecules listed herein or known in the art and as such include but are not limited to TRITC; Cy5; Cy3; YFP; 6-FAM; LC Red 640; Alexa Fluor 546; fluorescein; tetramethylrhodamine; Dabcyl (acceptor); BODIPY FL; QSY 7, QSY 9, QSY 21 and BBQ-650 dyes. Exemplary FRET pairs can include but are not limited to CFP:YFP; 6-FAM:Cy5; Cy5:Cy7; Cy5:IRdye800CW; FITC:TRITC; Cy3:Cy5; EGFP:Cy3; EGFP:YFP; 6-FAM: LC Red 640 or Alexa Fluor 546; fluorescein:tetramethylrhodamine; IAEDANS:fluorescein; EDANS:Dabcyl; fluorescein:fluorescein; BODIPY FL:BODIPY FL; and fluorescein:QSY 7 and QSY 9 dyes.

In some embodiments, the cargo moiety C, compound T and/or quencher moiety Q are or comprise a fluorescent moiety including but not limited to a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. Nos. 4,452,720; 5,227,487; and 5,543,295.

In some embodiments, a cargo moiety C and/or quencher moiety Q are or comprise fluorescein dyes. Typical fluorescein dyes include, but are not limited to, 5-carboxyfluorescein, fluorescein-5-isothiocyanate and 6-carboxyfluorescein; examples of other fluorescein dyes can be found, for example, in U.S. Pat. Nos. 6,008,379, 5,750,409, 5,066,580, and 4,439,356. A cargo moiety C may include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®), and other rhodamine dyes. Other rhodamine dyes can be found, for example, in U.S. Pat. Nos. 6,080,852; 6,025,505; 5,936,087; 5,750,409. In some embodiments, a cargo moiety C and/or a compound T includes a cyanine dye, such as, for example, Cy3, Cy3B, Cy3.5, Cy5, Cy5.5, Cy 7.

In some embodiments, cargo moiety C, compound T and/or quencher moiety Q are or comprise fluorophores. Fluorophores are commercially available and any known and/or commercially available fluorophore can be employed as the cargo moiety C and/or compound T detectable entity for the present invention. In some embodiments, the fluorophore exhibits green fluorescence (such as for example 494 nm/519 nm), orange fluorescence (such as for example 554 nm/570 nm), red fluorescence (such as for example 590 nm/617 nm), or far red fluorescence (such as for example 651 nm/672 nm) excitation/emission spectra. In some embodiments, the fluorophore is a fluorophore with excitation and emission spectra in the range of about 350 nm to about 775 nm. In some embodiments the excitation and emission spectra are about 346 nm/446 nm, about 494 nm/519 nm, about 554 nm/570 nm, about 555 nm/572 nm, about 590 nm/617 nm, about 651 nm/672 nm, about 679 nm/702 nm or about 749 nm/775 nm. In some embodiments, the fluorophore can include but is not limited to AlexaFluor 3, AlexaFluor 5, AlexaFluor 350, AlexaFluor 405, AlexaFluor 430, AlexaFluor 488, AlexaFluor 500, AlexaFluor 514, AlexaFluor 532, AlexaFluor 546, AlexaFluor 555, AlexaFluor 568, AlexaFluor 594, AlexaFluor 610, AlexaFluor 633, AlexaFluor 647, AlexaFluor 660, AlexaFluor 680, AlexaFluor 700, and AlexaFluor 750 (Molecular Probes AlexaFluor dyes, available from Life Technologies, Inc. (USA)). In some embodiments, the fluorophore can include but is not limited to Cy dyes, including Cy2, Cy3, Cy3B, Cy3.5, Cy5, Cy5.5 and Cy7 (available from GE Life Sciences or Lumiprobes). In some embodiments the fluorophore can include but is not limited to DyLight 350, DyLight 405, DyLight 488, DyLight 550, DyLight 594, DyLight 633, DyLight 650, DyLight 680, DyLight 750 and DyLight 800 (available from Thermo Scientific (USA)). In some embodiments, the fluorophore can include but is not limited to a FluoProbes 390, FluoProbes 488, FluoProbes 532, FluoProbes 547H, FluoProbes 594, FluoProbes 647H, FluoProbes 682, FluoProbes 752 and FluoProbes 782, AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein), 5(6)-FAM cadaverine; 5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CR1 10 (5-Carboxyrhodamine 110); 6-CR1 10 (6-Carboxyrhodamine 110); 5-CR6G (5-Carboxyrhodamine 6G); 6-CR6G (6-Carboxyrhodamine 6G); 5(6)-Carboxyrhodamine 6G cadaverine; 5(6)-Caroxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamme; 6-TAMRA ethylenediamme; 5-TMR C6 maleimide; 6-TMR C6 maleimide; TR C2 maleimide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

Some of the above compounds or their derivatives will produce phosphorescence in addition to fluorescence, or will only phosphoresce. Some phosphorescent compounds include porphyrins, phthalocyanines, polyaromatic compounds such as pyrenes, anthracenes and acenaphthenes, and so forth, and in some embodiments are included in a compound T and/or a cargo moiety. In some embodiments, a cargo moiety and/or compound T include a fluorescence quencher, such as, for example, a (4-dimethylamino-phenylazo)benzoic acid (DABCYL) group.

In some embodiments, a cargo moiety and/or compound T is or comprises a fluorescent label. In some embodiments, a cargo moiety C, compound T and/or quencher moiety Q is indocarbocyanine dye, Cy5, Cy5.5, Cy7, IR800CW, or a combination thereof. In some embodiments, a cargo moiety is a MRI contrast agent. In some embodiments, a cargo moiety is Gd complex of [4,7,10-tris(carboxymethyl)-1,4,7,10-tetraazacyclododec-1-yl] acetyl.

In some embodiments, compound T (e.g., radiosensitizing agent T) and/or cargo C may include a chemotherapeutic moiety, such as a chemical compound useful in the treatment of cancer, or other therapeutic moiety, such as an agent useful in the treatment of ischemic tissue, or of necrotic tissue, or other therapeutic agent.

In some embodiments, compound T and/or cargo C may include a radiosensitization agent or moiety, such as a chemical compound useful in the radiosensitization of cancer.

Multiple membrane translocation signals (MTS) have been identified. For example, the Tat protein of the human immunodeficiency virus 1 (HIV-1) is able to enter cells from the extracellular environment. A domain from Antennapedia homeobox protein is also able to enter cells.

Molecules comprising a MTS may also be used to carry other molecules into cells along with them. The most important MTS are rich in amino acids such as arginine with positively charged side chains. Molecules transported into cell by such cationic peptides may be termed "cargo" or compound T (e.g., radiosensitizing agent T) and may be reversibly or irreversibly linked to the cationic peptides.

The uptake facilitated by molecules comprising a MTS can occur with specificity by including appropriate X and/or Y linkers as well as pre-targeting P moieties, enhancing uptake into most or all cells. It is desirable to have the ability to target the delivery of cargo to a type of cell, or to a tissue, or to a location or region within the body of an animal. Accordingly, we have identified a need for a MTS molecule with increased in vivo circulation.

In some embodiments, a MTS molecule disclosed herein has the formula according to one of the following:

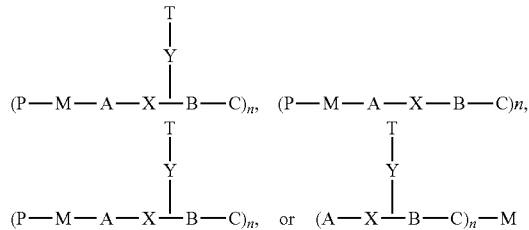

wherein C is a cargo moiety; T is a therapeutic compound; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X and/or Y is a linker that is cleavable by thrombin. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments, a MTS molecule disclosed herein has the formula according to one of the following:

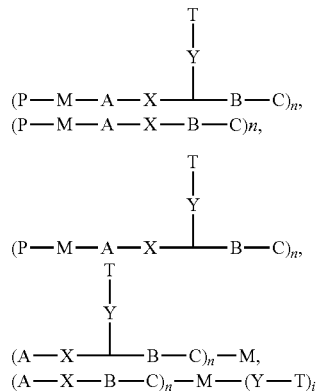

wherein C is a cargo moiety; T is a therapeutic moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X and/or Y is a linker that is cleavable by thrombin. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments, a MTS molecule disclosed herein has a formula according to one of the following:

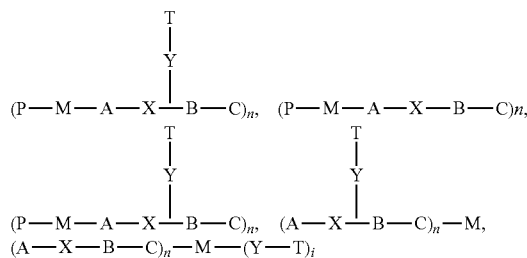

wherein C is a cargo moiety; T is a therapeutic compound; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X and/or Y is a linker that is cleavable by thrombin; M is a macromolecular carrier; and n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

Delivery of cargo C and/or compound T such as a fluorescent molecule may be used to visualize cells having a certain condition or cells in a region exhibiting a particular condition For example, thrombosis (clot formation) may be visualized by designing a linker X and/or Y to be cleaved by thrombin. Thus, fluorescent molecules are one example of a marker that may be delivered to target cells and regions upon release of a portion A upon cleavage of a linker X and/or Y.

In some embodiments, the cargo moiety and or compound T is selected from an imaging agent, a therapeutic agent, a lipid, a detection agent or a combination thereof.

In some embodiments, the cargo portion comprises at least two cargo moieties. In some embodiments, C comprises a marker cargo and a therapeutic cargo. Multiple cargo moieties can allow, for example, delivery of both a radioactive marker and an ultrasound or contrast agent, allowing imaging by different modalities. Alternatively, for example, delivery of radioactive cargo along with an anti-cancer agent, providing enhanced anticancer activity, or delivery of a radioactive cargo with a fluorescent cargo, allowing multiple means of localizing and identifying cells which have taken up cargo. Alternatively, delivery of a fluorescent or radioactive compound with a therapeutic compound can allow, for example, for identification of cells to which a therapeutic compound has been delivered.

In some embodiments, the compound T (e.g., radiosensitizing agent T) comprises at least two T moieties. In some embodiments, T comprises a marker cargo and a therapeutic compound. Multiple therapeutic moieties can allow, for example, delivery of both a radioactive marker and an ultrasound or contrast agent, allowing imaging by different modalities. Alternatively, for example, delivery of radioactive compound along with an anti-cancer agent, providing enhanced anticancer activity, or delivery of a radioactive cargo with a fluorescent cargo, allowing multiple means of localizing and identifying cells which have taken up compound. Alternatively, delivery of a fluorescent or radioactive compound with a therapeutic compound can allow, for example, for identification of cells to which a therapeutic compound has been delivered.

The cargo moiety is attached to B in any location or orientation. The cargo moiety need not be located at an opposite end of portion B than a linker X and/or Y. Any location of attachment of the cargo moiety to B is acceptable as long as that attachment remains after X is cleaved. For example, the cargo moiety may be attached to or near to an end of portion B with linker X and/or Y is attached to an opposite end of portion B. The cargo moiety may also be attached to or near to an end of portion B with linker X attached to or near to the same end of portion B.

In some embodiments, a cargo moiety C and/or compound T is a fluorescent molecule such as fluorescein. Fluorescent cargo moieties enable easy measurement by fluorescence microscopy or flow cytometry in unfixed cultured cells. In some embodiments, T is a therapeutic moiety capable of use in treating a variety of diseases, including inflammation, diabetes, cardiovascular diseases, neurodegenerative disorders and cancer.

In some embodiments, compound T and/or cargo C may include a radiosensitization agent or moiety, such as a chemical compound useful in the radiosensitization of cancer.

In some embodiments, a cargo moiety and/or compound T is labeled with a positron-emitting isotope (e.g., 18F) for positron emission tomography (PET), gamma-ray isotope (e.g., 99mTc) for single photon emission computed tomography (SPECT), a paramagnetic molecule or nanoparticle (e.g., Gd3+ chelate or coated magnetite nanoparticle) for magnetic resonance imaging (MRI), a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

In some embodiments, cargo C and/or compound T includes a radioactive moiety, for example a radioactive isotope such as $^{211}$At, $^{131}$I, $^{125}$I, $^{90}$Y, $^{186}$Re, $^{188}$Re, $^{153}$Sm, $^{212}$Bi, $^{32}$P, $^{64}$Cu, and $^{89}$Zr. In some embodiments, a cargo moiety is a radioactive moiety, for example a radioactive isotope such as $^{211}$At, $^{131}$I, $^{125}$S, $^{90}$Y, $^{186}$Re, $^{188}$Re, $^{148}$Sm, $^{133}$Ba, $^{212}$Bi, $^{12}$P, $^{3}$H, $^{14}$C, $^{32}$P, $^{35}$S, $^{87}$Rb, $^{90}$Sr, $^{115}$In, $^{123}$Te, $^{130}$Te, $^{131}$I, $^{137}$Cs, $^{138}$La, $^{144}$Nd, $^{147}$Sm, $^{148}$Sm, $^{176}$Lu, $^{187}$Re, $^{186}$Os, $^{222}$Rn, $^{226}$Ra, Barium-133, Cadmium-109, Cobalt-57, Cobalt-60, Europium-152, Manganese-54, Sodium-22, Zinc-65, Technetium-99m, Strontium-90, Thallium-204, Carbon-14, Tritium (Hydrogen-3), radioactive isotopes of Lu, Cu and Zr as well as others known to those of skill in the art.

In some embodiments, a cargo moiety and/or a therapeutic moiety are a therapeutic agent, such as a chemical compound useful in the treatment of cancer, ischemic tissue, or necrotic tissue.

For therapeutic purposes, for example, suitable classes of cargo moiety (C) and/or therapeutic moiety (T) include but are not limited to a) chemotherapeutic agents, b) radiation sensitizing agents, or c) peptides or proteins that modulate apoptosis, the cell cycle, or other crucial signaling cascades.

In some embodiments, a cargo moiety (C) or a therapeutic moiety (T) is or comprises an agent that treats a cardiovascular disorder. In some embodiments, the cargo moiety is a niacin, a fibrate, a statin, an Apo-Al mimetic peptide, an apoA-I transcriptional up-regulator, an ACAT inhibitor, a CETP modulator, or a combination thereof, a Glycoprotein (GP) IIb/IIIa receptor antagonist, a P2Y12 receptor antagonist, a Lp-PLA2-inhibitor, a leukotriene inhibitor, a MIF antagonist, or a combination thereof. In some embodiments the cargo moiety is atorvastatin, cerivastatin, fluvastatin, lovastatin, mevastatin, pitavastatin, pravastatin, rosuvastatin, simvastatin, simvastatin and ezetimibe, lovastatin and niacin, extended-release, atorvastatin and amlodipine besylate, simvastatin and niacin, extended-release, bezafibrate, ciprofibrate, clofibrate, gemfibrozil, fenofibrate, DF4 (Ac-D-W-F-K-A-F-Y-D-K-V-A-E-K-F-K-E-A-F-NH2XSEQ ID NO:77), DF5, RVX-208 (Resverlogix), avasimibe, pactimibe sulfate (CS-505), CI-1011 (2,6-diisopropylphenyl [(2, 4,6-triisopropylphenyl)acetyl]sulfamate), CI-976 (2,2-dimethyl-N-(2,4,6-trimethoxyphenyl)dodecanamide), VULM1457 (1-(2,6-diisopropyl-phenyl)-3-[4-(4'-mtrophenylthio)phenyl] urea), CI-976 (2,2-dimethyl-N-(2,4,6-trimethoxyphenyl)dodecanamide), E-5324 (n-butyl-N'-(2-(3-(5-ethyl-4-phenyl-1H-imidazol-1-yl)propoxy)-6-methylphenyl)urea), HL-004 (N-(2,6-diisopropylphenyl) tetradecylthioacetamide), KY-455 (N-(4,6-dimethyl-1-pentylindolin-7-yl)-2,2-dimethylpropanamide), FY-087 (N-[2-[N'-pentyl-(6,6-dimethyl-2,4-heptadiynyl)amino]ethyl]-(2-methyl-1-naphthyl-thio)acetamide), MCC-147 (Mitsubishi Pharma), F 1251 1 ((S)-2',3',5'-trimethyl-4'-hydroxy-alpha-dodecylthioacetanihde), SMP-500 (Sumitomo Pharmaceuticals), CL 277082 (2,4-difluoro-phenyl-N[[4-(2,2-dimethyl-propyl)phenyl]methyl]-N-(hepthyl)urea), F-1394 ((1s,2s)-2-[3-(2,2-dimethylpropyl)-3-nonylureido]aminocyclohexane-1-yl 3-[N-(2,2,5,5-tetramethyl-1,3-dioxane-4-carbonyl) amino]propionate), CP-113818 (N-(2,4-bis(methylthio)-6-methylpyridm-3-yl)-2-(hexylthio)decanoic acid amide), YM-750, torcetrapib, anacetrapid, JTT-705 (Japan Tobacco/ Roche), abciximab, eptifibatide, tirofiban, roxifiban, variabihn, XV 459 (N(3)-(2-(3-(4-formamidinophenyl)isox-azolm-5-yl)acetyl)-N(2)-(1-butyloxycarbonyl)-2,3-diaminopropionate), SR 121566A (3-[N-{4-[4-(aminoiminomethyl)phenyl]-1,3-thiazol-2-yl J-N-(I-carboxymethylpiperid-4-yl) aminol propionic acid, trihydrochloride), FK419 ((S)-2-acetylamino-3-[(R)-[1-[3-(piperidin-4-yl) propionyl] piperidin-3-ylcarbonyl] ammo] propionic acid trihydrate), clopidogrel, prasugrel, cangrelor, AZD6140 (AstraZeneca); MRS 2395 (2,2-Dimethyl-propionic acid 3-(2-chloro-6-methylaminopurin-9-yl)-2-(2,2-dimethyl-propionyloxymethyl)-propyl ester); BX 667 (Berlex Biosciences); BX 048 (Berlex Biosciences); darapladib (SB 480848); SB-435495 (GlaxoSmithKline); SB-222657 (GlaxoSmithKline); SB-253514 (GlaxoSmithKline); A-81834 (3-(3-(1,1-dimethylethylthio-5-(quinoline-2-yl-methoxy)-1-(4-chloromethylphenyl)indole-2-yl)-2,2-dimethylpropionaldehyde oxime-O-2-acetic acid; AME103 (Amira); AME803 (Amira); atreleuton; BAY-x-1005 ((R)-(+)-alpha-cyclopentyl-4-(2-quinolinylmethoxy)-Benzeneacetic acid); CJ-13610 (4-(3-(4-(2-Methyl-imidazol-1-yl)-phenylsulfanyl)-phenyl)-tetrahydro-pyran-4-carboxylic acid amide); DG-031 (DeCode); DG-051 (DeCode); MK886 (1-[(4-chlorophenyl)methyl]3-[(1, 1-dimethylethyl) thio]-α,α-dimethyl-5-(1-methylethyl)-1H-indole-2-propanoic acid, sodium salt); MK591 (3-(1-4[(4-chlorophenyl) methyl]-3-[(t-butylthio)-5-((2-quinoly)methoxy)-1H-indole-2]-, dimethylpropanoic acid); RP64966 ([4-[5-(3-Phenyl-propyl)thiophen-2-yl]butoxy] acetic acid); SA6541 ((R)—S-[[4-(dimethylamino)phenyl]methyl]-N-(3-mercapto-2methyl-1-oxopropyl-L-cysteine); SC-56938 (ethyl-l-[2-[4-(phenylmethyl)phenoxy] ethyl]-4-piperidine-carboxylate); VIA-2291 (Via Pharmaceuticals); WY-47,288 (2-[(1-naphthalenyloxy)methyl]quinoline); zileuton; ZD-2138 (6-((3-fluoro-5-(tetrahydro-4-methoxy-2H-pyran-4yl) phenoxy)methyl)-]-methyl-2(1H)-quinlolinone); or combinations thereof.

In some embodiments, a cargo moiety (C) or a therapeutic moiety (T) is or comprises a drug. In some embodiments, the drug is an agent that modulates death (e.g., via apoptosis or necrosis or modulates radiosensitization) of a cell. In some embodiments, the drug is a cytotoxic agent. In some embodiments, the drug is monomethyl auristatin E (MMAE), monomethyl auristatin F (MMAF), maytansine, methotrexate (RHEUMATREX®, Amethopterin); cyclophosphamide (CYTOXAN®); thalidomide (THALIDOMID®); paclitaxel; pemetrexed; pentostatin; pipobroman; pixantrone; plicamycin; procarbazine; proteasome inhibitors (e.g., bortezomib); raltitrexed; rebeccamycin; rubitecan; SN-38; salinosporamide A; satraplatin; streptozotocin; swainsonine; tariquidar; taxane; tegafur-uracil; temozolomide; testolactone; thioTEPA; tioguanine; topotecan; trabectedin; tretinoin; triplatin tetranitrate; tris(2-chloroethyl) amine; troxacitabine; uracil mustard; valrubicin; vinblastine; vincristine; vinorelbine; vorinostat; zosuquidar; or a combination thereof. In some embodiments, the drug is a pro-apoptotic agent. In some embodiments, the drug is an anti-apoptotic agent. In some embodiments, the drug is selected from: minocycline; SB-203580 (4-(4-Fluorophenyl)-2-(4-methylsulfinyl phenyl)-5-(4-pyridyl) 1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (5-(2-Amino-4-pyrimidinyl)-4-(4-fluorophenyl)-1-(4-piperidinlyl)imidazole); D-JNKI-I ((D)-hJIP 175-157-DPro-DPro-(D)-HIV-TAT57-48); AM-111 (Auris); SP600125 (anthra[1,9-cd]pyrazol-6(2H)-one); JNK Inhibitor I ((L)-HIV-T AT48-57-PP-JBD20); JNK Inhibitor III ((L)-HIV-T AT47-57-gaba-c-Jun633-57); AS601245 (1,3-benzothiazol-2-yl (2-[[2-(3-pyridinyl) ethyl] amino]-4 pyrimidinyl) acetonitrile); JNK Inhibitor VI (H2N-RP-KRPTTLNLF-NH2XSEQ ID NO:78); JNK Inhibitor VIII (N-(4-Amino-5-cyano-6-ethoxypyridin-2-yl)-2-(2,5-dimethoxyphenyl)acetamide); JNK Inhibitor IX (N-(3-Cyano-4,5,6,7-tetrahydro-1-benzothien-2-yl)-1-naphthamide); dicumarol (3,3'-Methylenebis(4-hydroxycoumarin)); SC-236 (4-[5-(4-chlorophenyl)-3-(trifluoromethyl)-1H-pyrazol-1-yl]benzene-sulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((+)-1-(3,6-Dibromocarbazol-9-yl)-3-piperazin-1-yl-propan-2-ol); Bax inhibiting peptide P5 (also known as Bax inhibitor peptide P5); Kp7-6; FAIM(S) (Fas apoptosis inhibitory molecule-short); FAIM(L) (Fas apoptosis inhibitory molecule-long); Fas:Fc; FAP-I; NOK2; F2051; Fl 926; F2928; ZB4; Fas M3 mAb; EGF; 740 Y-P; SC 3036 (KKHTDDGYMPMSPGVAXSEQ ID NO:79); PI 3-kinase Activator (Santa Cruz Biotechnology, Inc.); Pam3Cys ((S)-(2,3-bis(palmitoyloxy)-(2RS)-propyl)-N-palmitoyl-(R)-Cys-(S)-Ser(S)-Lys4-OH, trihydrochloride); Actl (NF-kB activator 1); an anti-IkB antibody; Acetyl-1 1-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMKWKK-TALDWSWLQTEXSEQ ID NO:80); NF-kB Activation Inhibitor (6-Amino-4-(4-phenoxyphenylethylamino)quinazoline); NF-kB Activation Inhibitor II (4-Methyl-Nl-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AAVALLPAVLLALLAPVQRKRQKLMP) (SEQ ID NO:81); Oridonin; Parthenolide; PPM-18 (2-Benzoylamino-1,4-naphthoquinone); RoI 06-9920; Sulfasalazine; TIRAP Inhibitor Peptide (RQIKIWFNRRMKWK-KLQLRDAAPGGAIVS) (SEQ ID NO:82); Withaferin A; Wogonin; BAY 1 1-7082 ((E)3-[(4-Methylphenyl)sulfonyl]-2-propenenitrile); BAY 1 1-7085 ((E)3-[(4-t-Butylphenyl) sulfonyl]-2-propenenitrile); (E)-Capsaicin; Aurothiomalate (ATM or AuTM); Evodiamine; Hypoestoxide; IKK Inhibitor m (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinyl)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401 (-[2-Methoxy-4-(methylthio)benzoyl]-4-(phenylmethyl)piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2,1-b]thiazole dihydrochloride); SB-200646 (N-(I-Methyl-1H-indol-5-yl)-N'-3-pyridinylurea); CMPD-I (2'-Fluoro-N-(4-hydroxyphenyl)-[1, 1'-biphenyl]-4-butanamide); EO-1428 ((2-Methylphenyl)-[4-[(2-amino-4-bromophenyl)amino]-2-chlorophenyl]methanone); SB-253080 (4-[5-(4-Fluorophenyl)-2-[4-(methylsulfonyl) phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl) 1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1, 1'-biphenyl)-4-yl)methyl)-1H-1-benzazepin-3-yl)-, (R)-); EPI 572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-V AD-FMK (Benzyloxycarbonyl-Val-Ala-Asp(OMe)-fluoromethylketone); (SEQ ID NO:83) z-LEHD-FMK (benzyloxycarbonyl-Leu-Glu(OMe)-His-Asp(OMe)-fluoromethylketone); B-D-FMK (boc-aspartyl (Ome)-fluoromethylketone); (SEQ ID NO:84) Ac-LEHD-CHO (N-acetyl-Leu-Glu-His-Asp-CHO); (SEQ ID NO:85) Ac-IETD-CHO (N-acetyl-Ile-Glu-Thr-Asp-CHO); (SEQ ID NO:86) z-IETD-FMK (benzyloxycarbonyl-Ile-Glu(OMe)-Thr-Asp(OMe)-fluoromethyl ketone); (SEQ ID NO:87) FAM-LEHD-FMK (benzyloxycarbonyl Leu-Glu-His-Asp-fluoromethyl ketone); (SEQ ID NO:88) FAM-LETD-FMK (benzyloxycarbonyl Leu-Glu-Thr-Asp-iluoromethyl ketone); Q-VD-OPH (Quinoline-Val-Asp-CH2-O-Ph); XIAP; cIAP-1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-t(phenylmethoxy)carbonyl]-L-leucyl-N-[(IS)-1-formyl-3-methylbutyl]-L-leucinamide); MYODUR; BN 82270 (Ipsen); BN 2204 (Ipsen); AHLi-11 (Quark Pharmaceuticals), an mdm2 protein, pifithrin-α (1-(4-Methylphenyl)-2-(4,5,6,7-tetrahydro-2-imino-3(2H)-benzothiazolyl)ethanone); trans-stilbene; cis-stilbene; resveratrol; piceatannol; rhapontin; deoxyrhapontin; butein; chalcon; isoliquirtigen; butein; 4,2',4'-trihydroxychalcone; 3,4,2',4',6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid*$H_2O$); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperazinyl) methyl)-3,4-dihydro-2,5,7,8-tetramethyl-2H-1-benzopyran-6-ol*2HCl); β-1'-5-methyl-nicotinamide-2'-deoxyribose; β-D-r-5-methyl-nico-tinamide-2'-deoxyribofuranoside; β-1'-4,5-dimethyl-nicotinamide-2'-de-oxyribose; β-D-1'-4,5-dimethyl-nicotinamide-2'-deoxyribofuranoside; 1-Naphthyl PP1 (1-(1,1-Dimethylethyl)-3-(1-naphthalenyl)-1H-pyrazolo[3, 4-d]pyrimidin-4-amine); Lavendustin A (5-[[(2, 5-Dihydroxyphenyl)methyl][(2-hydroxyphenyl)methy 1]amino]-2-hydroxybenzoic acid); MNS (3,4-Methylenedioxy-b-nitrostyrene), PP1 (1-(1,1-Dimethylethyl)-1-(4-methylphenyl)-1H-pyrazolo[3, 4-d]pyπmidin-4-amine), PP2 (3-(4-chlorophenyl) 1-(1, 1-dimethylethyl)-1H-pyrazolo[3,4-d] pyπmidin-4-amine), KX-004 (Kinex), KX-005 (Kinex), KX-136 (Kinex), KX-174 (Kinex), KX-141 (Kinex), KX2-328 (Kinex), KX-306 (Kinex), KX-329 (Kinex), KX2-391 (Kinex), KX2-377 (Kinex), ZD4190 (Astra Zeneca, N-(4-bromo-2-fluorophenyl)-6-methoxy-7-(2-(H-1,2,3-triazol-1-yl)ethoxy)quinazolin-4-amine), AP22408 (Ariad Pharmaceuticals), AP23236 (Ariad Pharmaceuticals), AP23451 (Ariad Pharmaceuticals), AP23464 (Ariad Pharmaceuticals), AZD0530 (Astra Zeneca), AZM475271 (M475271, Astra Zeneca), Dasatmib (N-(2-chloro-6-methylphneyl)-2-(6-(4-(2-hydroxyethyl)-piperazin-1-yl)-2-methylpynmidin-4-ylammo) thiazole-5-carboxamide), GN963 (trans-4-(6,7-dimethoxyqmnoxalm-2ylamino)cyclohexanol sulfate); Bosutimb (4-((2,4-dichloro-5-methoxyphenyl)ammo)-6-methoxy-7-(3-(4-methyl-1-piperazinyl)propoxy)-3-quinolinecarbonitrile), or combinations thereof. In some embodiments, a cargo moiety (C) or a therapeutic moiety (T) includes topoisomerase inhibitors (e.g., camptothecin, topotecan), and hypoxia-activated anthraquinone AQ4N; alkylating agents (e.g., temozolomide), agents involved in DNA repair pathways such as poly(ADP ribose)polymerase inhibitors (e.g., AG14361), agents that target Ras family proteins, agents that target epidermal growth factor receptors and associated kinases (e.g., including vandetanib [ZD6474], cetuximab and gefitinib), cyclooxygenase-2 (celecoxib), MMAE and auristatin and derivatives thereof. In some embodiments, T is a topoisomerase inhibitors (e.g., camptothecin, topotecan), and hypoxia-activated anthraquinone AQ4N; alkylating agents (e.g., temozolomide), agents involved in DNA repair pathways such as poly(ADP ribose) polymerase inhibitors (e.g., AG14361), agents that target Ras family proteins, agents that target epidermal growth factor receptors and associated kinases (e.g., including vandetanib [ZD6474], cetuximab and gefitinib), cyclooxygenase-2 (celecoxib), DM1 (mertansine), MMAE and auristatin. In some embodiments, C and/or T is DM1 (mertansine), auristatin, an auristatin derivative, monomethyl auristatin E (MMAE) or monomethyl auristatin F (MMAF).

In some embodiments, a MTS molecule as disclosed herein further comprises a lipid, L. In some embodiments, the MTS comprises a lipid L, A is a peptide with a sequence comprising 5 to 9 consecutive acidic ammo acids, wherein the amino acids are selected from aspartates and glutamates, B is a peptide with a sequence comprising 5 to 20 consecutive basic amino acids, X and/or Y is a linker, and n is an integer between 1 and 20, and wherein L is bound to an MTS as disclosed herein by a bond with a B.

In some embodiments, the lipid entraps a hydrophobic molecule. In some embodiments, the lipid entraps at least one agent selected from the group consisting of a therapeutic moiety and an imaging moiety.

In some embodiments, the lipid is PEGylated. In some embodiments, the lipid is PEG(2K)-phosphatidylethanolamine.

Disclosed herein, in certain embodiments, is a MTS molecule with increased in vivo circulation. In some embodiments, a MTS molecule disclosed herein has the formula according to one of the following:

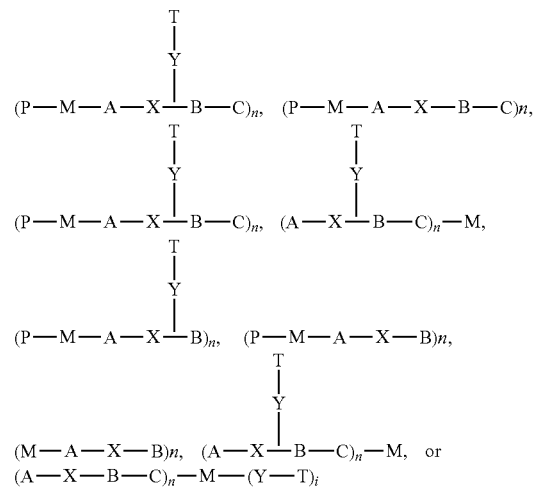

wherein C is a cargo moiety; T is a compound; A is a peptide with a sequence comprising 5 to 9 consecutive acidic ammo acids, wherein the amino acids are selected from aspartates and glutamates, B is a peptide with a sequence comprising 5 to 20 consecutive basic amino acids; X and/or Y is a linker; M is a macromolecular carrier; and n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

The term "macromolecular carrier" indicates an inert molecule that increases (a) plasma half-life and (b) solubility. In some embodiments, a macromolecular carrier decreases uptake of a MTS molecule into cartilage. In some embodiments, a macromolecular carrier decreases uptake of a MTS molecule into joints. In some embodiments, a macromolecular carrier decreases uptake of a MTS molecule into the liver. In some embodiments, a macromolecular carrier decreases uptake of a MTS molecule into kidneys.

In some embodiments, a macromolecular carrier M increases plasma half-life and solubility by reducing glomerular filtration. In some embodiments, a macromolecular carrier increases tumor uptake due to enhanced permeability and retention (EPR) of tumor vasculature.

In some embodiments, M is bound to A. In some embodiments, M is bound to A at the n-terminal poly glutamate. In some embodiments, M is bound to A (or, the n-terminal poly glutamate) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, M is bound to B. In some embodiments, M is bound to B at the c-terminal polyarginine. In some embodiments, M is bound to B (or, the c-terminal polyarginine) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond. In some embodiments, M is bound to A.

In some embodiments, M is selected from a protein, a synthetic or natural polymer, or a dendrimer. In some embodiments, M is a dendrimer, dextran (including for example but not limited to branched glucan/branched glucose molecules composed of chains of varying lengths ranging from 3 to 2000 kDa with molecular weights ranging from 3 kDa to 2,000 kDa, for example but not limited to 20 kDa, 40 kDa, 60 kDa and 100 kDa), a PEG polymer (e.g., PEG 5 kDa, PEG 10 kDa, PEG 12 kDa, PEG 15 kDa, PEG 20 kDa, PEG 40 kDa, PEG 50 kDa or PEG 100 kDa), albumin or fragments thereof, lipid-coated perfluorocarbon droplet or a combination thereof. In some embodiments, M is a PEG polymer.

In some embodiments, the size of the macromolecular carrier is between 50 kDa and 70 kDa. In some embodiments, small amounts of negative charge keep peptides out of the liver while not causing synovial uptake.

In some embodiments, the MTS molecule is conjugated to albumin. In certain instances, albumin is excluded from the glomerular filtrate under normal physiological conditions. In some embodiments, the MTS molecule comprises a reactive group such as maleimide that can form a covalent conjugate with albumin. A MTS molecule comprising albumin results in enhanced accumulation of cleaved MTS molecules in tumors in a cleavage dependent manner. In some embodiments, albumin conjugates have good pharmacokinetic properties but are difficult to work with synthetically.

In some embodiments, the MTS molecule is conjugated to a PEG polymer. In some embodiments, the MTS molecule is conjugated to a PEG 5 kDa polymer. In some embodiments, the MTS molecule is conjugated to a PEG 12 kDa polymer. In some embodiments, 5 kDa PEG conjugates behaved similarly to free peptides. In some embodiments, 12 kDa PEG conjugates had a longer half-life as compared to free peptides. See Example 5 for a detailed analysis of the effects of using a PEG polymer.

In some embodiments, the MTS molecule is conjugated to a dextran. In some embodiments, the MTS molecule is conjugated to a 70 kDa dextran. In some embodiments, dextran conjugates, being a mixture of molecular weights, are difficult to synthesize and purify reproducibly.

In some embodiments, the MTS molecule is conjugated to streptavidin.

In some embodiments, the MTS molecule is conjugated to a fifth generation PAMAM dendrimer.

In some embodiments, a macromolecular carrier is capped. In some embodiments, capping a carrier improves the pharmacokinetics and reduces cytotoxicity of a macromolecular carrier by adding hydrophilicity. In some embodiments, the cap is selected from: Acetyl, succinyl, 3-hydroxypropionyl, 2-sulfobenzoyl, glycidyl, PEG-2, PEG-4, PEG-8 and PEG-12.

In some embodiments, the macromolecular carrier comprises a dendrimer. As used herein, "dendrimer" means a poly-functional (or, poly-branched) molecule. In some embodiments, a dendrimer is a structure in which a central molecule branches repetitively and repetitiously. In some embodiments, the dendrimer is a nanoparticle. In some embodiments, the dendrimer comprises a reactive group such as maleimide that can form a covalent conjugate with albumin. In some embodiments, a dendrimer is conjugated to a MTS molecule via a maleimide linker at the C-terminal end of the MTS molecule. In some embodiments, when the MTS molecule comprises a dendrimer, the cargo and/or compound T is attached directly to D.

In some embodiments, conjugating a MTS molecule to a dendrimer increases plasma half-life as compared to an unconjugated (or, free) MTS molecule. In some embodiments, a MTS molecule conjugated to a dendrimer results in a decrease in acute toxicity as compared to unconjugated MTS molecules. In some embodiments, a MTS molecule conjugated to a dendrimer reduces uptake by synovium, cartilage and kidney as compared to unconjugated MTS molecules.

In some embodiments, a MTS molecule conjugated to a dendrimeric nanoparticle is used to target tumor associated macrophages. In some embodiments, a MTS molecule conjugated to a dendrimeric nanoparticle, wherein the nanoparticle further comprises Ricin A, is used to poison subcutaneous macrophages.

MTS molecules having features of disclosed herein may be synthesized by standard synthetic techniques, such as, for example, solid phase synthesis including solid phase peptide synthesis. (An example of peptide synthesis using Fmoc is given as Example 1 in WO 2005/042034). For example, conventional solid phase methods for synthesizing peptides may start with N-alpha-protected amino acid anhydrides that are prepared in crystallized form or prepared freshly in solution, and are used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1 to 2 reaction cycles are used for the first twelve residue additions, and 2 to 3 reaction cycles for the remaining residues.

After completing the growing peptide chains, the protected peptide resin is treated with a strong acid such as liquid hydrofluoric acid or trifluoroacetic acid to deblock and release the peptides from the support. For preparing an amidated peptide, the resin support used in the synthesis is selected to supply a C-terminal amide, after peptide cleavage from the resin. After removal of the strong acid, the peptide may be extracted into 1M acetic acid solution and lyophilized. The peptide can be isolated by an initial separation by gel filtration, to remove peptide dimers and higher molecular weight polymers, and also to remove undesired salts The partially purified peptide may be further purified by preparative HPLC chromatography, and the purity and identity of the peptide confirmed by amino acid composition analysis, mass spectrometry and by analytical HPLC (e.g., in two different solvent systems).

The invention also provides polynucleotides encoding MTS molecules described herein. The term "polynucleotide" refers to a polymeric form of nucleotides of at least 10 bases in length. The nucleotides can be ribonucleotides, deoxynucleotides, or modified forms of either type of nucleotide. The term includes single and double stranded forms of DNA. The term therefore includes, for example, a recombinant DNA which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

These polynucleotides include DNA, cDNA, and RNA sequences which encode MTS molecules having features of the invention, or portions thereof. Peptide portions may be produced by recombinant means, including synthesis by polynucleotides encoding the desired amino acid sequence. Such polynucleotides may also include promoter and other sequences, and may be incorporated into a vector for transfection (which may be stable or transient) in a host cell.

The construction of expression vectors and the expression of genes in transfected cells involves the use of molecular cloning techniques that are well known in the art. See, for example, Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc., most recent Supplement). Nucleic acids used to transfect cells with sequences coding for expression of the polypeptide of interest generally will be in the form of an expression vector including expression control sequences operatively linked to a nucleotide sequence coding for expression of the polypeptide. As used herein, "operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. The term "control sequences" is intended to include, at a minimum, components whose presence can influence expression, and can also include additional components whose presence is advantageous, for example, leader sequences and fusion partner sequences. As used herein, the term "nucleotide sequence coding for expression of a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Any suitable method is used to construct expression vectors containing the fluorescent indicator coding sequence and appropriate transcriptional/translational control signals. Any methods which are well known to those skilled in the art can be used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989). Transformation of a host cell with recombinant DNA may be carried out by conventional techniques as are well known to those skilled in the art.

Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukagotic Viral Vectors*, Cold Spring Harbor Laboratory, Gluzman ed., 1982). Techniques for the isolation and purification of polypeptides of the invention expressed in prokaryotes or eukaryotes may be by any conventional means such as, for example, preparative chromatographic separations and immunological separations such as those involving the use of monoclonal or polyclonal antibodies or antigen.

It will be understood that the compounds of the present invention can be formulated in pharmaceutically and or diagnostically useful compositions. Such pharmaceutical and diagnostically useful compositions may be prepared according to well-known methods. For example, MTS compounds having features of the invention, and having a cargo portion C that is, for example, a therapeutic moiety or a detection moiety, may be combined in admixture with a pharmaceutically acceptable carrier vehicle or a diagnostic buffering agent. Suitable vehicles and agents and their formulation, inclusive of other human proteins, e.g. human serum albumin are described, for example, in *Remington's Pharmaceutical Sciences* by E. W. Martin and, the techniques described in Maniatis, et al., Molecular Cloning A Laboratory Manual, Cold Spring Harbor Laboratory, N.Y., 1989-2013, which are hereby incorporated by reference. Such compositions will contain an effective amount of the compounds hereof together with a suitable amount of vehicle in order to prepare pharmaceutically acceptable compositions suitable for effective administration. Dosages and dosing regimens may be determined for the indications and compounds by methods known in the art, including determining (e.g., in experimental animals) the effective dose which causes half of those treated to respond to the treatment ($ED_{50}$) by providing a range of doses to experimental animals or subjects and noting the responses.

Methods of Use

The MTS molecules find use in a variety of ex vivo applications as described herein and such MTS molecules have been thoroughly described (see, WO 2005/042034, WO/2006/125134, WO2011008992 and WO2011008996; all of which are incorporated herein by reference in their entireties). As such, according to disclosure contained herein, this invention pertains to methods and compositions that find use in treatment, diagnostic, prognostic (e.g., patient prognosis) and characterization (e.g., histologic grade/stage) of neoplasia and neoplasma samples based on the ability of a tumor sample to cleave a MTS molecule of the present invention.

Methods of use and compositions comprising MTS molecules are disclosed. Molecules having features of the invention include peptide portions linked by a cleavable linker portion which may be a peptide. The inventors have found that these MTS molecules can find use in treatment, diagnostic, detection, screening, prognosis (e.g., patient prognosis) and characterization (e.g., histologic grade/stage) assays.

According to the present invention, such methods are based in part on cleavage of the MTS molecule and detection of that cleavage event. The presence of one or more proteases in a sample from a subject can be detected ex vivo based on cleavage of the peptide. Such cleavage is detected by detecting a change in a detectable label (detectable moiety) that is part of the MTS peptide. In some embodiments, the MTS molecule contains a detectable moieties which provide for an indication of a cleavage event. In some embodiments, cleavage could be detected by size changes in the length of the peptide (e.g., gel electrophoresis, size exclusion, column chromatography, immunofluorescence, etc.) or other biochemical and physical changes that occur to the MTS molecule. In some embodiments, the MTS molecule comprises a label which facilitates cleavage detection. In some embodiments, cleavage could be detected using a FRET-based pair (a reporter dye and an acceptor dye that are involved in fluorescence resonance energy transfer known as FRET), where a change in fluorescence is indicative of a cleavage event. See, for examples, Examples 1-3. Methods for detecting and monitoring cleavage of proteins are well known and any such methods could be employed in detecting cleavage of the MTS molecules of the invention.

In some embodiments, the invention provides an ex vivo method for detecting the presence of one or more protease activities in a neoplasia sample comprising a) combining ex vivo said sample from a subject with a molecule of the structure according to one of the following:

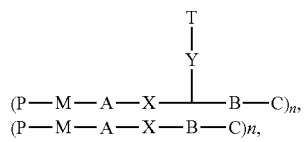

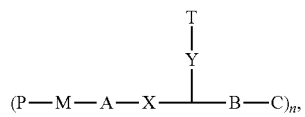

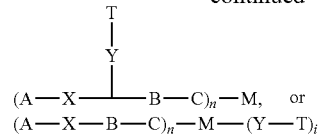

wherein cleavage of said molecule is indicative of the presence of protease activity and wherein P is an optional pre-targeting moiety; M is an optional macromolecular carrier; A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound (also referred to herein as a "warhead"); and n is an integer between 1 and 20; and C is a detectable moiety and b) detecting cleavage of said molecule by detecting a change in said detectable moiety C, wherein said change in C is indicative of cleavage and said cleavage is indicative of the presence of one or more protease activities in said neoplasia. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, the screening is small scale, involving screening of 1, 5, 10, 20 or 30 samples. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments, one protease activity can be detected. In some embodiments, 2, 3, 4, 5, 6, 7, 8, 9 or 10 protease activities can be detected. In some embodiments, one or more protease activities can be detected. In some embodiments, said portion A has between about 5 to about 9 acidic amino acid residues, and said portion B has between about 9 to about 16 basic amino acid residues.

In some embodiments, the invention provides an ex vivo method of screening for the presence of one or more protease activities in a neoplasia sample comprising combining ex vivo said neoplasia sample from a subject with a molecule of the structure according to one of the following:

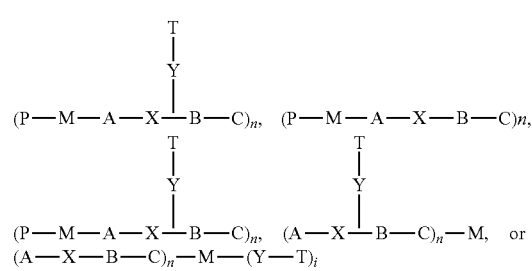

wherein cleavage of said molecule is indicative of the presence of protease activity and wherein P is an optional pre-targeting moiety; M is an optional macromolecular carrier; A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound (also referred to herein as a "warhead"); and n is an integer between 1 and 20; and C is a detectable moiety; and b) detecting cleavage of said molecule by detecting a change in said detectable moiety C, wherein said change in C is indicative of cleavage and said cleavage is indicative of the presence of one or more protease activities in said neoplasia. In some embodiments the MTS molecules can be used in screening assays to determine how many proteases and/or which proteases are expressed by a sample. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments, the screening is small scale, involving screening of 1, 5, 10, 20 or 30 samples. In some embodiments, screening is large scale, and involves screening of 100, 500, 1000, 10000, 100 000, 500000 or more samples. In some embodiments, samples are screened for 1, 2, 3, 4, 5, 6, 7, 8, 9, 10 or more protease activities using MTS molecules of the invention. In some embodiments, screening information can be employed to develop data bases and incorporated with other bioinformatic information in order to develop hydrogen peroxide profiles of samples. In some embodiments, said portion A has between about 5 to about 9 acidic amino acid residues, and said portion B has between about 9 to about 16 basic amino acid residues.

In some embodiments, the invention provides an ex vivo method of determining the protease profile of a neoplasia sample, comprising a) combining said sample from a subject with a molecule of the structure according to one of the following:

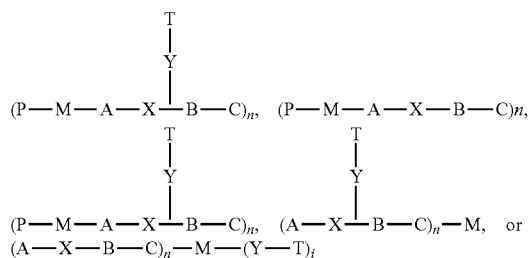

wherein cleavage of said molecule is indicative of the presence of protease activity and wherein P is an optional pre-targeting moiety; M is an optional macromolecular carrier; A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound (also referred to herein as a "warhead"); and n is an integer between 1 and 20; and C is a detectable moiety; and b) detecting cleavage of said molecule by detecting a change in said detectable moiety C, wherein said change in C is indicative of cleavage and said cleavage is indicative of the presence of one or more protease activities in said neoplasia. In some embodiments the MTS molecules can be used in screening assays to determine how many proteases and/or which proteases are expressed by a sample. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments, the MTS molecules are employed to develop a protease profile for one or more neoplasia samples. Hydrogen peroxide profiles can be employed to develop databases and can be incorporated with other information, including for example bioinformatic information, in order to develop hydrogen peroxide profiles of disease samples and for hydrogen peroxide profiles for patients with diseases. Diseases contemplated by the methods of the present invention include inflammatory diseases, neurodegenerative diseases, cardiovascular diseases, diabetes and neoplasia. In some embodiments, said portion A has between about 5 to about 9 acidic amino acid residues, and said portion B has between about 9 to about 16 basic amino acid residues. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments, the invention provides an ex vivo method of determining a treatment regimen based on the protease profile of a neoplasia sample, comprising a) combining ex vivo said neoplasia sample from a subject with a molecule of the structure according to one of the following:

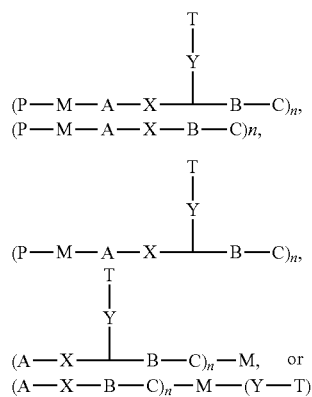

wherein cleavage of said molecule is indicative of the presence of protease activity and wherein P is an optional pre-targeting moiety; M is an optional macromolecular carrier; A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound (also referred to herein as a "warhead"); and n is an integer between 1 and 20; and C is a detectable moiety; and b) detecting cleavage of said molecule by detecting a change in detectable moiety C, wherein said change in C is indicative of cleavage and said cleavage is indicative of the presence of one or more protease activities and wherein the presence and/or absence of one or more protease activities allows for determining a medical treatment regimen. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments, the MTS molecules are employed to determine a treatment regimen. Matrix metalloproteinase (MMP), hydrogen peroxide or other cleavage information and/or profiles can be employed to develop databases and can be incorporated with other information, for example bioinformatic information, in order to develop cleavage profiles of samples. In some embodiments, such information can be combined with information regarding treatment and surgical options know to those of skill in the medical arts in order to determine and develop personalize treatment regimens for individual subjects. In some embodiments, the medical regimen is a surgical regimen. After detecting the presence or absence of one or more proteases based on MTS molecule cleavage, a determination of the usefulness of an MTS molecule in surgical procedures can be determined. Detection of cleavage of the MTS molecule would be indicative of the presence of one or more proteases and such information would allow for a determination of usefulness of the peptide in a surgical procedure in order to detect tumor borders and assist with surgical removal as previously described (See, e.g., see, WO 2005/042034, WO/2006/125134, WO2011008992 and WO2011008996). Non-detection of cleavage of the MTS molecule would be indicative of the absence of a protease and the non-usefulness of the peptide in a surgical procedure. In some embodiments, said portion A has between about 5 to about 9 acidic amino acid residues, and said portion B has between about 9 to about 16 basic amino acid residues. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments, the invention provides an ex vivo method of characterizing a neoplasia based on the protease profile of said neoplasia, comprising a) combining a sample of said neoplasia from a subject with a molecule of the structure according to one of the following:

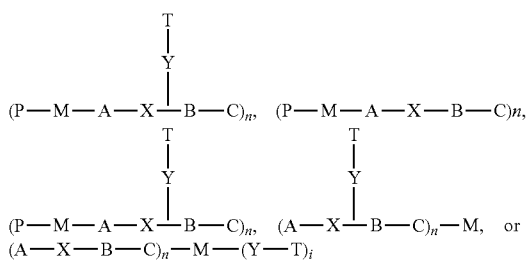

wherein cleavage of said molecule is indicative of the presence of protease activity and wherein P is an optional pre-targeting moiety; M is an optional macromolecular carrier; A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound (also referred to herein as a "warhead"); and n is an integer between 1 and 20; and C is a detectable moiety; and b) detecting cleavage of said molecule by detecting a change in detectable moiety C, wherein said change in C is indicative of cleavage and said cleavage is indicative of the presence of one or more protease activities and wherein the presence and/or absence of one or more protease activities allows for determining a medical treatment regimen. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments, the neoplasia is characterized based on histology, stage, grade, location, type, or any of a variety of characteristics known to those skilled in the medical arts. In some embodiments, the protease profile is correlated with histology, stage, grade, location, type, or any of a variety of characteristics known to those skilled in the medical arts in order to characterize the neoplasia. In some embodiments, the presence of the protease activity is indicative of neoplasia. In some embodiments, the presence of the protease activity is indicative of metastasis. In some embodiments, said portion A has between about 5 to about 9 acidic amino acid residues, and said portion B has between about 9 to about 16 basic amino acid residues. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments, the present invention provides a diagnostic composition for use in the methods of any of the preceding claims comprising: a molecule of the structure according to one of the following:

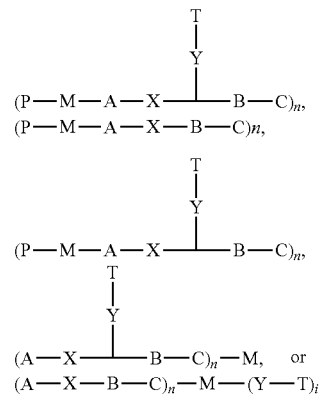

wherein cleavage of said molecule is indicative of the presence of protease activity and wherein P is an optional pre-targeting moiety; M is an optional macromolecular carrier; A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B and is cleavable under physiological conditions; Y is a second cleavable linker of about 2 to about 100 atoms, or about 3 to about 30 atoms, joining A-X-B with T and is cleavable under physiological conditions; T is a compound for delivery to a target, including for example a therapeutic compound (also referred to herein as a "warhead"); and n is an integer between 1 and 20; and C is a detectable moiety; and b) detecting cleavage of said molecule by detecting a change in detectable moiety C, wherein said change in C is indicative of cleavage and said cleavage is indicative of the presence of one or more protease activities and wherein the presence and/or absence of one or more protease activities allows for determining a medical treatment regimen. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments of the diagnostic composition, said portion A has between about 5 to about 9 acidic amino acid residues, and said portion B has between about 9 to about 16 basic amino acid residues. In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments, the present invention provides an array comprising: a plurality of molecules of the structure according to one or more of the following:

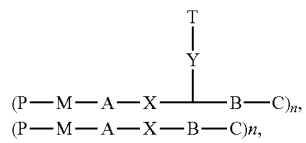

-continued

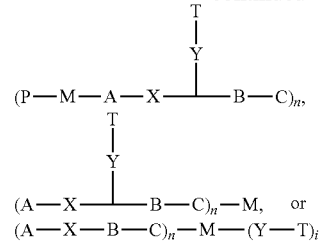

wherein cleavage of said molecule is indicative of the presence of protease activity and wherein P is an optional pre-targeting moiety; M is an optional macromolecular carrier; A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound (also referred to herein as a "warhead"); and n is an integer between 1 and 20; and C is a detectable moiety. In some embodiments of the array, said portion A has between about 5 to about 9 acidic amino acid residues, and said portion B has between about 9 to about 16 basic amino acid residues. In some embodiments, the array comprises a plurality of molecules of one or more of said structures and wherein the cleavable linker X comprises a plurality of cleavable linkers X. In some embodiments, the array comprises a plurality of molecules of one or more of said structures and wherein the cleavable linker Y comprises a plurality of cleavable linkers Y. In some embodiments of the array, the plurality of cleavable linkers X and/or Y linking a portion A to a portion B are cleavable by a single protease. In some embodiments of the array, the plurality of cleavable linkers X and/or Y linking a portion A to a portion B are cleavable by more than one protease. In some embodiments, an array of the invention would contain a plurality of one species (one type) of MTS molecules. In some embodiments, an array of the invention would contain a plurality of one species (one type) of MTS molecules and multiple samples could be screened for one protease activity type. In some embodiments, an array of the invention would contain a plurality of a plurality of species (multiple types) of MTS molecules. In some embodiments, an array of the invention would contain a plurality of a plurality of species (multiple types) of MTS molecules and one or more samples could be screened for one or more protease activity types. An array can include but is not limited to any substrate to which the MTS molecules can be bound, and can include for examples solid substrates, micro-arrays and microchips. Methods for making arrays are well known and can even be supplied by commercial suppliers. Arrays can be manually processed and/or automated or a combination thereof. Such arrays can be employed in low-throughput as well as high-throughput applications and can analyze one or more samples, one or more proteases or any combination thereof.

In some embodiments of molecules having features of the invention, n is an integer between 1 and 20. In some embodiments of molecules having features of the invention, n is an integer between 1 and 15. In some embodiments of molecules having features of the invention, n is an integer between 1 and 10. In some embodiments of molecules having features of the invention, n is an integer between 1 and 5. In some embodiments of molecules having features of the invention, n is an integer between 1 and 4. In some embodiments of molecules having features of the invention, n is an integer between 1 and 3. In some embodiments of molecules having features of the invention, n is an integer between 1 and 2. In some embodiments of molecules having features of the invention, n is 1. In some embodiments of molecules having features of the invention, n is an integer of 1, 2, 3, 4, 5, 6, 7, 8, 9, 10, 11, 12, 13, 14, 15, 16, 17, 18, 19, or 20. In some embodiments of molecules having features of the invention, i is an integer between 1 and 20. In some embodiments of molecules having features of the invention, i is an integer between 1 and 10. In some embodiments of molecules having features of the invention, i is an integer between 1 and 5. In some embodiments of molecules having features of the invention, i is an integer between 1 and 4. In some embodiments of molecules having features of the invention, i is an integer between 1 and 3. In some embodiments of molecules having features of the invention, i is an integer between 1 and 2. In some embodiments of molecules having features of the invention, i is 1. In some embodiments of molecules having features of the invention, i is an integer of 1, 2, 3, 4, 5, 6, 7, 8, 9, 10, 11, 12, 13, 14, 15, 16, 17, 18, 19, or 20. In some embodiments, the T-Y pair is attached to either end of B.

In some embodiments of the above described methods, ratiometric analysis can be employed to determine the level of enzyme activity and/or to assess the percentage of enzymatically positive tumors in a population. Such ratiometric analyses can be based on the ratio of cleaved to non-cleaved MTS molecules. In some embodiments, ratiometric analysis can be employed to correlate ex vivo cleavage with in vivo cleavage activities.

In some embodiments, the protease information can be correlated with histology, grade, type, characterization, etc. in order to better characterize neoplasias and to provide personalized prognosis and treatment regimens. Such information can be provided to those of skill in the medical arts and be employed to develop personalized medical treatment regimens for individuals.

Radiosensitization

The present invention also provides for methods of employing the MTS molecules of the present invention in radiosensitization.

In some embodiments, T is a radiosensitizing entity. Radiosensitizing drugs can include any substance that when administered to a tumor or cancer cell leads to increased sensitivity or susceptibility of the tumor or cancer cell to treatment with radiation therapy; also referred to as radiosensitizing agents. In some embodiments, T is an entity as described herein above.

Exemplary radiosensitizing agents can include but are not limited to any of the chemotherapeutic agents described herein above. In some embodiments, T is DM1 (mertansine), MMAE or auristatin or a derivative thereof.

The targeting mechanism according to the present invention involves several steps, a) binding of cRGD ligand to $\alpha v\beta 3$ receptor, b) proteolysis of ACPP by MMP-2, c) dissociation of MMAE-r9-Cy5 from cRGD-e9, d) uptake of MMAE-r9-Cy5 into cell through endocytosis, e) Cathepsin B induced cleavage of amide bond between Cit and PAB and subsequent release of MMAE, f) diffusion of MMAE across endosomal or lysosomal membrane into cytosol, g) MMAE interference with microtubules, and h) radiosensitization and subsequent cell death.

In some embodiments, the MTS molecules contain 1, 2, 3, 4, 5, 6, or more different T entities capable of radiosensitization.

In some embodiments, the MTS molecules containing 1, 2, 3, 4, 5, 6, or more different T entities capable of radiosensitization are administered to an individual with a cancer or tumor. In some embodiments, the MTS molecules containing 1, 2, 3, 4, 5, 6, or more different T entities capable of radiosensitization are administered to an individual with a cancer or tumor prior to administration of radiation therapy. In some embodiments, the MTS molecules containing 1, 2, 3, 4, 5, 6, or more different T entities capable of radiosensitization are administered to an individual with a cancer or tumor concurrently with administration of radiation therapy. Radiation therapy can be administered according to established standards of care, including dosages of 20-40 grays (Gy), 45-60 grays, 60-80 grays, as needed and as determined by a skilled physician in the art. In some cases the radiation dosage is administered as a single dosage or as multiple dosages. In some embodiments, the radiation therapy can be administered 1.8 to 2 gray per day or 2.67 to 2.75 Gy per day. In some embodiments, the radiation therapy can be administered 1, 2, 3, 4, or 5 days per week, including 1-5, 2-5, 3-5, or 4-5 days per week.

Imaging

A variety of methods of imaging fluorescent compounds are known in the art and those of skill in the art will understand application of such methods in the context of imaging the compounds of the present invention according to the methods described herein, Frozen block face imaging provides fluorescence maps of where the Cy5-labeled mAb or ACPP is ending up in a tumor and its surrounding tissue with minimal perturbation or manipulation to signal. In some embodiments, the tissue is fresh-frozen. In some embodiments, the freezing is sufficiently fast or rapid such as to minimize cellular damage. In some embodiments, there are no perfusion or fixation artifacts. In some embodiments, the absence of perfusion or fixation artifacts allows the signal in the blood and vessels to be preserved. In some embodiments, a block face is cut, up to a centimeter across. Such a cross section can then be imaged. In some embodiments, such imaging is on a Nikon confocal microscope. In some embodiments, the imaging occurs while the sample is still frozen. In some embodiments, the sample is insulated to keep the sample frozen.

Multiple tumor models are available and known to those in the art with GFP and others that can be labeled with an RFP. In some embodiments, tumors models labeled with GFP or RFP allow for visualization of the same sample on both a macro and a micro scale. In some embodiments, this will allow for a determination of whether the mAb or ACPP enters into the fluorescent tumor cells or is primarily confined to the tumor stroma. See, FIG. 46A-D for an exemplary comparison of Cy5 fluorescence showing different localizations of a mAb, cetuximab as compared to an ACPP ((SEQ ID NO:4) PLGC(Me)AG Cy5/Cy7-labeled RACPP).

In some embodiments, frozen block face imaging can be employed. In some embodiments, such imaging methods allow for a determination of the relative amounts of mAb or ACPP (MTS) loaded into tumor cells versus host macrophages and examination of the vascular endothelium. In some embodiments, such methods allow for identification of specific cell types in the stroma, including for example but not limited to macrophages, neutrophils and mast cells using a variety of labeled antibodies.

In some embodiments, mAb or ACPP uptake into tumor versus host cells can be compared using fixed tissue and a variety of antibodies against cell markers of interest (for example, in order to determine cell identity). In some embodiments, the tissue can be stained with Hoechst or other nuclear markers after chemoradiation treatment to assess relative survival rates of malignant cells as compared components of stroma and vasculature.

Imaging Methods for Warhead Distribution

In some embodiments Mass Spectrometry Imaging (MSI) can be employed to quantitatively measure warhead loading into biological tissue (see, Laskin J, et al., *Anal Chem.* 2016; 88(1):52-73; and Hsu C C, Dorrestein P C. *Clin Chem.* 2016; 62(1):111-23).

In some embodiments, mass spectrometry can be employed to record the spatial distribution of drug compound (i.e., Cargo C, compound T, radiosensitizing agent T, and/or "warhead") allows the loading to be observed in the absence of fluorescent tags. In such embodiments, the signal is an orthogonal signal to epifluorescence microscopy, even though the sample is prepared for the instrument in a similar way. In some embodiments, a frozen slice of tissue is thaw mounted on a glass slide. In some embodiments, the slice of tissue is about 5 µm, about 7.5 µm, about 10 µm, about 12.4 µm, or about ~15 µm thick. In some embodiments, the tissue is then placed in the mass spectrometer (MS) interface. In some embodiments, the tissue is then imaged by measuring discrete mass spectra over each pixel, in accordance with the spatial resolution. The type of MS interface is the main factor determining the spatial resolution.

In some embodiments, matrix assisted laser desorption time-of-flight mass spectrometry (MALDI-TOF) (Chaurand P, et al., *Curr Opin Biotechnol.* 2006; 17(4):431-6) can be employed for imaging purposes according to the present invention. In some embodiments, Desorption Electrospray Ionization (DESI), developed by Cooks (Cooks R G, et al., *Science.* 2006; 311(5767): 1566-70.) can be employed for imaging purposes according to the present invention. In some embodiments, DESI and related techniques, including nanoflow DESI (nanoDESI) are classed as ambient MSI (Laskin J, Lanekoff, I. *Anal Chem.* 2016; 88(1):52-73) because the sample is ionized at ambient pressure from a small liquid droplet formed on the tissue when mounted on a standard glass slide. The spatial resolution in nanoDESI is determined by the diameter of the droplet formed between two fused silica capillaries, currently ~150 µm. In some embodiments of these methods, the chemical components in the tissue are extracted into the droplet and introduced into the MS by nanoflow electrospray ionization.

Figure 47:
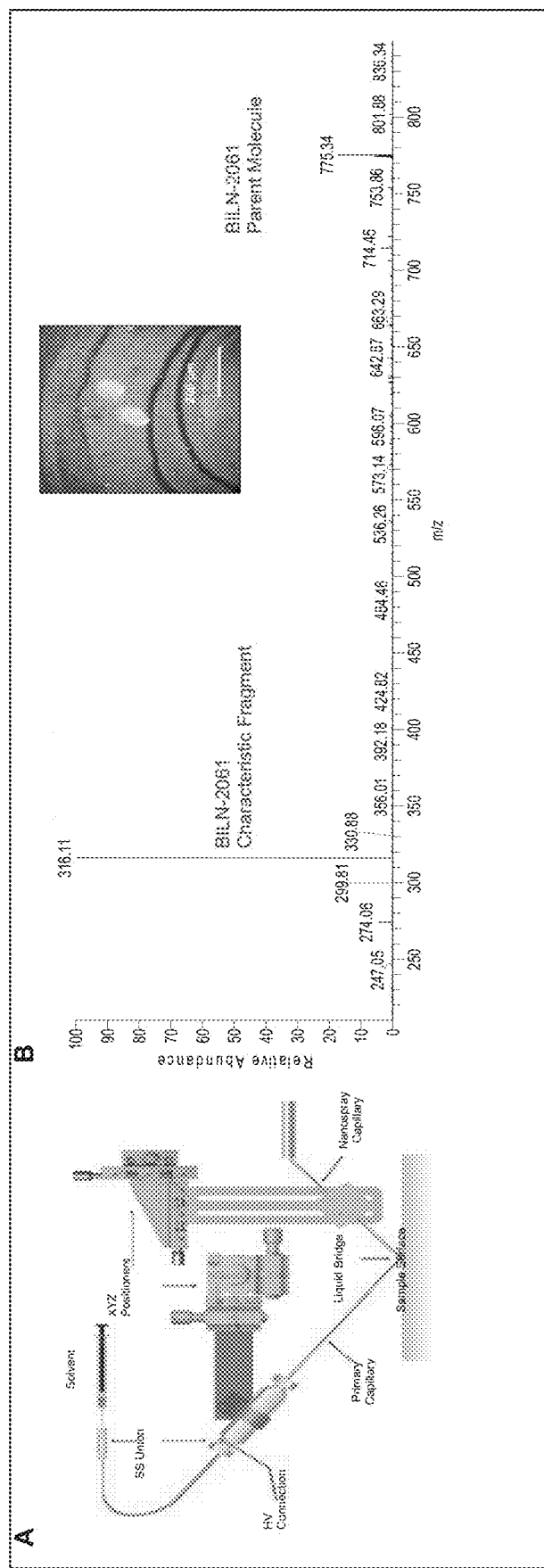
FIG. 47: A) Schematic of nanoDESI apparatus. B) BILN-2061 characteristic fragment detected in single sample site from mouse brain section after intra-cisternal injection of drug. Pale areas in inset show reproducibility of nanoDESI sampling sites.

In some embodiments, nanoDESI (Lanekoff I, et al., *Anal Chem.* 2012; 84(19):8351-6) can be employed to address where a warhead, a molecule T such as for example, MMAE, travels to the heterogeneous microenvironment of a tumor. In some embodiments, nanoDesi can be employed to determine the distribution of a molecule T. In some embodiments, a cross section of a sample, after injection of an ACPP (MTS) is examined. In some embodiments, the section is about 5 µm, about 10 µm, about 15 µm, about 20 µm, about 30 µm, about 40 µm, about 45 µm, about 50 µm, about 55 µm, about 60 µm, or about 65 µm. In some embodiments, the cross section is about 40 µm, about 45 µm, about 50 µm, about 55 µm, or about 60 µm. In some embodiments, the cross section is about 50 µm. In some embodiments, an apparatus as shown in FIG. 47 is employed. In some embodiments, the parent molecular ion forms from the intact ACPP (MTS) and is measured. In some embodiments, the characteristic fragment ion is formed from a molecular cleavage that occurs in the ionization process and is measured. In some embodiments, both ions can be measured and used for quantitation. In some embodiments, the tumor can be categorized based on the cleavage of the ACPP (MTS). In some embodiments, the tumor microenvironment can be categorized based on the cleavage of the ACPP (MTS). For example, the proteases expressed by the tumor can be determined by employing an ACPP (MTS) which contains protease cleavable linker which is only cleavable by a particular protease, such as MMP-9 or MMP-2, etc.

In some embodiments, lipids from cell membranes and extracellular spaces occur as negative ions in nanoDESI. In some embodiments, analytes that contain secondary amines or pyridyl groups in their structures are detected with good sensitivity as positive ions. In some embodiments, conditions are determined and employed to prevent suppression of the analyte ions by electrostatic attraction from ionized lipids. In such embodiments, the solvent for extracting the sample is first continuously flowed over the point of contact with the sample, so its organic content can be systematically varied while the mass spectral results are observed. In such embodiments, modifying reagents can be added secondarily to the solvent stream if desired, for example, to adjust the pH or other solubility parameters.

In some embodiments, NanoDESI is employed for quantitation, because the standard can be added in the flowing solvent (see, for example, Laskin J, Lanekoff I., *Anal Chem.* 2016; 88(1):52-73). In some embodiments, a second standard can also be added directly to the sample slice, to control for extraction efficiency. In some embodiments, two standards are thus used to calibrate for extraction and ionization independently. In such embodiments employed two standards, it is not as essential to match the properties of the analyte exactly. In some embodiments, this allows for avoidance of the synthesis of drug targets substituted with stable isotope atoms. In some embodiments, these calibration methods are semi-quantitative. In some embodiments, the semi-quantitativeness of the calibration methods depends on factors such as the consistency of solvent flow. In some embodiments, the average drug concentration in the tissue will be measured from bulk tissue homogenates. In some embodiments, the overall result will be compared with the distribution found in tissue in order to quantitatively determine the amount of compound T in a tissue. In some embodiments, the amount of compound T is a tissue can be determined.

In some embodiments, the present invention provides a method for imaging a tumor sample comprising:

i) administering to a subject in need thereof a molecule comprising the formula:

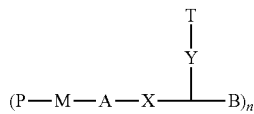

wherein the molecule comprises:
 an optional pre-targeting moiety P;
 an optional macromolecular carrier M;
 a peptide A with a sequence comprising 5 to 9 consecutive acidic amino acids, wherein the amino acids are selected from: aspartates and glutamates;

a first cleavable linker X;
a second cleavable linker Y;
a radiosensitizing agent T;
a peptide B with a sequence comprising 5 to 20 consecutive basic amino acids;
  the T-Y pair is attached to either end of B; and
  n is an integer between 1 and 20;
ii) obtaining a sample from the subject; and
iii) determining the location of compound T, using an imaging method.

In some embodiments of the method, the molecule is cleaved in vivo in the presence of a tumor in the subject.

In some embodiments of the method, the imaging method is NanoDESI.

In some embodiments of the method, determining the location of compound T allows for a determination of the tumor type and/or a categorization of the tumor microenvironment.

In some embodiments, the present invention provides a method for imaging a tumor sample comprising:
i) administering to a subject in need thereof a molecule comprising the formula:

$(A-X-B)_n$-M-$(Y-T)_i$ wherein the molecule comprises:
  a macromolecular carrier M bound to A or B;
  a peptide A with a sequence comprising 5 to 9 consecutive acidic amino acids, wherein the amino acids are selected from: aspartates and glutamates;
  a first cleavable linker X;
  a second cleavable linker Y;
  a compound T;
  a peptide B with a sequence comprising 5 to 20 consecutive basic amino acids; and
  n and i are independently selected integers between 1 and 20;
ii) obtaining a sample from the subject; and
iii) determining the location of compound T, using an imaging method.

In some embodiments of the method, the molecule is cleaved in vivo in the presence of a tumor in the subject.

In some embodiments of the method, the imaging method is NanoDESI.

In some embodiments of the method, determining the location of compound T allows for a determination of the tumor type and/or a categorization of the tumor microenvironment.

In some embodiments, the present invention provides a method for imaging a tumor sample comprising:
i) subjecting a sample from a subject to a molecule comprising the formula:

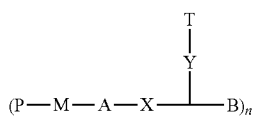

wherein the molecule comprises:
  an optional pre-targeting moiety P;
  an optional macromolecular carrier M;
  a peptide A with a sequence comprising 5 to 9 consecutive acidic amino acids, wherein the amino acids are selected from: aspartates and glutamates;
  a first cleavable linker X;
  a second cleavable linker Y;
  a radiosensitizing agent T;
  a peptide B with a sequence comprising 5 to 20 consecutive basic amino acids;
  the T-Y pair is attached to either end of B; and
  n is an integer between 1 and 20; and
ii) determining the location of compound T, using an imaging method.

In some embodiments of the method, the molecule is cleaved in vitro in the presence of a tumor sample.

In some embodiments, the imaging method is a fluorescent based imaging method. In some embodiments of the method, the imaging method is NanoDESI, MRI, or PET (positron-emission tomography).

In some embodiments of the method, determining the location of compound T allows for a determination of the tumor type and/or a categorization of the tumor microenvironment.

In some embodiments, the present invention provides a method for imaging a tumor sample comprising:
i) subjecting a sample from a subject in need thereof a molecule comprising the formula:

$(A-X-B)_n$-M-$(Y-T)_i$ wherein the molecule comprises:
  a macromolecular carrier M bound to A or B;
  a peptide A with a sequence comprising 5 to 9 consecutive acidic amino acids, wherein the amino acids are selected from: aspartates and glutamates;
  a first cleavable linker X;
  a second cleavable linker Y;
  a compound T;
  a peptide B with a sequence comprising 5 to 20 consecutive basic amino acids; and
  n and i are independently selected integers between 1 and 20; and
ii) determining the location of compound T, using an imaging method.

In some embodiments of the method, the molecule is cleaved in vitro in the presence of a tumor sample.

In some embodiments, the imaging method is a fluorescent based imaging method. In some embodiments of the method, the imaging method is NanoDESI, MRI (magnetic resonance imaging), or PET (positron-emission tomography). Such imaging methods can be used with the MTS molecules of the present invention.

In some embodiments of the method, determining the location of compound T allows for a determination of the tumor type and/or a categorization of the tumor microenvironment.

Pharmaceutical Compositions

The MTS molecules of the present invention can be administered with a suitable pharmaceutical excipient and/or buffer as necessary. One of skill will understand that the composition will vary depending on mode of administration and dosage unit.

The compositions typically include a conventional pharmaceutical carrier, buffer, or excipient and may additionally include other medicinal agents, carriers, adjuvants, diluents, tissue permeation enhancers, solubilizers, and the like. Preferably, the composition will contain about 0.01% to about 90%, about 0.1% to about 75%, about 0.1% to 50%, or about 0.1% to 10% by weight of a conjugate of the present invention or a combination thereof, with the remainder consisting of suitable pharmaceutical carrier and/or excipients. Appropriate excipients can be tailored to the particular composition and route of administration by methods well known in the art. See, e.g., REMINGTON'S PHARMACEUTICAL SCIENCES, 18TH ED., Mack Publishing Co., Easton, Pa. (1990).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The compositions can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; coloring agents; and flavoring agents. The compositions may also comprise biodegradable polymer beads, dextran, and cyclodextrin inclusion complexes.

For oral administration, the compositions can be in the form of tablets, lozenges, capsules, emulsions, suspensions, solutions, syrups, sprays, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the conjugate or combination of conjugates, any of the following: a diluent such as lactose, sucrose, dicalcium phosphate, and the like; a disintegrant such as starch or derivatives thereof, a lubricant such as magnesium stearate and the like; and a binder such a starch, gum acacia, polyvinylpyrrolidone, gelatin, cellulose and derivatives thereof. The conjugates can also be formulated into a suppository disposed, for example, in a polyethylene glycol (PEG) carrier.

Liquid compositions can be prepared by dissolving or dispersing a conjugate or a combination of conjugates and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The conjugates of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

One of ordinary skill in the art understands that the dose administered will vary depending on a number of factors, including, but not limited to, the particular peptide composition to be administered, the mode of administration, the type of application (e.g., prophylactic, therapeutic, etc.), the age of the patient, and the physical condition of the patient. Preferably, the smallest dose and concentration required to produce the desired result should be used. Dosage can be appropriately adjusted for children, the elderly, debilitated patients, and patients with cardiac and/or liver disease. Further guidance can be obtained from studies known in the art using experimental animal models for evaluating dosage. The MTS molecules of the present invention can be formulated without undue experimentation for administration to a mammal, including humans, as appropriate for the particular application. Additionally, proper dosages of the compositions can be determined without undue experimentation using standard dose-response protocols.

In some embodiments, the peptide comprising compositions of the present invention are administered to a subject at a particular dose of the peptide or are formulated for unit dosage administration of the peptide to a subject. In some embodiments, the dose administered to a subject is from about 0.001 to about 1000 mg per day. In some embodiments, the dose administered to a subject is from about 0.1 to about 500 mg per day. In some embodiments, the dose administered to a subject is from about 0.5 to about 100 mg per day. In some embodiments, the compositions of the present invention are formulated for unit dosage administration, wherein the unit dosage is from about 0.001 to about 1000 mg per day. In some embodiments, the compositions of the present invention are formulated for unit dosage administration, wherein the unit dosage is from about 0.1 to about 500 mg per day. In some embodiments, the compositions of the present invention are formulated for unit dosage administration, wherein the unit dosage is from about 0.5 to about 100 mg per day.

Methods of Administration

Administration of the peptides of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra joint, parenteral, intra-arteriole, intradermal, intraventricular, intracranial, intraperitoneal, intralesional, intranasal, rectal, vaginal, or by inhalation. Administration can be targeted directly to pancreatic tissue, e.g., via injection.

The MTS molecule compositions of the invention may be administered repeatedly, e.g., at least 2, 3, 4, 5, 6, 7, 8, or more times, or the composition may be administered by continuous infusion. Suitable sites of administration include, but are not limited to, dermal, mucosal, bronchial, gastrointestinal, anal, vaginal, eye, and ear. The formulations may take the form of solid, semi-solid, lyophilized powder, or liquid dosage forms, such as, for example, tablets, pills, lozenges, capsules, powders, solutions, suspensions, emulsions, suppositories, retention enemas, creams, ointments, lotions, gels, aerosols, or the like, preferably in unit dosage forms suitable for simple administration of precise dosages.

The term "unit dosage form" refers to physically discrete units suitable as unitary dosages for human subjects, each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a conjugate or a combination of conjugates.

Methods for preparing such dosage forms are known to those skilled in the art (see, for example, REMINGTON'S PHARMACEUTICAL SCIENCES, 18TH ED., Mack Publishing Co., Easton, Pa. (1990). The composition to be administered contains a quantity of the peptides of the invention in a pharmaceutically effective amount for improving beta islet cell survival. In addition, pharmaceutically acceptable salts of the peptides of the present invention (e.g., acid addition salts) may be prepared and included in the compositions using standard procedures known to those skilled in the art of synthetic organic chemistry and described, e.g., by March, Advanced Organic Chemistry: Reactions, Mechanisms and Structure, 4th Ed., New York, Wiley-Interscience (1992).

EXAMPLES

The methods system herein described are further illustrated in the following examples, which are provided by way of illustration and are not intended to be limiting.

Example 1: Tumor Specific Radiosensitization with Monomethyl Auristatin E and Activatable Cell Penetrating Peptide Targeting MMP-2/9 and Integrin αvβ3

Abstract

To improve tumor local control with radiotherapy, concurrent chemotherapy is used to radiosensitize tumors. However, a major obstacle to fully realize the clinical benefits of radiosensitization results from the failure of tumor specific delivery of potent radiosensitizers. A strategy using an integrin and MMP targeted activatable cell penetrating peptide as a tumor selective delivery vehicle for monomethyl auristatin E (ACPP-cRGD-MMAE) was tested to radiosensitize tumors. MMP cleavable ACPP that is pre-targeted by CyclicRGD is selectively activated in tumor microenvironment through tumor associated matrix metalloproteinase activity and RGD binding integrins. Once ACPP-cRGD-MMAE is cleaved, MMAE-conjugated polycation cell penetrating peptide is released and taken up by tumor cells. Studies with the powerful anti-mitotic agent MMAE demonstrated that MMAE radiosensitizes tumor cells by decreasing clonogenic survival and increasing DNA damage in cell culture. More importantly, combining ACPP-cRGD-MMAE with IR results in prolonged tumor regression in tumor xenograft models.

Introduction

Locally advanced gastrointestinal tumors are commonly treated with combination chemotherapy and radiotherapy. In randomized clinical trials, the addition of concurrent chemotherapy to radiotherapy has demonstrated improved local tumor control and overall survival in esophageal, gastric, pancreatic, and rectal carcinomas[1-4]. A rationale for using concurrent chemotherapy with radiotherapy is the ability of chemotherapy drugs to act as radiation sensitizers. Radiosensitizers increase IR mediated DNA damage and tumor cell kill[5-7]. To be clinically useful, radiation sensitizers must improve the therapeutic index, i.e. the level of sensitization of tumor cells must be greater than that of surrounding normal tissue. A major limitation to using more potent radiosensitizers is the inability to deliver such agents specifically to the tumor.

Activatable cell penetrating peptides (ACPP) can function as tumor targeted delivery vehicles[8-11]. ACPP consist of 4 regions: a polyanionic autoinhibitory domain, a protease sensitive peptide linker region, a cell penetrating polycationic peptide, and the payload to be delivered. Typically the polycationic cell penetrating peptide consists of nine D-arginines ($r_9$), and the autoinhibitory portion is nine D-glutamates ($e_9$). A flexible peptide linker separates these two domains. For therapeutic applications, anti-cancer drugs are the payload, conjugated to the polycationic cell penetrating peptide portion to facilitate their intracellular delivery[12]. While the ACPP is intact, the polyanion region prevents adhesion and uptake of the polycationic cell penetrating peptide plus payload. Upon protease attack on the linker region, drug conjugated-$r_9$ is released and taken up by cells. Tumor specific activation has been achieved by inserting a (SEQ ID NO:26) PLGLC(Me)AG linker sequence between the polyanionic and polycationic regions. Cleavage of this peptide linker is dependent on matrix metalloproteinases (MMP) 2 and 9. To further augment MMP activity and cleavage of (SEQ ID NO:4) PLGC(Me)AG, the substrate was designed to co-target αvβ3 integrin. αvβ3 integrin binds to the hemopexin domain of MMP-2 and enhances MMP activity[13]. Adding the integrin ligand cyclic RGD to the polyanion autoinhibitory domain (ACPP-cRGD) has shown improved tumor mediated cleavage of (SEQ ID NO:4) PLGC(Me)AG and release of the polycationic cell penetrating peptide[12].

Cell sensitivity to ionizing radiation (IR) varies throughout the cell cycle with $G_2/M$ being the most sensitive phase of the cell cycle to IR[14]. Chemotherapy drugs such as paclitaxel block cells in $G_2/M$, function as radiosensitizers, and are used clinically in combination with radiotherapy[15]. Monomethyl auristatin E (MMAE) is a synthetic derivative of dolastatin 10 and functions as a very potent anti-mitotic agent by inhibiting tubulin polymerization[16]. However like many potent anti-tumor agents, systemic delivery of MMAE is limited by normal tissue toxicity. When MMAE delivery is tumor restricted, its efficacy becomes clinically apparent. MMAE had been conjugated to a CD30 targeting antibody (brentuximab vedotin) for lymphomas[17]. In Hodgkins disease and anaplastic large cell leukemia, brentuximab vedotin has shown clinical efficacy with durable tumor responses in patients. MMAE has recently been conjugated to ACPP-cRGD as payload, abbreviated ACPP-cRGD-MMAE, and shown to have improved efficacy compared to free MMAE in murine models of breast cancer[12].

In these studies, we tested the therapeutic strategy of using tumor targeted ACPP-cRGD to deliver a potent tumoricidal agent that can also radiosensitize tumor cells. We show that MMAE blocks cells in $G_2/M$ in a dose dependent manner in the 1-5 nM range and has an $IC_{50}$ that is >6 fold lower than paclitaxel. Of significance, we demonstrate that in addition to its intrinsic anti-tumor activity, MMAE sensitized cells to IR mediated DNA damage in cell culture with decreased cell survival. To target and restrict MMAE to tumors, we tested the efficacy of ACPP-cRGD-MMAE in combination with IR. HCT-116 and PANC-1 tumor xenografts had MMP activity and preferentially cleaved and activated ACPP with (SEQ ID NO:4) PLGC(Me)AG protease sensitive linker in situ. Of therapeutic significance, combining ACPP-cRGD-MMAE with IR in either HCT-116 or PANC-1 tumor xenografts resulted in prolonged tumor xenograft regression that was not seen with IR or ACPP-cRGD-MMAE alone. Moreover in irradiated tumor xenografts, ACPP-cRGD tumor localized MMAE delivery improved tumor xenograft control compared to free MMAE non-targeted delivery. Our results lay the foundation for a therapeutic treatment paradigm in which improved tumor radiosensitization can be achieved through potent radiosensitizers conjugated to tumor targeted ACPP.

Materials and Methods

Cells and Reagents.

Human colorectal (HCT-116), pancreatic (PANC-1), breast (MDA-MB-231) adenocarcinoma cell lines were obtained from American Type Culture Collection. 779E is a limited passage, patient derived pancreatic adenocarcinoma. HCT-116, PANC-1 and 779E cells were cultured in DMEM supplemented with 10% FBS. Paclitaxel (Sigma) and MMAE (Concortis) were both diluted in DMSO at 10 mM. Vehicle treated cells were treated with DMSO.

Cell Cycle.

Cells were treated with 0, 1, 2, or 5 nM MMAE for 24 hours and then fixed in methanol. Cells were treated with RNAse, stained with propidium iodide and analyzed by FACS using FloJo software.

Alamar Blue Assay.

Cells were plated in 96 well plates at varying cell densities and exposed to range of concentrations of MMAE or paclitaxel for 72 hrs. Alamar Blue (also known as resazurin) was added to the cells and allowed to incubate for 2 hrs at 37° C. Plates were analyzed using a plate reader with fluorescence measured at 560 nm. For irradiated cells, cells were treated with MMAE overnight followed by 6 Gy.

Clonogenic Assay.

Cells were treated with 0, 1, 2, or 5 nM of MMAE for 24 hours and then irradiated with 0, 2, or 6 Gy. Following IR, cells were counted, re-plated at varying cell numbers in drug free media. Colonies were counted 10-14 after initial seeding. Colonies were then fixed and stained with crystal violet to quantify colonies.

Neutral Comet Assay:

Cells were treated for 24 hours with indicated doses of MMAE and then irradiated with 6 Gy. Cells were harvested 15 minutes post IR, suspended in agarose gel and lysed per assay directions (Trevigen). Samples underwent electrophoresis under neutral conditions and were then stained with Sybr Green. Comet tails were counted in multiple fields (>60 cells per sample) and analyzed using CometScore (TriTek Corp).

γH2Ax Immunostaining:

Cells were grown on glass cover slips were treated with indicated concentrations of MMAE overnight and then irradiated. Two hours post IR, cells were fixed in 4% paraformaldehyde. Samples were then permeabilized in 0.25% Triton X-100, blocked in 1% BSA, incubated with antibody to γH2Ax for 1 hr at room temperature, washed, and incubated in secondary antibody for 1 hour at room temperature. Samples were incubated for 1 minute in a 1:5000 dilution of DAPI to label nuclei. The number of foci per cell was counted. 6-8 high power fields were counted per each group.

Peptide Synthesis

Peptides were synthesized by following our reported procedure[12], briefly NH$_2$-e$_9$-o-PLGC(Me)AG-o-c-r$_9$-c(suc-Cy5) (where o=NH—CH$_2$—CH$_2$—O—CH$_2$—CO—, lower case letters refer to D-amino acids, "suc" refers to succinimido) was reacted with previously synthesized maleimido-caproyl-Val-Cit-PABC-MMAE (MC-Val-Cit-PABC-MMAE) to generate NH$_2$-e$_9$-o-PLGC(Me)AG-o-c[suc-(CH$_2$)$_2$-Val-Cit-PABC-MMAE]-r$_9$-c(suc-Cy5). This peptide was reacted with MAL-dpeg$_{12}$-NHS (Quanta Biodesign) through the N terminus, isolated and reacted with 2 molar equivalents of cyclic(RGDfC) (Peptide International) in DMSO to get the final compound. The product was purified using HPLC and the identity was verified using electrospray mass spectrometry. MC-Val-Cit-PABC-MMAE was synthesized by reacting MMAE (Concortis) with 2 molar equivalents of MC-Val-Cit-PABC-PNP (Synchem) in the presence of pyridine and purified using preparative HPLC.

Tumor Zenograft Gel Zymography

In Vivo Tumor Xenograft Optical Imaging:

All animal work was done in compliance with the principles and procedures outlined by the UCSD Institutional Animal Use and Care Committee. Immune-compromised 6-8 week old female nu/nu mice purchased from the UCSD Animal Care Program breeding colony were injected subcutaneously into the bilateral upper thighs with 5 million HCT-116 or PANC-1 tumor cells in 1:1 Matrigel (BD) and PBS solution. After tumors grew to >200 mm$^3$, the right tumor bearing hindlimb was focally irradiated while the remainder of the mouse including the left tumor bearing hindlimb were shielded from IR with custom designed lead blocking >95% of the dose as verified by dosimeters placed on the mouse. One day post IR, tumor xenografts were tail vein injected with either fluorescently (Cy5 and Cy7) labeled ratiometric ACPP or ACPP-cRGD-MMAE in anesthesized mice (1:1 of ketamine (100 mg/ml) and midazolam (5 mg/ml). For ACPP-cRGD-MMAE, 10 nmoles was injected by tail vein and animals images 6 hours later using Maestro Small Animal Imager with excitation filter of 620/22 nm and 645 nm log pass emission filter with dichroic filter tuned to 670 nm. Imaging was done both with skin on and after skin removal.

In Vivo Tumor Xenograft Experiments:

HCT-116 or PANC-1 tumor xenografts were established and tumor growth was measured with digital calipers. Tumor volume was calculated using the formula as ½*Length*Width$^2$. Mice were randomized into groups once the average tumor volume reached 250 mm$^3$. Mice were assigned to groups: Vehicle, ACPP-cRGD-MMAE, fractionated IR or the combination. ACPP-cRGD-MMAE lyophilized powder was suspended in sterile deionized water just prior to tail vein injection. MMAE doses and IR fractionation are as indicated in the Results.

Results

Cytotoxicity of MMAE Against Gastrointestinal Tumor Cell Lines.

Figure 3A:
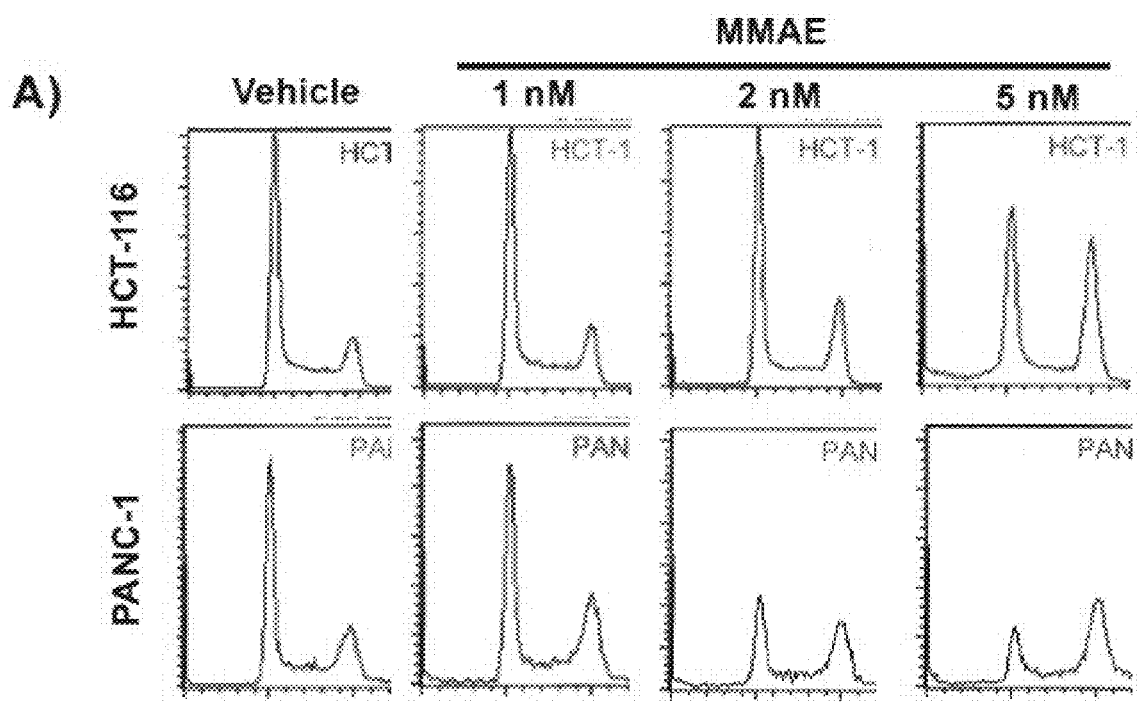
FIG. 3A-D: MMAE is an anti-mitotic agent with increased potency compared to paclitaxel in gastrointestinal tumor cells A) HCT-116 (top panel) and PANC-1 (bottom panel) cells were exposed to 0, 1, 2 and 5 nM of MMAE overnight. Cells were collected, stained with PI and cell cycle analyzed by FACS. B, C) HCT-116 and PANC-1 tumor cells were exposed to dose range of MMAE or paclitaxel for 72 hours. Cell viability was normalized to vehicle treated cells and plotted as percent survival±SD. D) $IC_{50}$ of MMAE and paclitaxel in HCT-116, PANC-1, and 779E cells. Data is plotted as mean $IC_{50}$±SD from triplicates.

The ability of MMAE to block proliferating tumor cell in G$_2$/M was first tested. Established tumor cell lines (HCT-116 and PANC-1) were exposed to varying doses of MMAE for 24 hrs and then the cells were collected. Cell cycle analysis was performed by FACS analysis using PI staining. HCT-116 and PANC-1 cells showed a dose response block of cells in the G$_2$/M phase of the cell cycle, with PANC-1 cells more sensitive to MMAE than HCT-116 cells (FIG. 3A). A dose of 5 nM MMAE resulted in 50% of HCT-116 cells blocked in G$_2$/M, while in PANC-1 cells a dose of 2 nM of MMAE produced a similar G$_2$/M block.

Figure 3B:
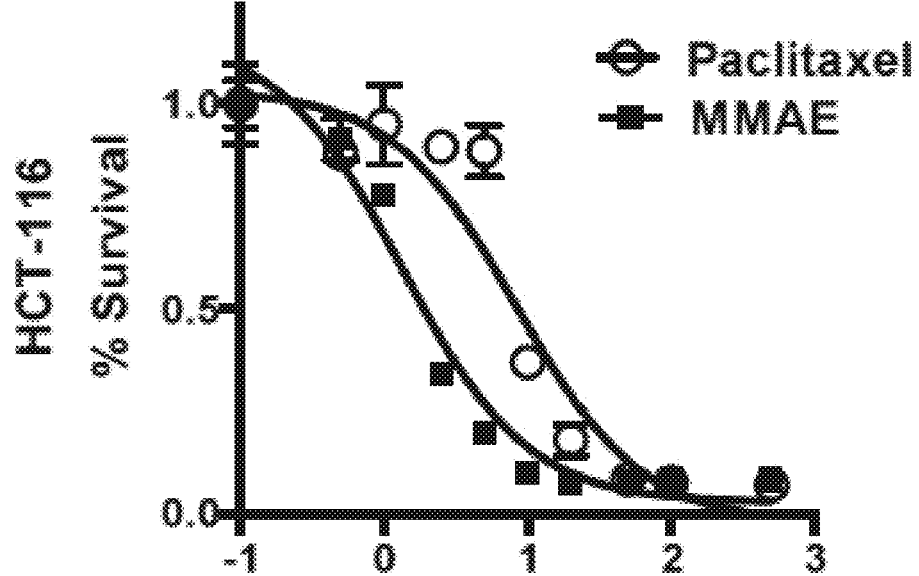
Figure 3C:
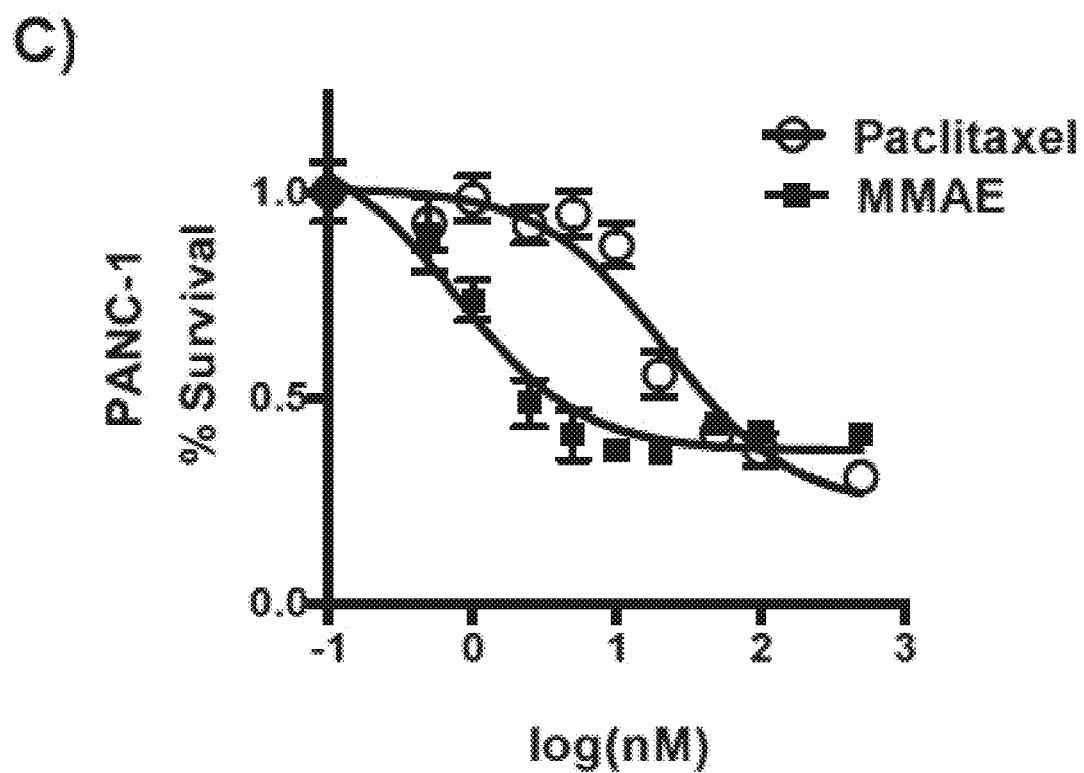
Figure 3D:
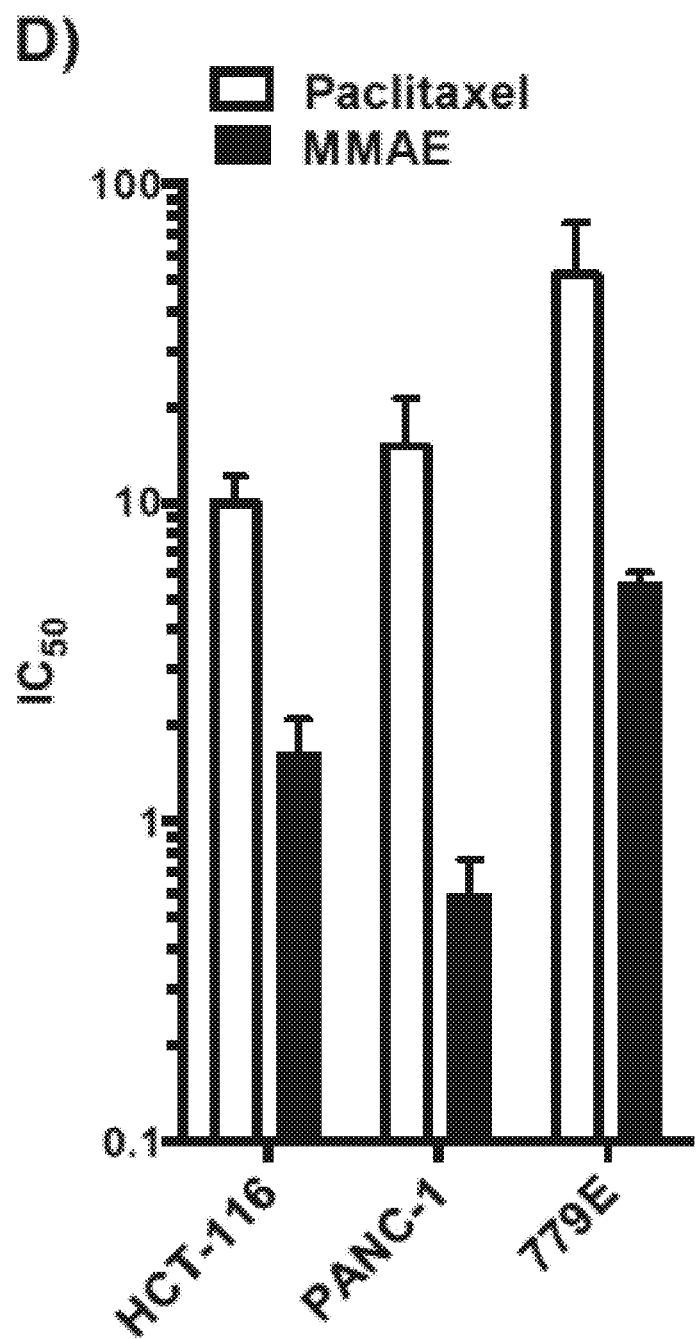

We next compared the cytotoxicity of MMAE to the anti-mitotic chemotherapy agent, paclitaxel. Tumor cell lines and were exposed to varying concentrations of MMAE or paclitaxel for 72 hours. Cell viability was assessed by Alamar Blue assay. For HCT-116, the IC$_{50}$ for paclitaxel compared to MMAE were 10.04 nM and 1.66 nM, p=0.003 (FIG. 3B, D). For PANC-1, the IC$_{50}$ for paclitaxel compared to MMAE were 15.09 nM and 0.60 nM, p=0.014 (FIG. 3C, D). We also tested a limited passage human pancreatic tumor cell line, 779E. While 779E was more resistant to antimitotic agents, it also showed increased cytotoxicity to MMAE compared to paclitaxel. The $IC_{50}$ following paclitaxel or MMAE exposure were of 51.95 nM and 5.61 nM respectively, p=0.028 (FIG. 3D).

Radiosensitization of Gastrointestinal Tumor Cell Lines by MMAE

Figure 4A:
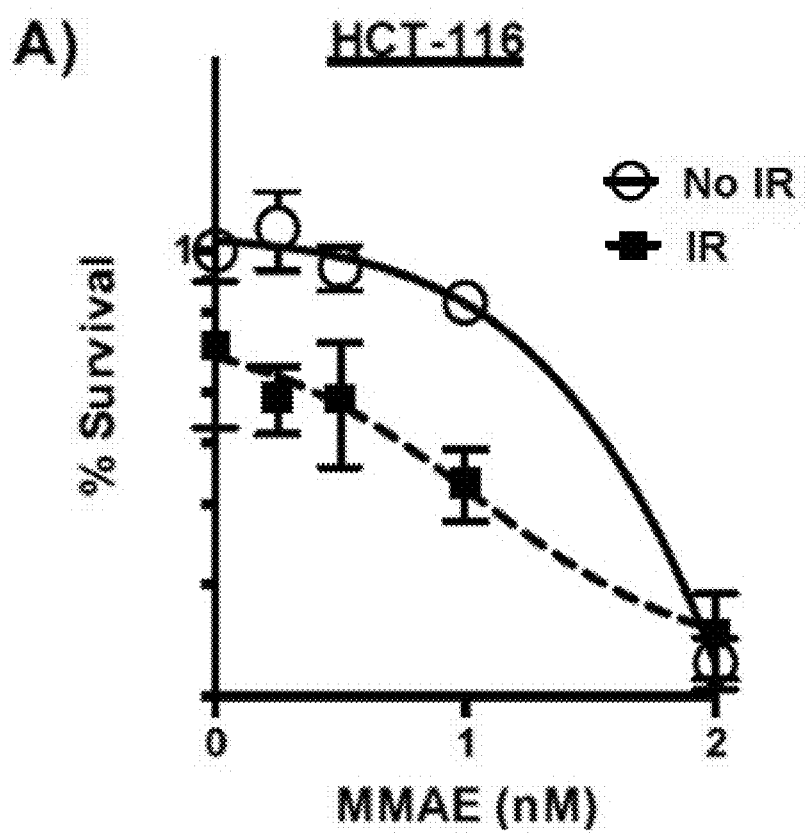
FIG. 4A-F: MMAE radiosensitizes gastrointestinal tumor cells. A, B) HCT-116 and PANC-1 cells were exposed to varying concentrations of MMAE overnight followed by 6 Gy. Cell viability was measured at 72 hrs. Cell viability was normalized to vehicle treated, non-irradiated cells and plotted as percent survival±SD. C, D) Clonogenic survival assay to measure radiosensitization. HCT-116 and PANC-1 cells were treated with 5 and 2 nM MMAE respectively overnight. Cells were then irradiated. Cells were re-plated in drug free media and colonies were allowed to grow out over 10-14 days. Colonies were counted and survival was normalized for both vehicle and MMAE treated cells to non-irradiated groups. Data is plotted as mean surviving fraction±SD. E, F) The effect of MMAE with 2 Gy on cell survival was measured by clonogenic survival. Cell were treated with 0-5 nM MMAE overnight and then exposed to 2 Gy. Cells were re-plated in drug-free media and colonies allowed to form over 10-14 days. Survival was normalized to non-irradiated cells for each concentration of MMAE. Data is plotted as mean survival±SD.
Figure 4B:
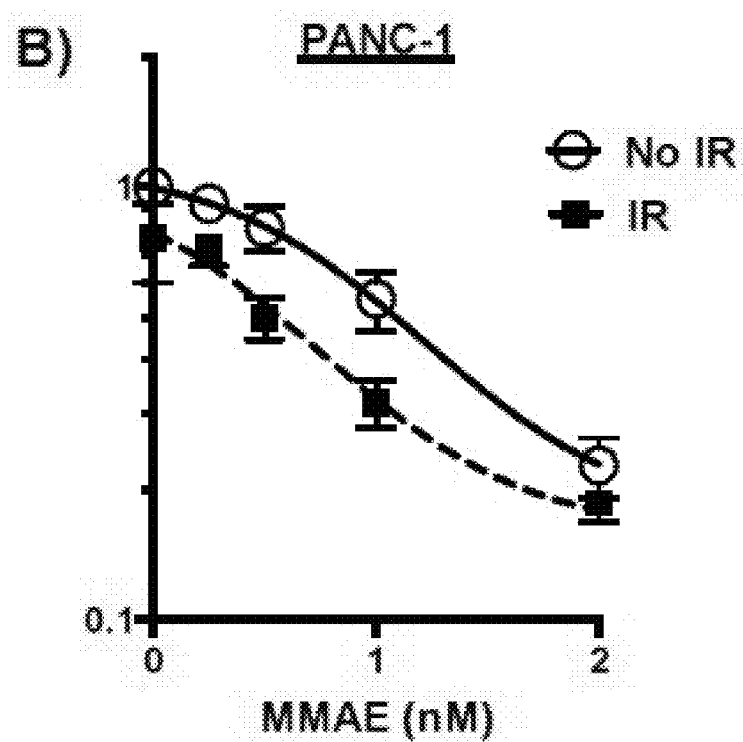

Since MMAE is a potent cytotoxic agent that blocks tumor cells in the radiosensitive $G_2/M$ phase of the cell cycle, we then tested the efficacy of combining IR and MMAE on tumor cell kill. In the first series of experiments, HCT-116 and PANC-1 tumor cell lines were incubated with varying doses of MMAE overnight and then irradiated with 6 Gy the following day. Cells were left in continuous exposure to MMAE, and tumor cell viability was measured 72 hours after initiation of MMAE treatment. In HCT116 cells, the $IC_{50}$ for MMAE decreased from 1.58 nM for MMAE alone treated cells to 0.78 nM in cells treated with MMAE and IR (FIG. 4A). In PANC-1 cells, a similar relative >50% reduction in the $IC_{50}$ of MMAE was observed from 0.81 nM in MMAE alone treated cells to 0.35 nM when IR was combined with MMAE (FIG. 4B).

Figure 4C:
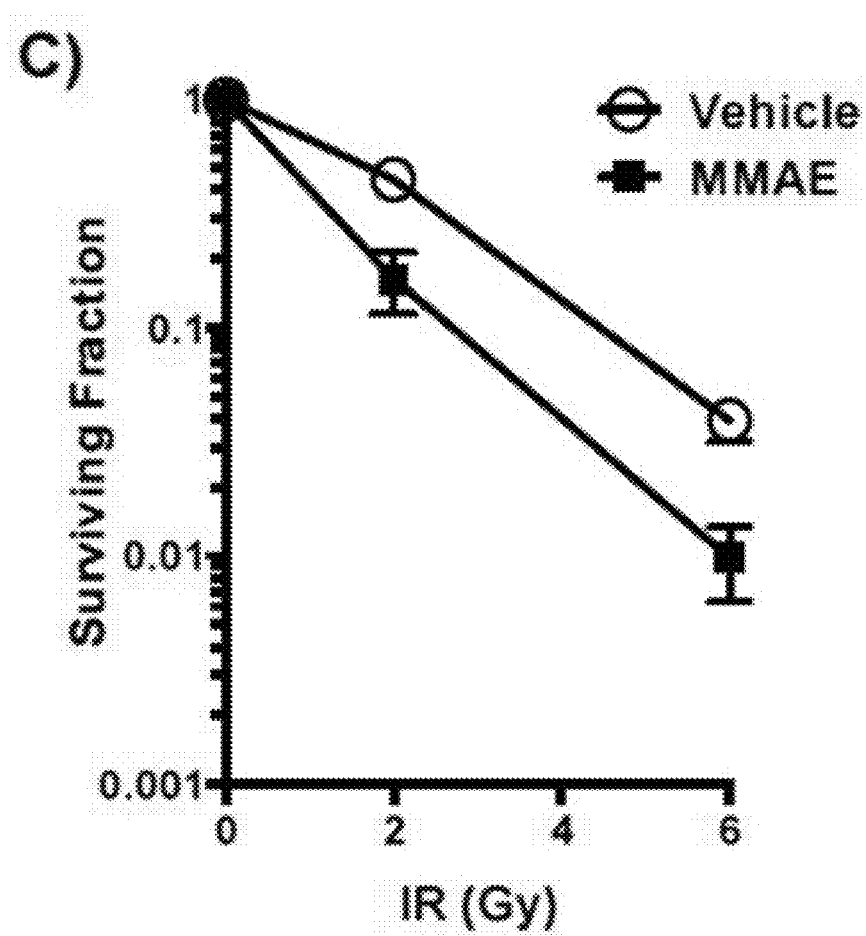
Figure 4D:
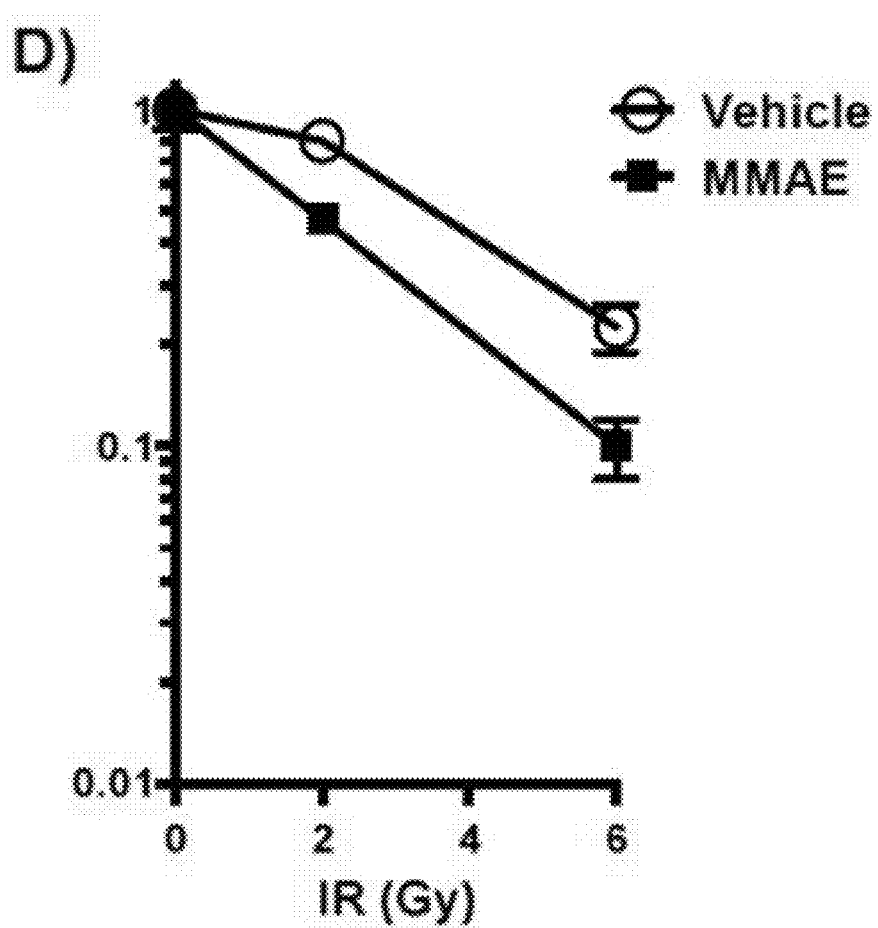
Figure 4E:
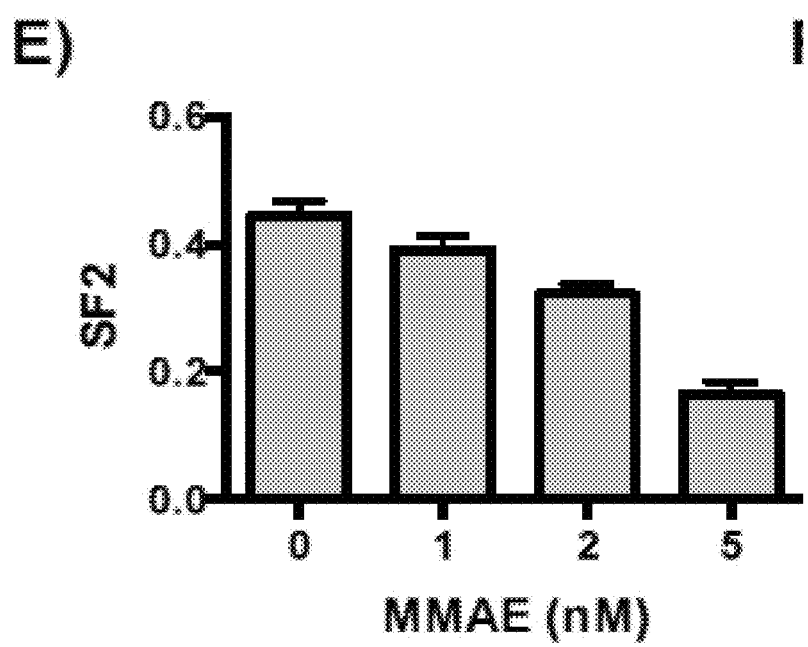
Figure 4F:
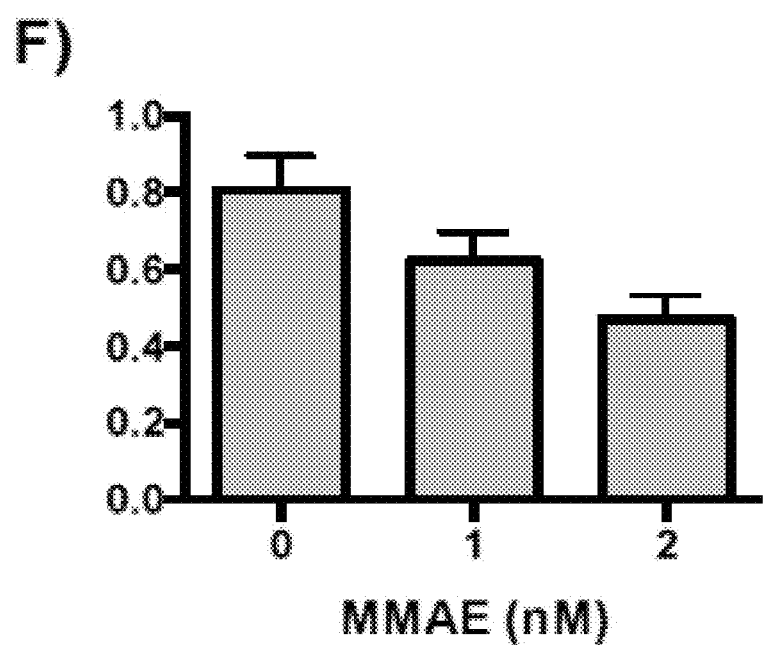

The primary mode of cell death following ionizing radiation is mitotic catastrophe through the DNA double strand breaks. Therefore, we first tested the ability of MMAE to radiosensitize tumor cells using clonogenic assays. HCT-116 or PANC-1 cells were exposed to MMAE overnight and then irradiated with 0, 2 or 6 Gy. Cells were then re-plated in drug free media at low cell density and colonies allowed to grow out over the following 10-14 days. Cell surviving fraction was normalized to 1 for non-irradiated cells treated with either vehicle or MMAE. Both HCT-116 and PANC-1 cells showed loss of the shoulder region of the survival curve at 2 Gy when pre-treated with MMAE compared to vehicle (FIG. 4C, D). Conventionally fractionated radiotherapy for locally advanced gastrointestinal tumors is often given with 2 Gy concurrently with chemotherapy. In tumor cells treated with 2 Gy, the surviving fraction by clonogenic assay (SF2) showed a dose response to overnight pre-exposure to MMAE. For HCT116, the SF2 for cells treated with 1 nM MMAE was not significantly different from vehicle treated cells. However, at doses of 2 and 5 nM MMAE there was a significant reduction in the SF2 compared to cells irradiated with vehicle, p<0.01 (FIG. 4E). Consistent with our above results with MMAE alone, PANC-1 cells were radiosensitized at lower doses of MMAE. The SF2 in PANC-1 cells was significantly reduced with 1 or 2 nM of MMAE compared to vehicle treated cells, p<0.01 (FIG. 4F). Too few colonies formed when PANC-1 cells were treated with 5 nM MMAE.

Figure 5A:
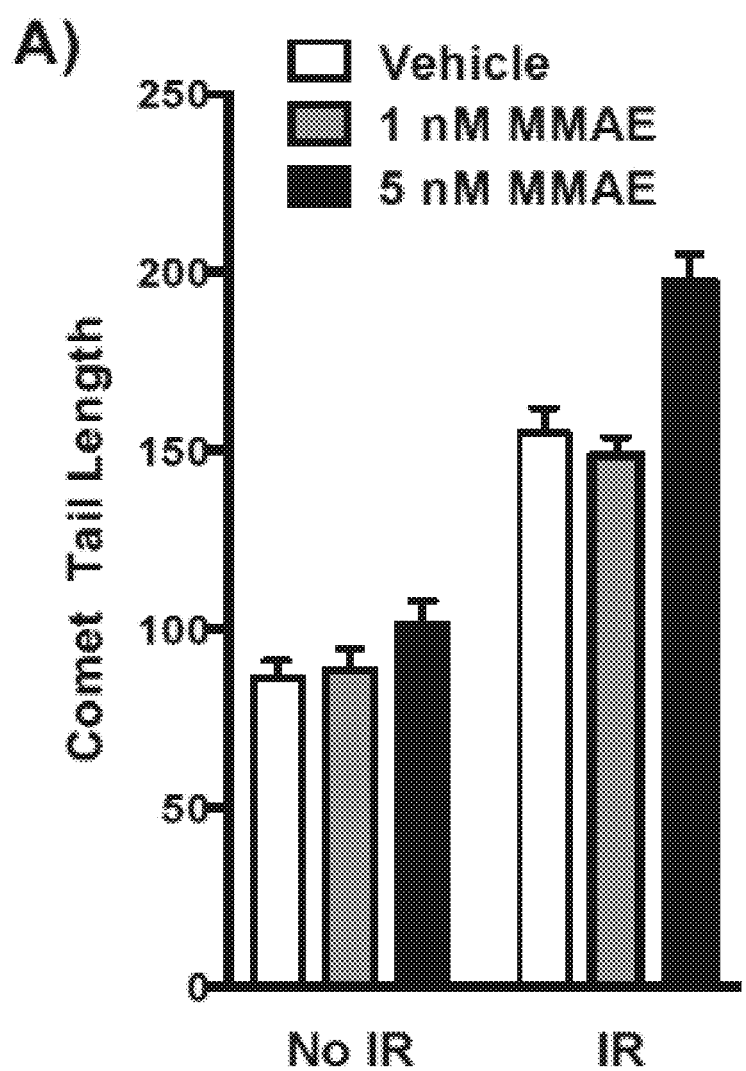
FIG. 5A-D: MMAE enhances radiation mediated DNA double strand break damage in gastrointestinal tumor cells. A, B) HCT-116 cells were treated with 0, 1, or 5 nM MMAE overnight and then irradiated with 6 Gy. Cells were collected 15 minutes post IR and DNA double strand breaks were quantitated using neutral comet assay to measure comet tail length. Data is plotted as mean comet tail length±SEM. Representative images from comet tail assay are shown for MMAE dose of 5 nM. C, D) PANC-1 cells were treated overnight with 1 nM of MMAE followed by 6 Gy. Cells were fixed 2 hours post IR and analyzed for γH2Ax foci formation by immunostaining (green). Nuclei were stained with DAPI (blue). Data are plotted as mean γH2Ax foci/nucleus±SEM. Representative images of γH2Ax foci formation are shown for each treatment group.
Figure 5B:
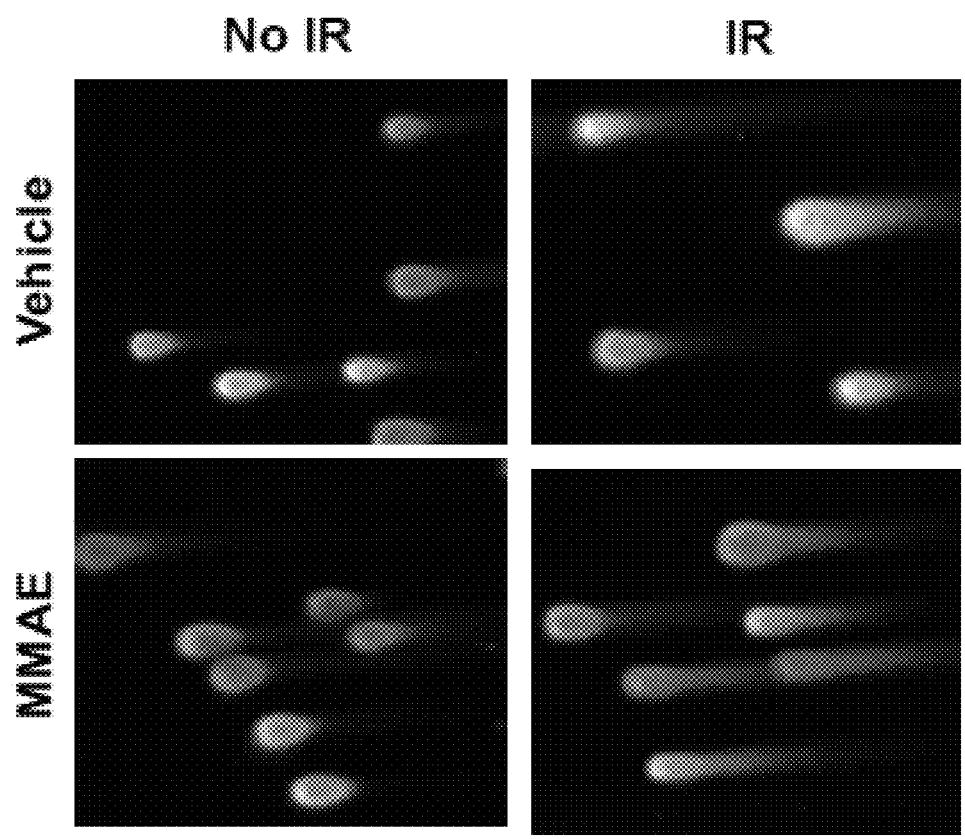
Figure 10:
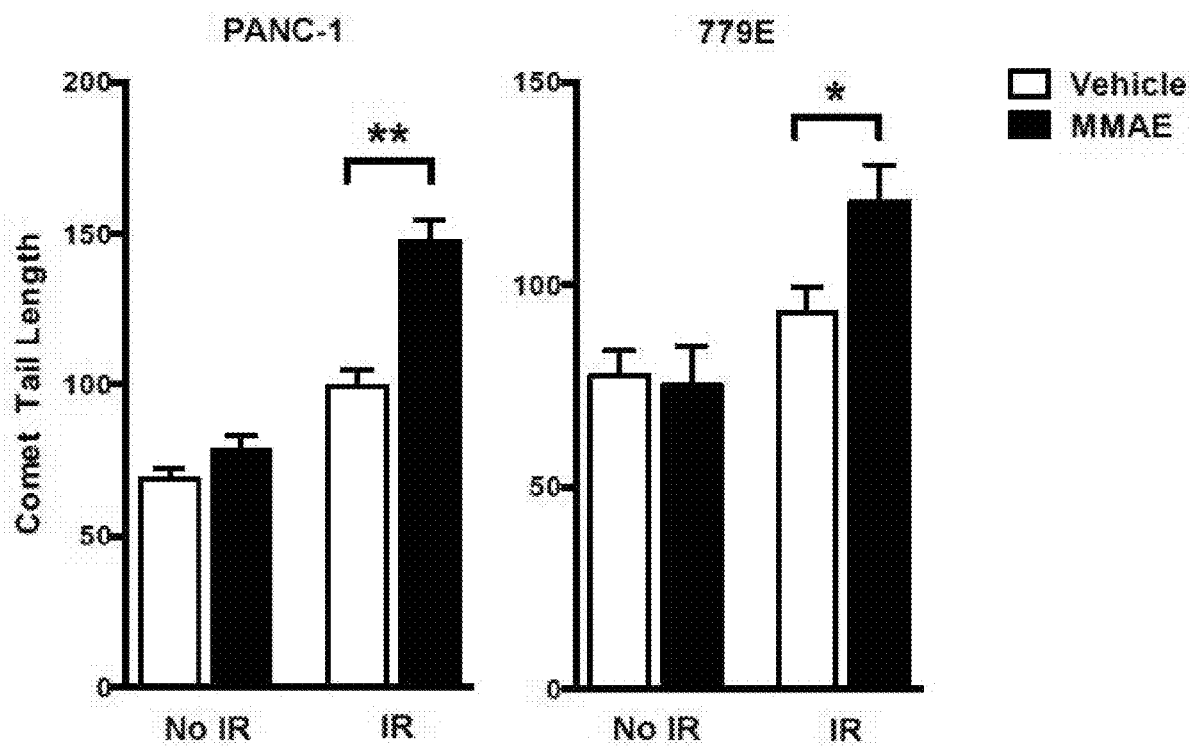
FIG. 10: MMAE enhances comet tail length following irradiation in pancreatic tumor cell lines. PANC-1 and 779E cells were treated with 0 or 1 nM MMAE overnight and then irradiated with 2 Gy. Cells were collected 15 minutes post IR and DNA double strand breaks were quantitated using neutral comet assay to measure comet tail length. Data is plotted as mean comet tail length±SEM, **$p<0.0001$, *$p=0.014$.

Since MMAE reduced clonogenic cell survival following IR, we then evaluated the ability of MMAE to modulate IR induced DNA double strand breaks through neutral comet assay or histone 2A phosphorylation on S139 ($\gamma$H2AX). Tumor cells were pre-treated with MMAE followed by IR. In non-irradiated HCT-116 cells, overnight exposure to 1 or 5 nM MMAE had no significant effect on comet tail length compared to vehicle treated cells (FIG. 5A, B). In vehicle treated cells, irradiation resulted in increased comet tail length compared to non-irradiated cells, p<0.0001. While pre-treating HCT-116 cells with 1 nM MMAE did not significantly increase IR alone induced comet tail length, 5 nM MMAE did result in a significant increase in IR mediated double-stranded DNA breaks compared to vehicle treated irradiated cells, p<0.0001. These results are consistent with dose response effects of MMAE on clonogenic survival (FIG. 4E). A similar increase in comet tail length in cells treated in combination with MMAE and IR was seen with PANC-1 and 779E cells (FIG. 10).

Figure 5C:
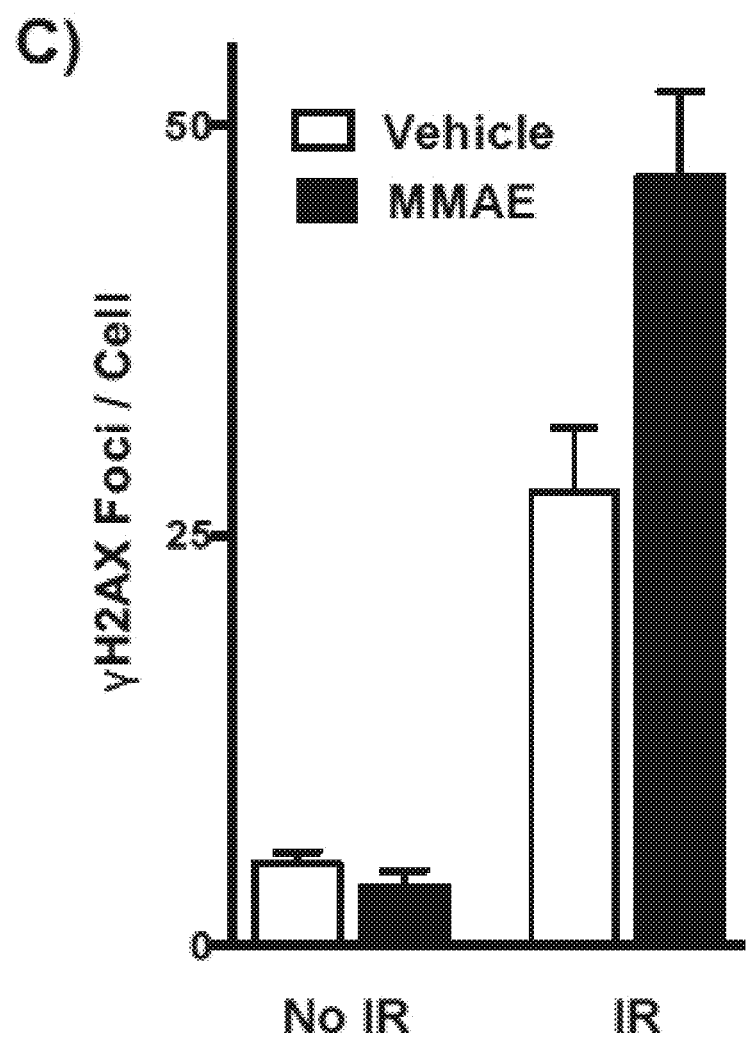
Figure 5D:
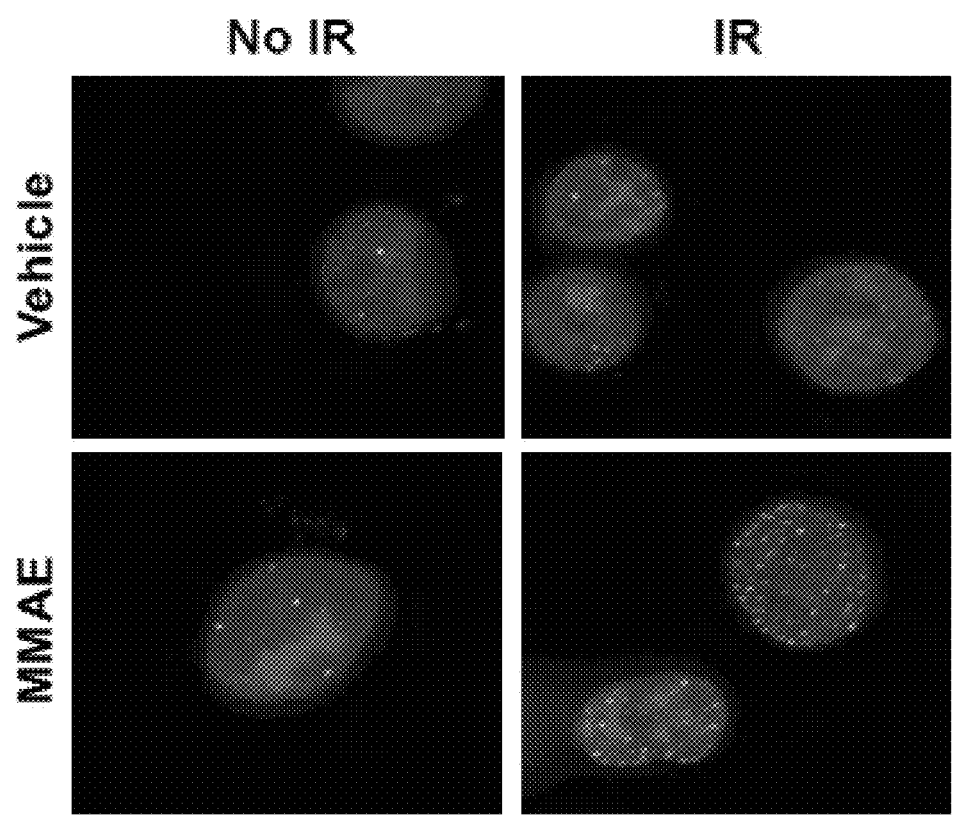
Figure 11:
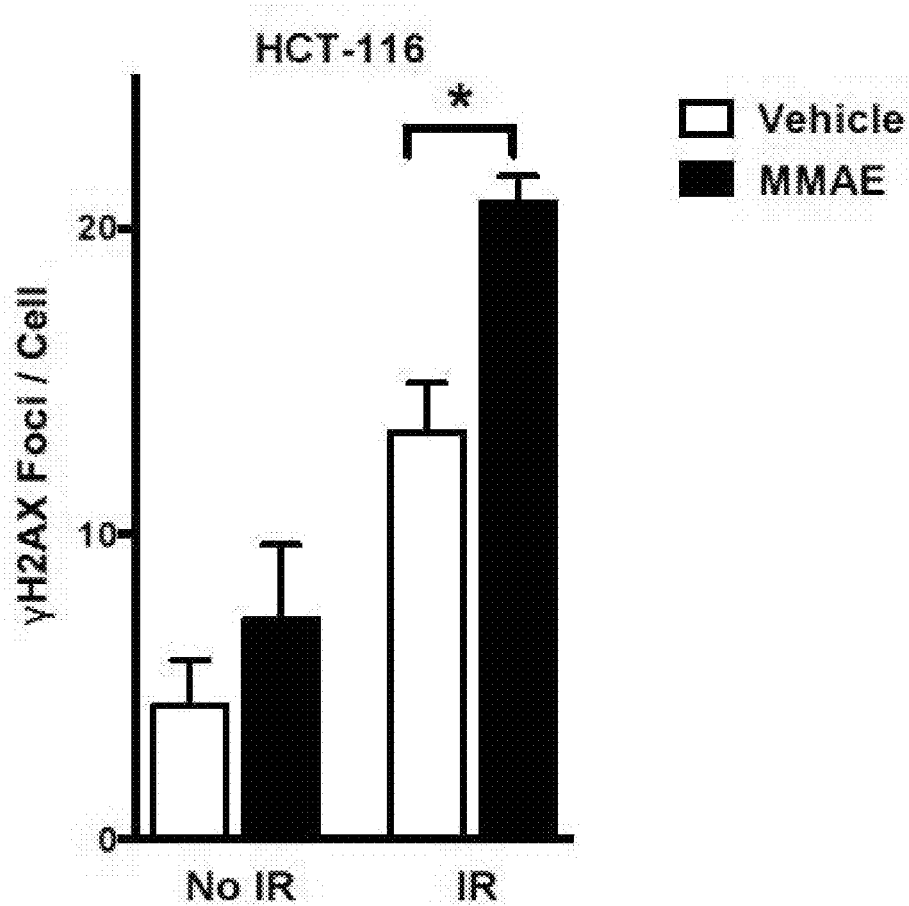
FIG. 11: MMAE enhances γH2Ax foci formation following irradiation. HCT-116 cells were treated overnight with 2 nM of MMAE followed by 2 Gy. Cells were fixed 2 hours post IR and analyzed for γH2Ax foci formation by immunostaining (green). Nuclei were stained with DAPI (blue). Data are plotted as mean γH2Ax foci/nucleus±SEM, *$p=<0.01$.

The ability of MMAE to increase IR induced DNA double strand breaks was validated through $\gamma$H2AX foci formation. In non-irradiated PANC-1 cells, MMAE did not significantly increase baseline $\gamma$H2AX staining compared to vehicle treated cells (FIG. 5C, D). In vehicle treated cells, IR significantly increased $\gamma$H2AX staining compared to non-irradiated cells, p<0.001. As observed with a neutral comet assay, pre-treating cells with MMAE followed by irradiation, resulted in a further significant enhancement of IR induced DNA double strand breaks as measured by $\gamma$H2AX foci formation was also seen in HCT-116 cells pre-treated with MMAE and followed by IR (FIG. 11).

Figure 6A:
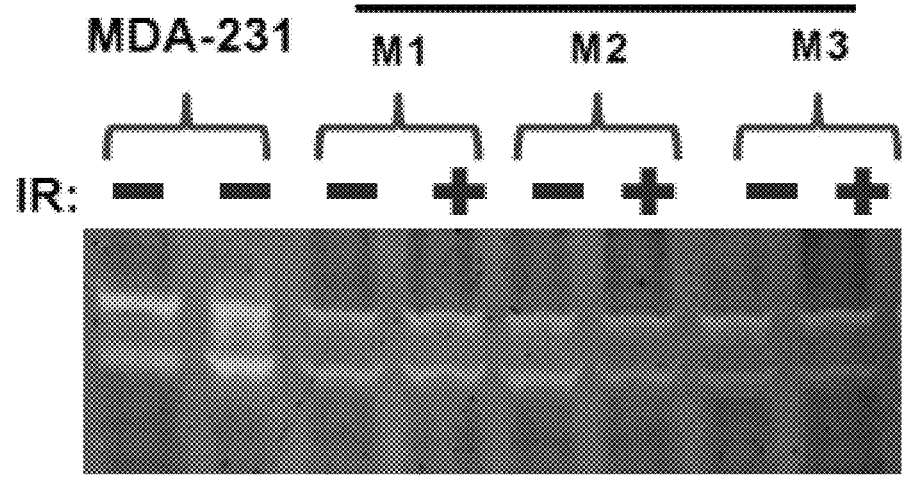
FIG. 6A-C: Gastrointestinal tumor xenografts have gelatinase activity and activate RACPP. HCT-116 or PANC-1 tumor xenografts were grown in both the left and right hindlimbs of nude mice. The right tumor was irradiated and the left tumor was shielded to block out >95% of the IR dose A, B) Zymography gels were used to asses MMP activity in non-irradiated and irradiated tumor xenografts. Non-irradiated MDA-MB-231 xenografts served as positive control for gelatinase activity. C) One day post IR, ratiometric ACPP was intravenously injected and Cy5:Cy7 emission ratio measured 2 hours later (pseudocolor scale at far right) by whole animal imaging with tumors in situ and after tumor excision.

Gastrointestinal Tumor Xenografts Express Protease Activity Against PLGC(Me)AG-ACPP Peptide Linker While MMAE is a potent cytotoxic molecule in cell culture and an effective radiosenstizer, normal tissue toxicity is a limiting factor to exploit its therapeutic application following systemic delivery in vivo. To restrict MMAE delivery to tumors following intravenous injection, MMAE has been conjugated to a dual integrin and MMP targeted ACPP, ACPP-cRGD-MMAE. In this molecule, the linker region of ACPP consists of the peptide sequence (SEQ ID NO:4) PLGC(Me)AG and is cleaved by MMP-2 and MMP-9. Therefore, we tested if HCT-116 and PANC-1 tumor xenografts had MMP-2 and MMP-9 activity. MDA-MB-231, HCT-116 and PANC-1 tumor xenografts were harvested and tumor lysates were loaded onto zymogram gels. MDA-231 tumor xenografts served as a positive control as they have been previously shown to have MMP activity by gel zymography. Non-irradiated MDA-MB-231, HCT-116, and PANC-1 tumor lysates all contained gelatinase activity as measured by gel zymography (FIG. 6A, B). We also tested if irradiation of tumor xenografts would alter MMP activity. Tumor xenografts were irradiated with a single dose of 6 Gy and harvested the following day. Irradiation of tumors did not hamper gelatinase activity.

Figure 6B:
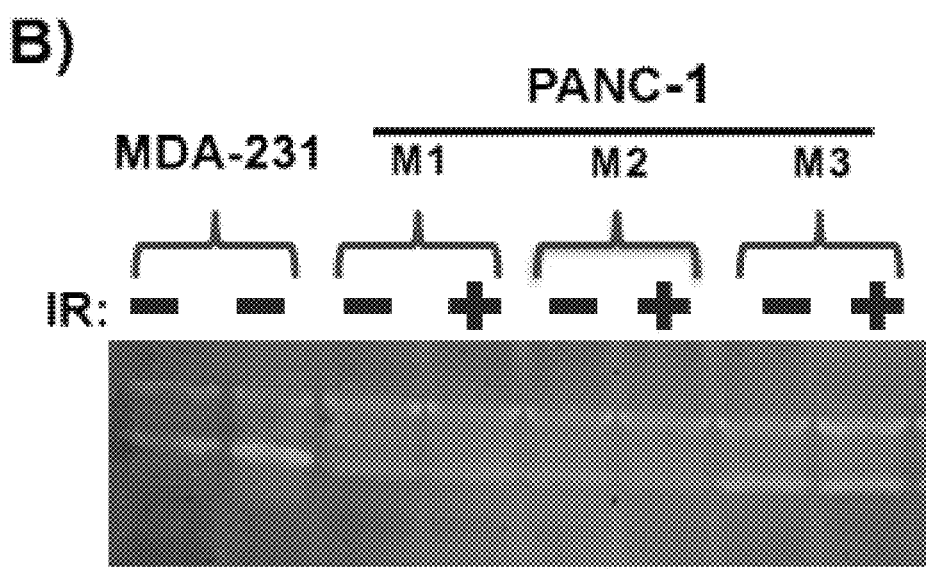
Figure 6C:
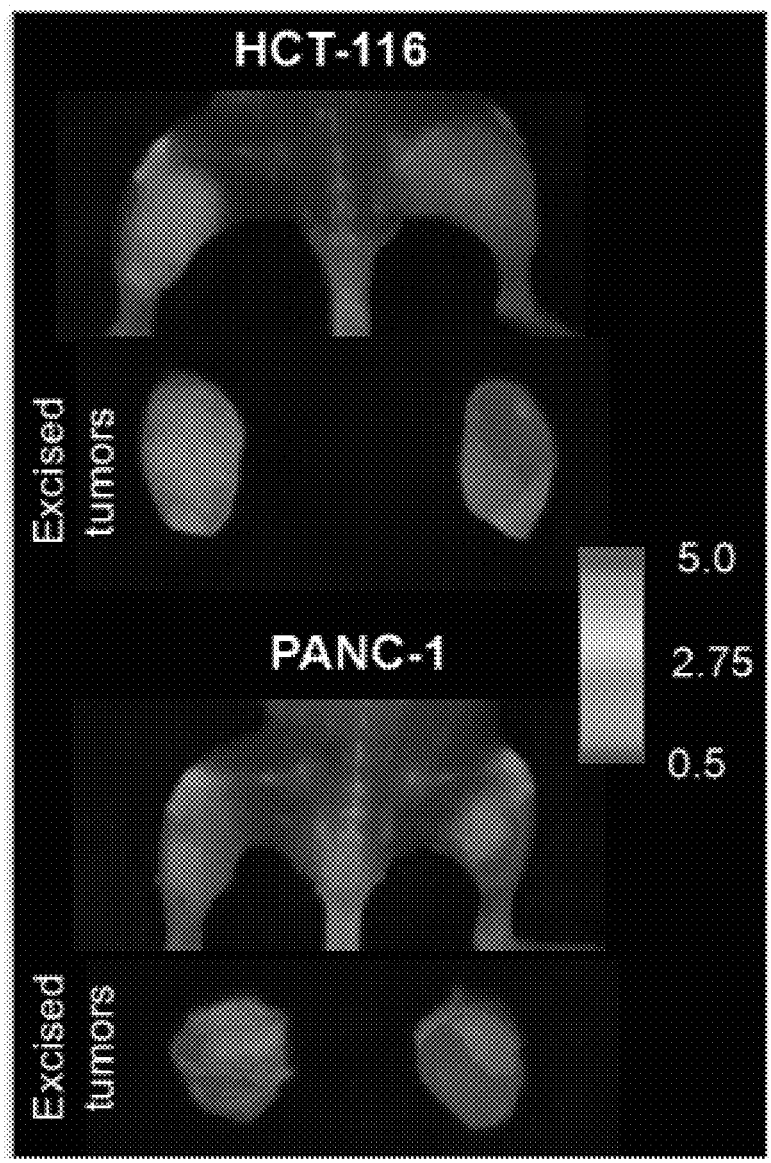
Figure 12A:
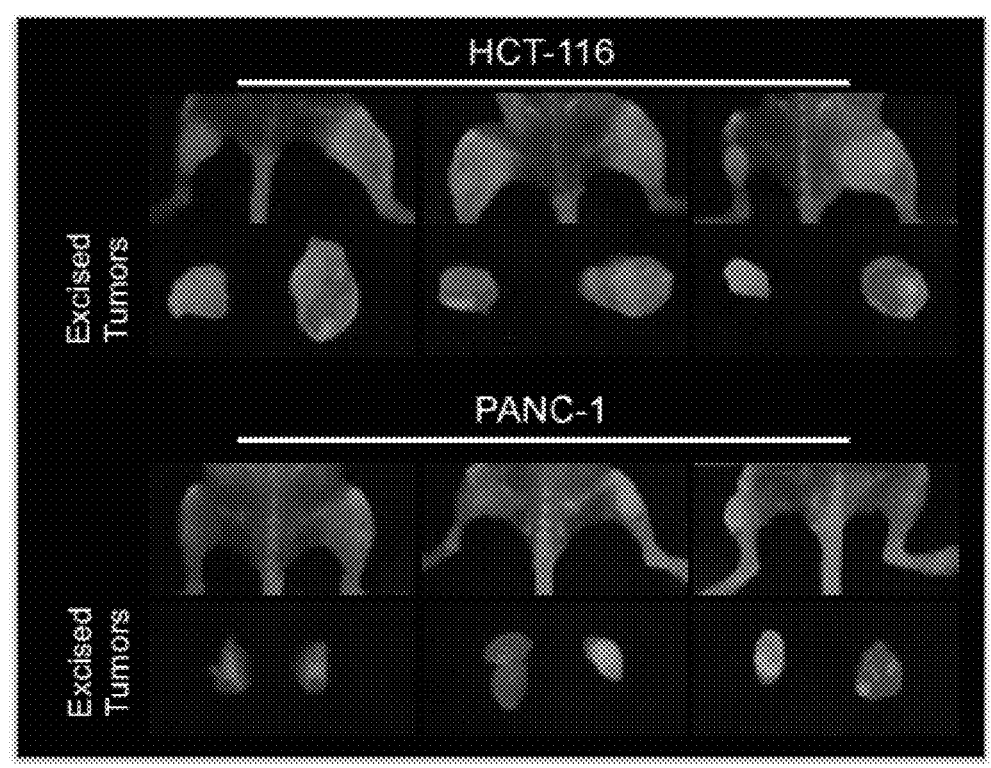
FIG. 12A-B: Gastrointestinal tumor xenografts show cleavage dependent tumor contrast with RACPP. HCT-116 or PANC-1 tumor xenografts were grown in both the left and right hindlimbs of nude mice. The right tumor was irradiated and the left tumor was shielded to block out >95% of the IR dose A) One day post IR, ratiometric ACPP was intravenously injected and Cy5:Cy7 emission ratio measured 2 hours later (pseudocolor scale at far right) by whole animal imaging with tumors "in situ" and after tumor excision. Imaging of an additional 3 mice with HCT-116 and PANC-1 tumor xenografts in addition to the mice shown in FIG. 6C. B) Quantification of Cy5:Cy7 emission ratio in non-irradiated and irradiated tumor xenografts.
Figure 12B:
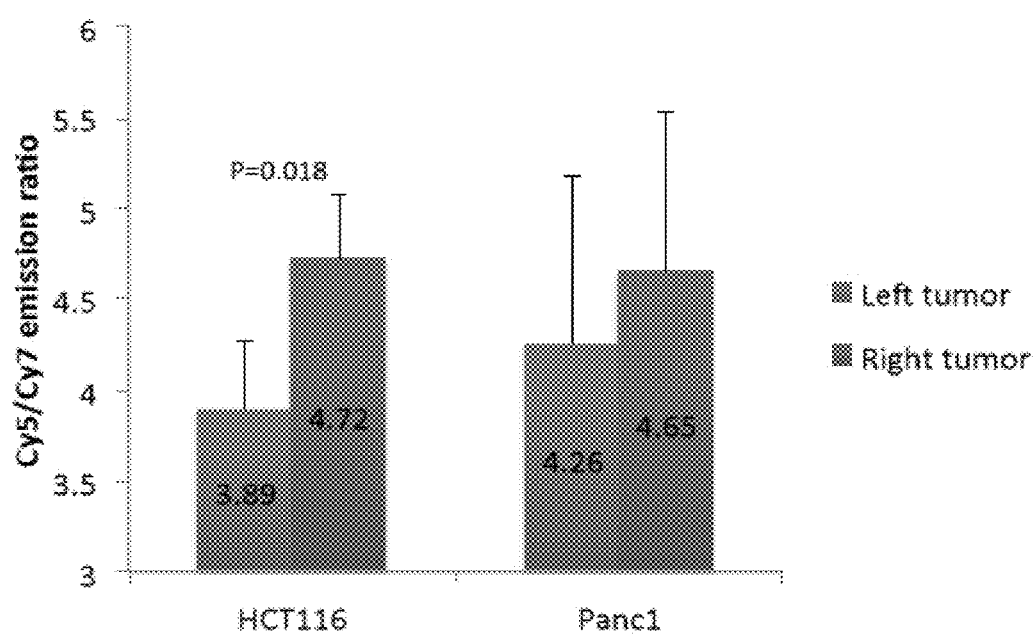

To directly assess if HCT-116 and PANC-1 tumor xenografts are able to cleave the (SEQ ID NO:4) PLGC(Me)AG linker region incorporated into ACPP-cRGD-MMAE, we used a ratiometric ACPP molecule with a (SEQ ID NO:4) PLGC(Me)AG linker[18]. Ratiometric ACPP has a Cy5 far red fluorescent donor and Cy7 near infrared fluorescent acceptor. While intact, the ACPP linker peptide results in Cy5 signal quenching in favor of Cy7 re-emission. However, linker cleavage results in an increase in Cy5:Cy7 emission ratio. Tumor xenografts were grown in the bilateral flank regions of athymic nude mice. The right hindlimb bearing tumor region was irradiated while the left hindlimb tumor was shielded. Ratiometric ACPP (10 nmoles) was injected intravenously the following day and mice were imaged 2 hours later using Maestro (CRI). Tumor xenografts were imaged in situ and after excision. In both HCT-116 and PANC-1 tumor xenografts, tumor xenografts had increase in Cy5:Cy7 emission ratio compared to surrounding normal tissue which is indicative of tumor protease activity to cleave the linker region within the ACPP molecule and release the polycationic cell penetrating peptide (FIG. 6C, FIG. 12A). Irradiation of tumors one day prior to ratiometric ACPP injection did not impede the Cy5:Cy7 emission ratio compared to non-irradiated tumors. Interestingly, there was a non-significant trend towards increase in Cy5:Cy7 emission ratio in irradiated HCT-116 and PANC-1 tumor xenografts compared to non-irradiated tumor xenografts (FIG. 12B).

Figure 7A:
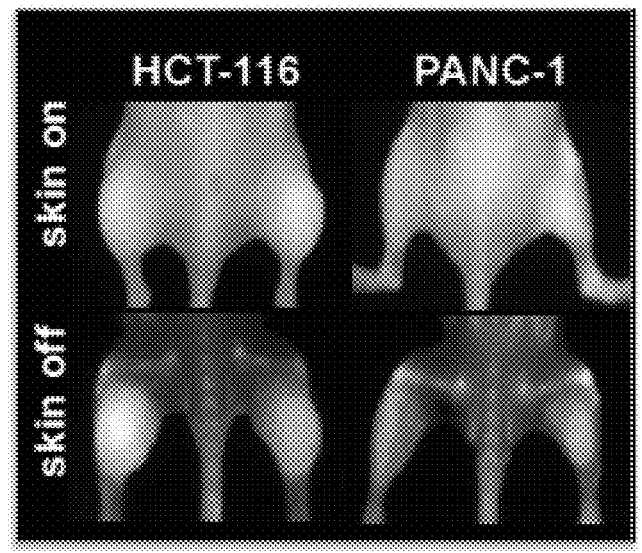
Figure 13:
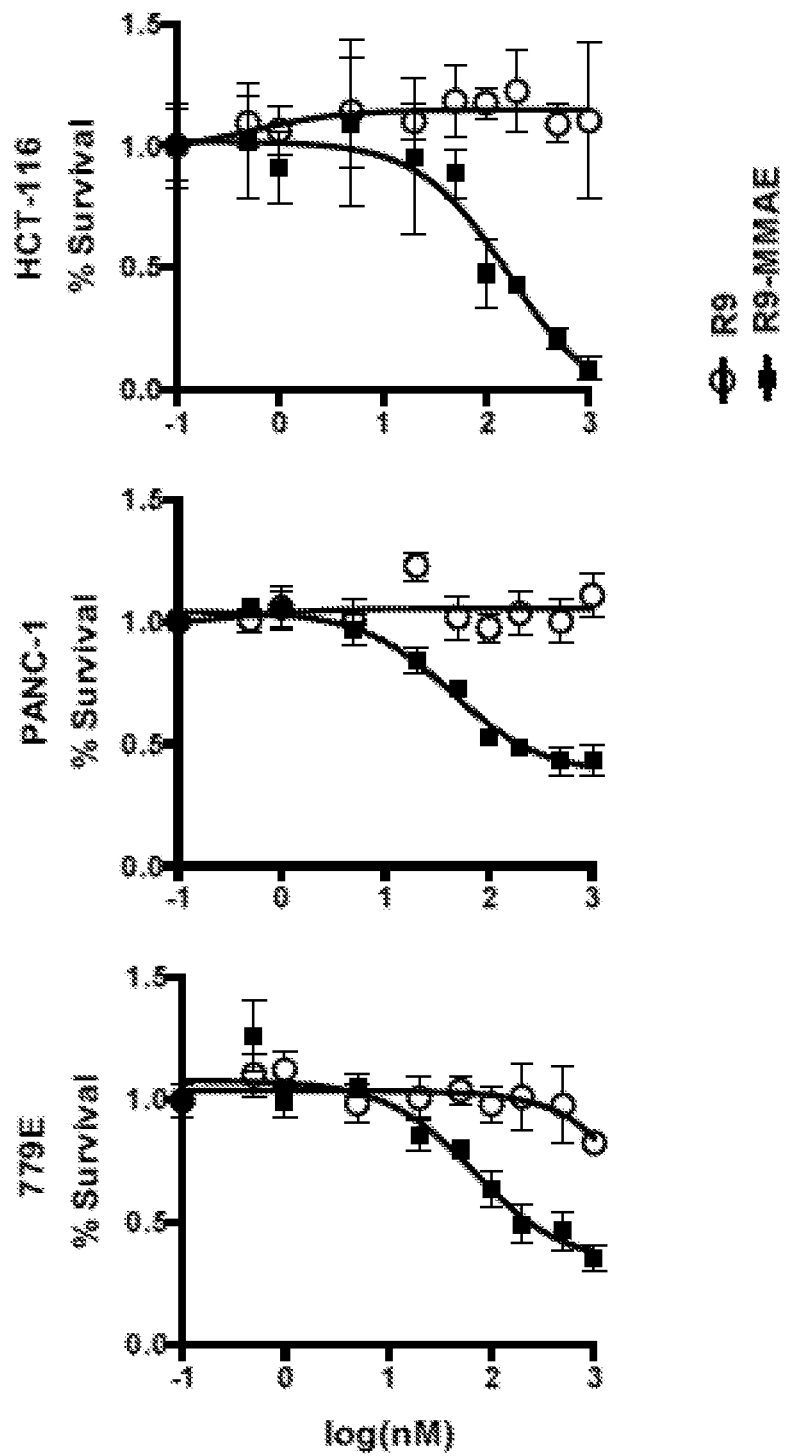
FIG. 13: Polycation conjugated MMAE is cytotoxic to gastrointestinal tumor cells HCT-116, PANC-1, and 779E cells were exposed to polycation alone ($r_9$) or conjugated to MMAE ($r_9$-MMAE) at varying concentrations for 72 hours. Cell viability was assessed by Alamar Blue assay. Cell viability was normalized to vehicle treated cells and plotted as percent survival±SD.

Therapeutic Efficacy of Combining an Integrin and MMP Targeted ACPP-cRGD-MMAE with Ionizing Radiation We next tested the therapeutic paradigm of using of ACPP-cRGD to deliver the potent cytotoxic agent/radiosensitizer, MMAE. First, we validated that MMAE conjugated to the polycation cell penetrating peptide ($r_9$) was cytotoxic to tumor cells. HCT-116, PANC-1 and 779E cells were exposed to varying concentrations of $r_9$ alone or $r_9$ conjugated to MMAE ($r_9$-MMAE). Cell viability was measured 72 hours later. Carrier $r_9$ alone had no cytotoxicity, whereas $r_9$-MMAE was cytotoxic to all three GI tumor cell lines (FIG. 13). We then validated that the integrin and MMP ACPP-cRGD accumulated in HCT-116 and PANC-1 tumor xenografts. ACPP-cRGD with a Cy5 dye attached to the polycation region was intravenously injected. Tumor xenografts were imaged 2 hours later. ACPP-cRGD accumulated in both non-irradiated and irradiated tumor xenografts (FIG. 7A).

Finally, we evaluated the efficacy of combining systemic intravenously injected MMAE with focal IR to inhibit tumor growth. We first tested targeted ACPP-cRGD tumor MMAE delivery compared to non-targeted free MMAE in combination with IR (FIG. 7B). PANC-1 tumor xenografts were grown to a mean of 200 mm³ prior to initiation of therapy. Free MMAE or ACPP-cRGD-MMAE was IV injected on days 0 and 1 (6 nmoles of MMAE/day). Fractionated IR of 3 Gy per day was given on day 1 and 2. On day 1 when MMAE and IR were both given, IR was delivered in the morning and MMAE in the afternoon. By day 20 following initiation of therapy, Two consecutive doses of 6 nmoles of free MMAE resulted in a modest, but statistically significant growth delay of PANC-1 tumor xenografts compared to untreated control tumor xenografts, p<0.01. As predicted from our above experiments in cell culture demonstrating MMAE radiosensitized tumor cells, free MMAE in combination with IR resulted in increased tumor xenograft regression compared to IR or free MMAE alone treated tumor xenografts (p<0.05). These results validate MMAE as a radiosensitizer not only in cell culture but also in a preclinical murine tumor xenograft model.

Next we tested the hypothesis that targeted MMAE delivery would increase IR mediated tumor xenograft regression when compared to free MAME delivery (FIG. 7B). ACPP-cRGD-MMAE resulted in improved tumor xenograft regression compared to free MMAE alone in colorectal and pancreatic tumor xenografts, which is consistent with prior studies with breast cancer models. More importantly in combination with IR, tumor targeted ACPP-cRGD delivery of MMAE resulted in prolonged tumor xenograft regression in contrast to free MMAE (p<0.05). By day 20, 9 of 10 tumor xenografts treated with ACPP-cRGD-MMAE were less than or equal to their starting tumor volume on day 0, when treatment was initiated (FIG. 9). In contrast only 2/10 IR treated and 4/10 free MMAE+IR tumor xenografts regressed. None of the control, free MMAE alone, or ACPP-cRGD-MMAE alone treated tumor xenografts were smaller than their starting tumor volumes. These findings demonstrate the utility of ACPP-cRGD tumor targeted delivery of radiosensitizers.

Figure 7C:
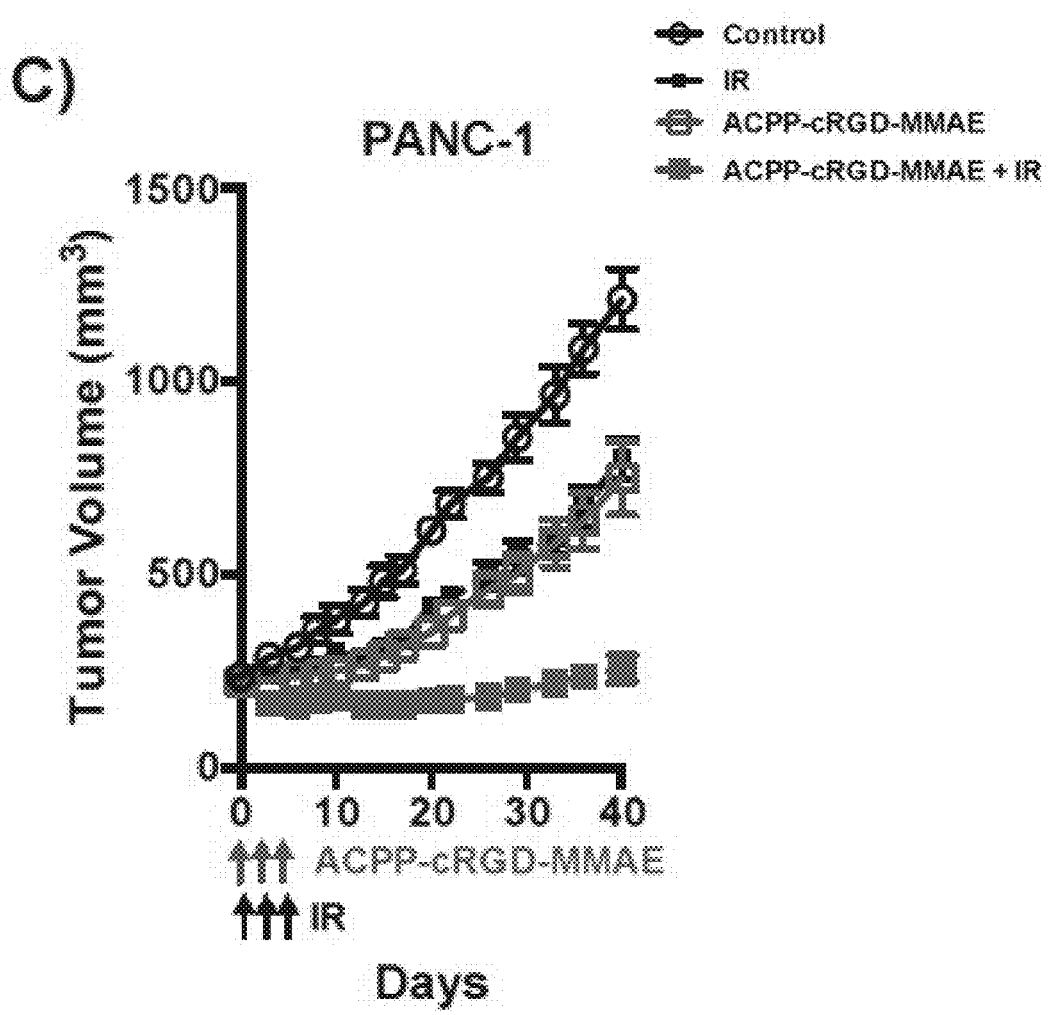

We then confirmed and extended our studies on ACPP-cRGD tumor targeted delivery of MMAE in combination with IR with increased IR fractionation and ACPP-cRGD-MMAE delivery. ACPP-cRGD-MMAE was given on days 0, 1, and 2 (6 nmoles/day, 18 nmoles total). Fractionated IR of 3 Gy per day was given on day 1, 2, and 3. Again on days when ACPP-cRGD-MMAE and IR were both given, IR was delivered in the morning and ACPP-cRGD-MMAE in the afternoon. As we observed above, combining ACPP-cRGD-MMAE with IR again produced significant and sustained tumor regression compared to IR or ACPP-cRGD-MMAE alone treated mice (FIG. 7C). By day 40, tumor volumes in the combined ACPP-cRGD-MMAE and IR mice remained statistically significant compared to all other groups, p<0.0001. More striking and of therapeutic significance, there was prolonged tumor regression in PANC-1 tumor xenografts upon combining ACPP-cRGD-MMAE with IR. By day 40, none of the control or IR alone treated tumors were smaller than their initial tumor volume on day 0 (FIG. 9). For the ACPP-cRGD-MMAE alone group, only 1 of 14 tumor xenografts was smaller than their initial tumor volumes. In contrast, 8 of 14 tumor xenografts in the combined ACPP-cRGD-MMAE and IR group were smaller than their initial tumor volume.

Figure 7D:
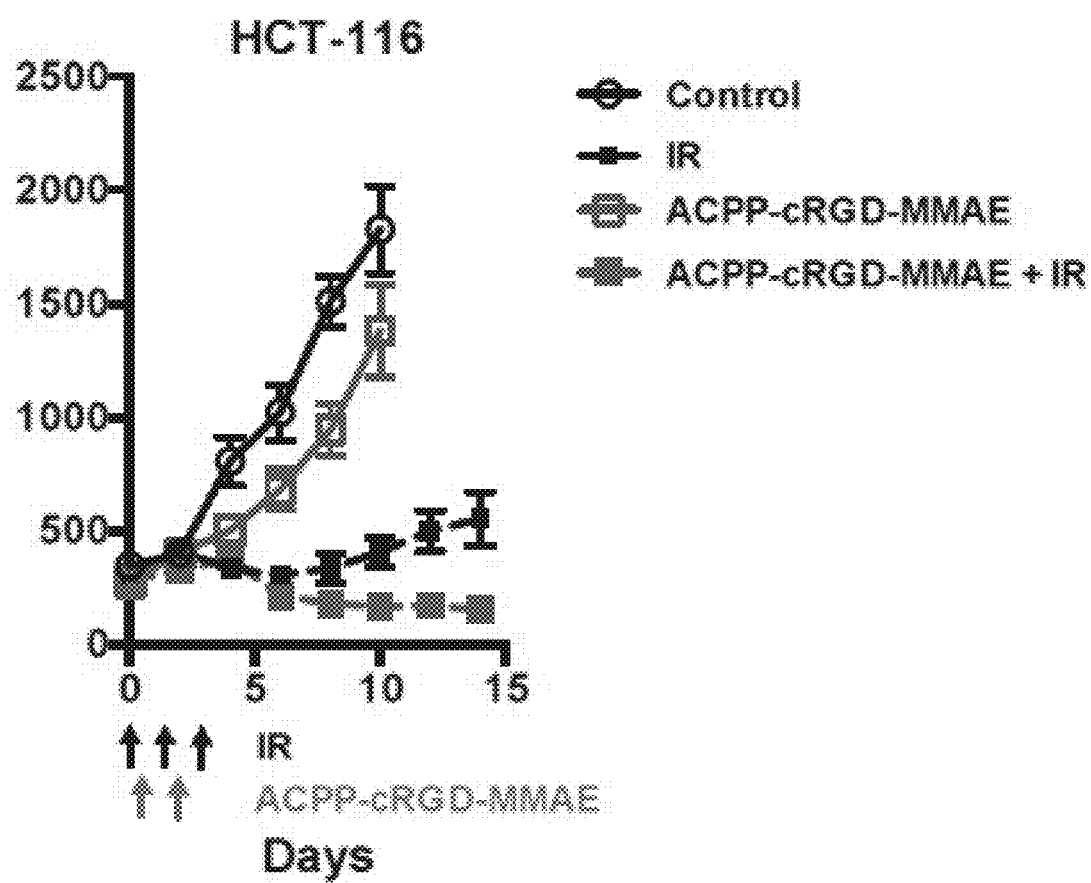

We next tested a different treatment schedule of ACPP-cRGD-MMAE and IR using HCT-116 tumor xenografts. HCT-116 tumor xenografts were grown to mean tumor volume of >270 mm³ prior to initiation of therapy. As shown in FIG. 6C and FIG. 12, 6 Gy of IR given to HCT-116 xenografts improved ratiometric ACPP probe cleavage. Therefore for irradiated mice, 6 Gy was given to irradiated tumor xenografts on day 0 followed by 3 Gy on days 1 and 2. For ACPP-cRGD-MMA, ACPP-cRGD-MMAE was IV injected on days 0 and 1, six hours following irradiation (7.5 nmoles each day). As seen in PANC-1 tumor xenografts, ACPP-cRGD-MMAE alone produced a modest growth delay compared to control untreated tumor xenografts (FIG. 7D). As expected, IR alone resulted in an initial tumor growth delay (especially prominent due to the 6 Gy dose on day 0), however by day 10, tumor volume began to rise. Interestingly, combining ACPP-cRGD-MMAE with IR again produced sustained significant tumor regression compared to IR alone starting at day 10 post initiation of therapy, p<0.006. By day 14, none of the control or ACPP-RGD-MMAE treated tumors were smaller than their initial tumor volume on day 0 (FIG. 9). For the IR alone group, only 3 of 10 tumor xenografts were smaller than their initial tumor volume. In contrast, 9 of 10 tumor xenografts in the combined ACPP-cRGD-MMAE and IR group were smaller than their initial tumor volume.

Discussion

Figure 8:
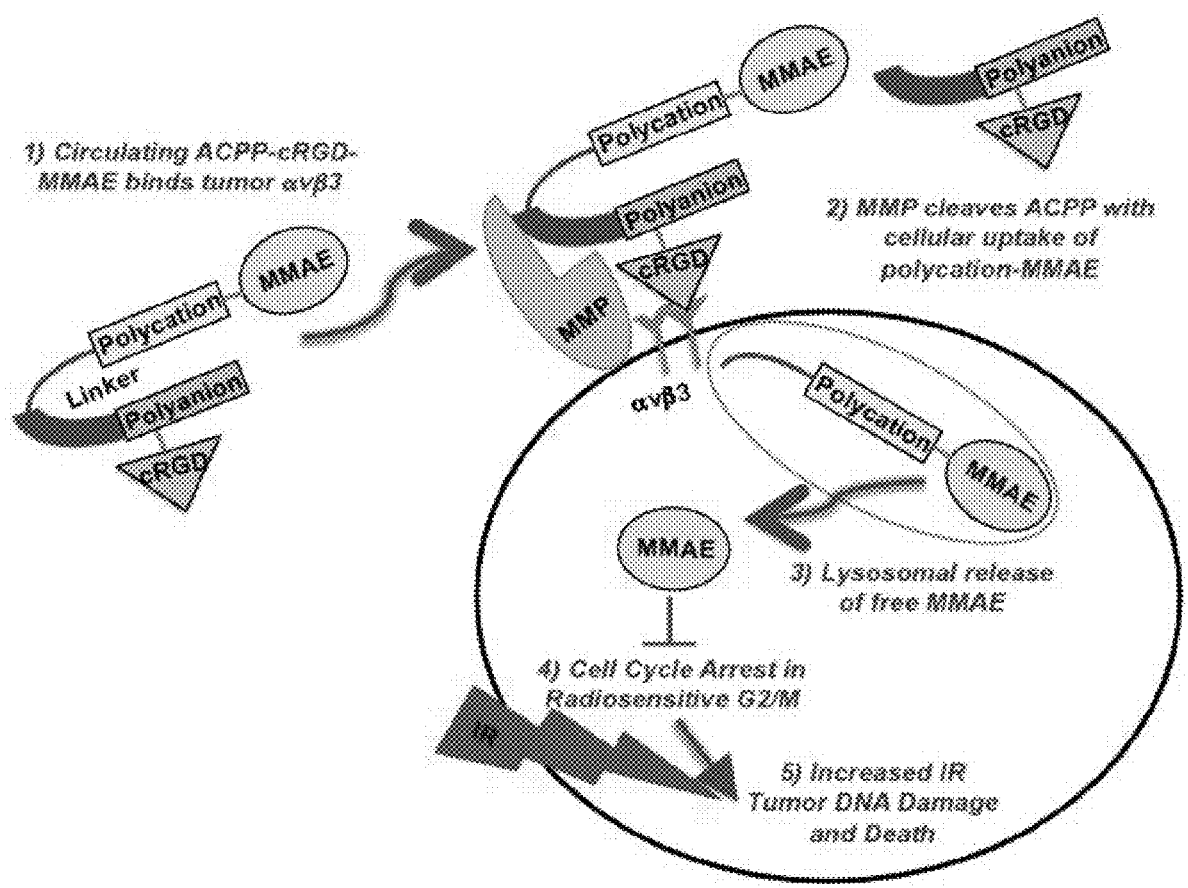
FIG. 8: Schematic model of combining tumor targeted ACPP with radiosensitizer delivery.

In these studies we have identified a new potent radiosensitizer that can be selectively delivered to tumor xenografts using activatable cell penetrating peptides (FIG. 8). We have discovered that MMAE, a synthetic derivative of dolastatin 10, sensitizes GI cancer cells to IR. Intrinsic tumor cell resistance to IR is dependent on a multitude of factors, including DNA repair pathways, tumor oxygenation status and cell cycle. By pharmacologically targeting these pathways, cells become more sensitive to the effects of IR. An optimal therapeutic agent to kill and radiosensitize tumors would have both single agent tumoricidal activity and also sensitize tumors to IR mediated cell death. MMAE is a candidate drug that meets such requirements, which we tested in gastrointestinal tumors including a limited patient passage patient derived pancreatic adenocarcinoma, MMAE had an $IC_{50}$ that is at least 6 fold lower than paclitaxel. Treating cancer cells with MMAE blocked cells in $G_2/M$ and increased IR induced DNA damage in a dose dependent manner with decreased clonogenic tumor cell survival. MMAE radiosensitized pancreatic and colorectal tumor cells in the 1-5 nM range indicating a dual therapeutic benefit. Since paclitaxel is routinely used in patients treated with radiotherapy, our results predict that there could be improved patient outcomes if MMAE was used instead of paclitaxel as a radiosensitizer.

We also have discovered that MMP and αvβ3 targeted ACPP delivery of radiosensitizers improves tumor xenograft regression in combination with focal IR. A major limitation to the therapeutic utility of radiosensitizers is the lack of tumor specific delivery. Radiosensitizer delivery that is non-targeted results in increased radiosensitization of not only tumor cell, but also the surrounding normal tissue. This results in no net gain in the therapeutic index of radiotherapy. Previous reports have tested nanoparticles as radiosensitizer delivery vehicles. Here, we have demonstrated the utility of ACPP technology to deliver the potent radiosensitizer MMAE specifically to tumors. Following MMP-2/9 tumor targeted delivery and release of MMAE conjugated cell penetrating from ACPP, tumor xenografts demonstrated prolonged tumor xenograft regression compared to IR alone. ACPP conjugated delivery of radiosensitizers is highly innovative and of clinical significance in that it solves the problem of non-selective radiosensitization of molecules for not only cancer cells but also surrounding normal tissue. Such a therapeutic paradigm can allow for the clinical development and testing of more potent radiosensitizers since systemic toxicity and collateral normal tissue damage would be decreased in such a therapeutic strategy. Since MMP activity is high in the tumor microenvironment, MMP-2/9 targeted ACPP may be a broadly applicable tumor selective delivery vehicle for radiosensitizers.

Meanwhile, the only immediately clinically approved vehicle for MMAE delivery is brentuximab vedotin, with a host of similar antibody-MMAE conjugates undergoing clinical trials. Our results showing radiosensitization by free MMAE in vitro (FIGS. 3-5, FIGS. 10-11) and in vivo (FIG. 7B, FIG. 9) suggest that antibody-MMAE conjugates should show similar radiosensitization, since the antibody is just a sophisticated targeting vector for MMAE. Viewed another way, IR may be a valuable adjunct to chemotherapy with antibody-drug conjugates.

IR results in tumor microenvironment changes including alterations of gene expression, tumor cell surface receptor expression and protease activity. The physics of IR allows for IR to be specifically deposited to tumor tissue and can allow it to serve as beaconing mechanism for systemically delivered therapeutic agents. Such a concept has been seen with combining IR with oncolytic viruses, where IR enhances the ability of both intratumoral and systemically delivered oncolytic viruses to replicate in irradiated tumor microenvironments[19-22]. IR has also been used to induce the expression of neo-antigens within tumors that can function receptors for peptide ligand targeted nanoparticles[23-26]. Interestingly, MMP activity has been reported to be induced in irradiated tumors, including patient derived rectal cancers[27-30]. Moreover, αvβ3 expression is also upregulated by IR and modulates cell response to IR[31-34]. While gelatin zymography of excised tumor xenografts did not reveal an increase in gelatinase activity in irradiated tumors compared to their non-irradiated counterparts, ratiometric (SEQ ID NO:4) PLGC(Me)AG linker ACPP showed a trend toward increase Cy5:Cy7 emission ratio in irradiated tumor xenografts compared to non-irradiated tumor xenografts. These results suggest that with further optimization of radiation dose-fraction schedule may improve cleavage and activation of ACPP. Moreover, a radiation activatable cell penetrating peptide could be constructed in which a flexible peptide linker region could be inserted that is cleaved by IR induced tumor protease activity. Our results provide a basis for IR controlled ACPP to be developed that could deliver potent radiosensitizers. In such a treatment paradigm, there would be preferential accumulation of the radiosensitizer with the irradiated tumor and reduced bioavailability of the radiosensitizer to normal tissue. Such technology is not limited to radiosensitizer delivery. IR could be used to induce a "proteolytic switch" in the irradiated tumor target microenvironment to facilitate localized delivery of systemically administered cytotoxic anti-tumor agents.

REFERENCES

1. Werner J, Combs S E, Springfeld C, Hartwig W, Hackert T, Büchler M W. Advanced-stage pancreatic cancer: therapy options. *Nat Rev Clin Oncol.* 10:323-33. 2013.
2. Gutt R, Liauw S L, Weichselbaum R R. The role of radiotherapy in locally advanced pancreatic carcinoma. *Nat Rev Gastroenterol Hepatol.* 7:437-47. 2010.
3. Aklilu M, Eng C. The current landscape of locally advanced rectal cancer. *Nat Rev Clin Oncol.* 8:649-59. 2011.
4. Pretz J L, Wo J Y, Mamon H J, Kachnic L A, Hong T S. Chemoradiation therapy: localized esophageal, gastric, and pancreatic cancer. *Surg Oncol Clin N Am.* 22:511-24. 2013.
5. Moding E J, Kastan M B, Kirsch D G. Strategies for optimizing the response of cancer and normal tissues to radiation. *Nat Rev Drug Discov.* 12:526-42. 2013.
6. Liauw S L, Connell P P, Weichselbaum R R. New paradigms and future challenges in radiation oncology: an update of biological targets and technology. *Sci Transl Med.* 5:173sr2. 2013.
7. Raleigh D R, Haas-Kogan D A. Molecular targets and mechanisms of radiosensitization using DNA damage response pathways. *Future Oncol.* 9:219-23. 2013.
8. Jiang T, Olson E S, Nguyen Q T, Roy M, Jennings P A, Tsien R Y. Tumor imaging by means of proteolytic activation of cell-penetrating peptides. *Proc Natl Acad Sci USA.* 101:17867-72. 2004.
9. Aguilera T A, Olson E S, Timmers M M, Jiang T, Tsien R Y. Systemic in vivo distribution of activatable cell penetrating peptides is superior to that of cell penetrating peptides. *Integr Biol (Camb)* 1:371-81. 2009.
10. Olson E A, Aguilera T A, Jiang, Ellies L G, Nguyen Q T, Wong E H, Gross L A, Tsien R Y. In vivo characterization of activatable cell penetrating peptides for targeting protease activity in cancer. *Integr Biol* (Camb) 1:382-93. 2009.
11. Whitney M, Crisp J L, Olson E S, Aguilera T A, Gross L A, Ellies L G, Tsien R Y. Parallel in vivo and in vitro selection using phage display identifies protease-dependent tumor-targeting peptides. *J Biol Chem.* 285:22532-41. 2010.
12. Crisp J L, Savariar E N, Glasgow H L, Ellies L G, Whitney M A, Tsien R Y. Synergistic targeting of integrin avb3 and matrix metalloprotienase-2 improves optical imaging of tumors and chemotherapeutic efficiency. *Molecular Cancer Therapeutics*, submitted.
13. Deryugina E I, Ratnikov B, Monosov E, Postnova T I, DiScipio R, Smith J W, Strongin A Y. MT1-MMP initiates activation of pro-MMP-2 and integrin alphavbeta3 promotes maturation of MMP-2 in breast carcinoma cells. *Exp Cell Res.* 263:209-23. 2001.
14. Terasima, T. and L. J. Tolmach, Variations in several responses of HeLa cells to x-irradiation during the division cycle. *Biophys J.* 3:11-33. 1963.

15. Tishler R B1, Schiff P B, Geard C R, Hall E J. Taxol: a novel radiation sensitizer. *Int J Radiat Oncol Biol Phys.* 122:613-7. 1992.
16. Bai R, Pettit G R, Hamel E. Dolastatin 10, a powerful cytostatic peptide derived from a marine animal. Inhibition of tubulin polymerization mediated through the vinca alkaloid binding domain. *Biochem Pharmacol.* 39:1941-49. 1990.
17. Doronina S O, Toki B E, Torgov M Y, Mendelsohn B A, Cerveny C G, Chace D F, DeBlanc R L, Gearing R P, Bovee T D, Siegall C B, Francisco J A, Wahl A F, Meyer D L, Senter P D. Development of potent monoclonal antibody auristatin conjugates for cancer therapy. *Nat Biotechnol.* 21:778-84. 2003.
18. Savariar E N, Felsen C N, Nashi N, Jiang T, Ellies L G, Steinbach P, Tsien R Y, Nguyen Q T. Real-time in vivo molecular detection of primary tumors and metastases with ratiometric activatable cell-penetrating peptides. *Cancer Res.* 73:855-64. 2013.
19. Hallahan D E, Mauceri H J, Seung L P, Dunphy E J, Wayne J D, Hanna N N, Toledano A, Hellman S, Kufe D W, Weichselbaum R R. Spatial and temporal control of gene therapy using ionizing radiation. *Nat Med.* 1:786-91. 1995.
20. Mezhir J J, Advani S J, Smith K D, Darga T E, Poon A P, Schmidt H, Posner M C, Roizman B, Weichselbaum R R. Ionizing radiation activates late herpes simplex virus 1 promoters via the p38 pathway in tumors treated with oncolytic viruses. *Cancer Res.* 65:9479-84. 2005.
21. Advani S J, Markert J M, Sood R F, Samuel S, Gillespie G Y, Shao M Y, Roizman B, Weichselbaum R R. Increased oncolytic efficacy for high-grade gliomas by optimal integration of ionizing radiation into the replicative cycle of HSV-1. *Gene Ther.* 18:1098-102. 2011.
22. Advani S J, Buckel L, Chen N G, Scanderbeg D J, Geissinger U, Zhang Q, Yu Y A, Aguilar R J, Mundt A J, Szalay A A. Preferential replication of systemically delivered oncolytic vaccinia virus in focally irradiated glioma xenografts. *Clin. Cancer Res.* 2012 18:2579-2590. 2012.
23. Hallahan D E, Qu S, Geng L, Cmelak A, Chakravarthy A, Martin W, Scarfone C, Giorgio T. Radiation-mediated control of drug delivery. *Am J Clin Oncol.* 24:473-80. 2001.
24. Hallahan D, Geng L, Qu S, Scarfone C, Giorgio T, Donnelly E, Gao X, Clanton J. Integrin-mediated targeting of drug delivery to irradiated tumor blood vessels. *Cancer Cell.* 3:63-74. 2003.
25. Hariri G, Yan H, Wang H, Han Z, Hallahan D E. Radiation-guided drug delivery to mouse models of lung cancer. *Clin Cancer Res.* 16:4968-77. 2010.
26. Passarella R J, Spratt D E, van der Ende A E, Phillips J G, Wu H, Sathiyakumar V, Zhou L, Hallahan D E, Harth E, Diaz R. Targeted nanoparticles that deliver a sustained, specific release of Paclitaxel to irradiated tumors. *Cancer Res.* 70:4550-9. 2010.
27. Fujita M, Otsuka Y, Yamada S, Iwakawa M, Imai T. X-ray irradiation and Rho-kinase inhibitor additively induce invasiveness of the cells of the pancreatic cancer line, MIAPaCa-2, which exhibits mesenchymal and amoeboid motility. *Cancer Sci.* 102:792-8. 2011.
28. Lee W H, Warrington J P, Sonntag W E, Lee Y W. Irradiation alters MMP-2/TIMP-2 system and collagen type IV degradation in brain. *Int J Radiat Oncol Biol Phys.* 82:1559-66. 2012.
29. Speake W J, Dean R A, Kumar A, Morris T M, Scholefield J H, Watson S A. Radiation induced MMP expression from rectal cancer is short lived but contributes to in vitro invasion. *Eur J Surg Oncol.* 31:869-74. 2005.
30. Kumar A, Collins H M, Scholefield J H, Watson S A. Increased type-IV collagenase (MMP-2 and MMP-9) activity following preoperative radiotherapy in rectal cancer. *Br J Cancer.* 82:960-5. 2000.
31. Xu W1, Luo T, Li P, Zhou C, Cui D, Pang B, Ren Q, Fu S. RGD-conjugated gold nanorods induce radiosensitization in melanoma cancer cells by downregulating $\alpha(v)\beta_3$ expression. *Int J Nanomedicine.* 7:915-24. 2012.
32. Abdollahi A, Griggs D W, Zieher H, Roth A, Lipson K E, Saffrich R, Gröne H J, Hallahan D E, Reisfeld R A, Debus J, Niethammer A G, Huber P E. Inhibition of alpha(v)beta3 integrin survival signaling enhances anti-angiogenic and antitumor effects of radiotherapy. *Clin Cancer Res.* 11:6270-79. 2005.
33. Egami T, Ohuchida K, Yasui T, Mizumoto K, Onimaru M, Toma H, Sato N, Matsumoto K, Tanaka M. Up-regulation of integrin beta3 in radioresistant pancreatic cancer impairs adenovirus-mediated gene therapy. *Cancer Sci.* 100:1902-7. 2009.
34. Rieken S, Habermehl D, Mohr A, Wuerth L, Lindel K, Weber K, Debus J, Combs S E. Targeting $\alpha v \beta 3$ and $\alpha v \beta 5$ inhibits photon-induced hypermigration of malignant glioma cells. *Radiat Oncol.* doi10.1186/1748-717X-6-132. 2011.
Akashi, Y., Okamoto, I., Suzuki, M., Tamura, K., Iwasa, T., Hisada, S., Satoh, T., Nakagawa, K., Ono, K. and Fukuoka, M. The novel microtubule-interfering agent TZT-1027 enhances the anticancer effect of radiation in vitro and in vivo. *British Journal of Cancer* 96: 1532-1539. 2007.

Example 2: Rethinking EGFR Based Radiosensitization: From Pathway Inhibition to Targeted Delivery of Potent Tumoricidal Agents Abstract Concurrent chemotherapy and radiotherapy form the foundation for curative organ sparing therapy in locally advanced, non-metastatic cancers. In addition to its intrinsic anti-tumor activity, concurrent chemotherapy has the advantage of radiosensitizing tumors. While concurrent cytotoxic chemotherapy and radiotherapy has demonstrated clinical efficacy, treatment related morbidity limits dose intensification and efficacy. To overcome these barriers, targeted tumor therapies have been tested with radiotherapy but their overall clinical utility has had very limited success. We hypothesized that therapeutic EGFR antibodies (cetuximab) could target delivery of potent radiosensitizers to EGFR expressing tumors. This would bypass signaling pathway inhibition strategies and instead localize and restrict tumoricidal and radiosensitization activity to EGFR expressing tumors. We have constructed a theranostic molecule in which cetuximab was conjugated to the potent anti-mitotic agent monomethyl auristatin E and Cy5 (cetuximab-MMAE-Cy5) to allow for fluorescent monitoring. Diagnostically, cetuximab-MMAE-Cy5 bound specifically to EGFR expressing tumor cells. Therapeutically, cetuximab-MMAE-Cy5 restricted MMAE cytotoxicity and radiosensitization to EGFR expressing cells. While free MMAE was potent to cell lines of various histologies, the surface availability of EGFR-1 directly correlated with the degree of potency of MMAE conjugated to cetuximab. In particular, Head and Neck Squamous Cell Cancer (HNSCC) cell lines demonstrated retained potency and radiosensitization of MMAE when conjugated to cetuximab. Finally, we evaluated the efficacy of concurrent cetuximab-MMAE-Cy5 with ionizing radiation in HNSCC tumor xenografts. Cetuximab-MMAE-Cy5 localized to EGFR-1 expressing tumors and blocked tumor cells in the radiosensitive $G_2/M$ phase of the cell cycle. Combining cetuximab-MMAE-Cy5 with ionizing radiation resulted in a significant decrease in CAL-27 HNSCC tumor xenograft growth. More importantly, in combination with ionizing radiation, MMAE conjugated to cetuximab produced significantly increased tumor regression compared to mice treated with equivalent doses of co-administered cetuximab and free MMAE. These studies lay the foundation for redesigning EGFR based radiosensitization therapies in the clinic using antibody based drug targeting rather than signaling pathway inhibition.

Introduction

For patients with locally advanced cancers, radiation therapy combined with concurrent radiosensitizing chemotherapy forms the backbone of organ sparing, curative therapy. Patient outcomes are significantly improved when radiation therapy is combined with chemotherapy, as part of multi-modality therapy. Combining chemotherapy and radiotherapy has several advantages. First, chemotherapy agents and radiotherapy kill tumor cells through different modes of action, potentially decreasing the survival of resistant tumor cells to either therapy alone. Also while increasing the dose of either chemotherapy or radiotherapy alone could theoretically result in a similar level of tumor cell kill as combined therapy, in practice the dose of chemotherapy or radiotherapy are constrained by normal tissue toxicity. Therefore, combination therapy can achieve a similar level of tumor control at lower, safer, and more tolerable doses of each individual treatment. More importantly, a key rationale for administering chemotherapy concurrently with ionizing radiation (IR) is that certain chemotherapies sensitize tumors to IR by increasing IR mediated tumor cell kill. To be clinically useful, radiosensitizers must improve the therapeutic index, i.e. the level of sensitization of tumor cells must be greater than that of surrounding normal tissue. This is a major limitation in realizing the clinical benefit of radiosensitizers. To improve the therapeutic index of radiosensitization, more specific radiosensitizers are being tested. One strategy is to use drugs that inhibit DNA damage responses. However achieving therapeutic levels of such drugs is also limited by off target effects that result in dose limiting toxicity. Moreover, they do not address the issue of tumor specific delivery over surrounding normal tissue, which again would negate any gain in the therapeutic index.

An alternative approach employs drugs targeting signaling pathways up-regulated in tumors, i.e. epidermal growth factor receptor (EGFR) signaling. While inhibition of EGFR signaling through antibody (cetuximab) or small molecules (erlotinib) radiosensitizes tumors, significant limitations to this approach have appeared. Inhibition of the EGFR pathway results in the emergence of bypass signaling pathways to circumvent EGFR blockade, thereby limiting the therapeutic benefit of EGFR inhibition strategies. While concurrent cetuximab and radiotherapy is more tolerable to patients in regards to treatment related side effects, recent retrospective clinical studies suggest concurrent cetuximab-radiotherapy has inferior patient survival when compared to concurrent cisplatin-radiotherapy in locally advanced HNSCC. Moreover, the addition of cetuximab to standard of care cytotoxic chemotherapy and radiotherapy has failed to demonstrate improved patient outcomes in randomized controlled trials.

Antibody drug conjugates (ADC) are an emerging tumor targeted delivery strategy, but they require potent tumoricidal agents given the limitations of receptor mediated internalization and tumor penetration. Maytansinoids and auristatins are potent anti-tubulin drugs that have been conjugated to antibodies and demonstrated clinical efficacy. Trastuzumab linked to emtansine (T-DM1; DM1 is also known as mertansine) and CD-30 antibody linked to monomethyl auristatin E (brentuximab vedotin) are used for HER2 overexpressing breast cancer and CD30 expressing lymphomas respectively. We have recently discovered that monomethyl auristatin E (MMAE) is a potent radiosensitizer, effective at the single nM level. MMAE blocks cell is the radiosensitive $G_2/M$ phase of the cell cycle. Systemic delivery of free MMAE is hampered by dose limiting normal tissue toxicity, which can be overcome by ADC conjugation. As an alternative radiosensitizing strategy to inhibition of EGFR signaling, we tested EGFR targeted delivery of MMAE to radiosensitize tumors.

We synthesized and tested a theranostic cetuximab, which is conjugated to both MMAE and Cy5 (cetuximab-MMAE-Cy5) to allow for fluorescent monitoring and therapeutic targeting. By monitoring Cy5 fluorescence, we ascertain that cetuximab-MMAE-Cy5 bound to EGFR-1 expressing HNSCC, non-small cell lung cancer (NSCLC) and colorectal cell lines, but not to the low EGFR expressing glioma cell line LN-229. Upon endocytosis of the cetuximab-MMAE-Cy5, the valine-citrulline linker between cetuximab and MMAE is cleaved by enzymes in the endolysosomes, releasing MMAE to diffuse across the endolysosomal membrane and bind to its target, cytosolic microtubules. Therapeutically, while free MMAE was tumoricidal to all tumor cell lines tested, cetuximab conjugation restricted MMAE anti-tumor activity and radiosensitization to EGFR-1 expressing cell lines. In addition, the cell surface receptor availability of EGFR-1 in cell lines based on cetuximab-MMAE-Cy5 fluorescence correlated with the potency of MMAE conjugated to cetuximab compared to free MMAE. HNSCC cell lines were exquisitely sensitive to cetuxmab-MMAE-Cy5. Moreover, cetuximab-MMAE-Cy5 had increased potency compared to routinely used HNSCC radiosensitizers cisplatin and cetuximab. We then tested the efficacy of concurrent cetuximab-MMAE-Cy5 with ionizing radiation in CAL-27 HNSCC tumor xenografts. Cetuximab-MMAE-Cy5 localized to CAL-27 tumor xenografts and increased the proportion of tumor cells in $G_2/M$. Therapeutically, combining cetuximab-MMAE-Cy5 with ionizing radiation resulted in a significant decrease in CAL-27 tumor xenograft growth. In combination with ionizing radiation, cetuximab-MMAE-Cy5 produced significantly increased tumor regression compared to cetuximab alone and MMAE alone or the co-injection of MMAE with cetuximab. These results demonstrate the potential of utilizing EGFR antibody drug conjugates as radiosensitizers in the clinic.

Material and Methods:

Cells and Reagents.

Human HNSCC (CAL-27, SCC-25), NSCLC (A549) and colorectal (HCT-116) were obtained from American Type Culture Collection. Human HNSCC SQ-9G, SCC-35 and SCC-61 were kindly provided from Ralph Weichselbaum, University of Chicago. CAL-27, A549 and HCT-116, cells were cultured in DMEM supplemented with 10% FBS. SQ-9G, SCC-25, SCC-35 and SCC-61 were cultured in DMEM/F12 supplemented with 20% FBS and 400 ng/ml hydrocortisone. Cisplatin (Enzo Biosciences), Paclitaxel (Sigma) and MMAE (Concortis) were reconstituted in DMSO.

Synthesis of Cetuximab Conjugated to MMAE and Cy5

Figure 23:
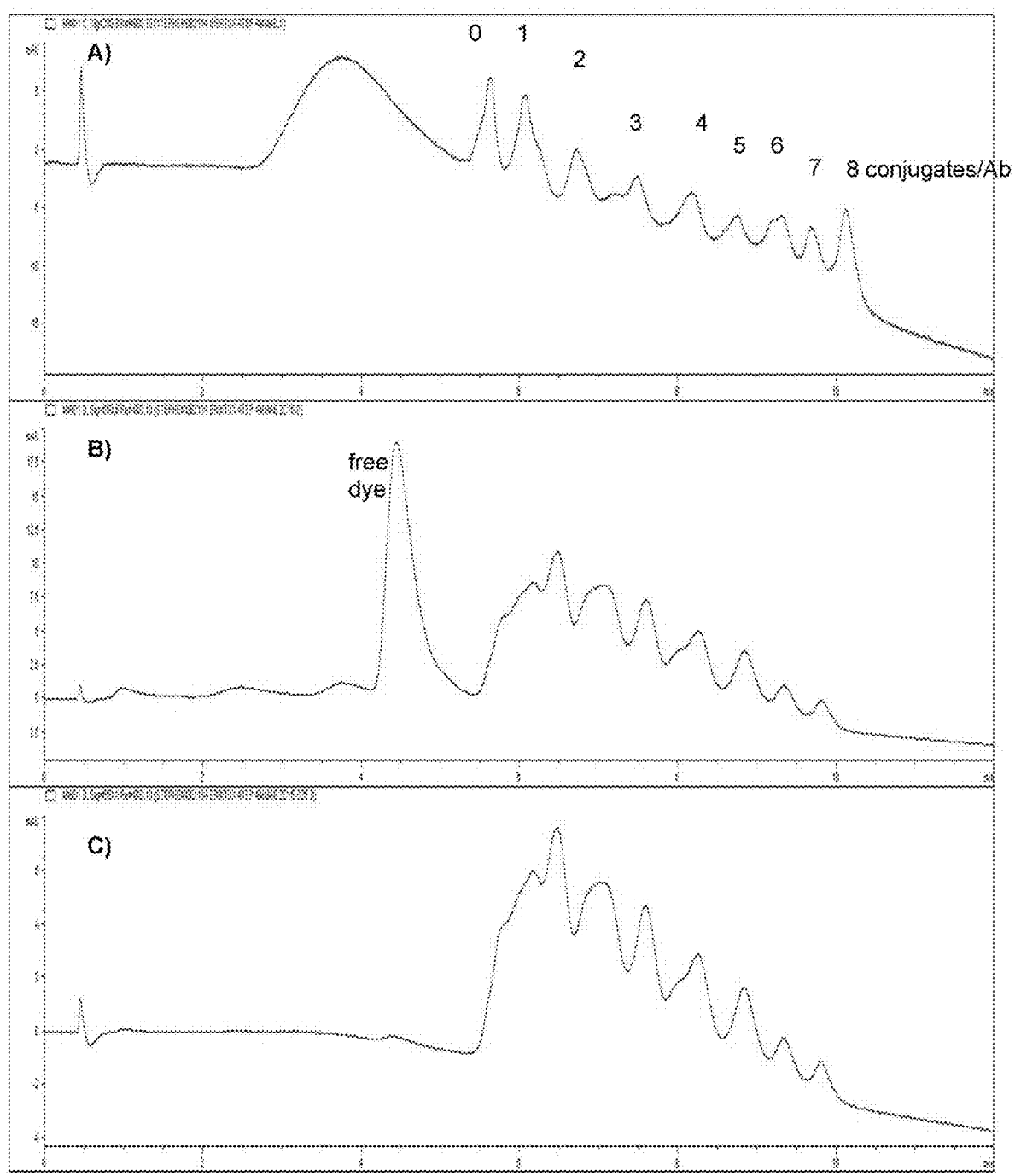
FIG. 23: Antibody labeling analysis with hydrophobic interaction chromatography. A) $A_{280}$ after 4 eq of MC-VC-MMAE. B) $A_{650}$ after 2 eq of Cy5-maleimide. C) $A_{650}$ after G25 purification.

A solution of cetuximab (Erbitux, ImClone 2 mg, 1 ml, 13.4 nmol) was treated with bicine (1 M solution adjusted to pH 8.3 with NaOH, 100 µl) and diethylenetriaminepentaacetic acid (DTPA, 100 mM adjusted to pH 7 with NaOH, 10 µl), reduced with tris(carboxyethyl)phosphine (TCEP, freshly-prepared 10 mM HCl salt, 4 eq, 5.4 µl, 54 nmol) at 37° C. for 2 h, and added to maleimidoylcaproyl-valine-citrulline-monomethylauristatin E (MC-VC-MMAE, Concortis, 1 mM in DMSO, 4 eq, 54 nmol, 54 µl). After 30 min at room temperature, the solution was added to Cy5-maleimide (27 nmol, 1 mM in DMSO, 27 µl) and after a further 30 min, gel-filtered (Sephadex G25, 0.6 g) eluting with 50 mM phosphate buffer pH 7.4. Following centrifugal concentration (Centricon 30 kD MWCO) to 500 µl, the concentrations of cetuximab and Cy5 were determined by absorbance using extinction coefficients of 210,000 $M^{-1}cm^{-1}$- and 12500 $M^{-1}cm^{-1}$ at 280 nm respectively and 250,000 $M^{-1}cm^{-1}$ for Cy5 at 650 nm. Hydrophobic interaction chromatography (HIC) of a reaction sample after labeling with MMAE revealed the expected 9 peaks corresponding to cetuximab modified with 0-8 MMAE derivatives (FIG. 23A). Subsequent Cy5-maleimide labeling gave 650 nm absorbance to each peak apart from that labeled with 8 MMAE as no cysteines are available for modification (FIG. 23B). Gel filtration and concentration removed unreacted Cy5-maleimide but not any MMAE, indicating stoichiometric labeling (FIG. 23C).

Cy5 Fluorescence Imaging.

Cells were exposed for cetuximab-Cy5 or cetuximab-MMAE-Cy5 for 30 minutes in media with 1% serum. Cells were then washed with PBS and incubated in media with 10% serum. At indicated times, cells were fixed in 4% paraformaldehyde and then stained with DAPI. Cells were imaged using a Nikon AIR confocal microscope.

Cetuximab-MMAE-Cy5 Cell Binding

Cells were collected and resuspended in cold PBS with 5% BSA. Cetuximab-MMAE-Cy5 was added to the cells at indicated concentrations for 15 minutes on ice. Cells were washed, resuspended in PBS with 5% BSA and 0.5 ug/ml propidium iodide, and analyzed by flow cytometry.

Cell Cycle.

Cells were treated with MMAE, cetuximab-Cy5 or cetuximab-MMAE-Cy5 for 24 hours and then fixed in methanol. Cells were treated with RNAse, stained with propidium iodide (PI) and analyzed by FACS using FloJo software.

Alamar Blue Assay

Cells were plated in 96 well plates and exposed to a range of concentrations of MMAE or paclitaxel for 72 hrs. Alamar Blue (resazurin) was added to the cells and allowed to incubate for 2 hrs at 37° C. Plates were analyzed using a plate reader with fluorescence measured at 560 nm.

Clonogenic Assay

Cells were treated with cetuximab-Cy5 or cetuximab-MMAE-Cy5 for 24 hours and then irradiated with 0-6 Gy. Following IR, cells were counted, re-plated at varying cell numbers in drug free media. 10-14 after initial seeding formed colonies were methanol fixed, stained with crystal violet and counted.

Neutral Comet Assay

Cells were treated for indicated times and doses of cetuximab-Cy5 or cetuximab-MMAE-Cy5 and then irradiated with 6 Gy. Cells were harvested 15 minutes post IR, suspended in agarose gel and lysed per assay directions (Trevigen). Samples underwent electrophoresis under neutral conditions and were then stained with Sybr Green. Comet tails were counted in multiple fields (>60 cells per sample) and analyzed using CometScore (TriTek Corp).

Immunoblotting

Cells were harvested and lysed in RIPA buffer (20 mM Tris pH 8, 150 mM NaCl, 5 mM EDTA, 1% Triton X-100) with protease and phosphatase inhibitors (Complete Protease Inhibitor Cocktail and Phos-Stop, Roche). Lysate protein was quantitated by BCA technique (Pierce). 20 µg of lysate underwent electrophoresis using 4-12% Bis-Tris gels (Life Technologies), transferred to PVDF membranes (iBlot) and incubated with indicated primary antibodies (Cell Signaling Technology) at manufacturer recommended dilutions. Blots were developed by ECL (Pierce).

Immunohistochemistry

Xenograft tumor tissue was fixed in formalin, processed, and embedded in paraffin wax. Four micron thick tissue sections were cut and mounted on positively-charged glass slides. The tissue was then stained with H&E and an antibody to pS10 histone H3 using a Ventana Discovery Ultra (Ventana Medical Systems). The primary antibody was used at a 1:250 dilution and was visualized using DAB as a chromagen with the UltraMap system (Ventana Medical Systems).

In Vivo Tumor Xenograft Optical Imaging

All animal work was done in compliance with the UCSD Institutional Animal Use and Care Committee. 6-8 week old female athymic nu/nu mice purchased from the UCSD Animal Care Program breeding colony were injected subcutaneously into the bilateral upper thighs with $5 \times 10^6$ CAL-27, SQ9-G, SCC-35, SCC-61, A549, HCT-116 or LN-229 tumor cells in a 1:1 Matrigel (BD) and PBS solution. After tumors grew to >100 $mm^3$ they were injected with 0.5 nmoles of cetuximab-Cy5 or cetuximab-MMAE-Cy5 as described above. For imaging, mice were anesthetized (1:1 mixture of 100 mg/ml of ketamine and 5 mg/ml of midazolam). Animals were imaged using a Maestro Small Animal Imager (CRI) with excitation filter of 620/22 nm and 645 nm long pass emission filter with dichroic filter tuned to 670 nm. Imaging was done both with skin on and after skin removal to decrease autofluorescence and scattering.

In Vivo Tumor Xenograft Experiments

CAL-27 tumor xenografts were established and tumor growth was measured with digital calipers. Tumor volume was calculated using the formula as $\frac{1}{2} \ast Length \ast Width^2$. Mice were randomized into groups once the average tumor volume reached >150 $mm^3$. Mice were assigned to indicated groups in the Results. MMAE, cetuximab-Cy5 or cetuximab-MMAE-Cy5 was intravenously injected in 50 µl. For irradiated mice, the tumor bearing hindlimbs were focally irradiated while the remainder of the mouse was shielded from IR with custom designed lead blocking >95% of the dose as verified by dosimeters placed on the mouse. Free MMAE was injected on an equimolar basis to ACPP-cRGD-MMAE in final volume of 3% DMSO. MMAE doses and IR fractionation are as indicated in the Results.

Statistical Analysis:

Unpaired 2-sided t tests were performed for $IC_{50}$ and radiosensitization experiments in cell culture. In tumor regression studies, 2-way ANOVA analysis was performed with Tukey's multiple comparison group. All statistical analyses were performed using Prism software (GraphPad). Statistical significance was defined as $p<0.05$.

Results

Cetuximab-MMAE-Cy5 Binds to Cells in an EGFR-1 Dependent Manner

Figure 24:
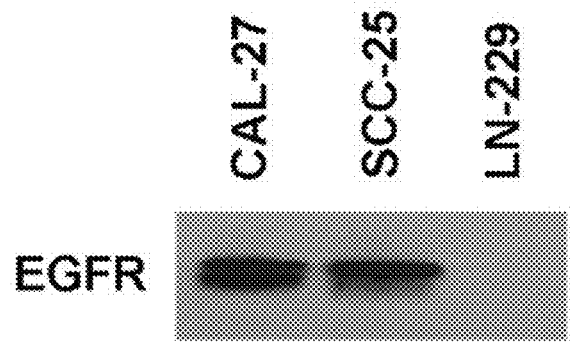
FIG. 24: EGFR expression in cell lines. Immunoblot for total EGFR in whole cell lysates of indicated cell lines.
Figure 25:
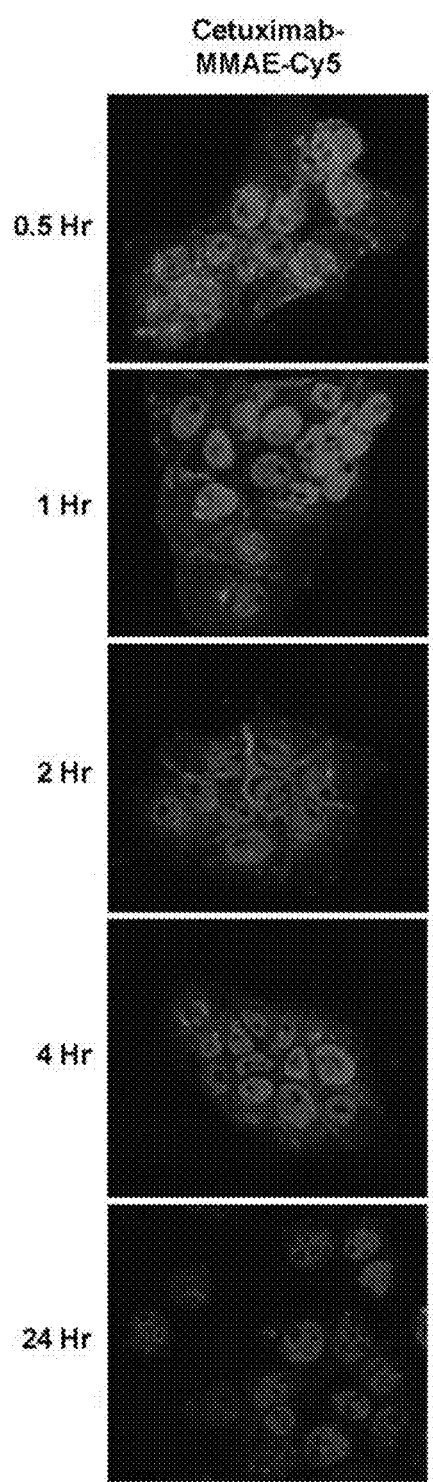
FIG. 25: Kinetics of cetuximab-MMAE-Cy5 binding and internalization. CAL-27 cells were exposed to cetuximab-MMAE-Cy5 for 30 minutes, then washed and incubated in drug free media. Cells were fixed at indicated times and imaged for Cy5 fluorescence.

We first tested if our synthesized cetuximab-Cy5 and cetuximab-MMAE-Cy5 bound to cells in an EGFR-1 dependent manner. CAL-27 (HNSCC) cells express EGFR-1 and were treated with 2 nM cetuximab-Cy5 at 37°. Cells were fixed at 2, 24 and 48 hrs and imaged by direct fluorescence (FIG. 24, FIG. 17A). By 2 hrs, Cy5 fluorescence localized to the cell surface and was internalized, and Cy5 fluorescence persisted intracellularly through 48 hrs. We next evaluated cell surface binding of our synthesized cetuximab-MMAE-Cy5 molecule. CAL-27 cells were incubated with 0-5 nM of cetuximab-MMAE-Cy5 on ice for 15 minutes. Cetuximab-MMAE-Cy5 surface binding was analyzed by flow cytometry for Cy5 fluorescence (FIG. 17B). CAL-27 cells bound cetuximab-MMAE-Cy5 in a dose dependent manner. Confocal fluorescence microscopy confirmed that cetuximab-MMAE-Cy5 was internalized in CAL-27 cells (FIG. 17C, FIG. 25). To test the specificity of our antibody drug conjugate, we exposed LN-229 cells (low EGFR-1 expression) to cetuximab-MMAE-Cy5 (FIG. 24, FIG. 17C). Of significance, cetuximab-MMAE-Cy5 did not bind appreciably to LN-229 cells.

Cetuximab Conjugation Restricts MMAE Toxicity to EGFR-1 Expressing Cells

Figure 18:
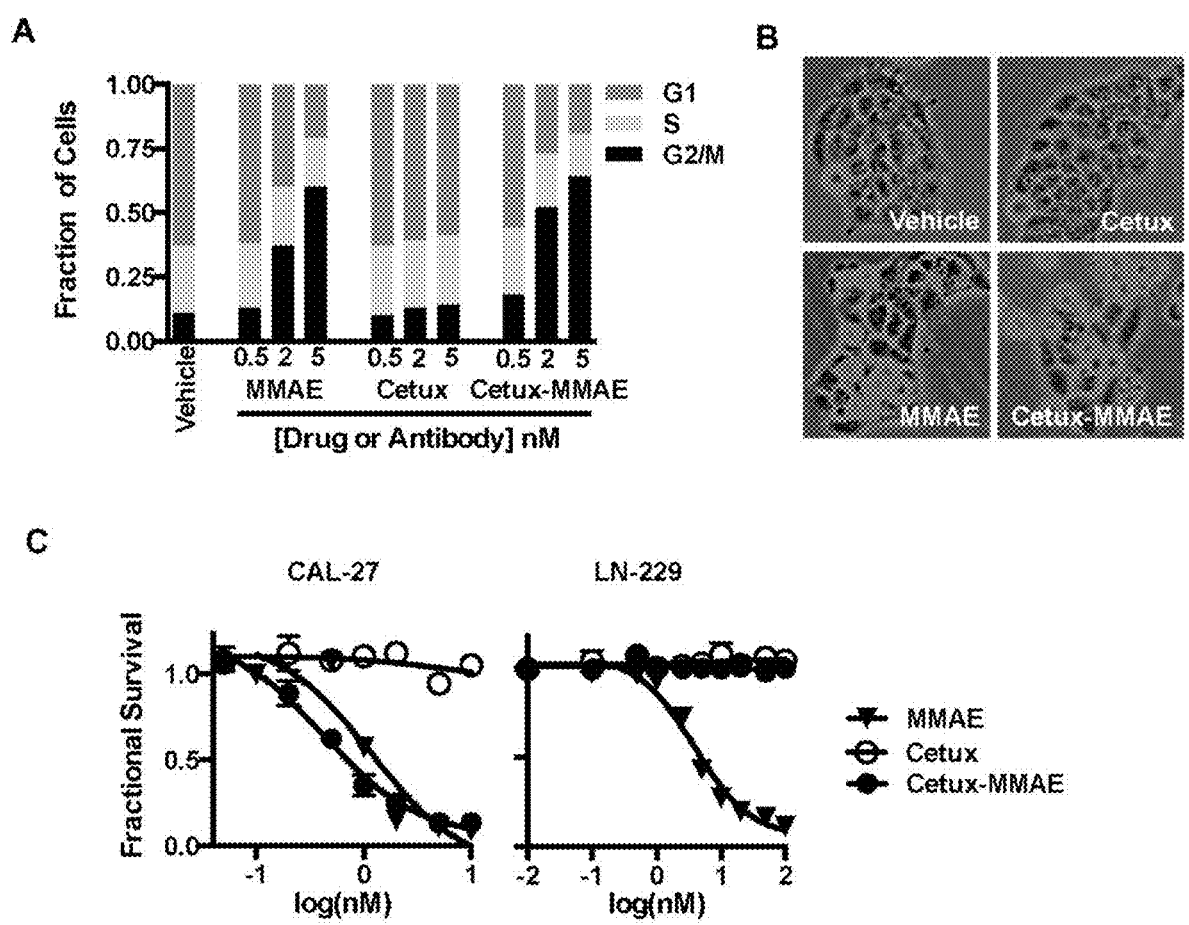
FIG. 18: Cetuximab conjugation restricts MMAE toxicity to EGFR-1 expressing cells. A) Cell cycle profile of CAL-27 cells treated with increasing concentrations of MMAE, cetuximab-Cy5 (Cetux), or cetuximab-MMAE-Cy5 (Cetux-MMAE) overnight and then stained with propidium iodide. B) Phase contrast microscopy images of CAL-27 cells treated with 2 nM MMAE, Cetux, or Cetux-MMAE overnight. C) CAL-27 and LN-229 tumor cells were exposed to dose range of MMAE, Cetux or Cetux-MMAE for 72 hours. Cell viability was measured, normalized to vehicle treated cells and plotted as fractional survival±SD.

We next determined if the MMAE conjugated to cetuximab retained its functional activity. MMAE is a potent anti-tubulin agent that arrests cells in the $G_2/M$ phase of the cell cycle. CAL-27 cells were treated with increasing concentrations of free MMAE, cetuximab-Cy5 or cetuximab-MMAE-Cy5. Cells were collected 24 hrs later, long enough for the conjugate to be endocytosed and hydrolyzed. Cell cycle analysis was performed by flow cytometry (FIG. 18A). Compared to vehicle treated control cells, free MMAE blocked cells in $G_2/M$ in a dose dependent manner. At 5 nM of MMAE, 60% of cells accumulated in $G_2/M$. Cetuximab-MMAE-Cy5 resulted in a cell cycle profile mirroring free MMAE, with 64% of cells in $G_2/M$ when treated with 5 nM. In the dose range of 0-5 nM, cetuximab alone had minimal influence on cell cycle distribution of CAL-27 cells compared to control cells. At 5 nM of cetuximab, only 14% of the cell population was in $G_2/M$, which was similar to vehicle treated cells, 11%. Morphologically, CAL-27 cells treated with either free MMAE or cetuximab-MMAE-Cy5 appeared identical with increased number of cells rounding up, indicative of $G_2/M$ (FIG. 18B). We next tested the ability of cetuximab conjugation to restrict MMAE toxicity to EGFR-1 expressing cells (FIG. 18C). CAL-27 and LN-229 cells were treated with increasing concentrations of free MMAE, cetuximab-Cy5, and cetuximab-MMAE-Cy5 and cell viability was measured 72 hours later. In EGFR-1 expressing CAL-27 cells, both free MMAE and cetuximab-MMAE-Cy5 were tumoricidal with an $IC_{50}$ of 1.1 nM and 0.4 nM respectively. At a dose of 10 nM, cetuximab-Cy5 without MMAE had minimal effect on cell survival. In the low EGFR-1 expressing LN-229 cell line, free MMAE effectively decreased cell viability, $IC_{50}$ of 3.8 nM. However, cetuximab conjugation reversed LN-229 sensitivity to MMAE with both cetuximab-Cy5 and cetuximab-MMAE-Cy5 having no appreciable effect on cell viability at concentrations of up to 100 nM.

Figure 19:
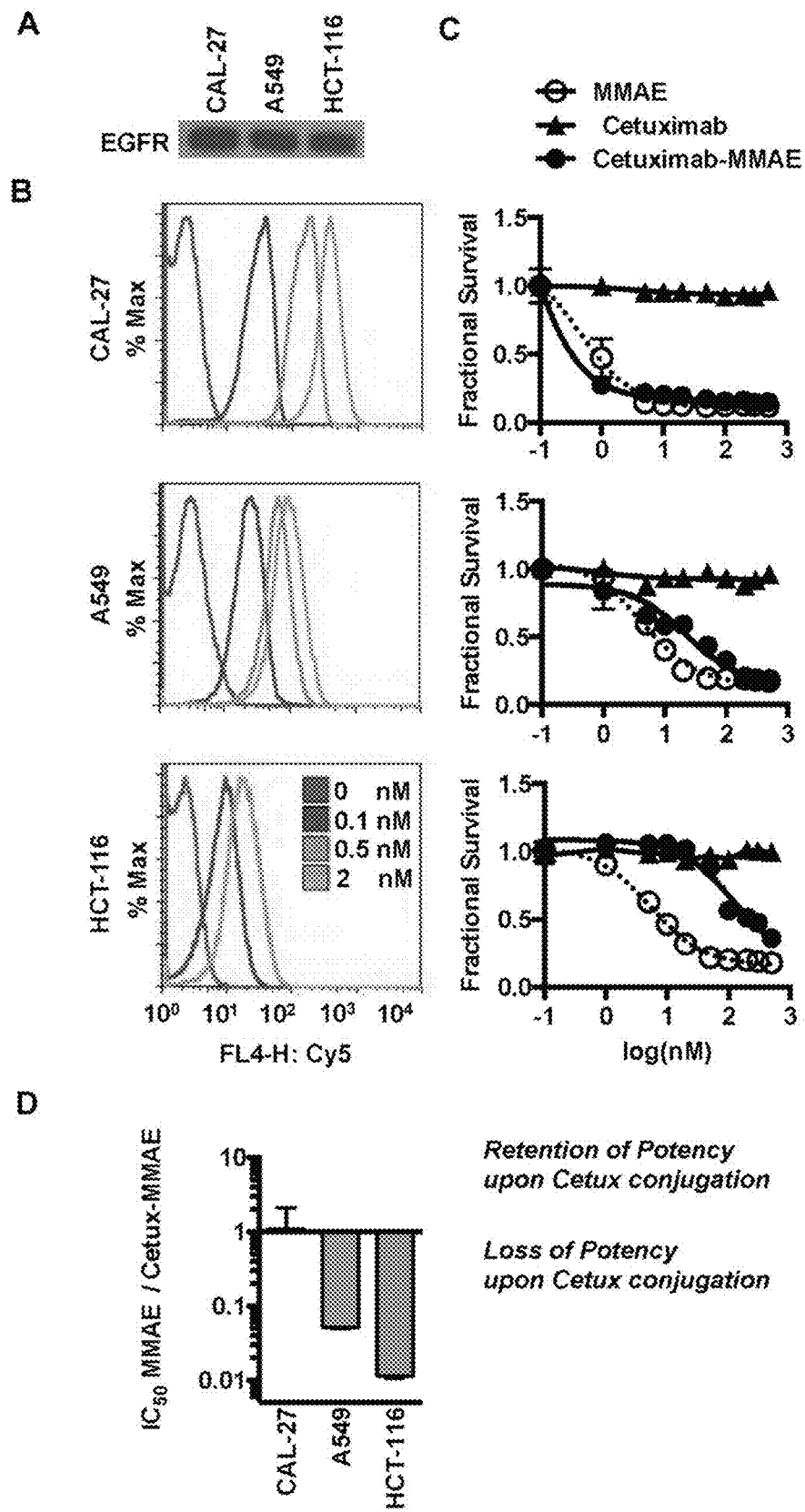
FIG. 19: EGFR-1 receptor availability correlates with cetuximab-MMAE toxicity. A) Immunoblot for total EGFR in whole cell lysates from indicated cell lines. B) Flow cytometry assessment of cetuximab-MMAE-Cy5 cell surface binding. Tumor cells were incubated on ice with increasing concentrations of cetuximab-MMAE-Cy5. C) Tumor cells were exposed to dose range of MMAE, cetuximab or cetuximab-MMAE for 72 hours. Cell viability was measured, normalized to vehicle treated cells and plotted as fractional survival±SD. D) Ratio of $IC_{50}$ for MMAE and cetuximab-MMAE. Values<1 indicate decreased potency of MMAE when conjugated to cetuximab compared to free MMAE.

EGFR-1 Cell Surface Receptor Availability Correlates with Potency of Cetuximab-MMAE We next tested the efficacy of MMAE conjugated to cetuximab in models of cancers clinically treated with EGFR inhibition strategies, HNSCC (CAL-27), NSCLC (A549), and colorectal (HCT-116). In whole cell lysates, all three cell lines expressed abundant levels of EGFR-1 (FIG. 19A). However, cell surface receptor binding on live cells demonstrated differing EGFR-1 receptor availability/saturation levels (FIG. 19B). CAL-27 cells showed continued dose responsive cell surface binding from 0-2 nM. Both A549 and HCT-116 cells had decreased Cy5 cell surface fluorescence. While free MMAE was potent in all 3 cell lines, the potency upon conjugation to cetuximab was concordant with cell surface receptor availability (FIG. 19C). In CAL-27 cells, the potency of cetuximab-MMAE overlaid free MMAE. In contrast, in A549 and HCT-116, cetuximab conjugation resulted in loss of MMAE potency, as the $IC_{50}$ of cetuximab-MMAE was up to 100-fold higher than that of free MMAE (FIG. 19D).

Figure 26:
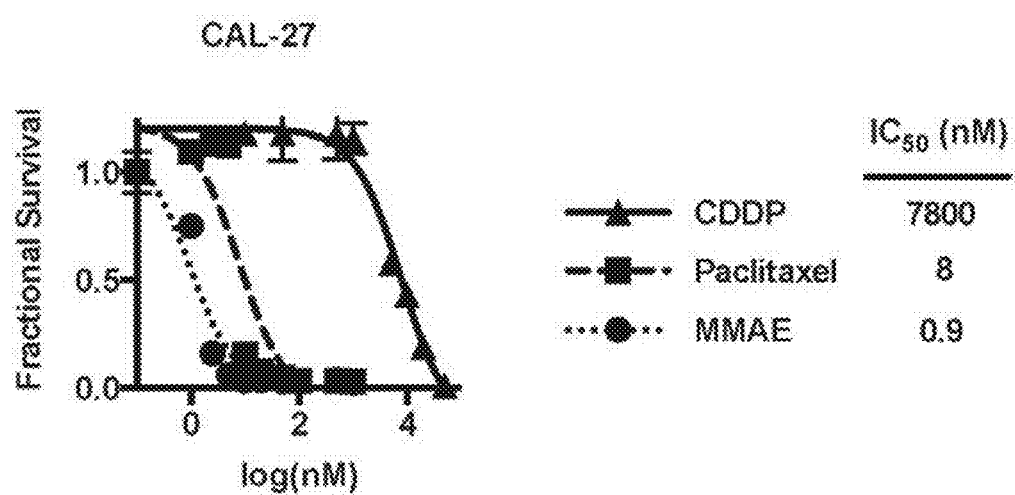
FIG. 26: MMAE is a more potent anti-tumor agent than standard cytotoxic chemotherapies used in HNSCC. CAL-27 cells were exposed to a dose range of cisplatin (CDDP), paclitaxel or MMAE for 72 hours. Cell viability was normalized to vehicle treated cells and plotted as fractional survival±SD. $IC_{50}$ was calculated.
Figure 27:
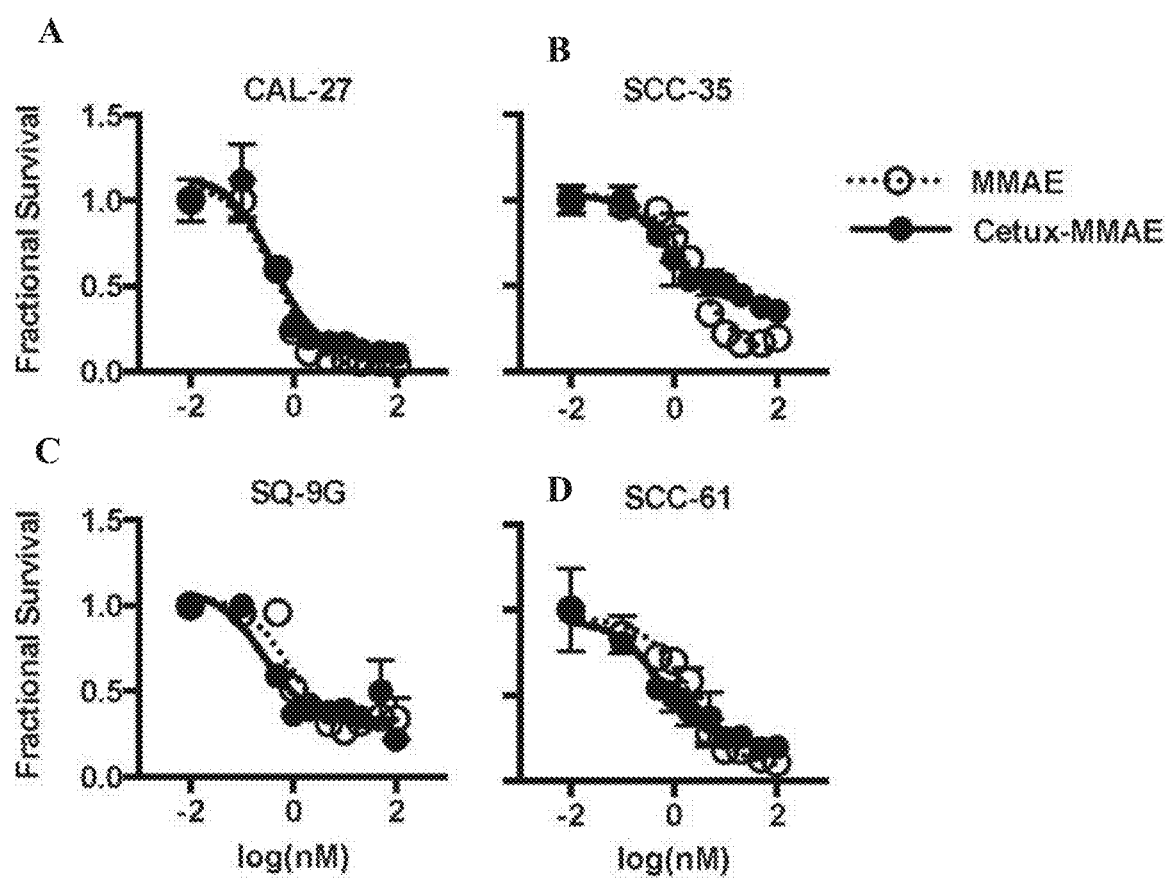
FIG. 27: Cetuximab conjugation does not alter the potency of MMAE in a panel of HNSCC cell lines. CAL-27, SQ-9G, SCC-35 and SCC-61 cells were treated with increasing concentrations of MMAE or cetuximab-MMAE-Cy5 for 72 hours. Cell viability was normalized to vehicle treated cells and plotted as fractional survival±SD.

Cetuximab-MMAE-Cy5 has Increased Potency Compared to Chemotherapies Given Concurrently with Radiotherapy for HNSCC One of the key features in the clinical development of MMAE is its potency, which we confirmed in CAL-27 cells compared to standard cytotoxic chemotherapy drugs cisplatin and paclitaxel (FIG. 26). Since MMAE conjugated to cetuximab retained its therapeutic efficacy in HNSCC CAL-27 cells, we further tested cetuximab-MMAE-Cy5 in a panel of HNSCC cell lines (SQ-9G, SCC-35 and SCC-61). We first tested the binding and internalization of cetuximab-MMAE-Cy5 by confocal microscopy at 4 hrs following exposure (FIG. 20A). As with CAL-27 cells, SQ-9G, SCC-35 and SCC-61 all internalized cetuximab-MMAE-Cy5. We next compared the potency of free or cetuximab conjugated MMAE in our panel of HNSCC cell lines (FIG. 27). The HNSCC cells were treated with free MMAE or cetuximab-MMAE-Cy5 and cell viability measured at 72 hours. In all four HNSCC cell lines tested, the potency of cetuximab-MMAE-Cy5 was similar to that of free MMAE. For locally advanced HNSCC, concurrent chemoradiotherapy is standard of care with either cisplatin or cetuximab. Therefore, we next compared the potency of cetuximab-MMAE-Cy5 to either cisplatin or cetuximab-Cy5. Cells were exposed to drug for 72 hours and cell viability measured (FIG. 20B). The $IC_{50}$ for cisplatin for CAL-27, SQ-9G, SCC-35 and SCC-61 were 5,000, 13,000, 30,000 and 10,000 nM. For cetuximab-Cy5, CAL-27 and SCC-61 were relatively resistant at doses up to 100 nM. The cell lines SCC-35 and SQ-9G showed modest sensitivity to cetuximab-Cy5 at dose above 10 nM. In contrast, cetuximab conjugated MMAE had significantly increased potency in all 4 HNSCC cell lines with an $IC_{50}$ of 0.3, 0.2, 0.6, and 1.2 nM for CAL-27, SQ-9G, SCC-35, and SCC-61 respectively.

Cetuximab-MMAE-Cy5 Radiosensitization is Restricted by EGFR Expression

Figure 28:
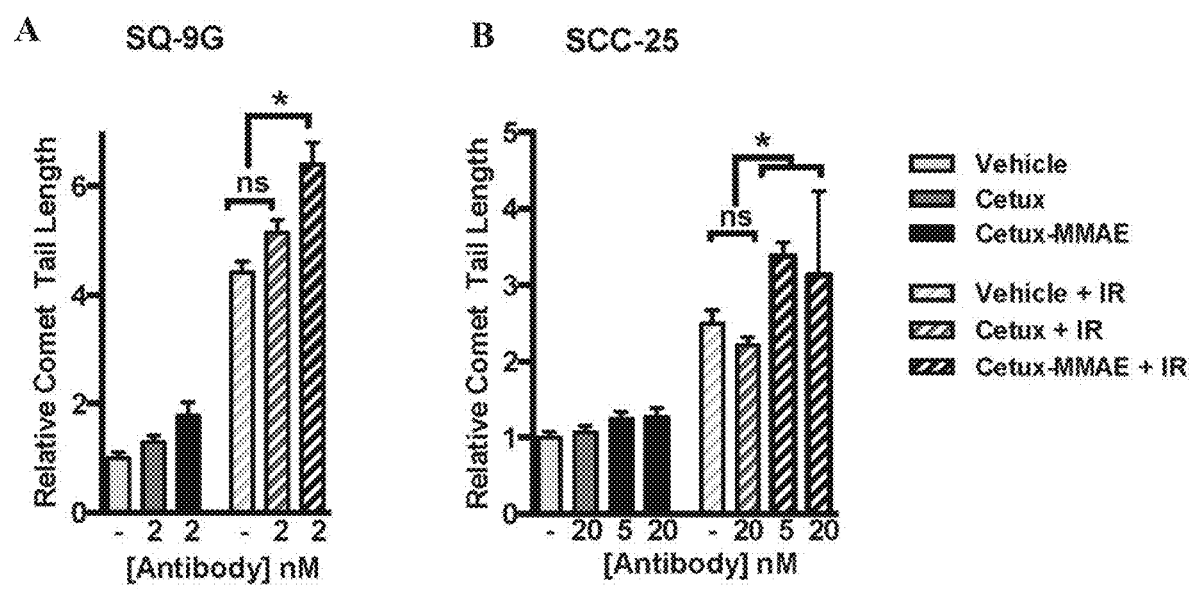
FIG. 28: Cetuximab-MMAE-Cy5 radiosensitizes HNSCC cell lines. SQ-9G or SCC-25 cells were treated with cetuximab-Cy5 or cetuximab-MMAE-Cy5 overnight at indicated concentrations and then irradiated with 6 Gy. Comet tail length was measured using neutral comet assay and normalized to vehicle treated, non-irradiated cells. Data is plotted as relative comet tail length±SEM. *P<0.05.

We had previously shown that MMAE radiosensitizes tumor cells. Since MMAE is highly potent against HNSCC cell lines and concurrent chemoradiotherapy is standard of care for locally advanced HNSCC, we evaluated if cetuximab conjugation restricted MMAE radiosensitization to EGFR expressing tumor cells. IR induces DNA double strand breaks that result in cell death through mitotic catastrophe. CAL-27 and LN-229 cells were treated with cetuximab-MMAE-Cy5 overnight followed by an IR dose of 6 Gy. Cells were collected 15 minutes following IR and DNA double strand breaks were measured by neutral comet assay (FIG. 21A). Comet tail length was normalized to vehicle-treated non-irradiated cells for each cell line. In non-irradiated CAL-27 cells, there was no significant increase in comet tail length following treatment with cetuximab-Cy5 or cetuximab-MMAE-Cy5. Irradiation of vehicle-treated CAL-27 cells resulted in a 3.6 fold increase in comet tail length that was not significantly enhanced by 5 nM cetuximab-Cy5. However, cetuximab-MMAE-Cy5 pre-treatment significantly increased comet tail length in irradiated CAL-27 cells compared to either vehicle or cetuximab-Cy5 irradiated cells in a dose dependent manner. A significant increase in comet tail length was seen as low as 0.5 nM cetuximab-MMAE-Cy5. In the HNSCC cell lines SQ-9G and SCC-25, cetuximab-MMAE-Cy5 treatment also significantly increased comet tail length in irradiated cells (FIG. 28). Importantly, cetuximab conjugation restricted MMAE radiosensitization. In low EGFR expressing LN-229 cells, irradiation of vehicle-treated cells resulted in a 2.5 fold increase in comet tail length. In contrast to our results in HNSCC cell lines, there was no further increased comet tail length with cetuximab-Cy5 or cetuximab-MMAE-Cy5 pretreatment in LN-229 cells.

As a result of IR induced DNA double strand breaks, cells predominantly die through mitotic catastrophe. CAL-27 cells were treated with 2 nM cetuximab-Cy5 or cetuximab-MMAE-Cy5 overnight followed by 0-6 Gy and cell survival was measured by clonogenic assay (FIG. 21B). CAL-27 cells treated with cetuximab-Cy5 showed a cell survival curve similar to vehicle treated cells. In contrast, treating cells overnight with cetuximab-MMAE-Cy5 significantly decreased the surviving fraction upon irradiation at doses as low as 2 Gy. For concurrent chemotherapy and radiotherapy in patients, IR doses are typically around 2 Gy. Therefore we measured clonogenic survival with 2 Gy and varied doses of cetuximab-MMAE-Cy5. The surviving fraction at 2 Gy significantly decreased in CAL-27 cells treated with either 0.5 nM or 2 nM cetuximab-MMAE-Cy5 (FIG. 21C). In contrast, 2 nM cetuximab-Cy5 did not affect survival of irradiated cells compared to control irradiated cells.

Cetuximab-MMAE-Cy5 and Ionizing Radiation Enhance Tumor Xenograft Regression

Figure 22:
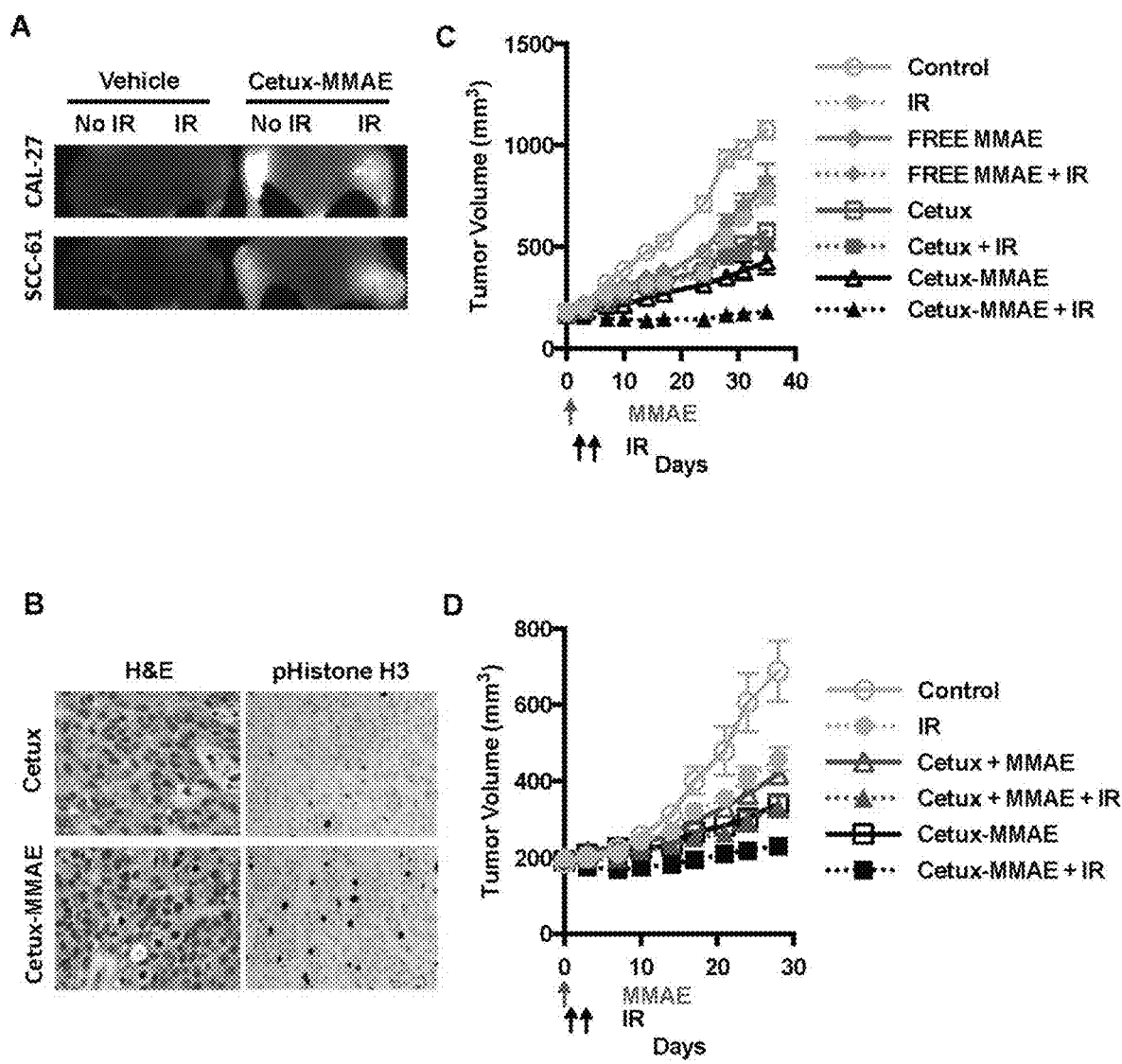
FIG. 22: Cetuximab-MMAE in combination with IR inhibits tumor xenograft growth. A) CAL-27 and SCC-61 tumor xenografts were grown in the bilateral thighs of athymic nude mice. 0.5 nmoles of cetuximab-MMAE-Cy5 was intravenously injected. 24 hours later the right thigh bearing tumors were irradiated with 3 Gy. Tumors were imaged 24 hours post IR for Cy5 fluorescence. B) CAL-27 tumor xenograft bearing mice were injected with cetuximab-Cy5 or cetuximab-MMAE-Cy5 and harvested 24 hours later, formalin fixed and stained with H&E or pS10 histone H3. C,D) Mice bearing CAL-27 tumor xenografts were IV injected on day 0 with C) free MMAE, cetuximab-Cy5 or cetuximab-MMAE-Cy5 or D) conjugated cetuximab-MMAE-Cy5 or free MMAE in combination with cetuximab-Cy5. In both experiments for IR treated mice, 3 Gy was delivered on days 1 and 2. Tumors were measured twice a week and plotted as mean tumor volume±SEM.
Figure 30:
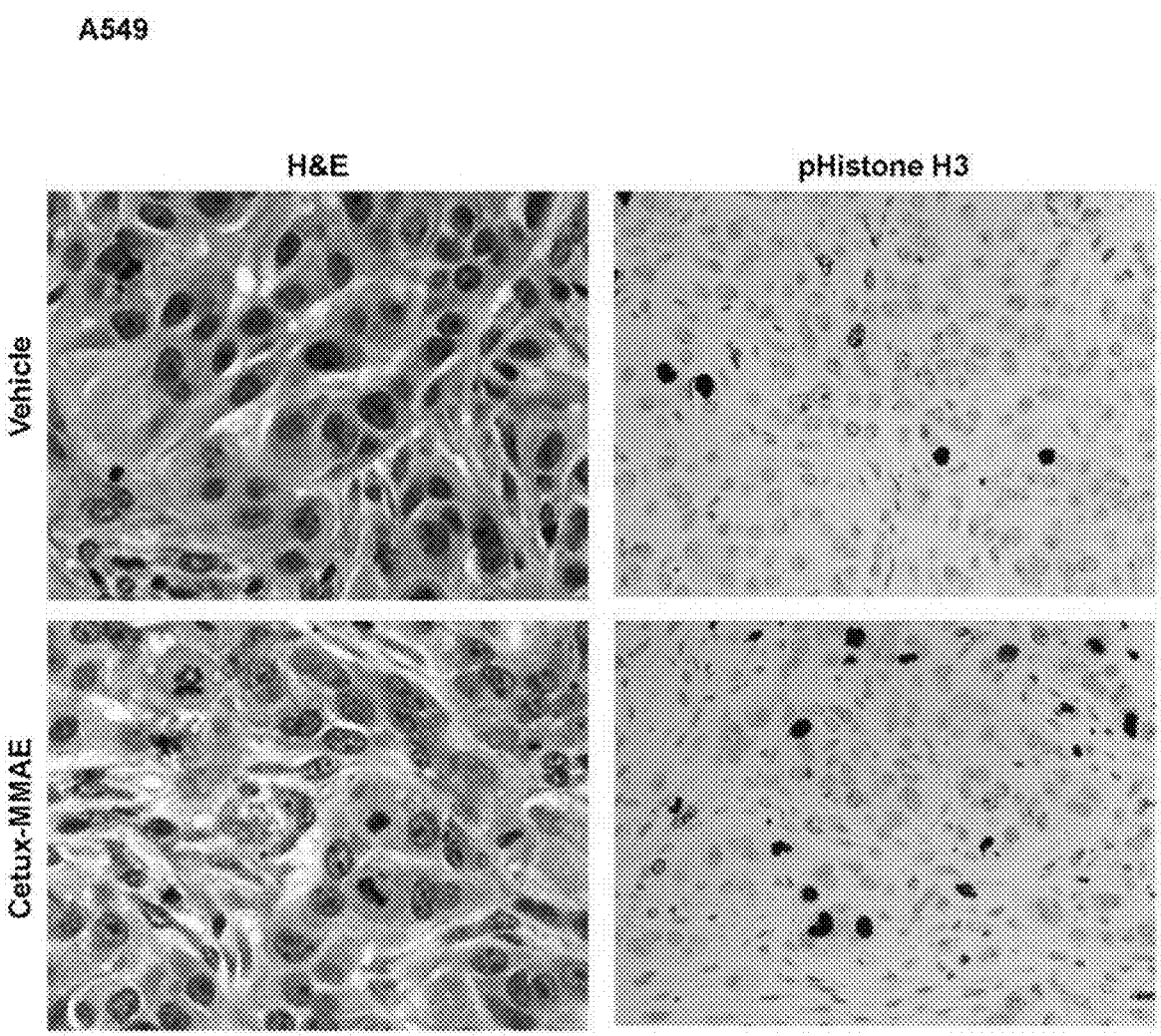
FIG. 30: Cetuximab-MMAE increases $G_2/M$ arrest in A549 tumor xenografts. A549 tumor xenograft bearing mice were injected with vehicle or 0.5 nmoles of cetuximab-MMAE-Cy5 and harvested 24 hours later, formalin fixed and stained with H&E or for pS10 histone H3.
Figure 31:
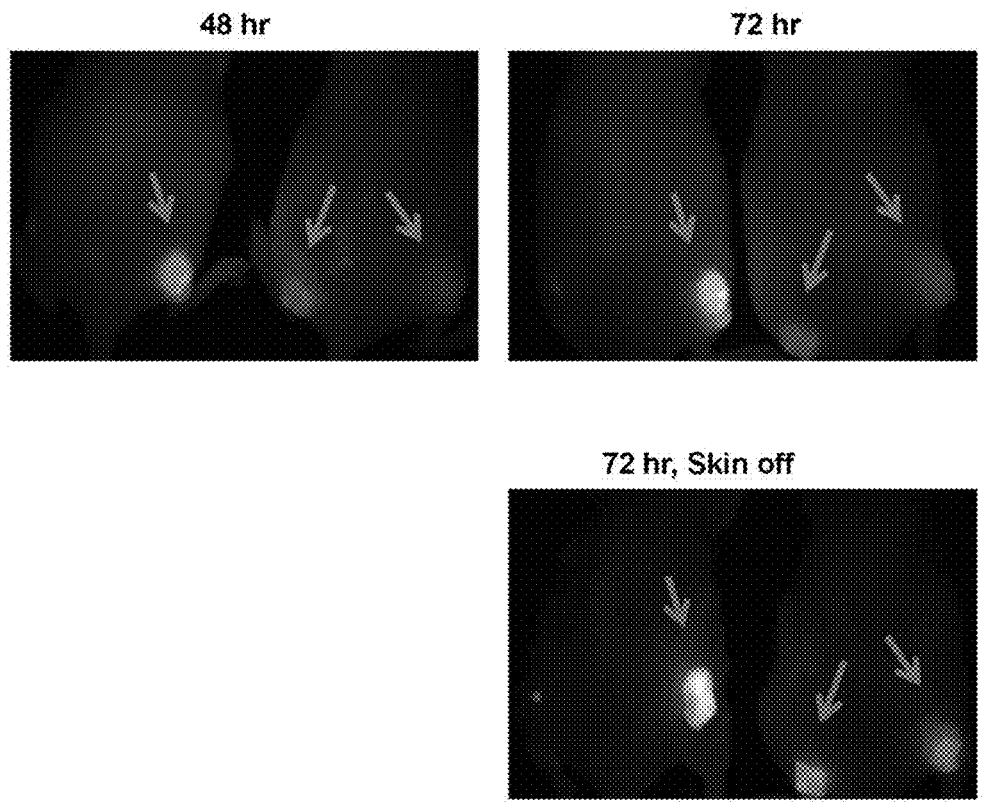
FIG. 31: Cetuximab-MMAE-Cy5 is retained in EGFR expressing tumor xenografts for 72 hrs. CAL-27 tumor xenografts were grown and 0.5 nmoles of cetuximab-MMAE-Cy5 was IV injected into tumor bearing mice. Mice were imaged 48 or 72 hrs later with for Cy5 fluorescence. Red arrows point to tumor Cy5 fluorescence.

We next tested the therapeutic efficacy of combining cetuximab-MMAE-Cy5 with IR on subcutaneous tumor xenografts. We first determined if cetuximab-MMAE-Cy5 localized to tumor xenografts upon intravenous injection. Tumor bearing mice were injected with 0.5 nmoles of cetuximab-MMAE-Cy5 and imaged for Cy5 fluorescence. HNSCC (CAL-27, SCC-61, SCC-35 and SQ-9G), NSCLC (A549) and colorectal (HCT-116) tumor xenografts showed strong Cy5 signal while tumor xenografts from low EGFR expressing LN-229 did not (FIG. 22A, FIG. 29). Next we tested if tumors harvested from mice injected with cetuximab-MMAE-Cy5 had increased accumulation in $G_2$/M due to MMAE. CAL-27 tumor xenografts were harvested 1 day after mice were injected with cetuximab-Cy5 or cetuximab-MMAE-Cy5 (FIG. 22B). Tumor sections were probed for the mitotic marker pS10 histone H3. CAL-27 tumor xenografts treated with cetuximab-MMAE-Cy5 had a 75% increase in staining for pS10 histone H3 compared to cetuximab-Cy5. A549 tumor xenografts also had an increased fraction of tumor cells arrested in G2/M following cetuximab-MMAE-Cy5 injections (FIG. 30).

To test the therapeutic efficacy of cetuximab-MMAE-Cy5 and IR, CAL-27 tumor xenografts were grown to a mean tumor volume of 150 mm$^3$ in the hindlimb of athymic nude mice. Mice were treated systemically with vehicle, free MMAE, cetuximab-Cy5, or cetuximab-MMAE-Cy5 on day 0 by tail vein injection (FIG. 22C). Cetuximab-Cy5 and cetuximab-MMAE-Cy5 were injected at a dose of 0.5 nmoles. Since an average of four molecules of MMAE were conjugated to each antibody molecule, a dose of 2 nmoles of free MMAE was injected to maintain MMAE dose equivalence. We had observed that cetuximab-MMAE-IR persisted in tumor cells and murine xenografts for at least 48 hrs (FIG. 17A, FIG. 22B, FIGS. 29 and 31), so irradiated tumor xenografts were given 3 Gy on day 1 and 2 (total dose of 6 Gy) to the tumor focally, with the remainder of the mouse shielded with lead. By day 35, untreated tumors had grown to >1000 mm$^3$ and were significantly larger than all treatment groups, p<0.0001. In non-irradiated tumors, either free MMAE or cetuximab-Cy5 alone delayed tumor growth, which was further increased in mice treated with conjugated cetuximab-MMAE-Cy5, p<0.01. Moreover, the addition of IR to cetuximab-MMAE-Cy5 increased tumor xenograft growth delay, p<0.001 to all experimental groups. There was no overt toxicity of treatment as measured by mouse body weight (FIG. 32). To ascertain the advantage of using MMAE conjugated to cetuximab, we tested if MMAE conjugated to cetuximab was more effective than co-administration of free MMAE with cetuximab in combination with irradiation (FIG. 22D). In non-irradiated mice, there was a non-significant decrease in tumor volume in cetuximab-MMAE compared to cetuximab and MMAE co-delivery. However in irradiated tumor xenografts, mean volume of tumors treated with conjugated cetuximab-MMAE-Cy5 was significantly smaller than after co-administration of cetuximab and MMAE, p<0.01.

Discussion

We have demonstrated the feasibility and applicability of targeting EGFR tumors with a potent tumoricidal and radiosensitizing drug conjugated to cetuximab. We synthesized a theranostic antibody drug conjugate, by conjugating a fluorophore (Cy5) and a therapeutic drug (MMAE) to cetuximab. MMAE was conjugated to the antibody by a valine-citrulline dipeptide linker. The valine-citrulline linker is stable in serum yet allows for release of MMAE intracellularly by the action of cathepsin B in endolysosomes. Our synthesized cetuximab-MMAE-Cy5 molecule has both diagnostic and therapeutic capabilities. The conjugated fluorophore Cy5 provided a label to evaluate binding to tumor cells in vitro and to monitor accumulation in tumor xenografts in vivo. Importantly, the activity of MMAE was restricted by conjugation to cetuximab. Whereas free MMAE was toxic to cells irrespective of EGFR expression, cetuximab-MMAE-Cy5 was non-toxic to low EGFR expressing tumor cells (i.e. LN-229). In EGFR-1 expressing cells, the potency of free versus cetuximab conjugated MMAE mirrored the cell surface receptor availability of EGFR-1, as expected from the selective lability of the ADC. The restriction of MMAE activity by cetuximab to EGFR-1 expressing cells resulted in selective radiosensitization.

Concurrent chemo-radiotherapy strategies in the clinic are for the most part reliant on the use of cytotoxic chemotherapies, i.e. cisplatin, taxanes and 5-FU. While targeted therapies have seen advancement as single agent therapy, few have been successfully tested with concurrent radiotherapy. The sole success to date has been cetuximab. This was based on a landmark clinical trial in locally advanced HNSCC patients randomized to radiotherapy alone or radiotherapy with concurrent cetuximab. However, cetuximab-radiotherapy has not been successfully compared to cisplatin-radiotherapy in clinical trials. Moreover, recent retrospective studies suggest that cetuximab-radiotherapy may be inferior to cisplatin-radiotherapy. The addition of cetuximab to concurrent chemo-radiotherapy in NSCLC or HNSCC patients has not proven to improve clinical outcomes. While targeting EGFR is appealing since the EGFR signaling pathway inhibition sensitizes tumor cells to IR, blocking EGFR signaling has resulted in bypass resistance pathways, including PI3K, Ras and AXL.

To overcome the limitations of EGFR based radiosensitization strategies, we have initially tested an ADC approach where MMAE was conjugated to cetuximab. We have recently demonstrated that MMAE is a potent radiosensitizer. In addition, MMAE has already shown clinical efficacy in lymphomas when conjugated to a CD30 targeting antibody to form brentuximab vedotin. Cetuximab was chosen based on its routine use in the clinic. In cell culture, our tested cell lines were relatively resistant to cetuximab, however MMAE conjugation resulted in potent nanomolar radiosensitization (FIG. 21, FIG. 28). An advantage of targeted radiosensitizer delivery is the ability to achieve higher local concentrations of drug delivery. In our tumor xenograft experiment, cetuximab-MMAE-Cy5 resulted in significant tumor growth delay when compared to co-administration of free MMAE with cetuximab, both in combination with IR (FIG. 22D).

In our therapeutic paradigm, the EGFR serves as a localizing beacon to deliver radiosensitizers. Patient selection would be based on tumor cell receptor surface availability and not on tumor histology, thereby allowing for personalized radiosensitization strategies. Our theranostic cetuximab-MMAE-Cy5 allowed for identification of tumor cell lines that high increased EGFR-1 surface receptor availability. Potency of MMAE directly correlated with Cy5 cell surface fluorescence when both are conjugated to cetuximab. Tumors can have abundant total EGFR histologically yet express very little of it on their cell surface (FIG. 3), presumably because the EGFR remains largely trapped in internal organelles. For such difficult cases, an alternative strategy is activatable cell penetrating peptides, which do not require specific receptors, yet which deliver imaging, chemotherapeutic, and radiosensitizing cargoes.

When antibody conjugation of the radiosensitizer works, it can greatly improve the therapeutic index. We have initially used a potent single agent cytotoxic drug that also functions as a radiosensitizer (MMAE). Given the expression of EGFR receptors on normal tissue, further improvement in the therapeutic index could be achieved by conjugation of drugs that specifically inhibit the DNA damage response and double strand break repair. Such drugs would have increased activity in irradiated cells thereby decreasing off-target toxicity inherent to broadly cytotoxic agents such as MMAE. Moreover, our antibody targeted radiosensitization strategy could be applicable to other tumors for which overexpressed receptors are identified and therapeutic antibodies identified. For example, trastuzumab-DM1 (DM1 is also known as mertansine) is clinically approved in the metastatic breast setting. HER2 overexpression has been identified on a proportion of lung, esophageal and gastric cancers. These tumor types are routinely treated with concurrent chemo-radiotherapy with significant morbidity and less than optimal tumor control rates.

Example 3: Tumor Radiosensitization by Monomethyl Auristatin E: Mechanism of Action and Targeted Delivery Abstract Intrinsic tumor resistance to radiotherapy limits the efficacy of ionizing radiation (IR). Sensitizing cancer cells specifically to IR would improve tumor control and decrease normal tissue toxicity. The development of tumor-targeting technologies allows for developing potent radiosensitizing drugs. We hypothesized that the anti-tubulin agent monomethyl auristatin E (MMAE), a component of a clinically approved antibody-directed conjugate, could function as a potent radiosensitizer and be selectively delivered to tumors using an activatable cell-penetrating peptide targeting matrix metalloproteinases and RGD-binding integrins (ACPP-cRGD-MMAE). We evaluated the ability of MMAE to radiosensitize both established cancer cells and a low-passage cultured human pancreatic tumor cell line using clonogenic and DNA damage assays. MMAE sensitized colorectal and pancreatic cancer cells to IR in a schedule- and dose-dependent manner, correlating with mitotic arrest. Radiosensitization was evidenced by decreased clonogenic survival and increased DNA double-strand breaks in irradiated cells treated with MMAE. MMAE in combination with IR resulted in increased DNA damage signaling and activation of CHK1. To test a therapeutic strategy of MMAE and IR, PANC-1 or HCT-116 murine tumor xenografts were treated with non-targeted free MMAE or tumor-targeted MMAE (ACPP-cRGD-MMAE). While free MMAE in combination with IR resulted in tumor growth delay, tumor-targeted ACPP-cRGD-MMAE with IR produced a more robust and significantly prolonged tumor regression in xenograft models. Our studies identify MMAE as a potent radiosensitizer. Importantly, MMAE radiosensitization can be localized to tumors by targeted activatable cell-penetrating peptides.

Introduction

Locally advanced tumors are commonly treated with combination chemotherapy and radiotherapy. In randomized clinical trials, concurrent chemotherapy-radiotherapy has demonstrated improved local tumor control and overall survival, including gastrointestinal tumors (1-4). A principal rationale for using concurrent chemotherapy with radiotherapy is the ability of chemotherapy drugs to radiosensitize. Radiosensitizers increase ionizing radiation (IR)-mediated DNA damage and tumor cell kill (5-7). To be clinically useful, radiation sensitizers must improve the therapeutic index, that is, the level of sensitization of tumor cells must be greater than that of normal tissue. A major limitation to using more potent radiosensitizers is the inability to deliver such agents specifically to the tumor.

Cell sensitivity to IR varies throughout the cell cycle with $G_2$-M being the most sensitive phase (8). Chemotherapy drugs such as paclitaxel block cells in $G_2$-M, function as radiosensitizers, and are used clinically with radiotherapy (9). Monomethyl auristatin E (MMAE) is a synthetic derivative of dolastatin 10 and functions as a potent antimitotic agent by inhibiting tubulin polymerization (10). We therefore tested the ability of MMAE to function as a radiosensitizer. However like many potent antitumor agents, systemic delivery of MMAE is limited by toxicity. When MMAE delivery is tumor restricted by conjugation to a CD30 targeting antibody (brentuximab vedotin), its efficacy becomes clinically apparent for lymphomas (11, 12).

To evaluate the ability of targeted MMAE tumor delivery to radiosensitize tumors, we used activatable cell-penetrating peptide (ACPP) technology. ACPP can function as tumor-targeted delivery vehicles (13-16). MMAE has recently been conjugated to ACPP-cRGD as a therapeutic payload (ACPP-cRGD-MMAE) in murine models of breast cancer (17). ACPPs consist of 4 regions: a polyanionic autoinhibitory domain, a protease-sensitive peptide linker region, a cell-penetrating polycationic peptide, and the payload to be delivered. The polycationic cell-penetrating peptide consists of 9 D-arginines ($r_9$) and the autoinhibitory portion is 9 D-glutamates (e9). A flexible peptide linker separates these 2 domains. For therapeutic applications, anticancer drugs are the payload conjugated to the polycationic cell-penetrating peptide portion to facilitate their intracellular delivery (17). While the ACPP is intact, the polyanion region prevents adhesion and uptake of the polycationic cell-penetrating peptide plus payload. Upon extracellular protease attack on the linker region, drug-conjugated $r_9$ is released and taken up by cells, where a second protease in the endocytic pathway releases the drug from the $r_9$. Tumor-specific activation of ACPP has been achieved by inserting a (SEQ ID NO:4) PLGC(Me)AG linker sequence between the polyanionic and polycationic regions. Cleavage of this peptide linker is dependent on gelatinases, MMP-2 and -9. To augment MMP activity and cleavage of (SEQ ID NO:4) PLGC(Me)AG, the ACPP was designed to co-target RGD-binding integrins. $\alpha_v\beta_3$ integrin binds to the hemopexin domain of MMP-2 and enhances MMP activation (18).

Here, we evaluated the ability of MMAE to radiosensitize tumor cells and to be targeted to tumor xenografts in combination with IR. We show MMAE arrests cells in $G_2$-M in the 1 to 5 nmol/L range and has an $IC_{50}$ that is >6-fold lower than paclitaxel. Of significance, we demonstrate that in addition to its intrinsic antitumor activity, MMAE sensitized cells to IR. MMAE radiosensitization showed both schedule and dose dependency, with MMAE radiosensitization directly correlating with accumulation of cells in $G_2$-M. In irradiated cells treated with MMAE, there was decreased clonogenic survival and increased activation of the DNA damage response. We then evaluated a therapeutic strategy of combining MMAE with IR in murine tumor xenograft models. We tested both nontargeted and tumor targeted MMAE delivery in PANC-1 and HCT-116 xenografts. For tumor-targeted delivery, we used ACPP-cRGD-MMAE. Combining ACPP-cRGD-MMAE with IR in either HCT-116 or PANC-1 tumor xenografts resulted in prolonged tumor xenograft regression that was not observed with IR or ACPP-cRGD-MMAE alone. Moreover, the advantage of tumor-targeted MMAE delivery was demonstrated in irradiated tumor xenografts. ACPP-cRGD-MMAE tumor-targeted delivery increased tumor xenograft control compared with free MMAE. Our results provide for a therapeutic treatment paradigm in which selective and potent radiosensitization can be achieved with tumor-targeted ACPP.

Materials and Methods

Cells and Reagents

Human colorectal HCT-116 (ATCC CCL-247) and pancreatic PANC-1 (ATCC CRL-1469) adenocarcinomacell lines were directly obtained from ATCC (STR tested) and passaged for less than 6 months following resuscitation. 779E is a limited passage pancreatic adenocarcinoma cell line developed in the Lowy laboratory from patient-derived pancreatic adenocarcinoma xenograft. 779E has been whole-exome sequenced in 2014 for mutational status and also was confirmed to be human origin. The XPA-1 cell line was initially derived from a patient-derived pancreatic xenograft from Johns Hopkins (Baltimore, Md.) and provided by the Lowy laboratory. Cells were negative for mycoplasma before use in experiments. Cells were cultured in DMEM supplemented with 10% FBS. For patient-derived pancreatic adenocarcinoma xenografls (PDX), primary tumors from patients were directly implanted orthotopically into NOD/SCID gamma (NSG) mice and passaged serially by orthotopic re-implantation. Paclitaxel (Sigma) and MMAE (Concortis) were both reconstituted in DMSO. ACPP and ratiometric ACPP peptides were synthesized as previously reported (17, 19).

Cell Cycle and Apoptosis

Cells were treated with MMAE for 24 hours and then fixed in methanol. Cells were treated with RNAse, stained with propidium iodide (PI), and analyzed by FACS using FlowJo software.

Alamar Blue Assay

Cells were plated in 96-well plates and exposed to MMAE or paclitaxel for 72 hours and analyzed at 560 nm. For irradiated cells, cells were treated with MMAE overnight followed by 6 Gy.

Clonogenic Assay

Cells were treated with MMAE for 24 hours and then irradiated with 0 to 8 Gy. Following IR, cells were replated in drug-free media. Colonies formed over 10 to 14 days and were counted.

Neutral Comet Assay

Cells were treated for indicated length and doses of MMAE followed by 6 Gy. Cells were harvested 15 minutes after IR and underwent neutral electrophoresis (Trevigen). Comet tails were counted in multiple fields (>60 cells per sample) and analyzed using CometScore (TriTek Corp).

γH2Ax Immunostaining

Cells grown on glass coverslips were treated with MMAE overnight and then irradiated. Two hours after IR, cells were fixed, permeabilized, and stained with antibody to 7H2Ax. Nuclei were stained with 4',6-diamidino-2-phenylindole (DAPI). Foci were counted in 6 to 8 high-power fields per group.

Immunoblotting

MMAE- and IR-treated cells were harvested and lysed in RIPA buffer with protease and phosphatase inhibitors (Roche). Thirty micrograms of lysate underwent electrophoresis using 4% to 12% Bis-Tris gels (Life Technologies), transferred to polyvinylidene difluoride (PVDF) membranes, and incubated with indicated primary antibodies (Cell Signaling Technology). Blots were developed by ECL (Pierce).

Tumor Xenograft Gel Zymography

All animal work was done in compliance with the UCSD Institutional Animal Use and Care Committee. Six- to 8-week-old female athymic nu/nu mice (UCSD Animal Care Program) were injected subcutaneously into thighs with $5\times10^6$ HCT-116 or PANC-1 cells in a 1:1 Matrigel (BD) and PBS solution. After tumors grew to >200 $mm^3$, the right tumor hindlimb was focally irradiated whereas the remainder of the mouse including the left tumor hindlimb was shielded from IR with custom lead blocking >95% of the dose as verified by dosimeters placed on the mouse. Tumors were excised from animals 1 day after IR. Nonirradiated pancreatic adenocarcinoma PDX tumors were also tested for gelatinase activity. Tris-SDS buffer was added at a ratio of 9 μL buffer per mg of tissue. Tumors were homogenized, centrifuged, and the supernatant diluted 1:1 with PBS. Tris-glycine sample buffer (2×) was added and the samples were run on zymography gels (Life Technologies). The gels were placed in renaturing buffer and then transferred to developing buffer (Life Technologies).

Immunohistochemistry

Mice were treated with IR or intravenous injection of ACPP-cRGD-MMAE, tumor tissue was harvested, formalin fixed, and paraffin embedded followed by staining with indicated antibodies (Ventana Medical Systems). The primary antibody was used at a 1:250 dilution and was visualized using DAB as a chromogen with the UltraMap system (Ventana Medical Systems).

In Vivo Tumor Xenograft Optical Imaging

Tumor xenografts were irradiated as described above. One day after IR, mice were anesthetized (1:1 mixture of 100 mg/mL of ketamine and 5 mg/mL of midazolam) and intravenously injected with either fluorescently labeled ratiometric ACPP (Cy5 and Cy7) or ACPP-cRGD-MMAE (Cy5). Animals were imaged using a Maestro Small Animal Imager (CRI) with excitation filter of 620/22 nm and 645 nm long-pass emission filter with dichroic filter tuned to 670 nm. Imaging was done both with skin on and after skin removal to decrease autofluorescence and scattering.

In Vivo Tumor Xenograft Experiments

HCT-116 or PANC-1 tumor growth was measured with digital calipers. Tumor volume was calculated using the formula as ½×length×width$^2$. Mice were randomized into groups as indicated in Results once the average tumor volume reached >200 mm$^3$. Free MMAE was injected on an equimolar basis to ACPP-cRGD-MMAE.

Statistical Analysis

Unpaired 2-sided t tests were performed for $IC_{50}$ and radio-sensitization experiments in cell culture. In tumor regression studies, 2-way ANOVA analysis was performed with Tukey multiple comparison group. All statistical analyses were performed using Prism software (GraphPad).

Results

Cytotoxicity of MMAE Against Tumor Cell Lines

We first tested the ability of MMAE to block proliferating tumor cells in $G_2$-M.

Established tumor cell lines (HCT-116 and PANC-1) were exposed to MMAE for 24 hours and then collected. HCT-116 and PANC-1 cells showed a dose-response accumulation of cells in the $G_2$-M, with PANC-1 cells more sensitive to MMAE than HCT-116 cells (FIG. 33A). MMAE at 5 nmol/L resulted in 50% of HCT-116 cells blocked in $G_2$-M and at 2 nmol/L in PANC-1 cells.

We next compared the cytotoxicity of MMAE to paclitaxel. Tumor cells were exposed to MMAE or paclitaxel for 72 hours and cell viability was assessed. For HCT-116, the $Ic_{50}$ values for paclitaxel and MMAE were 10.0 and 1.7 nmol/L (FIGS. 33B and 33D). For PANC-1, the $IC_{50}$ values for paclitaxel and MMAE were 15.1 and 0.6 nmol/L (FIGS. 33C and 33D). We also tested a limited passage human pancreatic tumor cell line, 779E. 779E was more resistant to both antimitotic agents; however, it also showed increased sensitivity to MMAE. The $IC_{50}$ values following paclitaxel or MMAE exposure were 52.0 and 5.6 nmol/L, respectively (FIG. 33D).

Interaction of MMAE and IR to Increase DNA Double-Strand Breaks

Figure 39:
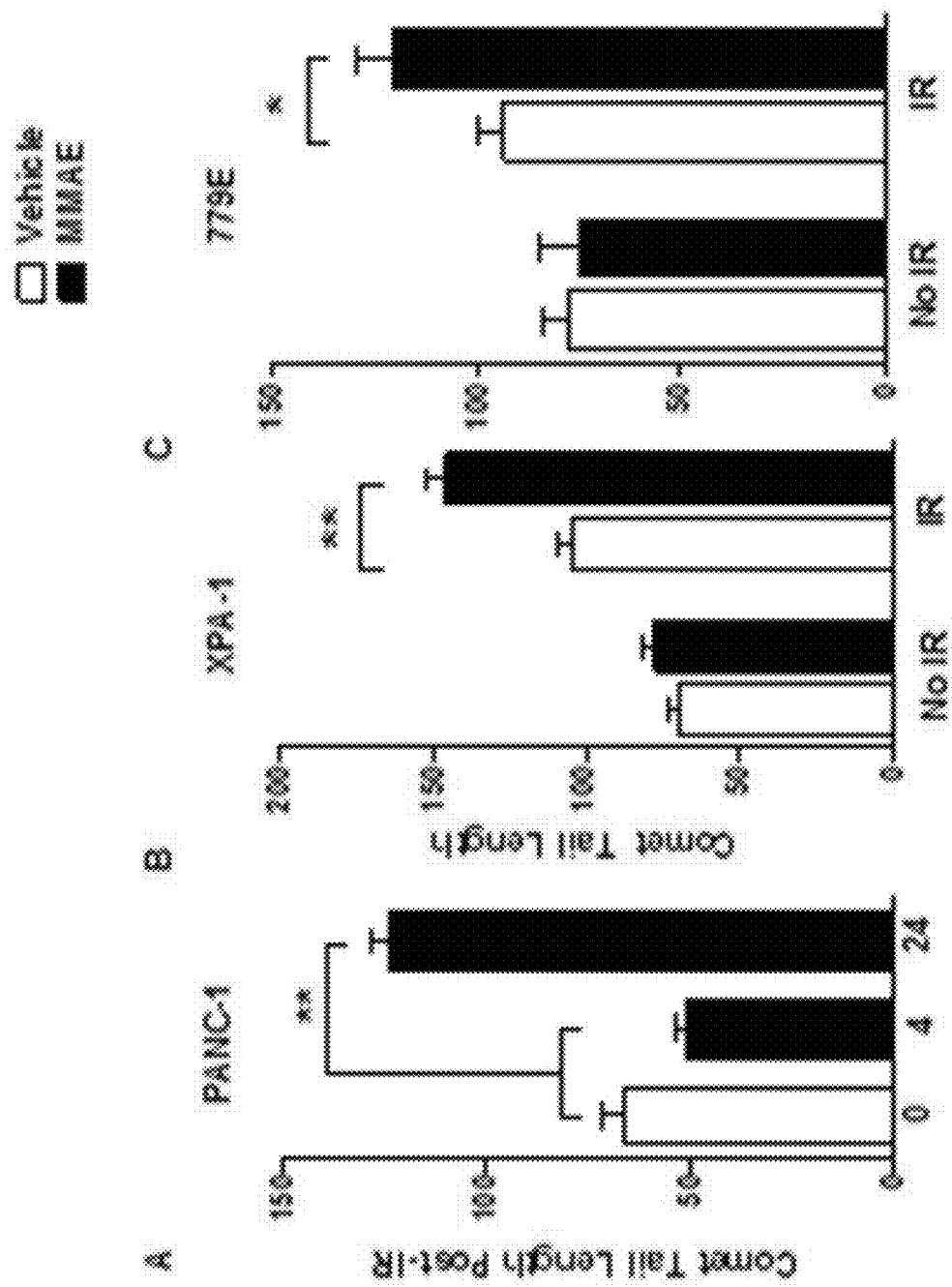
FIG. 39: MMAE enhances comet tail length following irradiation in pancreatic tumor cell lines. A) PANC-1 cells were treated with vehicle or MMAE for 4 or 24 hours followed by 6 Gy. Cells were collected 15 minutes post IR and DNA double strand breaks were quantitated using neutral comet assay to measure comet tail length. Data was normalized to non-irradiated samples. Data is plotted as mean comet tail length±SEM. B), C) XPA-1 and 779E cells were treated with 0 or 1 nM MMAE overnight followed by 2 Gy. Cells were collected 15 minutes post IR and DNA double strand breaks were quantitated using neutral comet assay to measure comet tail length. Data is plotted as mean comet tail length±SEM. **p<0.0001, *p=0.014.

Because MMAE blocks cells in the radiosensitive G2-M phase of the cell cycle, we tested whether MMAE specifically interacted with IR. We hypothesized that while a short exposure to MMAE would not influence radiosensitivity, prolonged MMAE exposure with cells accumulating in $G_2$-M would increase sensitivity to IR. DNA double-stand breaks are a hallmark of IR damage and can be measured by neutral comet assay. HCT-116 cells were treated with 5 nmol/L MMAE for varying lengths of time (0, 2, 4, or 24 hours) and then irradiated (FIG. 34A). Irradiation of cell exposed to MMAE for 2 or 4 hours did not increase comet tail length compared with IR alone. However, 24-hour exposure to MMAE significantly increased comet tail length in irradiated cells compared with vehicle or shorter MMAE exposure time. Immunoblotting for cell phase-specific cyclins demonstrated that 24-hour MMAE exposure resulted in the specific accumulation of the $G_2$-M cyclin B compared with nonmitotic cyclins. A similar schedule dependence of MMAE on IR-induced DNA damage was observed in PANC-1 cells (FIG. 39A).

Next, we evaluated whether 24-hour exposure to MMAE increased IR-induced DNA breaks in a dose-dependent manner. In irradiated HCT-116 cells, treating with 1 nmol/L MMAE did not increase DNA damage over IR alone. However, 5 nmol/L MMAE resulted in a significant increase in IR-induced DNA double-stranded breaks. These results are concordant with dose-response effects of MMAE on cell cycle in HCT-116 cells, where 1 nmol/L of MMAE did not alter the cell-cycle profile but 5 nmol/L did (FIG. 33A). Overnight MMAE exposure also significantly increased comet tail length following IR in XPA-1 and 779E cells (FIGS. 39B and 39C).

MMAE Decreases Clonogenic Survival in Irradiated Cells

Figure 35:
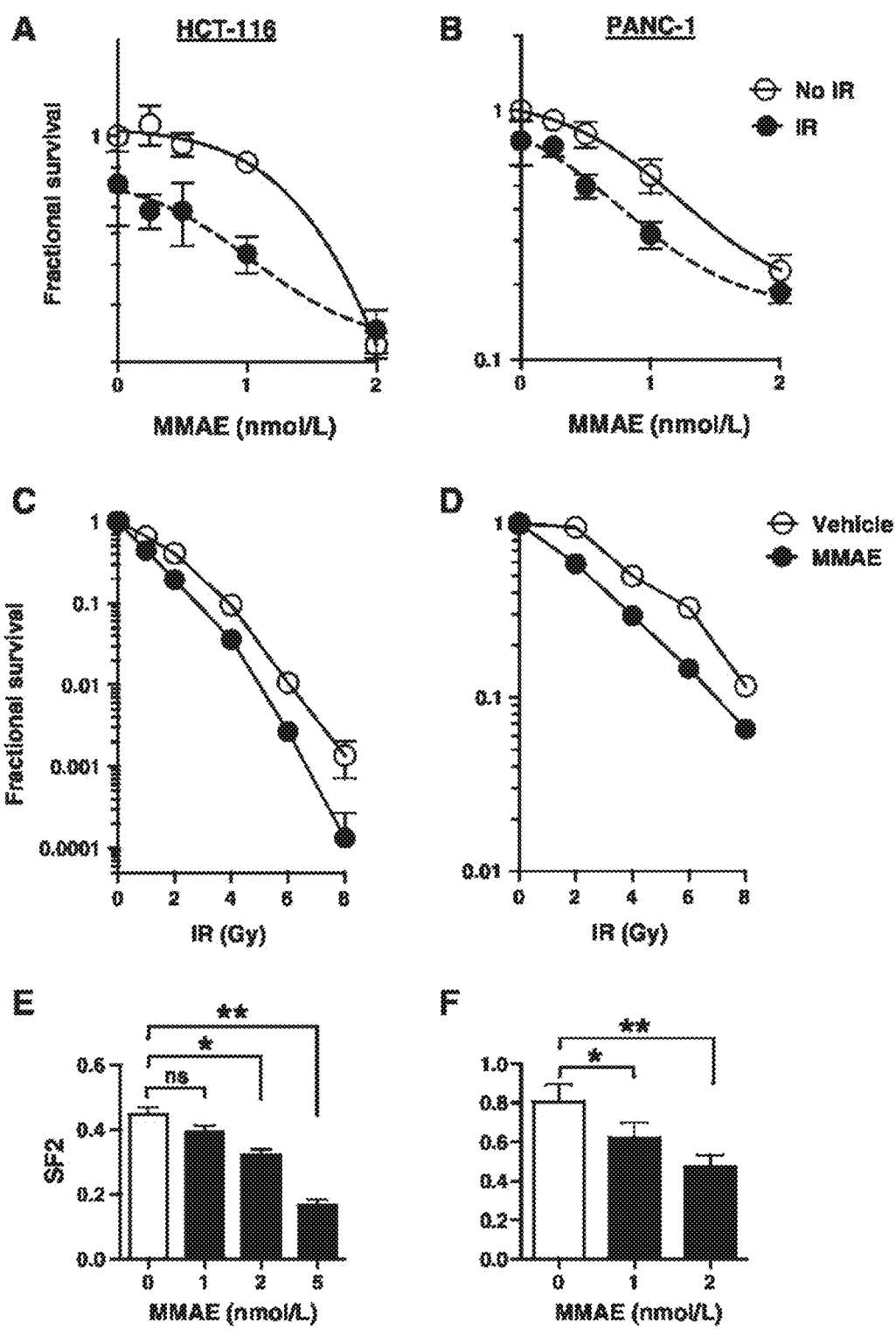
FIG. 35: MMAE decreases clonogenic survival of irradiated tumor cells. A) and B), HCT-116 and PANC-1 cells were exposed to varying concentrations of MMAE overnight followed by 6 Gy. Cell viability was normalized to vehicle-treated, nonirradiated cells and plotted as fractional survival±SD. C) and D), clonogenic survival assay to measure radiosensitization. HCT-116 and PANC-1 cells were treated with 5 and 2 nmol/L MMAE and then irradiated. Data are plotted as mean surviving fraction±SD. E) and F), the effect of MMAE with 2 Gy on cell survival was measured by clonogenic survival. Survival was normalized to nonirradiated cells for each concentration of MMAE. Data are plotted as mean survival±SD. *, P<0.01; **, P<0.0001.

Because MMAE increased IR-induced DNA double-strand breaks, we determined whether MMAE decreased survival in irradiated cells. In the first series of experiments, HCT-116 and PANC-1 tumor cell lines were incubated with varying doses of MMAE overnight and then irradiated with 6 Gy the following day. Cells were continuously exposed to MMAE, and tumor cell viability was measured 72 hours after initiation of MMAE treatment. In HCT116 cells, the $IC_{50}$ for MMAE decreased from 1.6 nmol/L for MMAE alone treated cells to 0.8 nmol/L in cells treated with MMAE and IR (FIG. 35A). In PANC-1 cells, a similar relative reduction (~50%) in the $IC_{50}$ of MMAE was observed. In non-irradiated PANC-1 cells, the $_{IC50}$ value for MMAE was 0.8 nmol/L, which decreased to 0.4 nmol/L when IR was combined with MMAE (FIG. 35B).

The primary mode of cell death following IR is mitotic catastrophe. Therefore, we tested the ability of MMAE to decrease clonogenic cell survival. HCT-116 or PANC-1 cells were exposed to MMAE overnight and then irradiated with 0 to 8 Gy. On the basis of the cell-cycle dose response to MMAE from FIG. 33A, we treated HCT-116 cells with 5 nmol/L and PANC-1 cells with 2 nmol/L of MMAE. Following irradiation, cells were replated in drug-free media at low cell density and colonies grew out over 10 to 14 days. Cell-surviving fractions were normalized to 1 for nonirradiated cells treated with either vehicle or MMAE. MMAE resulted in increased tumor cell kill at doses as low as 2 Gy (FIGS. 35C and 35D). Because conventionally fractionated radiotherapy for tumors is often given with 2 Gy concurrently with chemotherapy, we measured the surviving fraction at 2 Gy (SF2) with varying doses of MMAE. For HCT116, the SF2 for cells treated with 1 nmol/L MMAE was not significantly different from vehicle-treated cells. However, at doses of 2 and 5 nmol/L MMAE, there was a significant reduction in the SF2 compared with cells irradiated with vehicle (FIG. 35E). Consistent with our above results with MMAE alone, irradiated PANC-1 cells showed increased sensitivity at lower MMAE doses. The SF2 in PANC-1 cells was significantly reduced with 1 or 2 nmol/L of MMAE compared with vehicle-treated cells (FIG. 35F).

MMAE Increases DNA Damage Response in Irradiated Cells

Figure 36:
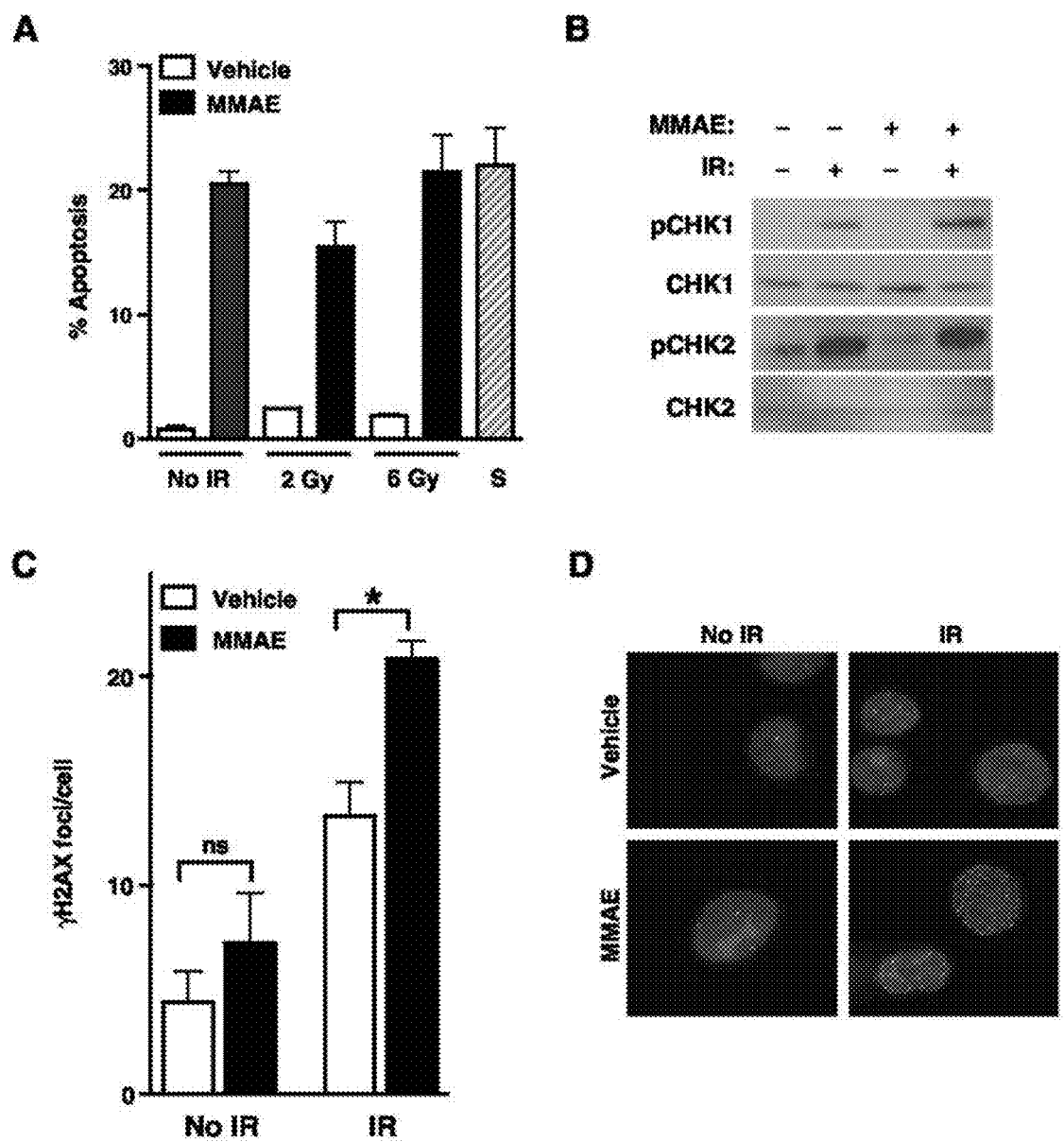
FIG. 36: MMAE increases DNA damage response in irradiated tumor cells. A), HCT-116 cells were treated with MMAE for 24 hours, irradiated, and 24 hours later, apoptosis was measured. Staurosporine-treated cells were used as a positive apoptosis control. B) and C), HCT-116 cells were treated with MMAE for 24 hours before 6 Gy and were collected 2 hours later. Lysates were immunoblotted for activation of CHK1 (pS345) and CHK2 (pT68) or cells were fixed and analyzed by immunofluorescence for gH2Ax foci formation. D), representative images of gH2AX foci formation in PANC-1-treated cells (green). Nuclei were stained with DAPI (blue). *, P<0.05.
Figure 40:
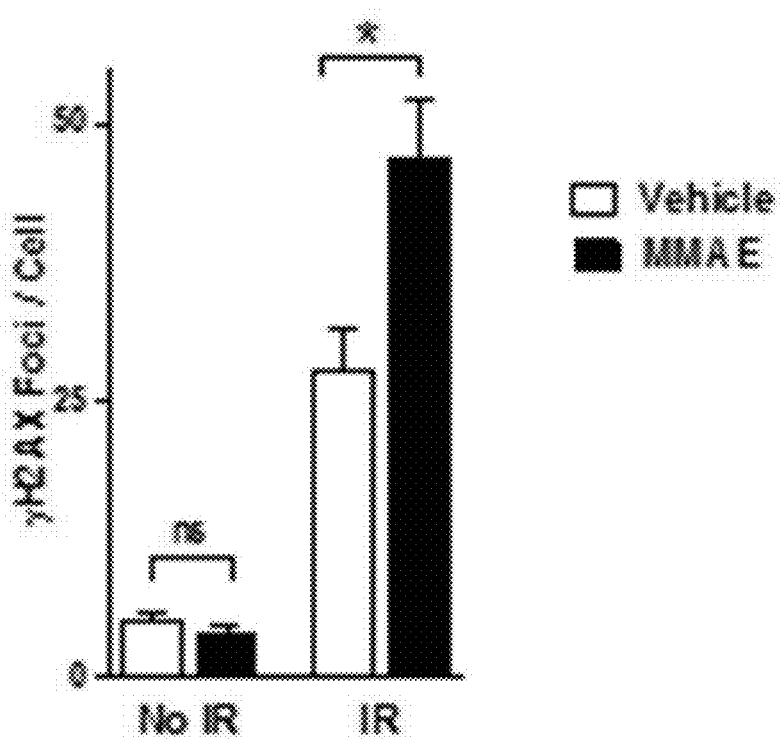
FIG. 40: MMAE enhances 7H2Ax foci formation following irradiation. PANC-1 cells were treated overnight with 0.5 nM MMAE followed by 6 Gy. Cells were fixed 2 hours post IR and analyzed for 7H2Ax foci formation by immunostaining. Nuclei were stained with DAPI. Data are plotted as mean 7H2Ax foci/nucleus±SEM, *p=<0.01.

Because MMAE reduced clonogenic cell survival following IR, we tested whether MMAE increased apoptosis in irradiated cells. HCT-116 cells were treated with MMAE for 24 hours followed by IR. Cells were collected 24 hours after IR and the sub-$G_1$ population (apoptotic) was measured. MMAE alone resulted in a significant increase in apoptosis compared with vehicle-treated cells (FIG. 36A). However, there was no further increase in apoptosis when IR was combined with MMAE. Because MMAE increased DNA double-strand breaks in irradiated cells (FIG. 34), we then evaluated whether MMAE altered the DNA damage response in irradiated cells. HCT-116 cells were treated with MMAE for 24 hours followed by 6 Gy. Cells were collected 1 hour after IR, and activation of the DNA damage checkpoint proteins CHK1 (pS345) and CHK2 (pT68) was ascertained (FIG. 36B). Interestingly, MMAE enhanced CHK1 activation in irradiated cells, whereas CHK2 activation was not affected. Upon DNA damage, histone H2A becomes phosphorylated at S139, γH2AX. MMAE significantly increased γH2AX foci formation in irradiated HCT116 and PANC-1 cells (FIG. 36C-36D and FIG. 40). In nonirradiated cells, MMAE did not alter DNA damage.

Figure 41:
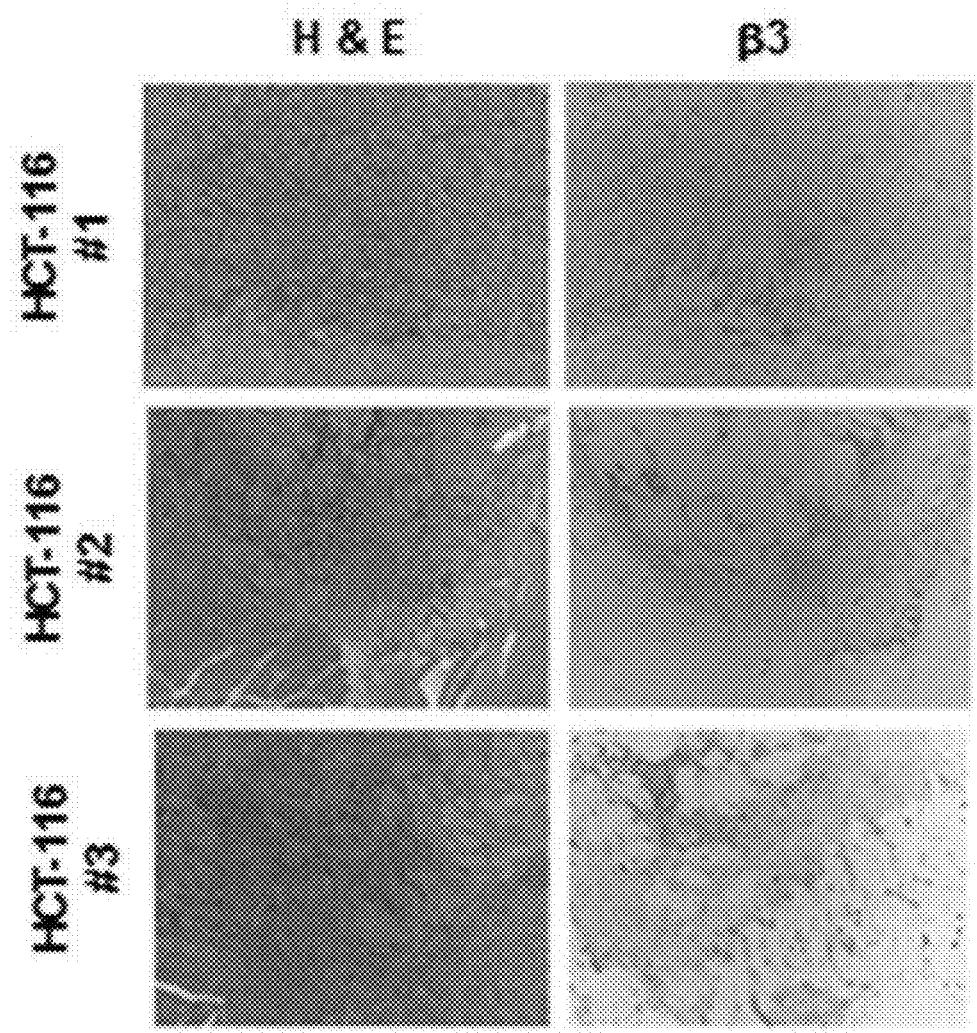
FIG. 41: HCT-116 tumor xenografts have β3 integrin expression. HCT-116 in the hindlimbs of nude mice. β3 integrin expression by IHC in non-irradiated HCT-116 tumors.

Pancreatic and Colorectal Tumor Xenografts Express Protease Activity Against PLGC(Me)AG-ACPP Peptide Linker While MMAE is a potent cytotoxic molecule in cell culture and an effective radiosensitizer, normal tissue toxicity is a limiting factor to exploit it therapeutically in vivo. To target MMAE to tumors, we used MMAE conjugated to a dual integrin and MMP targeted ACPP, ACPP-cRGD-MMAE (17). The linker region of this ACPP is a substrate for MMP-2 and MMP-9. We first tested whether orthotopically grown patient-derived pancreatic adenocarcinoma xenografts (PDX) expressed MMP activity. Two unique PDX xenografts both contained gelatinase activity (FIG. 37A). Next, we tested whether HCT-116 and PANC-1 tumor xenografts had gelatinase activity. Nonirradiated HCT-116 and PANC-1 tumor lysates both contained gelatinase activity as measured by gel zymography (FIG. 37B). We also tested whether tumor irradiation altered MMP activity. Tumor xenografts were irradiated with a single dose of 6 Gy and harvested the following day. Irradiation of tumors did not hamper gelatinase activity. Because ACPP-cRGD-MMAE is co-targeted to cRGD-binding integrin $\alpha_v\beta_3$, we analyzed $\beta_3$ integrin expression and found that PANC-1 and HCT-116 tumors expressed $\beta_3$ integrin (FIG. 37C and FIG. 41). One day after IR, irradiated tumors also abundantly expressed R3 integrin.

To directly assess whether HCT-116 and PANC-1 tumor xenografts can cleave the (SEQ ID NO:4) PLGC(Me)AG linker region incorporated into ACPP-cRGD-MMAE, we used a ratiometric ACPP probe with the same MMP substrate sequence (19). Ratiometric ACPP has a Cy5 far red fluorescent donor and Cy7 near-infrared fluorescent acceptor. While intact, the peptide will favor Cy7 re-emission when excited with Cy5 excitation wavelengths, resulting in a low Cy5:Cy7 emission ratio (blue pseudocolor). However, when the peptide is cleaved, Cy5 emission is no longer quenched, resulting in a higher Cy5:Cy7 emission ratio (red pseudocolor). Tumors were grown in the bilateral hindlimbs. The right hindlimb tumor-bearing region was irradiated, whereas the left hindlimb tumor was shielded. The following day ratiometric ACPP (10 nmoles) was injected intravenously and mice were imaged 2 hours later. Tumors were imaged in situ and after excision. In both HCT-116 and PANC-1 tumors, tumors had increase in Cy5:Cy7 emission ratio compared with surrounding normal tissue, which is indicative of tumor protease activity cleaving the linker region within the ACPP molecule and releasing the polycationic cell penetrating peptide (FIG. 37D and FIG. 42A). Irradiation of tumors 1 day before ratiometric ACPP injection did not diminish peptide cleavage compared with nonirradiated tumors. Interestingly, there was a trend toward increased Cy5:Cy7 emission ratio in irradiated tumors compared with nonirradiated tumors (FIG. 42B).

Therapeutic Efficacy of Combining an Integrin and MMP-Targeted ACPP-cRGD-MMAE with IR We next tested a therapeutic paradigm of using of ACPP-cRGD to deliver the potent radiosensitizer, MMAE. We first validated that MMAE conjugated to the polycationic cell penetrating peptide ($r_9$) was cytotoxic to tumor cells. HCT-116, PANC-1, and 779E cells were exposed to $r_9$ alone or $r_9$ conjugated to MMAE ($r_9$-MMAE). Carrier $r_9$ alone had no cytotoxicity, whereas $r_9$-MMAE produced cytotoxicity in all 3 tumor cell lines (43). We then tested whether ACPP-cRGD-MMAE accumulated in HCT-116 and PANC-1 tumor xenografts. ACPP-cRGD-MMAE with a Cy5 dye attached to the polycation region was intravenously injected. Tumors were imaged 6 hours later. As with ratiometric ACPP (FIG. 37D), ACPP-cRGD-MMAE accumulated in both the non-irradiated and irradiated tumor xenografts (FIG. 38A). To determine whether ACPP-cRGD-MMAE delivered functionally active MMAE within the tumor, HCT-116 tumor xenografts were harvested 24 hours following ACPP-cRGD-MMAE intravenous injection and stained for the mitotic marker, pS10 histone H3 (FIG. 38B). In mice intravenously injected with ACPP-cRGD-MMAE, tumor xenografts demonstrated a 32% increase in pS10 histone H3 staining compared with vehicle treatment, P=0.002.

We then evaluated the efficacy of combined MMAE with focal IR to inhibit tumor xenograft growth. First, we tested the hypothesis that MMAE tumor-targeted delivery would increase tumor regression compared with free MMAE delivery (FIG. 38C). PANC-1 tumor xenografts were grown to a mean volume of 200 mm3 before initiation of therapy. Free MMAE or ACPP-cRGD-MMAE was intravenously injected on days 0 and 1 (6 nmoles of MMAE/d). This dose of MMAE was chosen based on prior studies on animal toxicity associated with free MMAE delivery. Fractionated IR of 3 Gy per day was given on days 1 and 2. On day 1, when MMAE and IR were both given, IR was delivered in the morning and MMAE in the afternoon. By day 30 following initiation of therapy, free MMAE treatment resulted in a small but statistically significant growth delay of PANC-1 tumors compared with untreated control tumors, P<0.0001. The average tumor volume of free MMAE-treated mice was 75% of untreated controls. More importantly, free MMAE in combination with IR resulted in profound tumor xenograft regression compared with IR or free MMAE alone (P<0.0001). In comparing targeted and free MMAE delivery in the absence of IR, ACPP-cRGD-MMAE resulted in significantly greater tumor regression compared with free MMAE, which is consistent with prior studies involving breast cancer models (17). Of significance, IR combined with ACPP-cRGD-MMAE resulted in prolonged tumor regression when compared with free MMAE and IR (P<0.01). Longer follow-up of tumors demonstrated that 2 of 10 PANC-1 tumors treated with ACPP-cRGD-MMAE and IR were less than or equal to their starting tumor volume on day 0 (Table 1). Of significance, such prolonged and sustained tumor regression was observed with only 2 doses of both MMAE and IR and the initial tumor volume was greater than 200 mm³. Moreover, no other treatment group showed long-term tumor regression.

Figure 44:
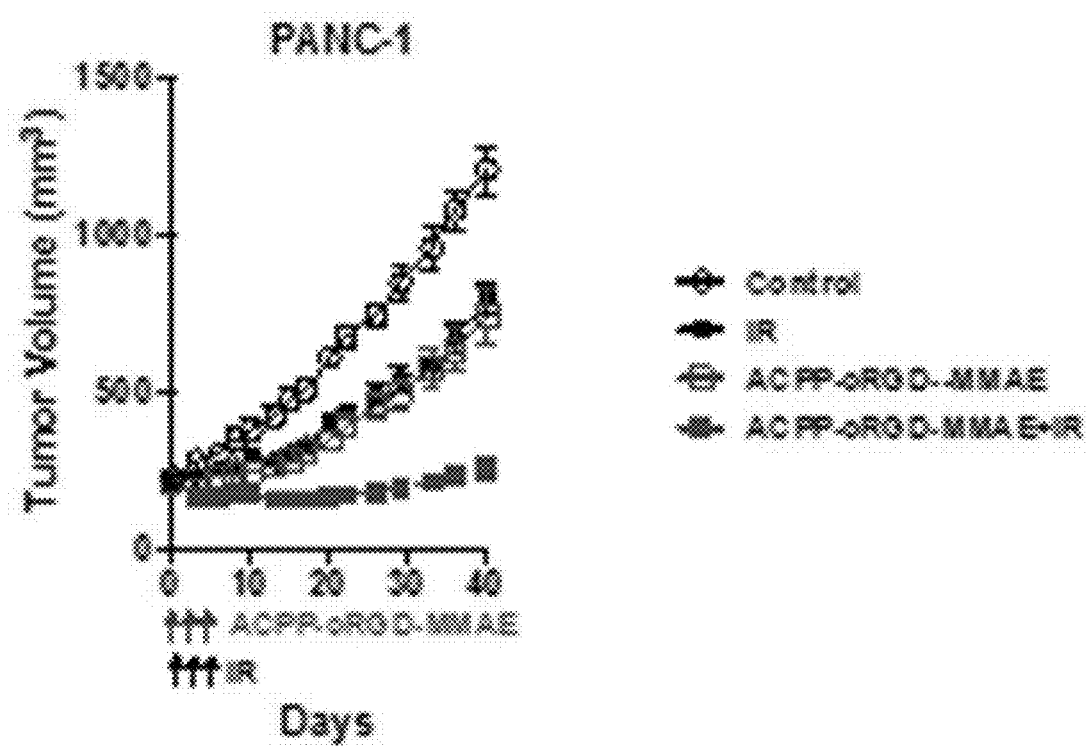
FIG. 44: Combination of increased delivery of ACPP-cRGD-MMAE with IR significantly improved tumor regression. PANC-1 tumor xenografts bearing mice were IV injected with 6 nmoles of ACPP-cRGD-MMAE days 0, 1, and 2. For IR treated tumors, 3 Gy was delivered on days 1, 2 and 3. On days 1 and 2, IR was given 6 hrs after IV injection of ACPP-cRGD-MMAE. PANC-1 tumors were measured twice a week.

We extended our studies on ACPP-cRGD-MMAE and IR by increasing the dosing schedule to see whether it would result in further improvement in long-term regression. ACPP-cRGD-MMAE was given on days 0, 1, and 2 (6 nmoles/day, 18 nmoles total). Fractionated IR of 3 Gy per day was administered on days 1 to 3. Again on days when ACPP-cRGD-MMAE and IR were both given, IR was delivered in the morning and ACPP-cRGD-MMAE in the afternoon. As we observed in FIG. 38C, combining ACPP-cRGD-MMAE with IR again produced significant tumor regression compared with IR or ACPP-cRGD-MMAE alone treated mice (FIG. 44). Tumor volumes in the combined ACPP-cRGD-MMAE and IR mice remained statistically significant compared with all other groups, P<0.0001. More striking and of therapeutic importance, the majority of treated tumors had prolonged tumor regression in PANC-1 tumors upon combining ACPP-cRGD-MMAE with IR By day 40, none of the control or IR alone treated tumors were smaller than their initial tumor volume on day 0 (Table 1).

For the ACPP-cRGD-MMAE alone group, only 1 of 14 tumors was smaller than their initial tumor volumes. In contrast, 8 of 14 tumors in the combined ACPP-cRGD-MMAE and IR group were smaller than their initial tumor volume.

Figure 42:
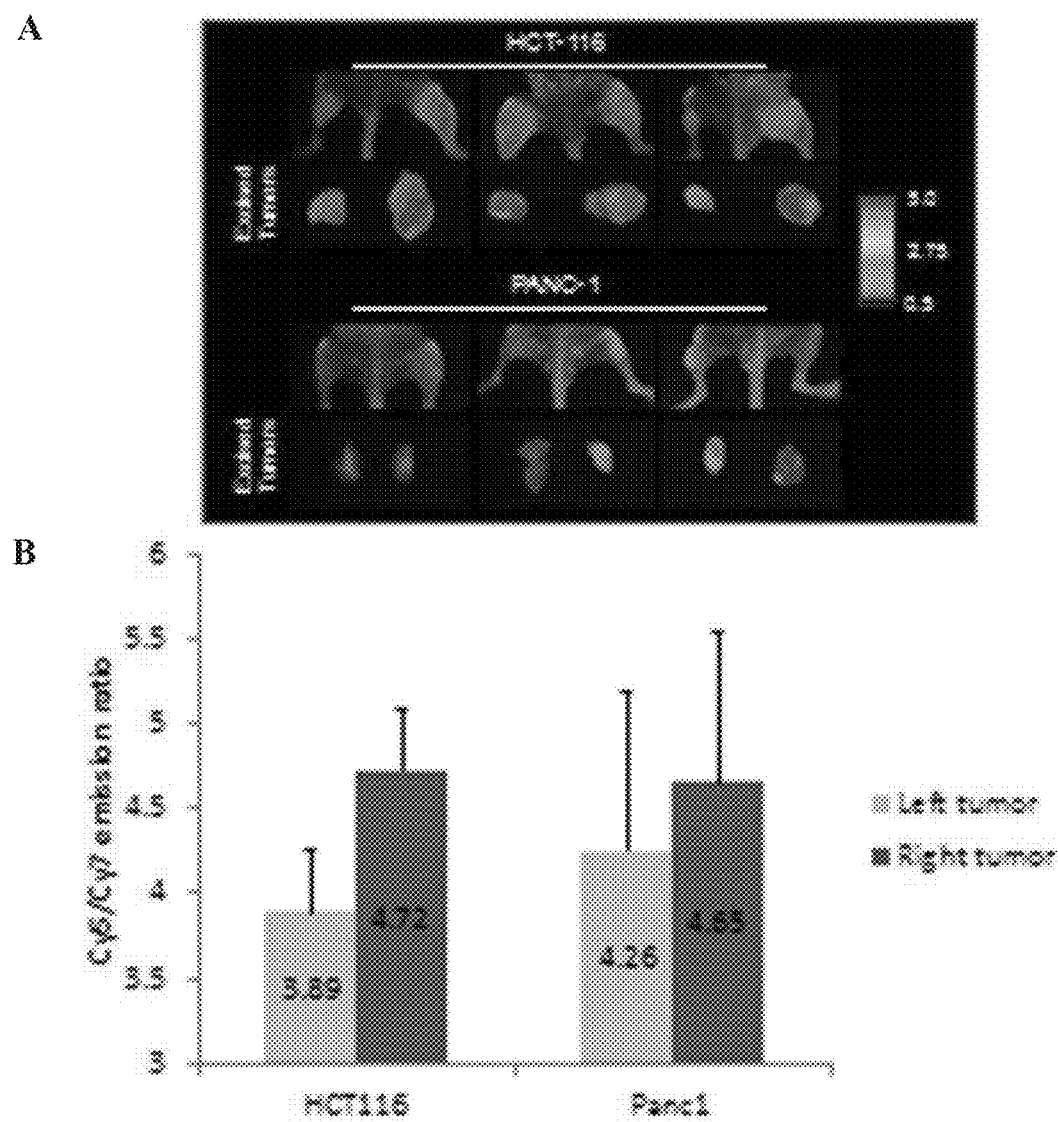
FIG. 42: Tumor xenografts show cleavage dependent tumor contrast with ratiometric ACPP. HCT-116 or PANC-1 tumor xenografts were grown in both the left and right hindlimbs of nude mice. The right tumor was irradiated and the left tumor was shielded to block out >95% of the IR dose A) One day post IR, ratiometric ACPP was intravenously injected and Cy5:Cy7 emission ratio measured 2 hours later (pseudocolor scale at far right) by whole animal imaging with tumors "in situ" and after tumor excision. Imaging of an additional 3 mice with HCT-116 and PANC-1 tumor xenografts in addition to the mice shown in FIG. 36C. B) Quantification of Cy5:Cy7 emission ratio in non-irradiated (LEFT) and irradiated (RIGHT) tumors.

We then tested a modified treatment schedule of ACPP-cRGD-MMAE and IR using HCT-116 tumor xenografts. HCT-116 tumors were grown to mean tumor volume of >270 mm$^3$ before initiation of therapy. We had observed that 6 Gy given to HCT-116 xenografts improved ratiometric ACPP probe cleavage (FIG. 37D and FIG. 42). Therefore in irradiated tumors, we delivered 6 Gy on day 0 followed by 3 Gy on days 1 and 2. ACPP-cRGD-MMAE was intravenously injected on days 0 and 1, 6 hours following irradiation (7.5 nmoles/day). The dose of ACPP-cRGD-MMAE was increased compared with PANC-1, as HCT116 cells had a higher IC$_{50}$ for MMAE. As seen in PANC-1 tumors, ACPP-cRGD-MMAE alone produced a modest growth delay compared with untreated control tumors (FIG. 38D). As expected, IR alone resulted in an initial tumor growth delay (especially prominent due to the 6 Gy dose on day 0); however by day 10, tumor volume began to increase. Combining ACPP-cRGD-MMAE with IR again produced sustained tumor regression compared with IR alone starting at day 10 after the initiation of therapy, P<0.006. By day 14, none of the control or ACPP-RGD-MMAE-treated tumors were smaller than their initial tumor volume on day 0 (Table 1). For the IR alone group, only 3 of 10 tumors were smaller than their initial tumor volume. In contrast, 9 of 10 tumors in the combined ACPP-cRGD-MMAE and IR group were smaller than their initial tumor volume.

TABLE 1

Sustained tumor growth inhibition following treatment with ACPP-cRGD-MMAE and IR

| | V(end)/V(0) ≤ 1 | | |
|---|---|---|---|
| | PANC-1, expt 1 | PANC-1, expt 2 | HCT-116 |
| Control | 0% | 0% | 0% |
| IR | 0% | 0% | 30% |
| Free MMAE | 0% | — | — |
| Free MMAE + IR | 0% | — | — |
| ACPP-cRGD-MMAE | 0% | 7% | 0% |
| ACPP-cRGD-MMAE + IR | 20% | 57% | 90% |

NOTE:
The percentage of treated PANC-1 and HCT-116 tumor xenografts at days 30, 40, 14 [PANC-1 (FIG. 37B), PANC-1 (FIG. 43), HCT-116 (FIG. 37C), respectively] after initiation of treatment were smaller than the initial tumor volume on day 0, V(end)/V(0) ≤ 1.

Discussion

Figure 45:
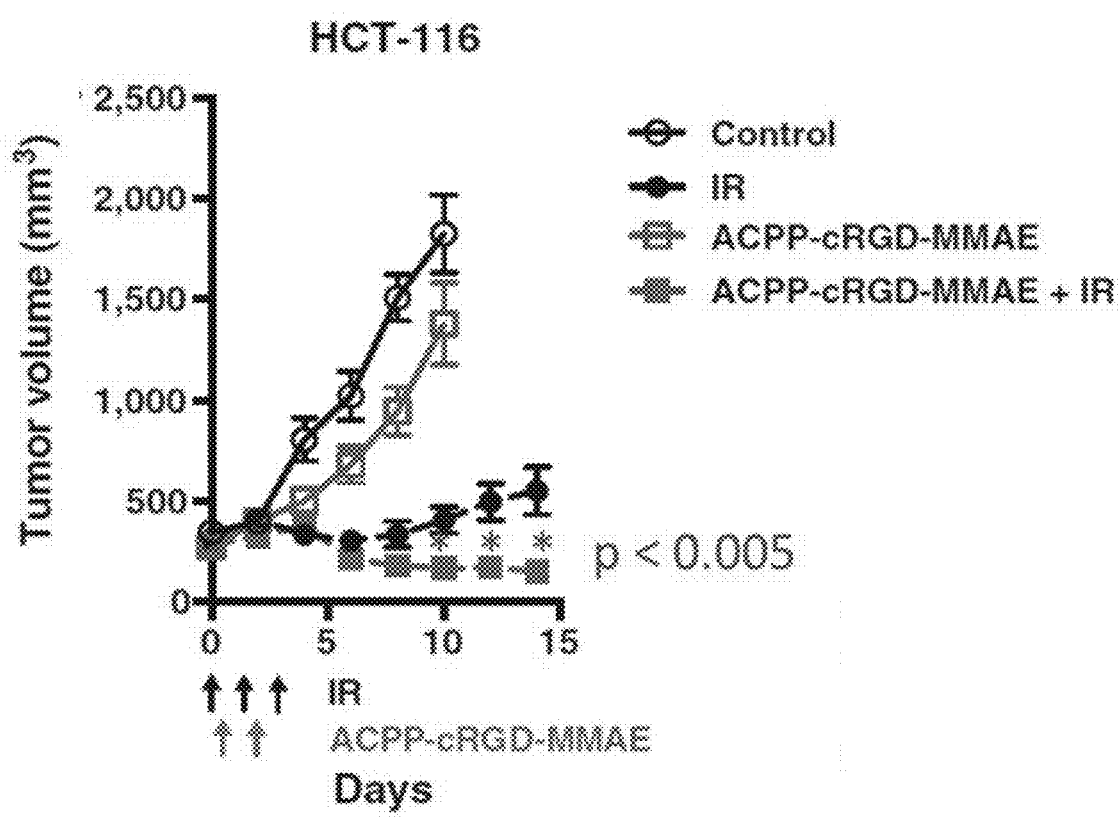
FIG. 45: ACPP-cRGD-MMAE are radiosensitizers, i.e. give more durable tumor regressions with ionizing radiations than any treatment alone. HCT-116 were treated with 6 Gy on day 0 and then 3 Gy on days 1 and 2. A dose of 7.5 nmoles ACPP-cRGD-MMAE was intravenously injected on both days 0 and 1, 6 hrs after IR.
Figure 46:
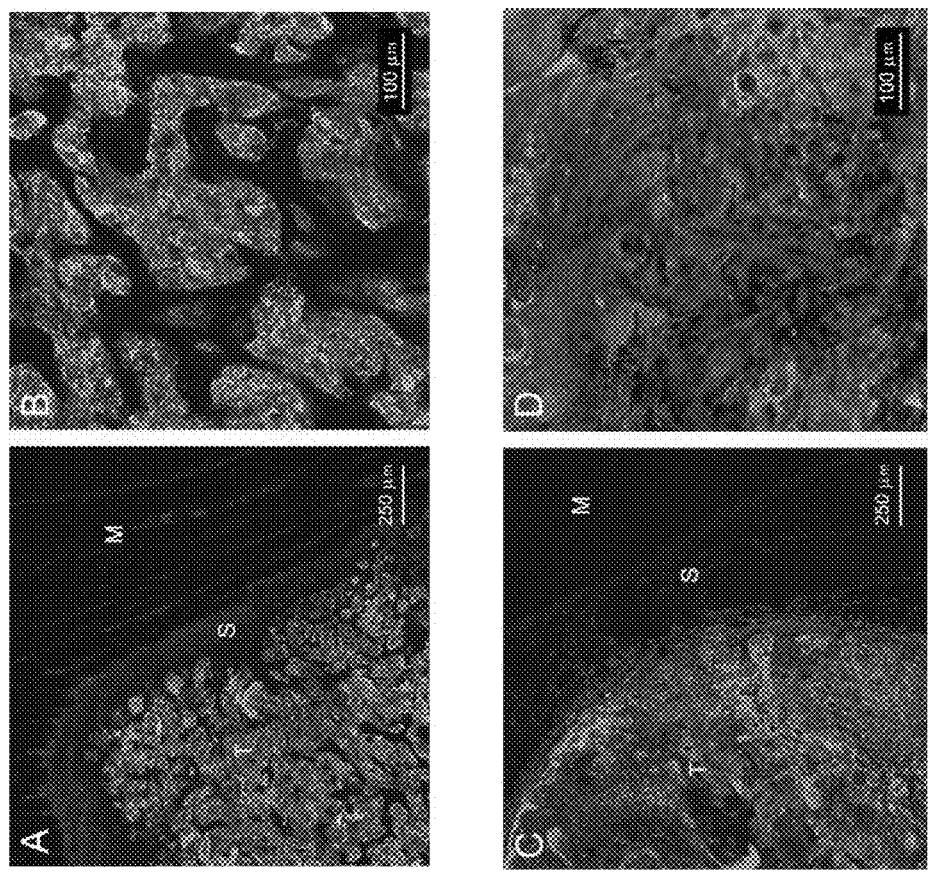
FIG. 46: Mice harboring Cal-27 GFP flank tumors were IV dosed with either A)-B) 5 nanomoles of cetuximab-Cy5 24 hr ago or C)-D) 10 nanomoles (SEQ ID NO:4) PLGC (Me)AG Cy5/Cy7-labeled RACPP (magenta) 2 hr ago. Both sets of tumors were flash frozen in liquid $N_2$ and imaged using the frozen block face technique. Green is GFP expressed in the tumor cells, magenta is Cy5 fluorescence. Magenta is used for the benefit of colorblind referees: see Wong (2011) *Nature Methods* 8: 441. A) and C) are lower magnification images that show labeling of the tumor cells (T) in the context of stroma (S) and surrounding normal muscle (M). B) and D) are higher magnification images that illustrate cetuximab homing to EGFR expressing tumor cells and RACPP being activated by MMP2 and 9 and taken up predominantly in stromal regions of the tumor microenvironment.

In these series of studies, we have identified that MMAE can radiosensitize tumor cells and enhance tumor xenograft regression in combination with IR. Moreover, we tested a therapeutic paradigm whereby a potent radiosensitizer such as MMAE can be selectively delivered to tumors using ACPP to increase tumor response to IR (FIG. 45). MMAE, a synthetic derivative of dolastatin 10, sensitizes cancer cells to IR-mediated DNA damage and cell kill (10). Intrinsic tumor cell resistance to IR is dependent on a multitude of factors, including activity of DNA repair pathways, tumor oxygenation status, and the cell cycle (5-7). By pharmacologically targeting these pathways, cells become more sensitive to the effects of IR. An optimal cancer therapeutic agent would have the dual benefit of single-agent potent tumoricidal activity and also sensitize tumors to IR. Our data support MMAE as a candidate that meets such requirements.

Figure 33:
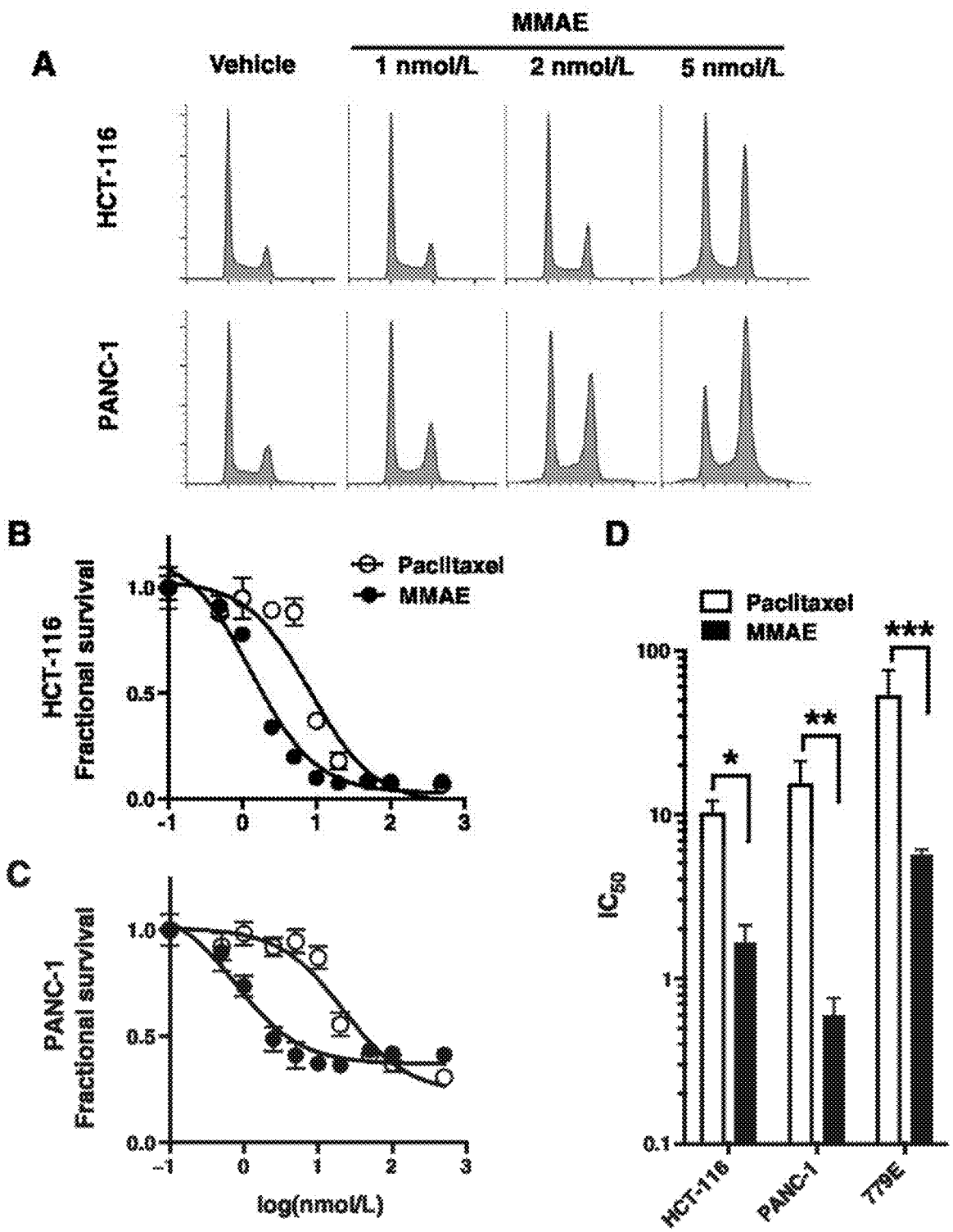
FIG. 33: MMAE has increased potency compared with paclitaxel in tumor cells. A) HCT-116 (top) and PANC-1 (bottom) cells were exposed to 0, 1, 2, and 5 nmol/L of MMAE for 24 hours. Cells were collected, stained with PI, and cell cycleanalyzed by FACS. B) and C), HCT-116 and PANC-1 tumor cells were exposed to dose range of MMAE or paclitaxel for 72 hours. Cell viability was normalized to vehicle-treated cells and plotted as fractional survival±SD. D), IC50 of MMAE and paclitaxel in HCT-116, PANC-1, and 779E cells. Data are plotted as mean IC50±SD from triplicates. *, P=0.003; , P=0.014; *, P=0.028.
Figure 34:
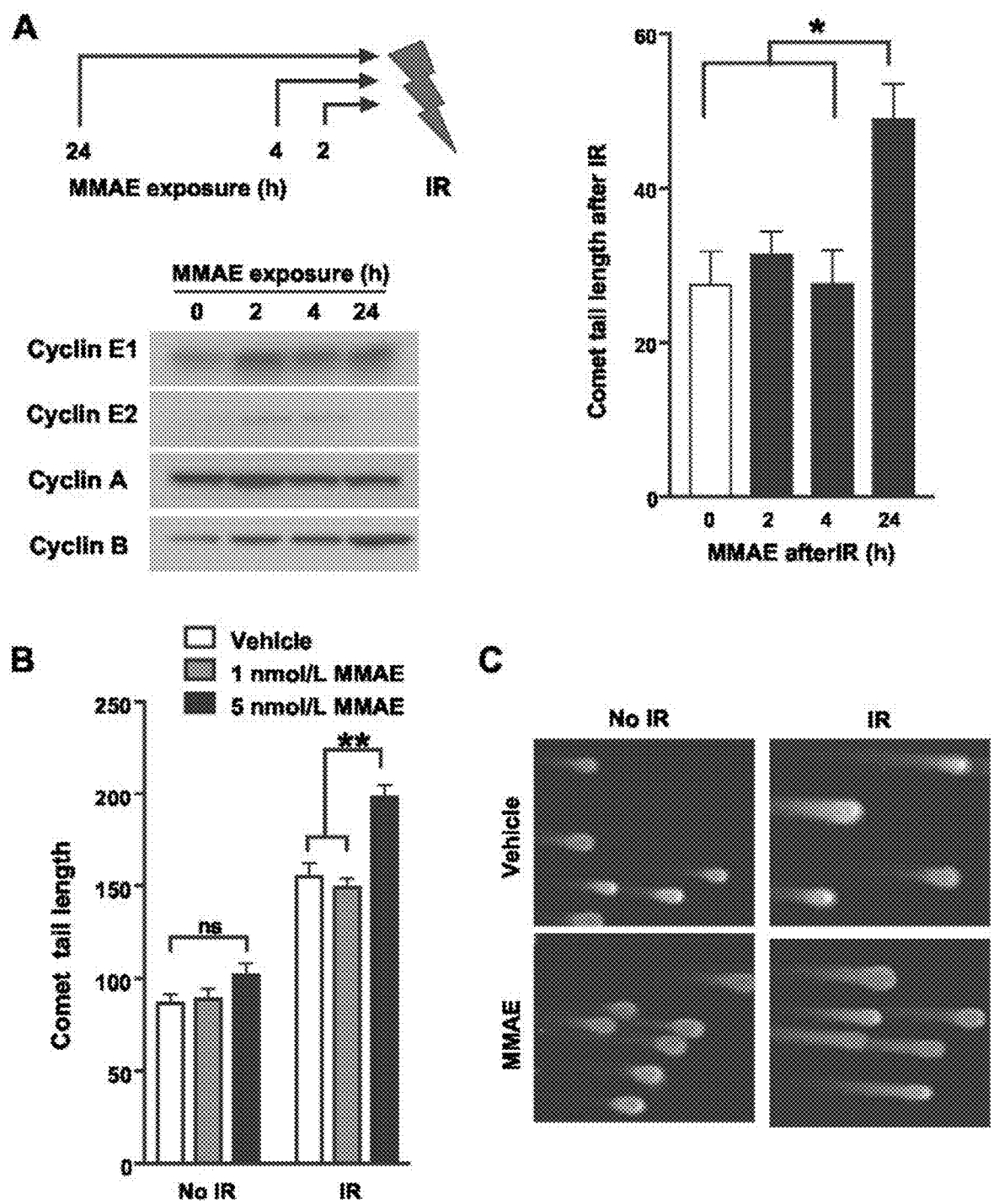
FIG. 34: MMAE increases IR-induced DNA doublestrand breaks in a schedule- and dosedependent manner. A), HCT-116 cells were treated with 5 nmol/L MMAE for 2, 4, or 24 hours followed by 6 Gy. Accumulation of cyclins was assessed by immunoblotting at time of irradiation. Comet tail length was measured using neutral comet assay 15 minutes after IR. Data are plotted as mean comet tail length±SEM with nonirradiated comet tail length subtracted. B) and C), HCT-116 cells were treated with 0, 1, or 5 nmol/L MMAE for 24 hours and then irradiated with 6 Gy. Comet tail length was measured using neutral comet assay. Data are plotted as mean comet tail length±SEM. Representative images from comet tail assay are shown for MMAE dose of 5 nmol/L. *, P<0.01; **, P<0.0001.

MMAE has previously been shown to have single-agent antitumor efficacy against a broad panel of tumor histologies when appropriately delivered (17, 20, 21). In our own studies with established cancer cells and a limited patient passage patient-derived pancreatic adenocarcinoma cell line, MMAE had an IC$_{50}$ that is at least 6-fold lower than paclitaxel (FIG. 33). MMAE is an anti-tubulin agent that blocks cells in G$_2$-M, and the G$_2$-M phase of the cell cycle is the most sensitive to the IR (8). We demonstrated that MMAE increased IR induced DNA double-strand breaks in both a schedule- and a dose-dependent manner that directly correlated with the accumulation of cells in G$_2$-M (FIG. 33 and FIG. 34). MMAE also decreased clonogenic survival of pancreatic and colorectal cancer cells in the 1 to 5 nmol/L range in combination with IR indicative of its application as a potent radio-sensitizer. Mechanistically, MMAE increased clonogenic cell death in irradiated cells. The decreased cell survival following combined IR and MMAE was not due to apoptosis, suggesting mitotic catastrophe as the cause of MMAE enhanced cell death in irradiated cells. In support of this, MMAE enhanced the DNA damage response pathway in irradiated cells. Both γH2AX foci formation and activation of CHK1 were increased in cells treated with MMAE before irradiation. Understanding the cellular response to MMAE can allow for future rational drug combinations with MMAE to further augment radiosensitization by inhibiting survival pathways induced by MMAE.

Figure 38:
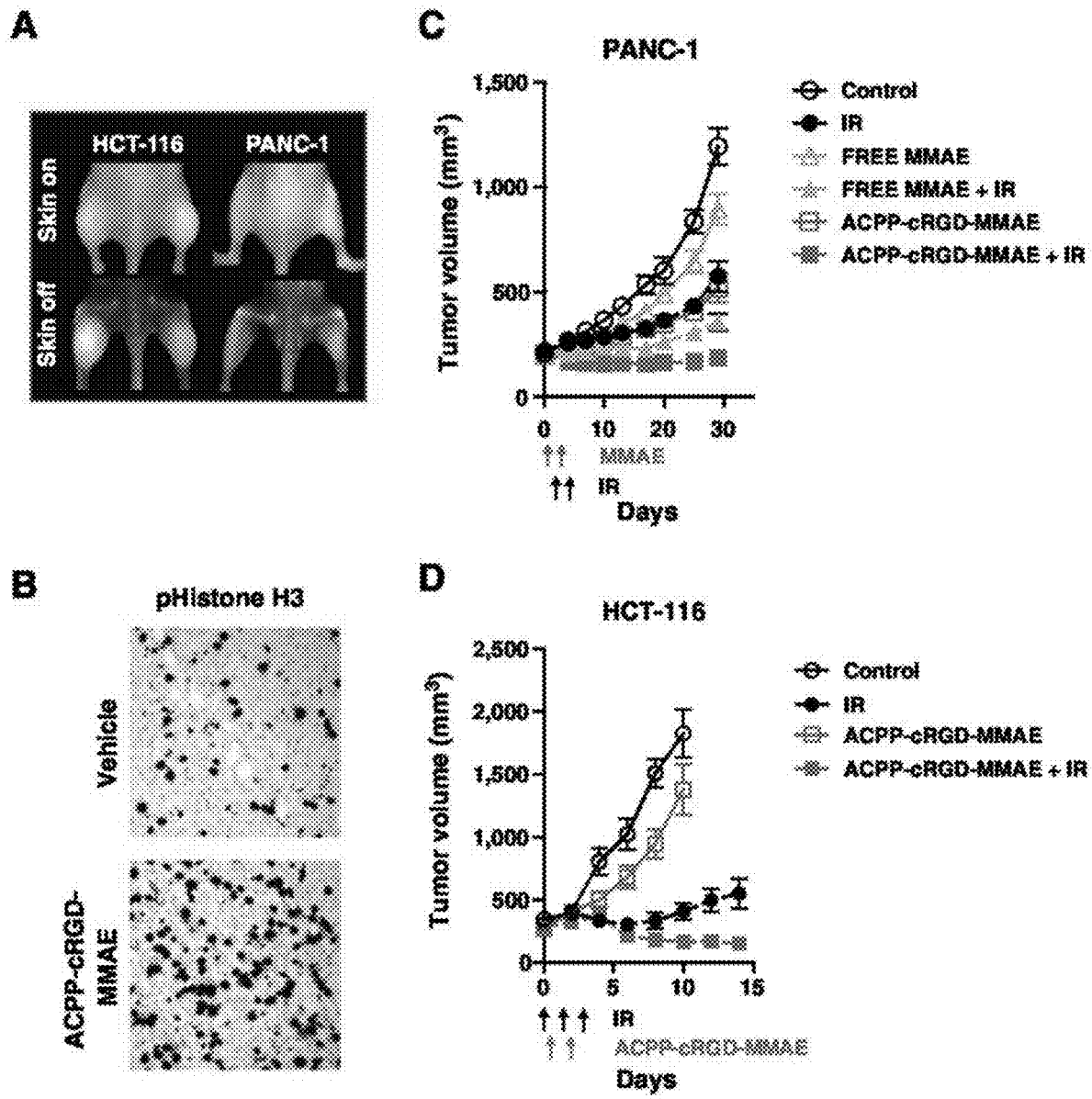
FIG. 38: ACPP-cRGD-MMAE in combination with IR significantly reduces tumor growth. HCT-116 or PANC-1 tumor xenografts were grown subcutaneously in athymic nude mice. A), ACPP-cRGD-MMAE localizes to tumor xenografts following intravenous administration. The right hindlimb tumor was irradiated (3 Gy), whereas the leftsided tumor was shielded to block >95% of the delivered IR dose. Cy5-labeled ACPP-cRGD-MMAE was intravenously injected into tumor-bearing mice and mice were imaged 6 hours later with skin on (top) and skin removed (bottom). B), mice with HCT-116 tumor xenografts were intravenously injected with vehicle or 6 nmoles of ACPP-cRGD-MMAE. Tumor xenografts were harvested the following day, paraffin embedded, and stained for mitotic marker pS10 histone H3. C), PANC-1 tumor xenografts-bearing mice were intravenously injected with 6 nmoles of free MMAE or ACPP-cRGD-MMAE on days 0 and 1. For IR-treated tumor xenografts, 3 Gy was delivered on days 1 and 2. Tumors were measured twice a week. D), HCT-116 tumors were treated 6 Gy on day 0 and then 3 Gy on days 1 and 2. A dose of 7.5 nmoles ACPP-cRGD-MMAE was intravenously injected on both days 0 and 1, 6 hours after IR. Tumors were measured every other day.

While MMAE is a potent radiosensitizer in vitro, it requires tumor-targeted delivery to achieve a clinically meaningful therapeutic index in vivo. We have therefore initially evaluated a strategy using MMP and cRGD-binding integrin targeted ACPP delivery of MMAE in combination with focal IR (17). A major limitation to the therapeutic use of radiosensitizers is the lack of tumor-specific delivery (22, 23). Radiosensitizer delivery that is nontargeted can result in increased radiosensitization of not only tumor cells but also surrounding normal tissue. This results in no net gain in the therapeutic index of radiotherapy. Previous reports have tested nanoparticles as radiosensitizer delivery vehicles (24-27). Here, we have demonstrated the efficacy of ACPP technology to deliver the potent radiosensitizer MMAE specifically to tumors. Following MMP-2/-9 and αvβ3 integrin targeted delivery and release of MMAE conjugated cell-penetrating peptide from the ACPP, tumor xenografts demonstrated prolonged regression in combination with IR compared with nontargeted free MMAE delivery (FIG. 38 and Table 1). Moreover at equimolar systemic intravenous injection, ACPP-cRGD-MMAE improved tumor xenograft regression when compared with nontargeted MMAE for both nonirradiated and irradiated tumors. We also tested altering the order of delivery of IR and ACPP-cRGD-MMAE. In the PANC-1 xenograft experiments, ACPP-cRGD-MMAE was initially injected 1 day before 3 Gy fractions of IR (FIG. 38 and FIG. 44). These experiments were designed on the basis of MMAE functioning as a radiosensitizer by blocking tumor cells in G$_2$-M. Therefore, MMAE was injected into mice before irradiation. To test the ability of IR to modulate the tumor environment and increase ACPP-cRGD-MMAE tumor accumulation, we altered the treatment scheduling, with a larger 6 Gy dose given 1 day before ACPP-cRGD-MMAE injection in HCT-116 xenografts (FIG. 38D). The rationale for an initial 6 Gy in the HCT-116 tumor xenograft experiment was 2-fold. First, HCT-116 tumors grow more rapidly in our tumor model compared with PANC-1 tumor xenografts. Second, a dose of 6 Gy increased ratiometric ACPP activation in irradiated tumors compared with nonirradiated tumors (FIG.

37D and FIG. 42). Therefore, we hypothesized that preirradiation would increase ACPP-mediated delivery of MMAE to irradiated tumor xenografts. Following the initial 6 Gy dose to increase ACPP-mediated MMAE delivery, 2 doses of 3 Gy were given after ACPP-cRGD-MMAE. Even with a total dose delivered of 12 Gy to HCT-116 tumors over 3 days, the majority of HCT-116 tumors began to regrow in contrast to combined treatment with ACPP-cRGD-MMAE. While the treatment regimens in the 3 xenograft experiments varied from each other, a strength is that their conclusions consistently demonstrated that combining ACPP-cRGD-MMAE with IR resulted in sustained tumor xenograft regression (Table 1).

ACPP-conjugated delivery of radiosensitizers is innovative and of clinical significance in that it offers a solution to the problem of nonselective radiosensitization of molecules for not only cancer cells but also surrounding normal tissue. In addition, it provides a mechanism for efficient intracellular delivery and release of the conjugated drug payload, that is, MMAE. MMAE is conjugated to the polycationic cell-penetrating peptide portion of ACPP through a cathepsin B-sensitive linker (valine-citrulline; ref. 17). Once the ACPP peptide linker is cleaved in the tumor microenvironment, the cell-penetrating peptide MMAE is internalized and free MMAE released from lysosomes through the action of cathepsin B. Because MMP activity is high in the tumor microenvironment, MMP-2/-9-targeted ACPP may also be a broadly applicable tumor-selective delivery vehicle for radiosensitizers. Meanwhile, the only immediately clinically approved vehicle for MMAE delivery is brentuximab vedotin, with a host of similar antibody-MMAE conjugates undergoing clinical trial (11, 28). Our results showing radiosensitization by free MMAE in vitro suggest that antibody-MMAE conjugates should show similar radiosensitization, as the antibody is another mechanistic targeting vector for MMAE. Viewed another way, IR may be a valuable adjunct to chemotherapy with antibody-drug conjugates.

Figure 37:
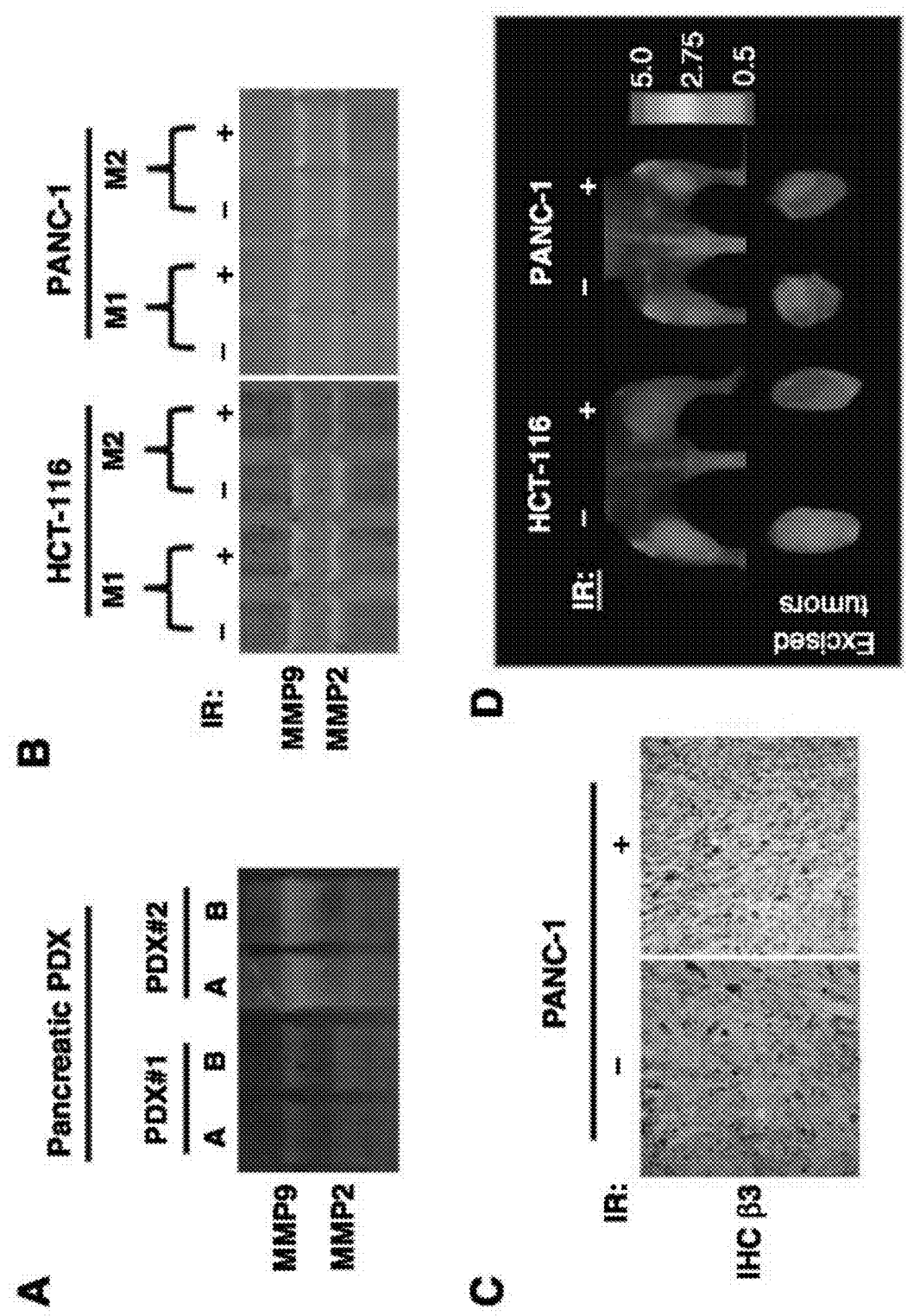
FIG. 37: ACPPs are cleaved in irradiated tumor microenvironments. A), orthotopic pancreatic adenocarcinoma PDX were harvested and zymography gels used to assess gelatinase activity, lysates. For each PDX, lysates were run in duplicate (lanes A and B). B)-D), HCT-116 or PANC-1 tumor xenografts were grown in both the left and right hindlimbs of nude mice. The right tumor was irradiated with 6 Gy and the left tumor was shielded to block out >95% of the IR dose. B), zymography gels were used to asses MMP activity in nonirradiated and irradiated tumors. C), β3 integrin expression by IHC in nonirradiated and irradiated PANC-1 tumors. D), one day after IR, ratiometric ACPP was intravenously injected and Cy5:Cy7 emission ratio measured (right, pseudocolor scale) by whole-animal imaging with tumors in situ and after tumor excision.

IR results in changes in the tumor microenvironment including alterations of tumor permeability and retention, gene expression, tumor cell surface receptor expression, and protease activity. The physics of IR allows for IR to be specifically deposited to tumor tissue and can allow it to serve as beaconing mechanism for systemically delivered therapeutic agents. Such a concept has been seen with combining IR with oncolytic viruses, where IR enhances the ability of both intratumoral and systemically delivered oncolytic viruses to replicate in irradiated tumor microenvironment (29-32). IR has also been used to induce the expression of neoantigens within tumors that can function as receptors for peptide ligand-targeted nanoparticles (33-36). Interestingly, MMP activity has been reported to be induced in irradiated tumors, including patient-derived rectal cancers (37-40). Moreover, the cRGD-binding integrin $\alpha_v\beta_3$ expression is also upregulated by IR and modulates cell response to IR (41-44). While gelatin zymography of excised tumor xenografts did not reveal an increase in gelatinase activity in irradiated tumors compared with their nonirradiated counterparts, ratiometric PLGC(Me)AG linker ACPP showed a trend toward increase Cy5:Cy7 emission ratio in irradiated tumor xenografts compared with nonirradiated tumor xenografts (FIG. 37 and FIG. 42). Our ratiometric PLGC(Me)AG linker ACPP contains both Cy5 (polycationic side) and Cy7 (polyanionic side), and real-time ratiometric monitoring of tumors in mice has demonstrated tumor-specific cleavage of this ratiometric probe (19). While Cy5 has increased tissue attenuation than Cy7, in our experience, the greater extinction coefficient, quantum yield, and chemical stability of Cy5 compared with Cy7 make up for the somewhat greater attenuation (45). In addition, we have not found a ratiometric FRET donor-acceptor pair in which the donor is Cy7 and the acceptor is about 100 nm longer in wavelength.

An alternative explanation for the enhanced accumulation of ACPP within irradiated tumors as opposed to nonirradiated tumors is the concept of enhanced permeability and retention (EPR) of systemically delivered macromolecular agents of ≥40 kDa (46-48). IR has been shown to decrease the tumor interstitial pressure, especially with delivery of doses>10 Gy. By decreasing tumor interstitial pressure, IR can augment diffusion of macromolecular drugs into the tumor. However, the ACPP-cRGD-MMAE is only 6.9 KDa, so it may not be affected as much by EPR. Using ratiometric ACPP probes, further optimization of radiation dose fraction schedule may improve cleavage and activation of ACPP through increased expression of cRGD binding integrins and MMP-2/-9 activity or increased tumor EPR (FIG. 37 and FIG. 42). Our results provide a basis for IR-controlled ACPP to be developed that could deliver potent radiosensitizers. In such a treatment paradigm, there would be preferential accumulation of the radiosensitizer with the irradiated tumor and reduced bioavailability of the radiosensitizer to normal tissue. Such technology is not limited to radiosensitizer delivery.

REFERENCES

1. Werner J, Combs S E, Springfeld C, Hartwig W, Hackert T, B€uchler MW. Advanced-stage pancreatic cancer: therapy options. Nat Rev Clin Oncol 2013; 10:323-33.
2. Gutt R, Liauw S L, Weichselbaum R R. The role of radiotherapy in locally advanced pancreatic carcinoma. Nat Rev Gastroenterol Hepatol 2010; 7: 437-47.
3. Aklilu M, Eng C. The current landscape of locally advanced rectal cancer. Nat Rev Clin Oncol 2011; 8:649-59.
4. Pretz J L, Wo J Y, Mamon H J, Kachnic L A, Hong T S. Chemoradiationtherapy: localized esophageal, gastric, and pancreatic cancer. Surg Oncol Clin N Am 2013; 22:511-24.
5. Moding E J, Kastan M B, Kirsch D G. Strategies for optimizing the response of cancer and normal tissues to radiation. Nat Rev Drug Discov 2013; 12:526-42.
6. Liauw S L, Connell P P, Weichselbaum R R. New paradigms and future challenges in radiation oncology: an update of biological targets and technology. Sci Transl Med 2013; 5:173sr2.
7. Raleigh D R, Haas-Kogan D A. Molecular targets and mechanisms of radio-sensitization using DNA damage response pathways. Future Oncol 2013; 9:219-23.
8. Terasima T, Tolmach L J. Variations in several responses of HeLa cells to x-irradiation during the division cycle. Biophys J 1963; 3:11-33.
9. Tishler R B, Schiff P B, Geard C R, Hall E J. Taxol: a novel radiation sensitizer. Int J Radiat Oncol Biol Phys 1992; 122:613-7.
10. Bai R, Pettit G R, Hamel E. Dolastatin 10, a powerful cytostatic peptide derived from a marine animal. Inhibition of tubulin polymerization mediated through the *vinca* alkaloid binding domain. Biochem Pharmacol 1990; 39:1941-49.
11. Doronina S O, Toki B E, Torgov M Y, Mendelsohn B A, Cerveny C G, Chace D F, et al. Development of potent monoclonal antibody auristatin conjugates for cancer therapy. Nat Biotechnol 2003; 21:778-84.

12. Sievers E L, Senter P D. Antibody-drug conjugates in cancer therapy. Annu Rev Med 2013; 64:15-29.
13. Jiang T, Olson E S, Nguyen Q T, Roy M, Jennings P A, Tsien R Y. Tumor imaging by means of proteolytic activation of cell-penetrating peptides. Proc Natl Acad Sci USA 2004; 101:17867-72.
14. Aguilera T A, Olson E S, Timmers M M, Jiang T, Tsien R Y. Systemic in vivo distribution of activatable cell penetrating peptides is superior to that of cell penetrating peptides. Integr Biol (Camb) 2009; 1:371-81.
15. Olson E A, Aguilera T A, Jiang T, Ellies L G, Nguyen Q T, Wong E H, et al. In vivo characterization of activatable cell penetrating peptides for targeting protease activity in cancer. Integr Biol (Camb) 2009; 1:382-93.
16. Whitney M, Crisp J L, Olson E S, Aguilera T A, Gross L A, Ellies L G, et al. Parallel in vivo and in vitro selection using phage display identifies protease-dependent tumor-targeting peptides. J Biol Chem 2010; 285: 22532-41.
17. Crisp J L, Savariar E N, Glasgow H L, Ellies L G, Whitney M A, Tsien R Y. Synergistic targeting of integrin avb3 and matrix metalloprotienase-2 improves optical imaging of tumors and chemotherapeutic efficiency. Mol Cancer Therapeutics 2014; 13:1514-25.
18. Deryugina E I, Ratnikov B, Monosov E, Postnova T I, DiScipio R, Smith J W, et al. MT1-MMP initiates activation of pro-MMP-2 and integrin alphavbeta3 promotes maturation of MMP-2 in breast carcinoma cells. Exp Cell Res 2001; 263:209-23.
19. Savariar E N, Felsen C N, Nashi N, Jiang T, Ellies L G, Steinbach P, et al. Real-time in vivo molecular detection of primary tumors and metastases with ratiometric activatable cell-penetrating peptides. Cancer Res 2013; 73:855-64.
20. Ma D, Hopf C E, Malewicz A D, Donovan G P, Senter P D, Goeckeler W F, et al. Potent antitumor activity of an auristatin-conjugated, fully human monoclonal antibody to prostate-specific membrane antigen. Clin Cancer Res 2006; 12:2591-6.
21. Breij E C, de Goeij B E, Verploegen S, Schuurhuis D H, Amirkhosravi A, Francis J, et al. An antibody-drug conjugate that targets tissue factor exhibits potent therapeutic activity against a broad range of solid tumors. Cancer Res 2014; 74:1214-26.
22. Liu F F, Okunieff P, Bernhard E J, Stone H B, Yoo S, Coleman C N, et al. Lessons learned from radiation oncology trials. Clin Cancer Res 2013; 19: 6089-100.
23. Lin S H, George T J, Ben-Josef E, Bradley J, Choe K S, Edelman M J, et al. Opportunities and challenges in the era of molecularly targeted agents and radiation therapy. J Natl Cancer Inst 2013; 105:686-93.
24. Miller S M, Wang A Z. Nanomedicine in chemoradiation. TherDeliv 2013; 4: 239-50.
25. Werner M E, Cummings N D, Sethi M, Wang E C, Sukumar R, Moore D T, et al. Preclinical evaluation of Genexol-PM, a nanoparticle formulation of paclitaxel, as a novel radiosensitizer for the treatment of non-small cell lung cancer. Int J Radiat Oncol Biol Phys 2013; 86:463-8.
26. Joh D Y, Sun L, Stangl M, Al Zaki A, Murty S, Santoiemma P P, Davis J J, et al. Selective targeting of brain tumors with gold nanoparticle-induced radio-sensitization. PLoS One 2013; 8:e62425.
27. Wang Y, Mo L, Wei W, Shi X. Efficacy and safety of dendrimer nanoparticles with coexpression of tumor necrosis factor-a and herpes simplex virus thymidine kinase in gene radiotherapy of the human uveal melanoma OCM-1 cell line. Int J Nanomedicine 2013; 8:3805-16.
28. Mullard A. Maturing antibody-drug conjugate pipeline hits 30. Nat Rev Drug Discov 2013; 12:329-32.
29. Hallahan D E, Mauceri H J, Seung L P, Dunphy E J, Wayne J D, Hanna N N, et al. Spatial and temporal control of gene therapy using ionizing radiation. Nat Med 1995; 1:786-91.
30. Mezhir J J, Advani S J, Smith K D, Darga T E, Poon A P, Schmidt H, et al. Ionizing radiation activates late herpes simplex virus 1 promoters via the p38 pathway in tumors treated with oncolytic viruses. Cancer Res 2005; 65:9479-84.
31. Advani S J, Markert J M, Sood R F, Samuel S, Gillespie G Y, Shao M Y, et al. Increased oncolytic efficacy for high-grade gliomas by optimal integration of ionizing radiation into the replicative cycle of HSV-1. Gene Ther 2011; 18:1098-102.
32. Advani S J, Buckel L, Chen N G, Scanderbeg D J, Geissinger U, Zhang Q, et al. Preferential replication of systemically delivered oncolytic vaccinia virus in focally irradiated glioma xenografts. Clin. Cancer Res 2012; 18: 2579-90.
33. Hallahan D E, Qu S, Geng L, Cmelak A, Chakravarthy A, Martin W, et al. Radiation-mediated control of drug delivery. Am J Clin Oncol 2001; 24: 473-80.
34. Hallahan D, Geng L, Qu S, Scarfone C, Giorgio T, Donnelly E, et al. Integrin-mediated targeting of drug delivery to irradiated tumor blood vessels. Cancer Cell 2003; 3:63-74.
35. Hariri G, Yan H, Wang H, Han Z, Hallahan D E. Radiation-guided drug delivery to mouse models of lung cancer. Clin Cancer Res 2010; 16: 4968-77.
36. Passarella R J, Spratt D E, van der Ende A E, Phillips J G, Wu H, Sathiyakumar V, et al. Targeted nanoparticles that deliver a sustained, specific release of Paclitaxel to irradiated tumors. Cancer Res 2010; 70:4550-9.
37. Fujita M, Otsuka Y, Yamada S, Iwakawa M, Imai T. X-ray irradiation and Rho-kinase inhibitor additively induce invasiveness of the cells of the pancreatic cancer line, MIAPaCa-2, which exhibits mesenchymal and amoeboid motility. Cancer Sci 2011; 102:792-8.
38. Lee W H, Warrington J P, Sonntag W E, Lee Y W. Irradiation alters MMP-2/TIMP-2 system and collagen type IV degradation in brain. Int J Radiat Oncol Biol Phys 2012; 82:1559-66.
39. Speake W J, Dean R A, Kumar A, Morris T M, Scholefield J H, Watson S A. Radiation induced MMP expression from rectal cancer is short lived but contributes to in vitro invasion. Eur J Surg Oncol 2005; 31:869-74.
40. Kumar A, Collins H M, Scholefield J H, Watson S A. Increased type-IV collagenase (MMP-2 and MMP-9) activity following preoperative radiotherapy in rectal cancer. Br J Cancer 2000; 82:960-5.
41. Xu W, Luo T, Li P, Zhou C, Cui D, Pang B, et al. RGD-conjugated gold nanorods induce radiosensitization in melanoma cancer cells by downregulating a(v)fl3 expression. Int J Nanomedicine 2012; 7: 915-24.
42. Abdollahi A, Griggs D W, Zieher H, Roth A, Lipson K E, Saffrich R, et al. Inhibition of alpha(v)beta3 integrin survival signaling enhances antiangiogenic and antitumor effects of radiotherapy. Clin Cancer Res 2005; 11:6270-79.
43. Egami T, Ohuchida K, Yasui T, Mizumoto K, Onimaru M, Toma H, et al. Up-regulation of integrin beta3 in radioresistant pancreatic cancer impairs adenovirus-mediated gene therapy. Cancer Sci 2009; 100:1902-7.

44. Rieken S, Habermehl D, Mohr A, Wuerth L, Lindel K, Weber K, et al. Targeting avβ3 and avβ5 inhibits photon-induced hypermigration of malignant glioma cells. Radiat Oncol 2011; 6:132.
45. Nguyen Q T, Tsien R Y. Fluorescence-guided surgery with live molecular navigation—a new cutting edge. Nat Rev Cancer 2013; 13:653-62.
46. Znati C A, Rosenstein M, Boucher Y, Epperly M W, Bloomer W D, Jain R K. Effect of radiation on interstitial fluid pressure and oxygenation in a human tumor xenograft. Cancer Res 1996; 56:964-68.
47. Li C, Ke S, Wu Q P, Tansey W, Hunter N, Buchmiller L M, et al. Tumor irradiation enhances the tumor-specific distribution of poly(L-glutamic acid)-conjugated paclitaxel and its antitumor efficacy. Clin Cancer Res 2000; 6:2829-34.
48. Giustini A J, Petryk A A, Hoopes P J. Ionizing radiation increases systemic nanoparticle tumor accumulation. Nanomedicine 2012; 8:818-21.

Example 4: MMAE Imaging

Abstract
MMAE

We first prepared and tested ACPP-MMAE (Crisp J L, et al., *Mol Cancer Ther.* 2014; 13(6):1514-25) for purely chemotherapeutic purposes as an alternative to the well-established antibody-MMAE conjugates, one of which (brentuximab vedotin) had gained FDA approval. We took advantage of the known close association between MMP2 and integrin $\alpha v\beta 3$ (Brooks P C, et al., *Cell.* 1996; 85(5): 683-93) to provide two mutually reinforcing mechanisms for tumor localization based on ACPP proteolysis and cyclic (RGD) affinity respectively in the same molecule. The two mechanisms were quantitatively much better than either one alone. This drug delivery system was able to significantly raise the efficacy of conjugated MMAE over an equimolar doses of free MMAE (Crisp J L, et al., *Mol Cancer Ther.* 2014; 13(6):1514-25). One obvious advantage over antibody drug conjugates (ADCs) is the comparative universality of the ACPP mechanism and cyclic(RGD) affinity, even cross-species, whereas antibody binding varies from patient to patient and from tumor type to tumor type. However, ADCs have much more prolonged circulatory half-lives (weeks instead of hours), which are greatly advantageous for traditional chemotherapy.

MMAE acts to block mitotic microtubules and to arrest cells in the $G_2/M$ phase of the cell cycle, which is when the cells are most sensitive to IR. Therefore MMAE is expected to be a radiosensitizer provided enough time is given for most cells to accumulate at the $G_2/M$ block. Surprisingly, this prediction had not yet been tested. We showed (Buckel L, et al., *Cancer Res.* 2015; 75(7): 1376-87; see, Example 3) that MMAE was just such a radiosensitizer, at doses at least an order of magnitude lower than taxanes. This paper for the first time shifted the focus to radiosensitization rather than mere chemotherapeutic efficacy.

Once we had shown that ACPPs could target MMAE, we hypothesized that therapeutic antibodies to ErbB receptors could also direct delivery of potent anti-tubulin drugs in a receptor restricted manner and radiosensitize tumors. We synthesized ADCs in which MMAE was linked to cetuximab C-MMAE. C-MMAE and T-MMAE bound specifically to and restricted MMAE activity and toxicity to EGFR and HER2 expressing tumor cells respectively. Importantly while free MMAE radiosensitized indiscriminately, cetuximab antibody conjugation targeted MMAE radiosensitization to EGFR. From another point of view, radiation provides a third therapeutic mode to synergize with the cetuximab and MMAE.

GEMMs in Immunocompetent Mice: Pancreatic Adenocarcinoma

We used orthotopic breast cancer models including xeno-grafted MDA-MB-231 tumors in nude mice and syngenic Py230 tumors in immunocompetent mice for showing ACPP-MMAE was effective as a chemotherapeutic(16). Four xenograft models, PANC-1 (pancreas), HCT-116 (colon), Cal-27 (HNSCC), and OE19 (esophageal) showed radiosensitization (Adams S R, Yang H C, Savariar E N, Aguilera J, Crisp J L, Lippman S M, Cohen E E, Tsien R Y, Advani S J. Anti-tubulin drugs conjugated to antibodies to ErbB are selective radiosensitizers. *Nature Communications.* 2016; under review; Buckel L, et al., *Cancer Res.* 2015; 75(7):1376-87). However, we are interested in incorporating genetically-engineered mouse models (GEMMs) or spontaneous tumors because of their greater realism to clinical etiology, with the caveats that such models take longer to develop and require more animals to see statistically significant changes in tumor growth. Initially we will focus on one model of one variety, with which we have experience from our imaging studies. For a GEMM, the famous KPC model (Hingorani S R, et al., *Cancer cell.* 2005; 7(5):469-83) of pancreatic adenocarcinoma is a good mimic for human disease, where radiation plays an essential role in therapy. Timing of tumorigenesis is dependent on K-ras genotype (i.e., G12D) and secondary alterations including mutated or deficient tumor suppressors such as p53. Tumorigenesis generally begins early after induced mutagenesis with animal survival varying from 2 months to over a year depending on specific mutations and time of oncogene induction (Guerra C, Barbacid M. *Mol Oncol.* 2013; 7(2):232-47). Such genetically engineered mouse models allow for evaluation of drug delivery and radiosensitization by better mimicking the desmoplastic stroma and inflammatory responses found in human pancreatic tumors. Tumor growth and effect of therapeutics (targeted radiosensitizer and IR) will be measured by high-resolution ultrasound, increased animal survival and immunohistochemistry on harvested tumors measuring DNA damage ($\gamma$H2AX) and target hit (Singh M, et al., *Nat Biotechnol.* 2010; 28(6):585-93). The selectivity of tumor radiosensitization will be measured by the same immunohistochemistry comparing harvested tumor with surrounding normal tissues, including liver, kidneys, bowel and normal pancreas.

Chemical Carcinogenesis Model in HNSCC

We have initiated the 4NQO carcinogen induced spontaneous tumor model (Vitale-Cross L, et al., *Cancer Prev Res (Phila).* 2009; 2(5):419-22), well known as a model for tobacco-induced HNSCC that avoids any genetic drift in established cell lines. Wild type mice (C57B16) were given the oral carcinogen 4-nitroquinoline oxide (4NQO, 50 µg/ml) in their drinking water for 16 weeks followed by normal drinking water. Physical examination of the oral cavity began at week 16 and continues to week 21. By week 21, we found that 13 of the 14 mice had oral cavity lesions as seen by white light reflectance that are confirmed HNSCC by H&E. Following IV injection of standard (SEQ ID NO:4) PLGC(Me)AG RACPP (10 nmol, 100 µl, i.v., 90 min circulation), we found that Cy5:Cy7 ratiometric fluorescence identifies 1.57 tumors per mouse (ratio intensity range=11 to 29%) which is comparable to 1.50 obtained by white light alone. In a few cases, ratiometric signal identified tumors inconspicuous by white light. We will try drug conjugates (ACPP-DCs and EGFR ADCs) and IR singly or together to determine whether radiosensitization occurs and if so, how to optimize it.

Imaging and Effects of Microenvironment

Relative Amounts of mAb or ACPP Loaded into Tumor Cells Vs Host Macrophages and Vascular Endothelium—Frozen Block Face Imaging Frozen block face imaging will give fluorescence maps of where the Cy5-labeled mAb or ACPP is ending up in a tumor and its surrounding tissue with minimal perturbation or manipulation to signal. The tissue is fresh-frozen, fast enough to minimize cellular damage, so there is no perfusion or fixation artifact, allowing the signal in the blood and vessels to be preserved. A block face is cut, up to a centimeter across, and imaged on a Nikon confocal microscope while still frozen, while keeping the objective thermal insulation. We already have multiple tumor models with GFP and intend to label others with a red FP, allowing for easy visualization on both a macro and a micro scale. This also permits us to determine if the mAb or ACPP is making it into the fluorescent tumor cells or is primarily confined to the tumor stroma. See, FIG. 46A-D for an exemplary comparison of Cy5 fluorescence showing different localizations of a mAb, cetuximab, vs. our standard ACPP ((SEQ ID NO:4) PLGC(Me)AG Cy5/Cy7-labeled RACPP). Within this stroma we have been able to identify cell types such as macrophages, neutrophils and mast cells using a variety of labeled antibodies. We can look at mAb or ACPP uptake in tumor vs host cells using fixed tissue and a variety of antibodies against interesting cell markers. We can also stain the tissue with Hoechst or other nuclear markers after chemoradiation treatment to assess relative survival rates of malignant cells vs. components of stroma and vasculature.

Imaging Mass Spectrometry of Warhead Distribution

We propose to use Mass Spectrometry Imaging (MSI) (Laskin J, Lanekoff I. *Anal Chem.* 2016; 88(1):52-73; Hsu C C, Dorrestein P C. *Curr Opin Biotechnol.* 2015; 31:24-34; and Ifa D R, Eberlin L S. *Clin Chem.* 2016; 62(1): 111-23) to quantitatively measure warhead loading (for example, MMAE) into biological tissue. Using mass spectrometry to record the spatial distribution of drug compound allows the loading to be observed in the absence of fluorescent tags. It is an orthogonal signal to epifluorescence microscopy, even though the sample is prepared for the instrument in a similar way. A frozen slice of tissue (~10 µm thick) is thaw mounted on a glass slide, placed in the mass spectrometer (MS) interface, and imaged by measuring discrete mass spectra over each pixel, in accordance with the spatial resolution. The type of MS interface is the main factor determining the spatial resolution. We are aware of matrix assisted laser desorption time-of-flight mass spectrometry (MALDI-TOF) (Chaurand P, Cornett D S, Caprioli R M. *Curr Opin Biotechnol.* 2006; 17(4):431-6) which could also be used. We plan to use Desorption Electrospray Ionization (DESI), developed by Cooks (Cooks R G, et al., *Science.* 2006; 311(5767): 1566-70). DESI and related techniques, including nanoflow DESI (nanoDESI) are classed as ambient MSI (Laskin J, Lanekoff I. *Anal Chem.* 2016; 88(1):52-73) because the sample is ionized at ambient pressure from a small liquid droplet formed on the tissue when mounted on a standard glass slide. The spatial resolution in nanoDESI is determined by the diameter of the droplet formed between two fused silica capillaries, currently ~150 µm.

The chemical components in the tissue are extracted into the droplet and introduced into the MS by nanoflow electrospray ionization. We plan to use nanoDESI (Lanekoff I, et al., *Anal Chem.* 2012; 84(19):8351-6) to address where a warhead such as those described herein (for example MMAE) goes into the heterogeneous microenvironment of tumor and how it is distributed. We have configured a nanoDESI MSI interface for testing with high resolution MS. We applied it to a 50 µm sagittal section of a mouse brain several hours after intracisternal injection of the drug BILN-2061, which crosses the blood-brain barrier poorly. FIG. 47A shows the apparatus (Watrous J, et al., *Proc Natl Acad Sci USA.* 2012; 109(26):E1743-52), and FIG. 47B shows an example of the mass spectrum for BILN-2061. The parent molecular ion (775.34 m/z) is formed from the intact drug. The characteristic fragment ion is formed from a molecular cleavage that occurs in the ionization process. Both ions can be used for quantitation.

Quantitation and limits of detection are the specific goals. Both require techniques to minimize interferences and enhance the target signal. A recent report (Eberlin L S, et al., *Proc Natl Acad Sci USA.* 2014; 111(29):10450-5) shows that lipids from cell membranes and extracellular spaces occur as negative ions in nanoDESI. Analytes that contain secondary amines or pyridyl groups in their structures are detected with good sensitivity as positive ions, so the warheads should be optimally detected. Conditions will be determined to prevent suppression of the analyte ions by electrostatic attraction from ionized lipids. The review by Laskin (Laskin J, Lanekoff I. *Anal Chem.* 2016; 88(1):52-73) discusses determining these conditions. First, the solvent for extracting the sample is continuously flowing over the point of contact with the sample, so its organic content can be systematically varied while the mass spectral results are observed. Second, modifying reagents can be added to the solvent stream if desired, to adjust the pH or other solubility parameters.

NanoDESI is useful for quantitation, because the standard can be added in the flowing solvent (Laskin J, Lanekoff I. *Anal Chem.* 2016; 88(1):52-73). A second standard can also be added directly to the sample slice, to control for extraction efficiency. If two standards are thus used to calibrate for extraction and ionization independently, it is not as essential to match the properties of the analyte exactly. The synthesis of drug targets substituted with stable isotope atoms can thereby be avoided. These calibration methods may be semi-quantitative, depending on factors such as the consistency of solvent flow. The average drug concentration in the tissue will be measured from bulk tissue homogenates. The overall result will be compared with the distribution found in tissue.

The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method for inducing radiosensitization comprising administering to a subject in need thereof a molecule comprising the formula:

(A-X-B)$_n$-M-(Y-T)$_i$ wherein the molecule comprises:
  a macromolecular carrier M bound to A or B;
  a peptide A with a sequence comprising 5 to 9 consecutive acidic amino acids, wherein the amino acids are selected from the group consisting of aspartates and glutamates;
  a first cleavable linker X;
  a second cleavable linker Y;
  a radiosensitizing agent T, wherein T is monomethyl auristatin E (MMAE) or a derivative thereof;
  a peptide B with a sequence comprising 5 to 20 consecutive basic amino acids; and
  n and i are independently integers between 1 and 20;
wherein said subject is radiosensitized.

2. The method of claim 1, wherein X is selected from the group consisting of DPRSFL (SEQ ID NO: 1), PPRSFL (SEQ ID NO:2), Norleucine-TPRSFL (SEQ ID NO:3), and PLGC(Me)AG (SEQ ID NO:4).

3. The method of claim 1, wherein M is a macromolecular carrier selected from the group consisting of a dendrimer, dextran, a PEG polymer, albumin, and lipid-coated perfluorocarbon droplet.

4. The method of claim 1, wherein Y is Val-Cit-(p-amido)benzyloxycarbonyl.

* * * * *

SEQUENCE LISTING

```
<160> NUMBER OF SEQ ID NOS: 91

<210> SEQ ID NO 1
<211> LENGTH: 6
<212> TYPE: PRT
<213> ORGANISM: Artificial Sequence
<220> FEATURE:
<223> OTHER INFORMATION: cleavable linker

<400> SEQUENCE: 1

Asp Pro Arg Ser Phe Leu
1               5

<210> SEQ ID NO 2
<211> LENGTH: 6
<212> TYPE: PRT
<213> ORGANISM: Artificial Sequence
<220> FEATURE:
<223> OTHER INFORMATION: cleavable linker

<400> SEQUENCE: 2

Pro Pro Arg Ser Phe Leu
1               5

<210> SEQ ID NO 3
<211> LENGTH: 6
<212> TYPE: PRT
<213> ORGANISM: Artificial Sequence
<220> FEATURE:
<223> OTHER INFORMATION: cleavable linker
<220> FEATURE:
<221> NAME/KEY: MOD_RES
<222> LOCATION: (1)..(1)
<223> OTHER INFORMATION: Xaa = Nle

<400> SEQUENCE: 3

Xaa Thr Pro Arg Ser Phe
1               5

<210> SEQ ID NO 4
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (4)..(4)
<223> OTHER INFORMATION: S-methylcysteine

<400> SEQUENCE: 4

Pro Leu Gly Cys Ala Gly
1               5

<210> SEQ ID NO 5
<211> LENGTH: 5
<212> TYPE: PRT
<213> ORGANISM: Artificial Sequence
<220> FEATURE:
```

```
<223> OTHER INFORMATION: synthetic polypeptide

<400> SEQUENCE: 5

Ser Ser Lys Leu Gln
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 6

Gly Pro Leu Gly Ile Ala Gly Gln
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (3)..(3)
<223> OTHER INFORMATION: Citrulline
<220> FEATURE:
<221> NAME/KEY: MOD_RES
<222> LOCATION: (5)..(5)
<223> OTHER INFORMATION: Homo Phenylalanine

<400> SEQUENCE: 7

Glu Pro Arg Gly Phe Tyr Leu
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 8

Pro Val Gly Leu Ile Gly
1               5

<210> SEQ ID NO 9

<400> SEQUENCE: 9

000

<210> SEQ ID NO 10
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 10

Pro Leu Gly Leu Ala Gly
1               5

<210> SEQ ID NO 11
<211> LENGTH: 6
<212> TYPE: PRT
<213> ORGANISM: Artificial Sequence
```

```
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: Pro is modified by 5-amino-3-oxopentanoyl
<220> FEATURE:
<221> NAME/KEY: MOD_RES
<222> LOCATION: (4)..(4)
<223> OTHER INFORMATION: S-methylcysteine
<220> FEATURE:
<221> NAME/KEY: MOD_RES
<222> LOCATION: (6)..(6)
<223> OTHER INFORMATION: Gly is modified by 5-amino-3-oxopentanoyl

<400> SEQUENCE: 11

Pro Leu Gly Cys Ala Gly
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (5)..(5)
<223> OTHER INFORMATION: acetylation

<400> SEQUENCE: 12

Arg Leu Gln Leu Lys Leu
1               5

<210> SEQ ID NO 13
<211> LENGTH: 8
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (3)..(3)
<223> OTHER INFORMATION: Citrulline
<220> FEATURE:
<221> NAME/KEY: MOD_RES
<222> LOCATION: (5)..(5)
<223> OTHER INFORMATION: Homo Phenylalanine

<400> SEQUENCE: 13

Arg Ser Arg Gly Phe Tyr Leu Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 14

Pro Leu Gly Leu Glu Glu Ala
1               5

<210> SEQ ID NO 15
<211> LENGTH: 10
<212> TYPE: PRT
<213> ORGANISM: Artificial Sequence
<220> FEATURE:
<223> OTHER INFORMATION: synthetic polypeptide
```

```
<400> SEQUENCE: 15

Cys Arg Pro Ala His Leu Arg Asp Ser Gly
1               5                   10

<210> SEQ ID NO 16
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 16

Ser Leu Ala Tyr Tyr Thr Ala
1               5

<210> SEQ ID NO 17
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 17

Asn Ile Ser Asp Leu Thr Ala Gly
1               5

<210> SEQ ID NO 18
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 18

Pro Pro Ser Ser Leu Arg Val Thr
1               5

<210> SEQ ID NO 19
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 19

Ser Gly Glu Ser Leu Ser Asn Leu Thr Ala
1               5                   10

<210> SEQ ID NO 20
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 20

Arg Ile Gly Phe Leu Arg
1               5

<210> SEQ ID NO 21
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
```

```
<222> LOCATION: (5)..(5)
<223> OTHER INFORMATION: acetylation

<400> SEQUENCE: 21

Arg Leu Gln Leu Lys Leu
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 22

Gly Val Ala Tyr Ser Gly Ala
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 23

Tyr Gly Arg Ala Ala Ala
1               5

<210> SEQ ID NO 24
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 24

Tyr Gly Pro Arg Asn Arg
1               5

<210> SEQ ID NO 25

<400> SEQUENCE: 25

000

<210> SEQ ID NO 26
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (5)..(5)
<223> OTHER INFORMATION: S-methylcysteine

<400> SEQUENCE: 26

Pro Leu Gly Leu Cys Ala Gly
1               5

<210> SEQ ID NO 27
<211> LENGTH: 19
<212> TYPE: PRT
<213> ORGANISM: Artificial Sequence
<220> FEATURE:
<223> OTHER INFORMATION: synthetic polypeptide
<220> FEATURE:
```

```
<221> NAME/KEY: MOD_RES
<222> LOCATION: (8)..(8)
<223> OTHER INFORMATION: Xaa = aminocaproic acid
<220> FEATURE:
<221> NAME/KEY: MOD_RES
<222> LOCATION: (18)..(18)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = cysteinamide modified by fluorescein

<400> SEQUENCE: 27

Glu Asp Asp Asp Asp Lys Ala Xaa Arg Arg Arg Arg Arg Arg Arg
1               5                   10                  15

Arg Xaa Xaa

<210> SEQ ID NO 28
<211> LENGTH: 22
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: Xaa = aminocaproic acid modified by fluorescein
<220> FEATURE:
<221> NAME/KEY: MOD_RES
<222> LOCATION: (12)..(12)
<223> OTHER INFORMATION: Xaa = aminocaproic acid

<400> SEQUENCE: 28

Xaa Cys Arg Arg Arg Arg Arg Arg Arg Arg Arg Xaa Glu Glu Glu Glu
1               5                   10                  15

Glu Glu Glu Glu Glu Cys
            20

<210> SEQ ID NO 29
<211> LENGTH: 17
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: Xaa = aminocaproic acid modified by fluorescein
<220> FEATURE:
<221> NAME/KEY: MOD_RES
<222> LOCATION: (7)..(7)
<223> OTHER INFORMATION: Xaa = aminocaproic acid

<400> SEQUENCE: 29

Xaa Cys Glu Glu Glu Glu Xaa Arg Arg Arg Arg Arg Arg Arg Arg
1               5                   10                  15

Cys

<210> SEQ ID NO 30
<211> LENGTH: 23
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (12)..(12)
<223> OTHER INFORMATION: Xaa = aminocaproic acid
<220> FEATURE:
<221> NAME/KEY: MOD_RES
```

```
<222> LOCATION: (22)..(22)
<223> OTHER INFORMATION: Xaa = aminocaproic acid
<220> FEATURE:
<221> NAME/KEY: MOD_RES
<222> LOCATION: (23)..(23)
<223> OTHER INFORMATION: Xaa = cysteinamide modified by fluorescein

<400> SEQUENCE: 30

Glu Glu Glu Glu Glu Asp Asp Asp Asp Lys Ala Xaa Arg Arg Arg
1               5                   10                  15

Arg Arg Arg Arg Arg Xaa Xaa
            20

<210> SEQ ID NO 31
<211> LENGTH: 19
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (8)..(8)
<223> OTHER INFORMATION: Xaa = aminocaproic acid
<220> FEATURE:
<221> NAME/KEY: MOD_RES
<222> LOCATION: (18)..(18)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = cysteinamide modified by fluorescein

<400> SEQUENCE: 31

Glu Asp Asp Asp Asp Lys Ala Xaa Arg Arg Arg Arg Arg Arg Arg
1               5                   10                  15

Arg Xaa Xaa

<210> SEQ ID NO 32
<211> LENGTH: 22
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (21)..(21)
<223> OTHER INFORMATION: Xaa = aminocaproic acid
<220> FEATURE:
<221> NAME/KEY: MOD_RES
<222> LOCATION: (22)..(22)
<223> OTHER INFORMATION: Xaa = cysteinamide modified by fluorescein

<400> SEQUENCE: 32

Glu Glu Glu Glu Glu Asp Asp Asp Asp Lys Ala Arg Arg Arg Arg
1               5                   10                  15

Arg Arg Arg Arg Xaa Xaa
            20

<210> SEQ ID NO 33

<400> SEQUENCE: 33

000

<210> SEQ ID NO 34
<211> LENGTH: 19
<212> TYPE: PRT
<213> ORGANISM: Artificial Sequence
<220> FEATURE:
```

```
<223> OTHER INFORMATION: synthetic polypeptide
<220> FEATURE:
<221> NAME/KEY: MOD_RES
<222> LOCATION: (18)..(18)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = cysteinamide modified by fluorescein

<400> SEQUENCE: 34

Asp Asp Asp Asp Asp Asp Lys Ala Arg Arg Arg Arg Arg Arg Arg Arg
1               5                   10                  15

Arg Xaa Xaa

<210> SEQ ID NO 35
<211> LENGTH: 23
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (10)..(10)
<223> OTHER INFORMATION: Xaa = aminocaproic acid
<220> FEATURE:
<221> NAME/KEY: MOD_RES
<222> LOCATION: (13)..(13)
<223> OTHER INFORMATION: Xaa = aminocaproic acid
<220> FEATURE:
<221> NAME/KEY: MOD_RES
<222> LOCATION: (16)..(16)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = aminocaproic acid
<220> FEATURE:
<221> NAME/KEY: MOD_RES
<222> LOCATION: (22)..(22)
<223> OTHER INFORMATION: Xaa = aminocaproic acid
<220> FEATURE:
<221> NAME/KEY: MOD_RES
<222> LOCATION: (23)..(23)
<223> OTHER INFORMATION: Xaa = cysteinamide modified by fluorescein

<400> SEQUENCE: 35

Glu Glu Asp Asp Asp Asp Lys Ala Arg Xaa Arg Arg Xaa Arg Arg Xaa
1               5                   10                  15

Arg Arg Xaa Arg Arg Xaa Xaa
            20

<210> SEQ ID NO 36

<400> SEQUENCE: 36

000

<210> SEQ ID NO 37
<211> LENGTH: 11
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (4)..(4)
<223> OTHER INFORMATION: Xaa = aminocaproic acid
<220> FEATURE:
<221> NAME/KEY: MOD_RES
<222> LOCATION: (10)..(10)
<223> OTHER INFORMATION: Xaa = aminocaproic acid
```

```
<220> FEATURE:
<221> NAME/KEY: MOD_RES
<222> LOCATION: (11)..(11)
<223> OTHER INFORMATION: Xaa = cysteinamide modified by fluorescein

<400> SEQUENCE: 37

Glu Asp Ala Xaa Arg Arg Arg Arg Arg Xaa Xaa
1               5                   10

<210> SEQ ID NO 38
<211> LENGTH: 19
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (8)..(8)
<223> OTHER INFORMATION: Xaa = aminocaproic acid
<220> FEATURE:
<221> NAME/KEY: MOD_RES
<222> LOCATION: (18)..(18)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = cysteinamide modified by doxorubicin

<400> SEQUENCE: 38

Glu Asp Asp Asp Asp Lys Ala Xaa Arg Arg Arg Arg Arg Arg Arg
1               5                   10                  15

Arg Xaa Xaa

<210> SEQ ID NO 39
<211> LENGTH: 23
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (12)..(12)
<223> OTHER INFORMATION: Xaa = aminocaproic acid
<220> FEATURE:
<221> NAME/KEY: MOD_RES
<222> LOCATION: (22)..(22)
<223> OTHER INFORMATION: Xaa = aminocaproic acid
<220> FEATURE:
<221> NAME/KEY: MOD_RES
<222> LOCATION: (23)..(23)
<223> OTHER INFORMATION: Tyr modified by iodination with 125-I and by
      amidation

<400> SEQUENCE: 39

Glu Glu Glu Asp Asp Asp Glu Glu Glu Asp Ala Xaa Arg Arg Arg Arg
1               5                   10                  15

Arg Arg Arg Arg Arg Xaa Tyr
            20

<210> SEQ ID NO 40

<400> SEQUENCE: 40

000

<210> SEQ ID NO 41

<400> SEQUENCE: 41

000
```

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49
<211> LENGTH: 23
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (12)..(12)
<223> OTHER INFORMATION: Xaa = aminocaproic acid
<220> FEATURE:
<221> NAME/KEY: MOD_RES
<222> LOCATION: (22)..(22)
<223> OTHER INFORMATION: Xaa = aminocaproic acid
<220> FEATURE:
<221> NAME/KEY: MOD_RES
<222> LOCATION: (23)..(23)
<223> OTHER INFORMATION: Xaa = cysteinamide modified by fluorescein

<400> SEQUENCE: 49

Glu Glu Glu Glu Glu Asp Asp Asp Asp Lys Ala Xaa Arg Arg Arg Arg
1               5                   10                  15

Arg Arg Arg Arg Arg Xaa Xaa
            20

```
<210> SEQ ID NO 50
<211> LENGTH: 22
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (21)..(21)
<223> OTHER INFORMATION: Xaa = aminocaproic acid
<220> FEATURE:
<221> NAME/KEY: MOD_RES
<222> LOCATION: (22)..(22)
<223> OTHER INFORMATION: Xaa = cysteinamide modified by fluorescein

<400> SEQUENCE: 50

Glu Glu Glu Glu Glu Asp Asp Asp Asp Lys Ala Arg Arg Arg Arg
1               5                   10                  15

Arg Arg Arg Arg Xaa Xaa
                20

<210> SEQ ID NO 51
<211> LENGTH: 19
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (8)..(8)
<223> OTHER INFORMATION: Xaa = aminocaproic acid
<220> FEATURE:
<221> NAME/KEY: MOD_RES
<222> LOCATION: (18)..(18)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = cysteinamide modified by fluorescein

<400> SEQUENCE: 51

Glu Asp Asp Asp Asp Lys Ala Xaa Arg Arg Arg Arg Arg Arg Arg
1               5                   10                  15

Arg Xaa Xaa

<210> SEQ ID NO 52
<211> LENGTH: 23
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (10)..(10)
<223> OTHER INFORMATION: Xaa = aminocaproic acid
<220> FEATURE:
<221> NAME/KEY: MOD_RES
<222> LOCATION: (13)..(13)
<223> OTHER INFORMATION: Xaa = aminocaproic acid
<220> FEATURE:
<221> NAME/KEY: MOD_RES
<222> LOCATION: (16)..(16)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = aminocaproic acid
<220> FEATURE:
<221> NAME/KEY: MOD_RES
<222> LOCATION: (22)..(22)
<223> OTHER INFORMATION: Xaa = aminocaproic acid
<220> FEATURE:
<221> NAME/KEY: MOD_RES
```

```
<222> LOCATION: (23)..(23)
<223> OTHER INFORMATION: Xaa = cysteinamide modified by fluorescein

<400> SEQUENCE: 52

Glu Glu Asp Asp Asp Asp Lys Ala Arg Xaa Arg Arg Xaa Arg Arg Xaa
1               5                   10                  15

Arg Arg Xaa Arg Arg Xaa Xaa
            20

<210> SEQ ID NO 53
<211> LENGTH: 19
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (18)..(18)
<223> OTHER INFORMATION: Xaa = aminocaproic acid
<220> FEATURE:
<221> NAME/KEY: MOD_RES
<222> LOCATION: (19)..(19)
<223> OTHER INFORMATION: Xaa = cysteinamide modified by fluorescein

<400> SEQUENCE: 53

Asp Asp Asp Asp Asp Asp Lys Ala Arg Arg Arg Arg Arg Arg Arg
1               5                   10                  15

Arg Xaa Xaa

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60
```

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77
<211> LENGTH: 18
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: acetylation

<400> SEQUENCE: 77

Asp Trp Phe Lys Ala Phe Tyr Asp Lys Val Ala Glu Lys Phe Lys Glu
1               5                   10                  15

Ala Phe

<210> SEQ ID NO 78
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 78

Arg Pro Lys Arg Pro Thr Thr Leu Asn Leu Phe
1               5                   10

<210> SEQ ID NO 79
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 79

```
Lys Lys His Thr Asp Asp Gly Tyr Met Pro Met Ser Pro Gly Val Ala
1               5                   10                  15
```

<210> SEQ ID NO 80
<211> LENGTH: 28
<212> TYPE: PRT
<213> ORGANISM: Artificial Sequence
<220> FEATURE:
<223> OTHER INFORMATION: synthetic polypeptide

<400> SEQUENCE: 80

```
Asp Arg Gln Ile Lys Ile Trp Phe Gln Asn Arg Arg Met Lys Trp Lys
1               5                   10                  15

Lys Thr Ala Leu Asp Trp Ser Trp Leu Gln Thr Glu
            20                  25
```

<210> SEQ ID NO 81
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 81

```
Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25
```

<210> SEQ ID NO 82
<211> LENGTH: 29
<212> TYPE: PRT
<213> ORGANISM: Artificial Sequence
<220> FEATURE:
<223> OTHER INFORMATION: synthetic polypeptide

<400> SEQUENCE: 82

```
Arg Gln Ile Lys Ile Trp Phe Asn Arg Arg Met Lys Trp Lys Lys Leu
1               5                   10                  15

Gln Leu Arg Asp Ala Ala Pro Gly Gly Ala Ile Val Ser
            20                  25
```

<210> SEQ ID NO 83
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (2)..(2)
<223> OTHER INFORMATION: Glu modified by O-methylation
<220> FEATURE:
<221> NAME/KEY: MOD_RES
<222> LOCATION: (4)..(4)
<223> OTHER INFORMATION: Asp modified by O-methylation and by attachment
      to fluoromethyl ketone (FMK)

<400> SEQUENCE: 83

```
Leu Glu His Asp
1
```

<210> SEQ ID NO 84
<211> LENGTH: 4
<212> TYPE: PRT
<213> ORGANISM: Artificial Sequence
<220> FEATURE:

```
<223> OTHER INFORMATION: synthetic polypeptide
<220> FEATURE:
<221> NAME/KEY: MOD_RES
<222> LOCATION: (1)..(1)
<223> OTHER INFORMATION: acetylation
<220> FEATURE:
<221> NAME/KEY: MOD_RES
<222> LOCATION: (4)..(4)
<223> OTHER INFORMATION: Asp modified by oxidation of the terminal
      backbone carboxyl group to an aldehyde

<400> SEQUENCE: 84

Leu Glu His Asp
1

<210> SEQ ID NO 85
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: acetylation
<220> FEATURE:
<221> NAME/KEY: MOD_RES
<222> LOCATION: (4)..(4)
<223> OTHER INFORMATION: Asp modified by oxidation of the terminal
      backbone carboxyl group to an aldehyde

<400> SEQUENCE: 85

Leu Glu Thr Asp
1

<210> SEQ ID NO 86
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: Ile modified by attachment to benzylcarbonyl
      group
<220> FEATURE:
<221> NAME/KEY: MOD_RES
<222> LOCATION: (2)..(2)
<223> OTHER INFORMATION: Glu modified by O-methylation
<220> FEATURE:
<221> NAME/KEY: MOD_RES
<222> LOCATION: (4)..(4)
<223> OTHER INFORMATION: Asp modified by O-methylation and by attachment
      to fluoromethyl ketone (FMK)

<400> SEQUENCE: 86

Ile Glu Thr Asp
1

<210> SEQ ID NO 87
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: Leu modified by attachment to benzylcarbonyl
      group
<220> FEATURE:
<221> NAME/KEY: MOD_RES
```

```
<222> LOCATION: (4)..(4)
<223> OTHER INFORMATION: Asp is modifed by attachment to fluoromethyl
      ketone

<400> SEQUENCE: 87

Leu Glu His Asp
1

<210> SEQ ID NO 88
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: Leu modified by attachment to benzylcarbonyl
      group
<220> FEATURE:
<221> NAME/KEY: MOD_RES
<222> LOCATION: (4)..(4)
<223> OTHER INFORMATION: Asp is modifed by attachment to iuoromethyl
      ketone

<400> SEQUENCE: 88

Leu Glu Thr Asp
1

<210> SEQ ID NO 89

<400> SEQUENCE: 89

000

<210> SEQ ID NO 90
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 90

Glu Glu Glu Glu Glu Glu Glu Glu
1               5

<210> SEQ ID NO 91
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 91

Arg Arg Arg Arg Arg Arg Arg Arg Arg
1               5
```